(12) United States Patent  
Campbell et al.

(10) Patent No.: US 8,415,295 B2
(45) Date of Patent: *Apr. 9, 2013

(54) HETEROCYCLIC BORONIC ACID COMPOUNDS

(75) Inventors: David Alan Campbell, San Diego, CA (US); David T. Winn, San Diego, CA (US); Juan Manuel Betancort, San Diego, CA (US)

(73) Assignee: Phenomix Corporation, Encinitas, CA (US)

( * ) Notice: Subject to any disclaimer, the term of this patent is extended or adjusted under 35 U.S.C. 154(b) by 442 days.

This patent is subject to a terminal disclaimer.

(21) Appl. No.: 12/692,276

(22) Filed: Jan. 22, 2010

(65) Prior Publication Data

US 2010/0120661 A1 May 13, 2010

Related U.S. Application Data

(63) Continuation of application No. 10/514,575, filed as application No. PCT/US2004/037820 on Nov. 12, 2004, now Pat. No. 7,674, 913.

(60) Provisional application No. 60/519,566, filed on Nov. 12, 2003, provisional application No. 60/557,011, filed on Mar. 25, 2004, provisional application No. 60/592,972, filed on Jul. 30, 2004.

(51) Int. Cl.
*A61K 38/28* (2006.01)
*A61K 31/69* (2006.01)
*C07F 5/02* (2006.01)
*C12N 9/99* (2006.01)
*C07D 205/02* (2006.01)
*A61P 3/10* (2006.01)

(52) U.S. Cl.
USPC ............... 514/3; 514/64; 548/405; 435/184; 546/13; 540/200; 544/229

(58) Field of Classification Search ............... None
See application file for complete search history.

(56) References Cited

U.S. PATENT DOCUMENTS

| | | | |
|---|---|---|---|
| 3,674,836 A | 7/1972 | Creger | |
| 3,983,140 A | 9/1976 | Endo et al. | |
| 4,027,009 A | 5/1977 | Grier et al. | |
| 4,231,938 A | 11/1980 | Monaghan et al. | |
| 4,346,227 A | 8/1982 | Terahara et al. | |
| 4,448,784 A | 5/1984 | Glamkowski et al. | |
| 4,450,171 A | 5/1984 | Hoffman et al. | |
| 4,572,912 A | 2/1986 | Yoshioka et al. | |
| 4,681,893 A | 7/1987 | Roth | |
| 4,759,923 A | 7/1988 | Buntin et al. | |
| 4,871,721 A | 10/1989 | Biller | |
| 4,924,024 A | 5/1990 | Biller | |
| 4,935,493 A * | 6/1990 | Bachovchin et al. | 530/331 |
| 5,006,530 A | 4/1991 | Angerbauer et al. | |
| 5,011,930 A | 4/1991 | Fujikawa et al. | |
| 5,177,080 A | 1/1993 | Angerbauer et al. | |
| 5,260,440 A | 11/1993 | Hirai et al. | |
| 5,273,995 A | 12/1993 | Roth | |
| 5,346,701 A | 9/1994 | Heiber et al. | |
| 5,354,772 A | 10/1994 | Kathawala | |
| 5,385,929 A | 1/1995 | Bjorge et al. | |
| 5,447,954 A | 9/1995 | Gribble et al. | |
| 5,462,928 A | 10/1995 | Bachovchin et al. | |
| 5,488,064 A | 1/1996 | Sher | |
| 5,491,134 A | 2/1996 | Sher et al. | |

(Continued)

FOREIGN PATENT DOCUMENTS

| CA | 2121369 | 4/1992 |
|---|---|---|
| CA | 2334155 | 12/1999 |

(Continued)

OTHER PUBLICATIONS

Pederson et al. in Diabetes vol. 47, Aug. 1998, 1253-1258.*
"U.S. Appl. No. 11/420,273, Notice of Allowance mailed Jan. 28, 2010", 7 pgs.
"U.S. Appl. No. 11/420,273, Response filed May 26, 2009 to Restriction Requirement mailed Mar. 23, 2009", 18 pgs.
"U.S. Appl. No. 11/420,273, Response filed Nov. 10, 2009 to Non Final Office Action mailed Jul. 31, 2009", 8 pgs.
"U.S. Appl. No. 11/833,063, Advisory Action mailed Oct. 31, 2010", 2 pgs.

(Continued)

*Primary Examiner* — Dennis Heyer
(74) *Attorney, Agent, or Firm* — Schwegman Lundberg & Woessner, P.A.

(57) ABSTRACT

Dipeptidyl peptidase IV (DPP-IV)-inhibiting compounds are provided that have formula I: wherein n is 1 to 3; X is $CH_2$, S; O; $CF_2$ or $C(CH_3)_2$; Z is H; halogen; hydroxyl; $(C_{1-6})$alkoxy; $(C_{1-12})$alkyl; $(C_{3-12})$cycloalkyl; phenyl; or heteroaryl; where the phenyl and heteroaryl groups are optionally mono- or independently plurisubstituted with R7; optionally, X together with an adjacent ring carbon and Z form a fused cyclopropyl; and optionally, one of the bonds in the ring containing X is a double bond; and $Cr^jR^{ii}$, $R^1$, $R^1$, $R^3$, $R^4$ and $R^5$ are as described herein. Methods for preparing these compounds, and methods for treating diabetes, especially Type II diabetes, and other related diseases are described using the compounds of formula I in pharmaceutical compositions which contain these compounds. Pharmaceutical compositions which contain combinations of these compounds with other antidiabetic agents are also described herein.

12 Claims, 1 Drawing Sheet

U.S. PATENT DOCUMENTS

| | | | |
|---|---|---|---|
| 5,541,204 A | 7/1996 | Sher et al. |
| 5,574,017 A | 11/1996 | Gutheil |
| 5,594,016 A | 1/1997 | Ueno et al. |
| 5,595,872 A | 1/1997 | Wetterau, II et al. |
| 5,614,492 A | 3/1997 | Habener |
| 5,631,224 A | 5/1997 | Efendic et al. |
| 5,686,104 A | 11/1997 | Mills et al. |
| 5,712,279 A | 1/1998 | Biller et al. |
| 5,712,396 A | 1/1998 | Magnin et al. |
| 5,739,135 A | 4/1998 | Biller et al. |
| 5,760,246 A | 6/1998 | Biller et al. |
| 5,770,615 A | 6/1998 | Cheng et al. |
| 5,776,983 A | 7/1998 | Washburn et al. |
| 5,827,875 A | 10/1998 | Dickson, Jr. et al. |
| 5,885,983 A | 3/1999 | Biller et al. |
| 5,952,301 A | 9/1999 | Drucker |
| 5,952,322 A | 9/1999 | Hoover et al. |
| 5,962,440 A | 10/1999 | Sulsky |
| 5,965,532 A | 10/1999 | Bachovchin |
| 5,998,463 A | 12/1999 | Hulin et al. |
| 6,011,155 A | 1/2000 | Villhauer |
| 6,040,145 A | 3/2000 | Huber et al. |
| 6,107,317 A | 8/2000 | Villhauer |
| 6,110,949 A | 8/2000 | Villhauer |
| 6,124,305 A | 9/2000 | Villhauer |
| 6,166,063 A | 12/2000 | Villhauer |
| 6,172,081 B1 | 1/2001 | Damon |
| 6,258,597 B1 | 7/2001 | Bachovchin et al. |
| 6,300,314 B1 | 10/2001 | Wallner et al. |
| 6,303,661 B1 | 10/2001 | Demuth et al. |
| 6,355,614 B1 | 3/2002 | Wallner |
| 6,380,398 B2 | 4/2002 | Kanstrup et al. |
| 6,395,767 B2 | 5/2002 | Robl et al. |
| 6,432,969 B1 | 8/2002 | Villhauer |
| 6,617,340 B1 | 9/2003 | Villhauer |
| 6,989,402 B1 | 1/2006 | Hangeland et al. |
| 7,317,109 B2 | 1/2008 | Campbell et al. |
| 7,576,121 B2 | 8/2009 | Campbell et al. |
| 7,674,913 B2 | 3/2010 | Campbell et al. |
| 7,767,828 B2 | 8/2010 | Campbell et al. |
| 7,884,217 B2 | 2/2011 | Campbell et al. |
| 7,906,658 B2 | 3/2011 | Campbell et al. |
| 2003/0100563 A1 | 5/2003 | Edmondson et al. |
| 2003/0153509 A1 | 8/2003 | Bachovchin et al. |
| 2006/0258621 A1 | 11/2006 | Campbell et al. |
| 2006/0264400 A1 | 11/2006 | Campbell et al. |
| 2006/0264401 A1 | 11/2006 | Campbell et al. |
| 2006/0276410 A1 | 12/2006 | Campbell et al. |
| 2007/0185061 A1 | 8/2007 | Campbell |
| 2007/0299036 A1 | 12/2007 | Campbell et al. |
| 2008/0182995 A1 | 7/2008 | Campbell et al. |

FOREIGN PATENT DOCUMENTS

| | | |
|---|---|---|
| CA | 2468192 | 6/2003 |
| CA | 2545311 C | 1/2012 |
| DE | 19616486 A1 | 10/1997 |
| EP | 0818448 B1 | 1/1998 |
| EP | 0896538 B1 | 2/1999 |
| EP | 0978279 A1 | 2/2000 |
| EP | 1041068 B1 | 4/2004 |
| IL | 175550 | 11/2011 |
| JP | 2009007377 A | 4/2000 |
| JP | 2007512254 | 5/2007 |
| JP | 2008220344 A | 9/2008 |
| KR | 20060121170 | 11/2006 |
| MX | 283828 B | 2/2011 |
| WO | WO-8903223 A1 | 4/1989 |
| WO | WO-9116339 A1 | 10/1991 |
| WO | WO-9308259 A2 | 4/1993 |
| WO | WO-9310127 A1 | 5/1993 |
| WO | WO-9511689 A1 | 5/1995 |
| WO | WO-9515309 A1 | 6/1995 |
| WO | WO-9639384 A1 | 12/1996 |
| WO | WO-9639385 A1 | 12/1996 |
| WO | WO-9712613 A1 | 4/1997 |
| WO | WO-9712615 A1 | 4/1997 |
| WO | WO-9721993 A2 | 6/1997 |
| WO | WO-9800439 A2 | 1/1998 |
| WO | WO-9819998 A2 | 5/1998 |
| WO | WO-9850046 A1 | 11/1998 |
| WO | WO-9900353 A1 | 1/1999 |
| WO | WO-9903850 A1 | 1/1999 |
| WO | WO-9926659 A1 | 6/1999 |
| WO | WO-9938501 A2 | 8/1999 |
| WO | WO-9943663 A1 | 9/1999 |
| WO | WO-0034241 A1 | 6/2000 |
| WO | WO-0038722 A1 | 7/2000 |
| WO | WO-0047206 A1 | 8/2000 |
| WO | WO-03045228 A2 | 6/2003 |
| WO | WO-03045977 A2 | 6/2003 |
| WO | WO-03045977 A3 | 6/2003 |
| WO | WO-03082817 A2 | 10/2003 |
| WO | WO-2004004661 A2 | 1/2004 |
| WO | WO-2004044661 A3 | 5/2004 |
| WO | WO-2005047297 A1 | 5/2005 |
| WO | WO-2005075426 A1 | 8/2005 |
| WO | WO-2006040625 A1 | 4/2006 |

OTHER PUBLICATIONS

"U.S. Appl. No. 11/833,063, Notice of Allowance mailed Nov. 3, 2010", 8 pgs.

"U.S. Appl. No. 11/833,063, Response filed Sep. 29, 2010 to Final Office Action mailed Aug. 25, 2010", 7 pgs.

"U.S. Appl. No. 11/833,063, Response filed Oct. 20, 2010 to Advisory Action mailed Aug. 25, 2010", 6 pgs.

"U.S. Appl. No. 11/930,337, Notice of Allowance mailed Sep. 22, 2010", 6 pgs.

"Canadian Application Serial No. 2,545,311, Office Action Response Filed Sep. 7, 2010", 24 pgs.

"Chile Application Serial No. 1034-06, Office Action mailed Oct. 12, 2010", 9 Pgs.

"Chinese Application Serial No. 200810215690.7, Office Action Response filed Aug. 6, 2010", 22 pgs.

"Japanese Application Serial No. 2006-539906 , Office Action Response filed Oct. 1, 2010", 11 pgs.

"Japanese Application Serial No. 2008-220344, Office Action Response Filed Oct. 1, 2010", 9 pgs.

"Mexican Application Serial No. PA/a/2006/005405, Office Action mailed Oct. 14, 2010", 1 pg.

"Taiwanese Application Serial No. 093134776, Office Action Mailed Sep. 15, 2010", 8 pgs.

"U.S. Appl. No. 10/514,575, Final Office Action mailed Nov. 10, 2009", 21 Pgs.

"U.S. Appl. No. 10/514,575, Non-Final Office Action mailed Dec. 29, 2008", 17 pgs.

"U.S. Appl. No. 10/514,575, Notice of Allowance mailed Jan. 13, 2010", 9 pgs.

"U.S. Appl. No. 10/514,575, Preliminary Amendment filed Nov. 6, 2006", 19 pgs.

"U.S. Appl. No. 10/514,575, Response filed Mar. 23, 2009 to Non Final Office Action mailed Dec. 29, 2008", 31 pgs.

"U.S. Appl. No. 10/514,575, Response filed Jul. 20, 2009 to Non Final Office Action mailed Dec. 29, 2008", 31 pgs.

"U.S. Appl. No. 10/514,575, Response filed Sep. 17, 2008 to Restriction Requirement mailed Aug. 19, 2008", 21 pgs.

"U.S. Appl. No. 10/514,575, Response filed Dec. 17, 2009 to Final Office Action mailed Nov. 10, 2009", 6 pgs.

"U.S. Appl. No. 10/514,575, Restriction Requirement mailed Aug. 19, 2008", 11 pgs.

"U.S. Appl. No. 10/514,575, Supplemental Preliminary Amendment filed Nov. 13, 2006", 21 pgs.

"U.S. Appl. No. 11/381,082, Final Office Action mailed Sep. 19, 2008", 14 pgs.

"U.S. Appl. No. 11/381,082, Non-Final Office Action mailed Mar. 17, 2008", 15 pgs.

"U.S. Appl. No. 11/381,082, Notice of Allowance mailed Apr. 17, 2009", 7 pgs.

"U.S. Appl. No. 11/381,082, Notice of Allowance mailed Dec. 31, 2008", 7 pgs.

"U.S. Appl. No. 11/381,082, Response filed Jun. 17, 2008 to Non Final Office Action mailed Mar. 17, 2008", 21 pgs.

"U.S. Appl. No. 11/381,082, Response filed Nov. 19, 2008 to Final Office Action mailed Sep. 19, 2008", 26 pgs.
"U.S. Appl. No. 11/381,085, Non-Final Office Action mailed Aug. 1, 2007", 9 pgs.
"U.S. Appl. No. 11/381,085, Notice of Allowance mailed Oct. 11, 2007", 4 pgs.
"U.S. Appl. No. 11/381,085, Response filed May 2, 2007 to Restriction Requirement mailed Apr. 2, 2007", 13 pgs.
"U.S. Appl. No. 11/381,085, Response filed Sep. 13, 2007 to Non-Final Office Action mailed Aug. 1, 2007", 9 pgs.
"U.S. Appl. No. 11/381,085, Restriction Requirement mailed Apr. 2, 2007", 12 pgs.
"U.S. Appl. No. 11/381,090 , Notice of Allowance mailed Jan. 12, 2010", 8 Pgs.
"U.S. Appl. No. 11/381,090 Response filed Aug. 6, 2009 to Non-Final Office Action mailed Jun. 9, 2009", 14 pgs.
"U.S. Appl. No. 11/381,090, Final Office Action Mailed Nov. 4, 2009", 10 pgs.
"U.S. Appl. No. 11/381,090, Final Office Action mailed Dec. 22, 2008", 11 pgs.
"U.S. Appl. No. 11/381,090, Non-Final Office Action mailed Jun. 9, 2009", 16 pgs.
"U.S. Appl. No. 11/381,090, Non-Final Office Action mailed Jun. 26, 2008", 11 pgs.
"U.S. Appl. No. 11/381,090, Response filed Mar. 17, 2008 to Restriction Requirement mailed Feb. 19, 2008", 3 pgs.
"U.S. Appl. No. 11/381,090, Response filed Mar. 20, 2009 to Final Office Action mailed Dec. 22, 2008", 13 pgs.
"U.S. Appl. No. 11/381,090, Response filed Sep. 23, 2008 to Non Final Office Action mailed Jun. 26, 2008", 25 pgs.
"U.S. Appl. No. 11/381,090, Response filed Dec. 16, 2009 to Final Office Action mailed Nov. 4, 2009", 11 pgs.
"U.S. Appl. No. 11/381,090, Restriction Requirement mailed Feb. 19, 2008", 12 pgs.
"U.S. Appl. No. 11/420,273, Non-Final Office Action mailed Jul. 31, 2009", 6 pgs.
"U.S. Appl. No. 11/420,273, Restriction Requirement mailed Mar. 23, 2009", 6 pgs.
"U.S. Appl. No. 11/556,944, Preliminary Amendment mailed Jul. 15, 2008", 9 pgs.
"U.S. Appl. No. 11/833,063, Non-Final Office Action mailed May 11, 2010", 16 pgs.
"U.S. Appl. No. 11/833,063, Preliminary Amendment filed Mar. 30, 2009", 9 pgs.
"U.S. Appl. No. 11/833,063, Preliminary Amendment mailed Feb. 11, 2010", 5 pgs.
"U.S. Appl. No. 11/833,063, Preliminary Amendment mailed Jun. 24, 2009", 10 pgs.
"U.S. Appl. No. 11/833,063, Response filed Jun. 14, 2010 to Non Final Office Action mailed May 11, 2010", 8 pgs.
"U.S. Appl. No. 11/930,337, Preliminary Amendment mailed Feb. 11, 2010", 5 pgs.
"Australian Application Serial No. 2004288831, First Examiner Report mailed Apr. 8, 2010", 3 Pgs.
"Australian Application Serial No. 2008229787, First Examiner Report mailed Apr. 9, 2010", 2 Pgs.
"Avasimibe: Treatment of Lipoprotein Disorders, ACAT Inhibitor", *Drugs of the Future* 24(1), Copyright 1999 PROUS Science, (1999), 9-15.
"Canadian Application Serial No. 2,545,311, Office Action mailed Mar. 17, 2009", 6 pgs.
"Canadian Application Serial No. 2,545,311, Office Action mailed Apr. 12, 2010", 2 pgs.
"Canadian Application Serial No. 2,602,772, Office Action Mailed Mar. 2, 2009", 32 pgs.
"Chilean Application Serial No. 1034-06, Office Action mailed Apr. 15, 2009", 6 pgs.
"Chilean Application Serial No. 1034-06, Office Action mailed Sep. 10, 2008", 10 pgs.
"Chinese Application Serial No. 200480037257.9, Office Action Mailed Dec. 5, 2008", 10 pgs.
"Chinese Application Serial No. 200810215690.7, Office Action mailed Mar. 22, 2010", 9 pages.
"Eurasian Application Serial No. 200600935, Notice of Allowance mailed Dec. 28, 2009", 1 pg.
"European Application Serial No. 08013650.0, Extended European Search Report Mailed Oct. 31, 2008", 4 pgs.
"European Application Serial No. 08013650.0, Office Action Mailed on Jun. 29, 2009", 1 pg.
"European Application Serial No. 04810839.3, Office Action mailed Oct. 23, 2008", 4 pgs.
"International Application Serial No. 04810839.3, Non-Final Office Action mailed Jul. 18, 2007", 4 pgs.
"International Application Serial No. 04810839.3, Supplemental European Search Report mailed Dec. 13, 2006", 3 pgs.
"International Application Serial No. 06015708.8, Non-Final Office Action mailed Aug. 17, 2007", 1 pgs.
"International Application Serial No. 06015708.8-2177, Extended European Search Report mailed Dec. 13, 2006", 16 pgs.
"International Application Serial No. 2,545,311, Non-Final Office Action mailed May 10, 2007", 1 pg.
"International Application Serial No. 200603077-9, Response filed Aug. 27, 2007 to Non-Final Office Action mailed May 29, 2007", 45 pgs.
"International Application Serial No. 200603077-9, Non-Final Office Action mailed Mar. 24, 2008", 4 pgs.
"International Application Serial No. 200603077-9, Non-Final Office Action mailed May 29, 2007", 4 pgs.
"International Application Serial No. 547752, Examination Report Mailed Nov. 6, 2008", 6 pgs.
"International Application Serial No. PCT/US04/37820, International Search Report and Written Opinion mailed Mar. 10, 2005", 9 pgs.
"International Application Serial No. PCT/US04/37820, International Search Report mailed Mar. 10, 2005", 5 pgs.
"International Application Serial No. PCT/US04/37820, Written Opinion mailed Mar. 10, 2005", 4 pgs.
"Israel Application Serial No. 175550 , Office Action mailed Mar. 23, 2010", 1 pg.
"Israeli Application Serial No. 175550, Office Action Mailed May 25, 2009", 2 pgs.
"Korean Application Serial No. 10-2006-7011419, Office Action mailed May 16, 2008", 10 pgs.
"Korean Application Serial No. 10-2006-7011419, Office Action mailed Apr. 8, 2008", 32 pgs.
"Korean Application Serial No. 10-2006-7011419, Office Action mailed Feb. 23, 2009", 2 pgs.
"New Zealand Application Serial No. 547752, Examiner Report mailed on Sep. 2, 2009", 2 pgs.
"Point Therapeutics", http://www.pther.com, [Online]. Retrieved from the Internet: <URL: http://webarchive.org/web/20070827113729/http://www.pther.com/>.
"Singapore Application Serial No. 200603077-9, Examination Report Oct. 6, 2008", 6 pgs.
"Taiwan Application Serial No. 093134766, Office Action mailed Jun. 8, 2010", 3 pgs.
"Taiwanese Application Serial No. 093134776, Office Action Mailed Feb. 12, 2010", 5 pgs.
Augustyns, K., et al., "The unique properties of dipeptidyl-peptidase IV (DPP IV / CD 26) and the therapeutic potential of DPP IV inhibitors", *Curr Med Chem.*, 6(4), (Apr. 1999), 311-27.
Bachovchin, W. W., et al., "Inhibition of IgA1 Proteinases from *Neisseria gonorrhoeae* and *Hemophilus influenzae* by Peptide Prolyl Boronic Acids", *Journal of Biological Chemistry*, 265(7), (Mar. 5, 1990), 3738-3743.
Balkan, B., et al., "Improved Insulin Secretion and Oral Glucose Tolerance after In Vivo Inhibition of DPP-IV in Obese Zucker Rats", *Diabetologia*, Suppl. 40, A131 Abstract, (1977), 1 page.
Balkan, B., et al., "Inhibition of dipeptidyl peptidase IV with NVP-DPP728 increases plasma GLP-1 (7-36 amide) concentrations and improves oral glucose tolerance in obese Zucker rats.", *Diabetologia*, 42(11), (Nov. 1999), 1324-31.
Biller, S. A., et al., "Communications to the Editor: Isoprenoid (Phosphinylmethyl)phosphonates as Inhibitors of Squalene Synthetase", *Journal of Medicinal Chemistry*, 31(10), (Oct. 1988), 1869-1871.

Biller, S. A., "Squalene Synthase Inhibitors", *Current Pharmaceutical Design*, 2(1), (1996), 1-40.

Chen, W. T, "DPPIV and seprase in cancer invasion and angiogenesis.", *Adv Exp Med Biol.*, 524, (2003), 197-203.

Conarello, S. L, et al., "Mice lacking dipeptidyl peptidase IV are protected against obesity and insulin resistance.", *Proc Natl Acad Sci U S A.*, 100(11), (May 27, 2003), 6825-30.

Corey, E. J., "Application of Unreactive Analogs of Terpenoid Pyrophosphates to Studies of Multistep Biosynthesis. Demonstration That "Presqualene Pyrophosphate" Is an Essential Intermediate on the Path to Squalene", *Journal of the American Chemical Society*, 98(5), (1976), 1291-1293.

Coutts, S. J, et al., "Two Efficient Methods for the Cleavage of Pinanediol boronate Esters Yielding the Free Boronic Acids", *Tetrahedron Letters*, 35(29), (1994), 5109-5112.

Coutts, Simon J., "Structure-Activity Relationships of Boronic Acid Inhibitors of Dipeptidyl Peptidase IV. 1. Variation of the P2 Position of Xaa-boroPro Dipeptides", *J. Med. Chem.* 39(10), (May 10, 1996), 2087-2094.

Dang, N. H, et al., "CD26: an expanding role in immune regulation and cancer.", *Histol Histopathol.*, 17(4), (Oct. 2002), 1213-26.

Deacon, C. F., et al., "Both Subcutaneously and Intravenously Administered Glucagon-Like Peptide I are Rapidly Degraded From the NH2-Terminus in Type II Diabetic Patients and in Healthy Subjects", *Diabetes*, 44(9), http://gateway.ut.ovid.com.floyd.lib.umn.edu/gw2/ovidweb.cgi, (1995), 1126-1131 (11 pgs.).

Deacon, C. F., et al., "Dipeptidyl Peptidase IV Inhibition as an Approach to the Treatment and Prevention of Type 2 Diabetes: a Historical Perspective", *Biochemical and Biophysical Research Communications* 294, (2002), 1-4.

Demuth, H.-U., et al., "Rebuttal to Deacon and Holst: "Metformin Effects on Dipeptidyl Peptidase IV Degradation of Glucagon-like Peptide-1" Versus "Dipeptidyl Peptidase Inhibition as an Approach to the Treatment and Prevention of Type 2 Diabetes: a Historical Perspective"", *Biochemical and Biophysical Research Communications* 296, (2002), 229-232.

Flentke, G. R., et al., "Inhibition of dipeptidyl aminopeptidase IV (DP-IV) by Xaa-boroPro dipeptides and use of these inhibitors to examine the role of DP-IV in T-cell function", *PNAS*, USA, 88., abstract obtained from CAPLUS database, accession No. 114:205351, (1991), 2 pgs.

Ghiselli, G., "The Pharmacological Profile of FCE 27677: A Novel ACAT Inhibitor with Potent Hypolipidemic Activity Mediated by Selective Suppression of the Hepatic Secretion of ApoB-100-Containing Lipoprotein", *Cardiovascular Drug Reviews*, 16(1), (1998), 16-30.

Hara, S., "Ileal Na+/bile Acid Cotransporter Inhibitors", *Drugs of the Future*, 24(4), published by Prous Science, (1999), 425-430.

Hinke, S. A., et al., "Metformin Effects on Dipeptidyl-Peptidase IV Degradation of Glucagon-like Peptide-1", *Biochemical and Biophysical Research Communications* 291, (2002), 1302-1308.

Holst, Jens J., et al., "Perspectives in Diabetes: Inhibition of the Activity of Dipeptidyl-Peptidase IV as a Treatment for Type 2 Diabetes", *Diabetes*, vol. 47, From the Department of Medical Physiology, University of Copenhagen, Copenhagen, Denmark., (Nov. 1998), 1663-1670.

Hughes, T. E, et al., "NVP-DPP728 (1-[[[2-[(5-cyanopyridin-2-yl)amino]ethyl]amino]acetyl]-2-cyano-(S)-pyrrolidine), a slow-binding inhibitor of dipeptidyl peptidase IV.", *Biochemistry*, 38(36), (Sep. 7, 1999), 11597-603.

Kelly, T. A., et al., "Immunosuppresive Boronic Acid Dipeptides Correlation Between Conformation and Activity", *Journal of the American Chemical Society*, 115(26), (1993), 12637-12638.

Kirkpatrick, P., "Giving nature a helping hand", *Nature Reviews Drug Discovery*,Jul. 1, 2002, (Jul. 2004), 486-487.

Krause, B. R., "ACAT Inhibitors: Physiologic Mechanisms for Hypolipidemic and Anti-Atherosclerotic Activities in Experimental Animals", Inflammation: Mediators and Pathways R.R. Ruffolo, Jr. and M.A. Hollinger, Ph.D (eds.), published by CRC Press, Boca Raton, FL, (1995), 173-198.

Kubota, T., et al., "Dipeptidyl Peptidase IV (DP IV) Activity in Serum and on Lymphocytes of MRL/Mp-Ipr/Ipr Mice Correlates With Disease Onset", *Clin Exp Immunol* 96, (1994), 292-296.

Lambeir, A M, et al., "Kinetic investigation of chemokine truncation by CD26/dipeptidyl peptidase IV reveals a striking selectivity within the chemokine family", *J Biol Chem.*, 276(32), (Aug. 10, 2001), 29839-45.

Lehninger,, A. .. L, "Prinzipien der Biochemie", (1987).

Marighetto, A, et al., "Further evidence for a dissociation between different forms of mnemonic expressions in a mouse model of age-related cognitive decline: effects of tacrine and S 17092, a novel prolyl endopeptidase inhibitor.", *Learn Mem.*, 7(3), (May-Jun. 2000), 159-69.

McClard, R W, "Novel Phosphonylphosphinyl (P-C-P-C-) Analogues of Biochemically Interesting Diphosphates. Syntheses and Properties of P-C-B-C-Analogues of Isopentenyl Diphosphate and Dimethylallyl Diphosphate", *J. Am. Chem. Soc.*, vol. 109, (1987), pp. 5544-5545.

Mentlein, R, "Dipeptidyl-peptidase IV (CD26)—role in the inactivation of regulatory peptides.", *Regul Pept.*, 85(1), (Nov. 30, 1999), 9-24.

Morain, P., et al., "Pharmacodynamic and pharmacokinetic profile of S 17092, a new orally active prolyl endopeptidase inhibitor, in elderly healthy volunteers. A phase I study.", *Br J Clin Pharmacol.*, 50(4), (Oct. 2000), 350-9.

Morissette, S. L, et al., "High-throughput crystallization: polymorphs,salts,co-crystals and solvates of pharmaceutical solids", *Advanced Drug Delivery Reviews 2004*,56., (2004), 275-300.

Murakami, K., "A Novel Insulin Sensitizer Acts as a Coligand for Peroxisome Proliferation—Activated Receptor Alpha (PPAR alpha) and PPAR gamma. Effect on PPAR alpha Activation on Abnormal Lipid Metabolism in Liver of Zucker Fatty Rats", *Diabetes*, vol. 47, (Dec. 1998), 1841-1847.

Nicolosi, Robert J., et al., "The ACAT Inhibitor, CI-1011 is Effective in the Prevention and Regression of Aortic Fatty Streak Area in Hamsters", *Atherosclerosis* 137, (1998), 77-85.

Ortiz De Montellano, P. R., "Inhibition of Squalene Synthetase by Farnesyl Pyrophosphate Analogues", *Journal of Medicinal Chemistry*, vol. 20, No. 2, (1977), 243-249.

Pauly, R. P., et al., "Inhibition of Dipeptidyl Peptidase IV (DP IV) in Rat Results in Improved Glucose Tolerance", *Abstracts from the 11th International Symposium on Regulatory Peptides*, (1996), p. 148.

Pederson, R. A, et al., "Improved glucose tolerance in Zucker fatty rats by oral administration of the dipeptidyl peptidase IV inhibitor isoleucine thiazolidide.", *Diabetes*, 47(8), (Aug. 1998), 1253-8.

Pospisilik, J. A, et al., "Dipeptidyl peptidase IV inhibitor treatment stimulates beta-cell survival and islet neogenesis in streptozotocin-induced diabetic rats.", *Diabetes*, 52(3), (Mar. 2003), 741-50.

Rosenblum, S. B., "Discovery of 1-(4-Fluorophenyl)-(3R)-[3-(4-fluorophenyl)-(3S)-hydroxypropyl]-(4S)-(4-hydroxyphenyl)-2-azetidinone (SCH 58235): A Designed, Potent, Orally Active Inhbitor of Cholesterol Absorption", *J. Med. Chem.* 41, (1998), 973-980.

Salisbury, B. G., "Hypocholesterolemic Activity of a Novel Inhibitor of Cholesterol Absorption, SCH 48461", *Atherosclerosis* 115, published by Elsevier Science Ireland Ltd., (1995), 45-63.

Scott, T., et al., "Concise Encyclopedia Biochemistry", (1988).

Sedo, A., et al., "Dipeptidyl peptidase IV-like molecules: homologous proteins or homologous activities?", *Biochim Biophys Acta.*, 1550(2), (Dec. 17, 2001), 107-16.

Sendobry, S. M., "Attenuation of Diet-Induced Atherosclerosis in Rabbits with a Highly Selective 15-lipoxygenase Inhibitor Lacking Significant Antioxidant Properties", *British Journal of Pharmacology*120, published by Stockton Press, (1997), 1199-1206.

Sliskovic, D. R., "ACAT Inhibitors: Potential Anti-atherosclerotic Agents", *Current Medicinal Chemistry*, vol. 1, No. 3, published by Bentham Science Publishers B.V., (1994), 204-225.

Smith, C., "RP 73163: A Bioavailable Alkylsulphinyl-Diphenylimidazole ACAT Inhibitor", *Bioorganic & Medicinal Chemistry Letters*, vol. 6, No. 1, published by Elsevier Science Ltd., (1996), 47-50.

Souillac, et al., "Characterization of Delivery Systems, Differential Scanning Calorimetry in Encyclopedia of controlled drug Delivery", (1999), 212-227.

Stout, D. M., et al., "Inhibitors of Acyl-CoA: Cholesterol O-Acyl Transferase (ACAT) as Hypocholesterolemic Agents. 6. The First Water-Soluble ACAT Inibitor With Lipid-Regulating Activity", *Chemtracts—Organic Chemistry*, vol. 8, (1995), 359-362.

Sudre, B., et al., "Chronic inhibition of circulating dipeptidyl peptidase IV by FE 999011 delays the occurrence of diabetes in male zucker diabetic fatty rats.", *Diabetes*, 51(5), (May 2002), 1461-9.

Tanaka, S, et al., "Suppression of Arthritis by the Inhibitors of Dipeptidyl Peptidase IV", *Ensho—Japanese Journal of Inflammation*, 18(3), (1998), 199-202.

Tanaka, Sumiko, et al., "Suppression of Arthritis by the Inhibitors of Dipeptidyl Peptidase IV", *International Journal of Immunopharmacology*, 19(1), (1997), 15-24.

Taylor, M. D., et al., *Peptide-Based Drug Design: Controlling Transport and Metabolism*, American Chemical Society, Washington, D.C., (1995), 84-85 & 395-396.

Umemura, K., et al., "Pharmacokinetics and safety of Z-321, a novel specific orally active prolyl endopeptidase inhibitor, in healthy male volunteers.", *J Clin Pharmacol.*, 39(5), (May 1999), 462-70.

Van Damme, J., et al., "The role of CD26/DPP IV in chemokine processing.", *Chem Immunol.*, 72, (1999), 42-56.

Vanhoof, G., et al., "Proline motifs in peptides and their biological processing.", *FASEB J.*, 9(9), (Jun. 1995), 736-44.

Vippagunta, et al., "Advanced Drug Delivery Reviews", vol. 48, (2001), 3-26.

U.S. Appl. No. 11/930,337, Response to Non Final Office Action mailed Jun. 25, 2010, 6 pgs.

U.S. Appl. No. 11/930,337, Non-Final Office Action mailed Jun. 25, 2010, 17 pgs.

U.S. Appl. No. 11/930,337, Response filed Jul. 13, 2010 to Non-Final Office Action mailed Jun. 25, 2010, 6 pgs.

Australian Application Serial No. 2004288831, Office Action Response mailed Jul. 14, 2010, 25 pgs.

Australian Application Serial No. 2008229787, Office Action Response Filed Jul. 14, 2010, 28 pgs.

Japanese Application Serial No. 2006-539906, Office Action mailed Jun. 11, 2010, 10 pgs.

Japanese Application Serial No. 2008-220344, Office Action mailed Jun. 11, 2010, 9 pgs.

U.S. Appl. No. 11/930,337, Final Office Action mailed Jul. 20, 2010, 12 pgs.

U.S. Appl. No. 11/930,337, Response filed Aug. 20, 2010 to Final Office Action mailed Jul. 20, 2010, 6 pgs.

U.S. Appl. No. 11/833,063, Final Office Action mailed Aug. 25, 2010, 14 pgs.

Israeli Patent Application No. 175550, Office Action Response Filed Jul. 11, 2010, 14 pgs.

"Argentine Application Serial No. 040104198, Amendment filed May 21, 2007", 32 pgs.

"Australian Application Serial No. 2004288831, Amendment filed Apr. 21, 2009", 10 pgs.

"Australian Application Serial No. 2004288831, Examiner's Report mailed Apr. 8, 2010", 3 pgs.

"Australian Application Serial No. 2007201757, Amendment filed Sep. 23, 2008", 9 pgs.

"Brazilian Application Serial No. PI 0416444-0, Amendment filed May 30, 2007".

"Canadian Application Serial No. 2,545,311, Notice of Allowance mailed Jun. 6, 2011", 1 pg.

"Canadian Application Serial No. 2,545,311, Office Action mailed May 10, 2007", 2 pgs.

"Canadian Application Serial No. 2,545,311, Office Action mailed Nov. 4, 2010", 2 pgs.

"Canadian Application Serial No. 2,545,311, Response filed Mar. 7, 2011 to Office Action mailed Nov. 4, 2010", 31 pgs.

"Canadian Application Serial No. 2,602,772, Amendment filed Jul. 25, 2008", 7 pgs.

"Chilean Application Serial No. 1034-06, International Search Report mailed Jun. 11, 2008", 1 pg.

"Chilean Application Serial No. 1034-06, Office Action mailed Jul. 11, 2006", 3 pgs.

"Chilean Application Serial No. 1034-06, Response filed Sep. 7, 2006 to Office Action mailed Jul. 11, 2006", 4 pgs.

"Chilean Application Serial No. 1034-06, Response filed Dec. 19, 2008 to Office Action mailed Sep. 10, 2008", 50 pgs.

"Chinese Application Serial No. 200480037257.9, Decision on Rejection mailed Sep. 5, 2011", 5 pgs.

"Chinese Application Serial No. 200480037257.9, Office Action mailed Mar. 16, 2012", w/ English Translation, 10 pgs.

"Chinese Application Serial No. 200480037257.9, Response filed Jun. 22, 2009 to Office Action mailed Dec. 5, 2008", 59 pgs.

"Chinese Application Serial No. 200710098129.0, Amendment filed Aug. 6, 2008", 7 pgs.

"Chinese Application Serial No. 200810215690.7, Office Action mailed Mar. 22, 2010", 6 pgs.

"Chinese Application Serial No. 200810215690.7, Response filed Aug. 11, 2011 to Office Action mailed Apr. 26, 2011", 22 pgs.

"Eurasian Application Serial No. 200600935, Office Action mailed Feb. 26, 2008", 2 pgs.

"Eurasian Application Serial No. 200600935, Office Action mailed Jul. 14, 2008", 2 pgs.

"Eurasian Application Serial No. 200600935, Response filed May 29, 2008 to Office Action mailed Feb. 26, 2008", 17 pgs.

"Eurasian Application Serial No. 200600935, Response filed Dec. 9, 2008 to Office Action mailed Jul. 14, 2008", 18 pgs.

"European Application Serial No. 04810839.3, Office Action mailed Jun. 6, 2011", 4 pgs.

"European Application Serial No. 04810839.3, Response filed Feb. 27, 2008 to Office Action mailed Jul. 14, 2007", 47 pgs.

"European Application Serial No. 04810839.3, Response filed Mar. 2, 2009 to Office Action mailed Oct. 23, 2008", 20 pgs.

"European Application Serial No. 04810839.3, Response filed Dec. 5, 2011 to Office Action mailed Jun. 6, 2011", 47 pgs.

"European Application Serial No. 06015708.8, Office Action mailed Jan. 27, 2009", 13 pgs.

"European Application Serial No. 06015708.8, Response filed Feb. 27, 2008 to Office Action mailed Aug. 17, 2007", 17 pgs.

"European Application Serial No. 06015708.8, Response filed Mar. 2, 2009 to Office Action mailed Jan. 27, 2009", 10 pgs.

"European Application Serial No. 06015708.8, Response filed Nov. 4, 2009 to Office Action mailed Jun. 29, 2009", 20 pgs.

"European Application Serial No. 08013650.0, Office Action mailed Jun. 6, 2011", 3 pgs.

"European Application Serial No. 08013650.0, Response filed Dec. 15, 2011 to Office Action mailed Jun. 6, 2011", 6 pgs.

"Israeli Application Serial No. 175550, Amendment filed Sep. 18, 2007", 20 pgs.

"Israeli Application Serial No. 175550, Office Action mailed Feb. 15, 2011", 3 pgs.

"Israeli Application Serial No. 175550, Response filed May 2, 2011 to Office Action mailed Feb. 15, 2011", 1 pg.

"Israeli Application Serial No. 175550, Response filed Aug. 11, 2009 to Office Action mailed May 25, 2009", 16 pgs.

"Japanese Application Serial No. 2006-539906, Amendment filed Apr. 11, 2007", 146 pgs.

"Japanese Application Serial No. 2006-539906, Examiner Decision mailed Jan. 11, 2012", 5 pgs.

"Japanese Application Serial No. 2006-539906, Office Action mailed Sep. 12, 2011", 21 pages.

"Japanese Application Serial No. 2006-539906, Response filed Dec. 8, 2011 to Office Action mailed Sep. 12, 2011", 12 pgs.

"Japanese Application Serial No. 2007-201372, Amendment filed Jul. 31, 2008", 14 pgs.

"Japanese Application Serial No. 2007-201372, Amendment filed Aug. 1, 2007", 11 pgs.

"Japanese Application Serial No. 2008-220344, Examiner Decision mailed Jan. 5, 2012", 5 pgs.

"Japanese Application Serial No. 2008-220344, Office Action mailed Sep. 8, 2011", 21 pgs.

"Japanese Application Serial No. 2008-220344, Response filed Dec. 8, 2011 to Office Action mailed Sep. 26, 2011", 19 pgs.

"Korean Application Serial No. 10-2006-7011419, Amendment filed Mar. 14, 2007", 67 pgs.

"Korean Application Serial No. 10-2006-7011419, Notice of Allowance mailed Jun. 18, 2009", 3 pgs.

"Korean Application Serial No. 10-2006-7011419, Response filed May 12, 2009 to Office Action mailed Feb. 23, 2009", 38 pgs.

"Korean Application Serial No. 10-2006-7011419, Response filed Oct. 20, 2008 to Office Action mailed Apr. 8, 2008", 110 pgs.

"Mexican Application Serial No. PA/a/2006/005405, Notice of Allowance mailed Jan. 20, 2011", 1 pg.

"Mexican Application Serial No. PA/a/2006/005405, Response filed Dec. 1, 2010", 1 pg.

"New Zealand Application Serial No. 547752, Amendment filed Feb. 16, 2007", 19 pgs.

"New Zealand Application Serial No. 547752, Response filed Aug. 10, 2009 to Office Action mailed Nov. 6, 2008".

"New Zealand Application Serial No. 547752, Response filed Nov. 18, 2009 to Office Action mailed Sep. 2, 2009".

"Singapore Application Serial No. 200603077-9, Amendment filed Feb. 9, 2007", 113 pgs.

"Singapore Application Serial No. 200603077-9, Response filed Aug. 20, 2008 to Office Action mailed Feb. 8, 2008", 11 pgs.

"Taiwanese Application Serial No. 093134766, Amendment filed Nov. 7, 2007".

"Taiwanese Application Serial No. 093134766, Notice of Allowance mailed Nov. 29, 2010".

"Taiwanese Application Serial No. 093134766, Office Action mailed Oct. 7, 2010", 1 pg.

"Taiwanese Application Serial No. 093134766, Response filed May 6, 2011 to Office Action mailed Feb. 6, 2010", 18 pgs.

"Taiwanese Application Serial No. 093134766, Response filed Oct. 29, 2010 to Office Action mailed Oct. 7, 2010", 4 pgs.

* cited by examiner

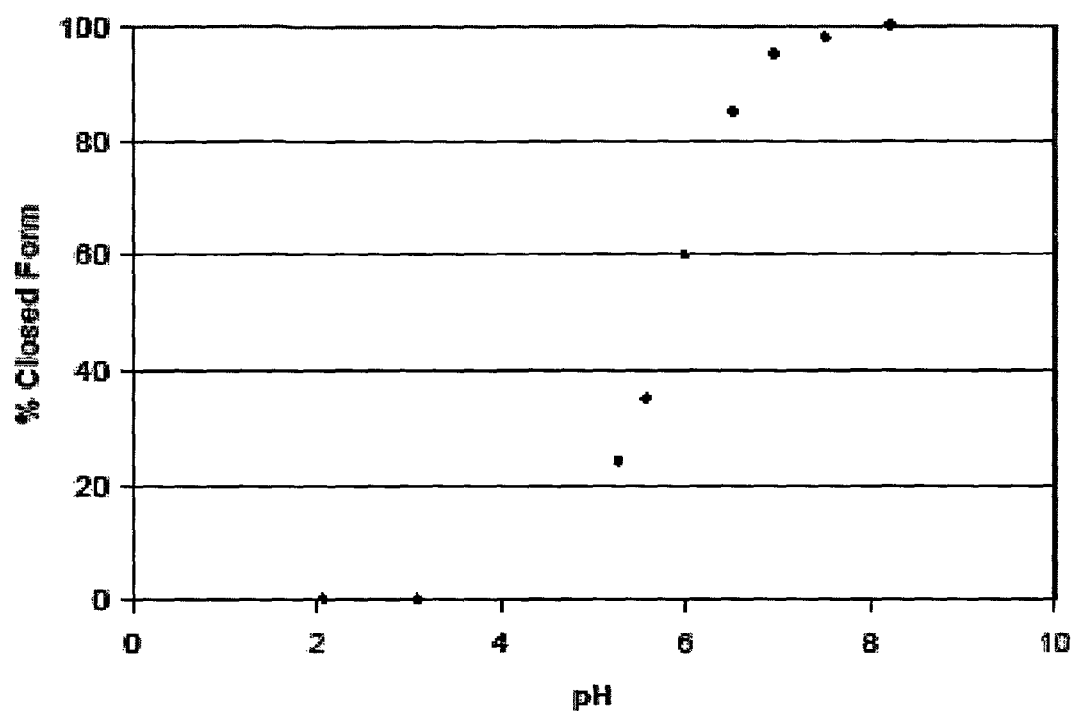

HETEROCYCLIC BORONIC ACID COMPOUNDS

This application is a continutation of U.S. application Ser. No. 10/514,575, filed Oct. 27, 2005, which is a U.S. National-Stage entry under 35 U.S.C. §371 based on International application no. PCT/US2004/037820, filed Nov. 12, 2004, and published in English as WO 2005/047297 on May 26, 2005, which designates the United States of America, and claims the priority of U.S. application No. 60/519,566, filed Nov. 12, 2003, and of U.S. application No. 60/557,011, filed Mar. 25, 2004, and of U.S. application No. 60/592,972, filed Jul. 30, 2004, each of which is incorporated herein by reference in its entirety.

FIELD OF THE INVENTION

The present invention relates to boronic acid compounds and their use as inhibitors of post-proline/alanine cleaving amino-dipeptidases. The invention also relates to methods of employing such inhibitors, alone or with another therapeutic agent, to treating DPP-IV-related diseases, such as Type II diabetes and diabetic complications, hyperglycemia, Syndrome X, hyperinsulinemia, obesity, atherosclerosis and related diseases, as well as various immunomodulatory diseases and chronic inflammatory bowel disease. Thus, the invention has applications in the medicinal chemical, pharmacological, and medical arts.

BACKGROUND OF THE INVENTION

The following background commentary is an aid to in understanding the present invention. Inclusion of this commentary is not an admission concerning the nature or content of the prior art.

Dipeptidyl peptidase-IV (DPP-IV) is a serine protease that belongs to a group of post-proline/alanine cleaving amino-dipeptidases. DPP-IV catalyzes the release of an N-terminal dipeptide only from proteins with N-terminal penultimate proline or alanine.

The physiological role of DPP-IV has not been established fully. It is believed to play an important role in neuropeptide metabolism, T-cell activation, gastric ulceration, functional dyspepsia, obesity, appetite regulation, impaired fasting glucose (IFG), and diabetes. In particular, DPP-IV has been implicated in the control of glucose metabolism because its substrates include the insulinotropic hormones, glucagon like peptide-1 (GLP-1) and gastric inhibitory peptide (GIP), which are inactivated by removal of their two N-terminal amino acids.

In vivo administration of synthetic inhibitors of DPP-IV prevents N-terminal degradation of GLP-1 and GIP, resulting in higher plasma concentrations of these hormones, increased insulin secretion and, therefore, improved glucose tolerance. Therefore, such inhibitors have been proposed for the treatment of patients with type II diabetes, a disease characterized by decreased glucose tolerance and insulin resistance.

Post-proline/alanine cleaving amino-dipeptidases have been discovered, including DPP7, DPP8, DPP9, and fibroblast activation protein (FAP), that have the substrate- and inhibitor-specificity of DPP-IV. Thus, inhibitors of this sort may affect multiple members of the enzyme group. The precise physiological role of each of these post-proline/alanine cleaving enzymes is not well defined. Consequently, inhibiting each of them separately, a subset of them, or all of them at the same time would have uncertain physiological effect(s).

Diabetic dyslipidemia is characterized by multiple lipoprotein defects, including moderately high serum levels of cholesterol and triglycerides, small LDL particles, and low levels of HDL cholesterol. The results of recent clinical trials reveal beneficial effects of cholesterol-lowering therapy in diabetic and nondiabetic patients, thus supporting increased emphasis on treatment of diabetic dyslipidemia. This need for intensive treatment of diabetic dyslipidemia was advocated by the National Cholesterol Education Program's Adult Treatment Panel III.

Obesity is a well-known risk factor for the development of many very common diseases such as atherosclerosis, hypertension and diabetes. The incidence of obese people and thereby also these diseases is increasing throughout the entire industrialized world. Except for exercise, diet and food restriction no convincing pharmacological treatment for reducing body weight effectively and acceptably currently exist. However, due to its indirect but important effect as a risk factor in mortal and common diseases it will be important to find treatment for obesity or appetite regulation. Even mild obesity increases the risk for premature death, diabetes, hypertension, atherosclerosis, gallbladder disease and certain types of cancer. In the industrialized western world the prevalence of obesity has increased significantly in the past few decades. Because of the high prevalence of obesity and its health consequences, its prevention and treatment should be a high public health priority.

At present a variety of techniques are available to effect initial weight loss. Unfortunately, initial weight loss is not an optimal therapeutic goal. Rather, the problem is that most obese patients eventually regain their weight. An effective means to establish and/or sustain weight loss is the major challenge in the treatment of obesity today.

Accordingly, a need exists for compounds that are useful for inhibiting DPP-IV without suppressing the immune system.

Several compounds have been shown to inhibit DPP-IV, but all of these have limitations in relation to the potency, stability, selectivity, toxicity, and/or pharmacodynamic properties. Such compounds have been disclosed, for example, in WO 98/19998, WO 00/34241, U.S. Pat. No. 6,124,305 (Novartis AG), and WO 99/38501 (Trustees of Tufts University).

SUMMARY OF THE INVENTION

The present invention provides DPP-IV inhibitors that are effective in treating conditions that may be regulated or normalized by inhibition of DPP-IV. More particularly, the invention relates to boronic acid-containing heterocycles and their derivatives that inhibit DPP-IV, and to methods for making such compounds. In addition, the invention provides pharmaceutical compositions comprising compounds of the invention, and combinations thereof including one or more other types of antidiabetic agents; methods for inhibiting DPP-IV comprising administering to a patient in need of such treatment a therapeutically effective amount thereof; and compounds for use as a pharmaceutical, and their use in a process for the preparation of a medicament for treating a condition that are regulated or normalized via inhibition of DPP-IV.

BRIEF DESCRIPTION OF THE DRAWING

FIG. 1 shows the pH dependence of the percentage of linear and cyclic isomeric forms present in aqueous solution of a compound of the invention.

DETAILED DESCRIPTION OF THE INVENTION

The present invention provides compounds of formula I:

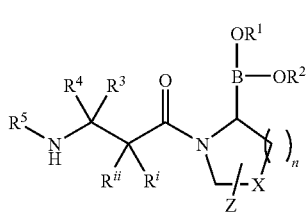

including all enantiomers, diastereoisomers, solvates, hydrates and pharmaceutically acceptable salts thereof, wherein:

n is 1 to 3;

X is $CH_2$; S; O; $CF_2$ or $C(CH_3)_2$;

Z is H; halogen; hydroxyl; $(C_{1-6})$alkoxy; $(C_{1-12})$alkyl; $(C_{3-12})$cycloalkyl; phenyl; or heteroaryl; where the phenyl and heteroaryl groups are optionally mono- or independently plurisubstituted with $R^7$;

optionally, X together with an adjacent ring carbon and Z form a fused cyclopropyl; and optionally, one of the bonds in the ring containing X is a double bond;

$R^1$ and $R^2$ independently or together are hydrogen; a boronic acid protecting group; or a group capable of being hydrolyzed to a hydroxyl group in an aqueous solution at physiological pH or in biological fluids;

$CR^iR^{ii}$ may be present or absent, wherein if $CR^iR^{ii}$ is present, then $R^i$, $R^{ii}$, $R^3$, $R^4$ and $R^5$ are selected from (aa), (bb) or (cc):

(aa) $R^i$, $R^{ii}$, $R^3$ and $R^4$ are hydrogen; and
$R^5$ is
  a) hydrogen;
  b) $(C_{1-12})$alkyl; $(C_{2-12})$alkenyl; $(C_{2-12})$alkynyl; $(C_{3-12})$ cycloalkyl; or $(C_{3-12})$cycloalkenyl; where the alkyl, alkenyl, alkynyl, cycloalkyl and cycloalkenyl groups are optionally mono- or independently plurisubstituted with $R^6$, and where the alkyl, alkenyl, alkynyl portions include linear or branched chains and may include cyclic portions;
    $R^6$ is $(C_{1-6})$alkyl; $(C_{1-6})$alkoxy; cycloalkyl; carboxy; acetamido; cyano; nitro; halogen; hydroxy; hydroxy$(C_{1-6})$alkyl; hydroxymethyl; trifluoromethyl; trifluoromethoxy; sulfamoyl; sulfonamido; carbamoyl; aryl; heteroaryl; where the aryl and heteroaryl groups are optionally mono- or independently plurisubstituted with $R^7$; amino, where the amino group is optionally mono- or independently plurisubstituted with $R^8$; $-SOR^8$; $-SO_2R^8$; $-COR^8$; $-CO_2R^8$; $-CONHR^8$; $-CON(R^8)_2$; $-OR^8$; or $-S-R^8$;
    $R^7$ is halogen; $(C_{1-10})$alkyl; $(C_{1-10})$alkoxy; $(C_{1-10})$ alkylamino; $(C_{1-10})$dialkylamino; benzyl; benzyloxy; hydroxyl$(C_{1-6})$alkyl; hydroxymethyl; nitro; trifluoromethyl; trifluoromethoxy; trifluoromethylthio; N-hydroxyimino; cyano; carboxy; acetamido; hydroxy; sulfamoyl; sulfonamido; or carbamoyl;
    $R^8$ is $(C_{1-10})$alkyl; $(C_{2-10})$alkenyl; $(C_{2-10})$alkynyl; $(C_{3-10})$cycloalkyl; $(C_{5-10})$cycloalkenyl; benzyl; phenethyl; aryl; or heteroaryl; where the alkyl, alkenyl, alkynyl, cycloalkyl, cycloalkenyl groups are optionally mono- or independently plurisubstituted with aryl or heteroaryl where the aryl and heteroaryl groups are optionally mono- or independently plurisubstituted with $R^7$; and where the aryl and heteroaryl groups are optionally mono- or independently plurisubstituted with $R^7$;
  c) aryl optionally fused to a $(C_{3-10})$cycloalkyl; or heteroaryl optionally fused to a $(C_{3-10})$cycloalkyl; where the aryl and heteroaryl groups are optionally mono- or independently plurisubstituted with $R^7$;
  d) indanyl; 1,2,3,4-tetrahydronaphthyl; $(CH_2)_j$adamantyl in which j is 0-3; or a [2.2.1] or [3.1.1] bicyclic carbocyclic moiety, including (4-pentylbicyclo[2.2.2]oct-1-yl)amine; where the indanyl, 1,2,3,4-tetrahydronaphthyl, $(CH_2)_j$adamantyl, and [2.2.1] or [3.1.1] bicyclic carbocyclic moieties are optionally mono- or independently plurisubstituted with hydroxy, $(C_{1-8})$alkoxy, $(C_{1-8})$alkanoyloxy, or $R^9R^{10}N-CO-O-$, where $R^9$ and $R^{10}$ are independently $(C_{1-8})$alkyl, or phenyl, where the alkyl and phenyl groups are optionally mono- or independently plurisubstituted with $(C_{1-8})$alkyl, $(C_{1-8})$ alkoxy, halogen, or trifluoromethyl, or $R^9$ and $R^{10}$ together are $(C_{3-6})$alkylene;
  e) $R^{11}(CH_2)_p-$ where $R^{11}$ is 2-oxopyrrolidinyl; $(C_{1-6})$alkoxy; phenyl; phenoxy; $(C_{1-8})$cycloalkyl; [3.3.3] bicyclic carbocyclic moiety; pyridinyl; naphthyl; cyclohexenyl; or adamantyl; where the 2-oxopyrrolidinyl, $(C_{1-6})$alkoxy, phenyl, pyridinyl, and naphthyl groups are optionally mono- or independently di- or independently trisubstituted with $R^{12}$; where the phenoxy group is optionally mono- or independently disubstituted with $(C_{1-4})$alkyl, $(C_{1-4})$alkoxy, or halogen; and where the [3.3.3] bicyclic carbocyclic moiety is optionally mono-or independently plurisubstituted with $(C_{1-8})$alkyl; and p is 0 to 3;
    $R^{12}$ is halogen; trifluoromethyl; cyano; nitro; $(C_{1-6})$ alkyl; $(C_{1-6})$alkoxy; cycloalkyl; carboxy; acetamido; hydroxy; hydroxy$(C_{1-6})$alkyl; hydroxymethyl; trifluoromethoxy; sulfamoyl; carbamoyl; sulfonamido; alkylsufonyl; phenylsulfonyl; aryl; heteroaryl; where the aryl and heteroaryl groups are optionally mono- or independently plurisubstituted with $R^7$;
  f) $(R^{13})_2CH(CH_2)_q-$, where $R^{13}$ is phenyl; in which the phenyl groups are independently optionally mono- or independently disubstituted with $R^{12}$; and q is 0 to 3;
  g) a group of the formula:

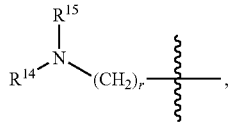

where $R^{14}$ and $R^{15}$ are independently hydrogen; $(C_{1-8})$alkyl; $(C_{1-6})$alkylcarbonyl; $(C_{3-12})$cycloalkyl ring; $(C_{3-12})$cycloalkenyl ring; benzyl; benzoyl; pyridine; pyrimidine; phenyl; phenylamino-carbonyl; alkylsulfonyl; or phenylsulfonyl; where the cycloalkyl ring is optionally substituted with hydroxy$(C_{1-6})$alkyl, and where the benzyl, benzoyl, pyridine, pyrimidine, phenyl, phenylaminocarbonyl, alkylsulfonyl, and phenylsulfonyl groups are optionally mono- or independently di-substituted with $R^{12}$; or $R^{14}$ and $R^{15}$ together form a $(C_{3-12})$cycloalkyl ring; and r is 2 to 6;

h) a group of the formula:

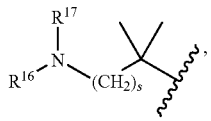

where $R^{16}$ and $R^{17}$ are each independently hydrogen; $(C_{1-8})$alkyl; $(C_{1-6})$alkylcarbonyl; di-$(C_{1-6})$alkylaminocarbonyl; benzyl; benzoyl; pyridine; pyrimidine; phenyl; phenylaminocarbonyl; alkylsulfonyl; or phenylsulfonyl; where the benzyl, benzoyl, pyridine, pyrimidine, phenyl, phenylaminocarbonyl, alkylsulfonyl, and phenylsulfonyl groups are optionally mono- or independently di-substituted with $R^{12}$; or $R^{16}$ and $R^{17}$ together form a $(C_{3-12})$cycloalkyl ring; and s is 1 to 6;

i) a group of the formula:

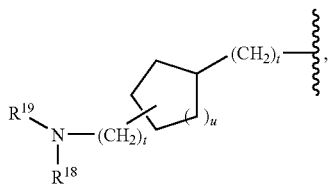

where $R^{18}$ and $R^{19}$ are independently hydrogen; $(C_{1-8})$alkyl; $(C_{1-6})$alkylcarbonyl; di-$(C_{1-6})$alkylaminocarbonyl; benzyl; benzothiazole; benzoyl; pyridine; pyrimidine; phenyl; phenylaminocarbonyl; alkylsulfonyl, or phenylsulfonyl; where the benzyl, benzoyl, benzothiazole, pyridine, pyrimidine, phenyl, phenylaminocarbonyl, alkylsulfonyl, and phenylsulfonyl groups are optionally mono- or independently di-substituted with $R^{12}$; or $R^{18}$ and $R^{19}$ together form a $(C_{3-12})$cycloalkyl ring; each t is independently 0 to 6; and u is 0 to 3;

j) a group of the formula:

(phenyl-CH$_2$—C(CH$_3$)$_2$—), where the phenyl group is optionally mono- or independently plurisubstituted with $R^{12}$;

k) a group of the formula:

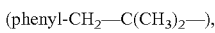

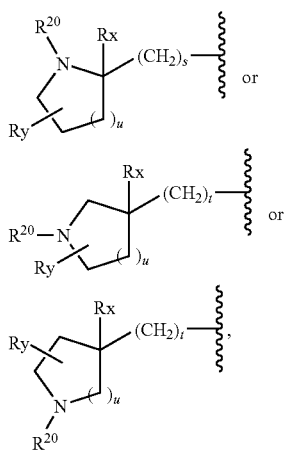

where $R^{29}$ is hydrogen; $(C_{1-8})$alkyl; $(C_{1-6})$alkylcarbonyl; di-$(C_{1-6})$alkylaminocarbonyl; $(C_{3-8})$cycloalkylcarbonyl; benzyl; benzoyl; $(C_{1-6})$alkyloxycarbonyl; arlkyloxycarbonyl, pyridine; pyrimidine; phenyl; phenyl substituted thiazole ring; phenylaminocarbonyl; alkylsulfonyl; or phenylsulfonyl; where the benzyl, benzoyl, pyridine, pyrimidine, phenyl, phenylaminocarbonyl, alkylsulfonyl, and phenylsulfonyl groups are optionally mono- or independently di-substituted with $R^{12}$; $R_x$ is hydrogen; $(C_{1-8})$alkyl; $(C_{3-12})$cycloalkyl; benzyl; phenyl; where the benzyl and phenyl, groups are optionally mono- or independently di-substituted on the ring with $R^{12}$; $R_y$ is absent or is halogen, $(C_{1-8})$alkyl, $(C_{1-8})$alkoxy, O-alkylcarboxylate, O-aralkylcarboxylate, N-alkylcarboxamido, N-aralkylcarboxamido; or phenyl;

s is 1 to 6; t is 0 to 6; and u is 0 to 3; or l) a group of the formula:

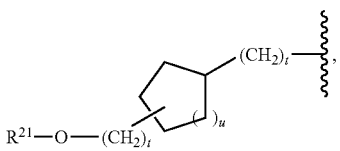

where $R^{21}$ is hydrogen; $(C_{1-8})$alkyl; benzyl; or phenyl; in which the benzyl and phenyl groups are optionally mono- or independently di-substituted on the ring with $R^{12}$; each t is independently 0 to 6; and u is 0 to 3;

(bb) $R^i$, $R^{ii}$, $R^3$, $R^4$ and $R^5$ are independently hydrogen; alkyl; alkenyl; alkynyl; cycloalkyl; cycloalkylalkyl; bicycloalkyl; tricycloalkyl; alkylcycloalkyl; hydroxyalkyl; hydroxyalkylcycloalkyl; hydroxycycloalkyl; hydroxybicycloalkyl; hydroxytricycloalkyl; bicycloalkylalkyl; alkylbicycloalkyl; alkylthioalkyl; arylalkylthioalkyl; cycloalkenyl; aryl, aralkyl; heteroaryl; heteroarylalkyl; cycloheteroalkyl or cycloheteroalkylalkyl; all optionally mono- or independently plurisubstituted with halogen, alkyl, polyhaloalkyl, alkoxy, haloalkoxy, polyhaloalkoxy, alkoxycarbonyl, alkenyl, alkynyl, cycloalkyl, cycloalkylalkyl, polycycloalkyl, heteroarylamino, arylamino, cycloheteroalkyl, cycloheteroalkylalkyl, hydroxy, hydroxyalkyl, nitro, cyano, amino, substituted amino, alkylamino, dialkylamino, thiol, alkylthio, alkylcarbonyl, acyl, alkoxycarbonyl, aminocarbonyl, alkynylamino-carbonyl, alkylaminocarbonyl, alkenylaminocarbonyl, alkylcarbonyloxy, alkylcarbonylamino, arylcarbonylamino, alkylsulfonylamino, alkylaminocarbonyl-amino, alkoxycarbonylamino, alkylsulfonyl, aminosulfinyl, aminosulfonyl, alkylsulfinyl, sulfonamido or sulfonyl; or $R^i$ together with $R^3$ or $R^4$, or together with $R^3$ or $R^4$, and the atoms to which they are attached form a 4 to 8 membered cyclic, polycyclic or heterocyclic ring system containing 1 to 3 heteroatoms selected from N, O, S, SO or SO$_2$; and includes single rings, fused bicyclic and tricyclic rings, which are optionally mono- or independently plurisubstituted with any of the groups set forth in (aa); or $R^4$ and $R^5$ together form —(CR$^{22}$R$^{23}$)$_m$— where m is 2 to 6, and $R^{22}$ and $R^{23}$ are independently hydrogen; hydroxyl; alkoxy; alkyl; alkenyl; alkynyl; cycloalkyl; halo; amino; substituted amino; cycloalkylalkyl; cycloalkenyl; aryl; arylalkyl; heteroaryl, heteroarylalkyl; cycloheteroalkyl; cycloheteroalkylalkyl; alkylcarbonylamino; arylcarbonylamino; alkoxycarbonylamino; aryloxycarbonyl-amino; alkoxycarbonyl; aryloxycarbonyl; or alkylaminocarbonylamino; or $R^4$ and $R^5$ together with the atoms to which they are attached form a 5 to 7 membered ring containing a total of 2 to 4 heteroatoms selected from N, O, S, SO, or $SO_2$; or $R^4$ and $R^5$ together with the atoms to which they are attached form a 4 to 8 membered cycloheteroalkyl ring wherein the cycloheteroalkyl ring optionally has an aryl, heteroaryl or 3 to 7 membered cycloalkyl ring fused thereto; or (cc) $R^i$ and $R^3$ are hydrogen; and $R^{ii}$ and $R^4$ together form a 4 to 8 membered cyclic, polycyclic or heterocyclic ring system containing 1 to 3 heteroatoms selected from N, O, S, SO and $SO_2$, and includes single rings, fused bicyclic and tricyclic rings, which are optionally mono- or independently plurisubstituted with any of the groups set forth in (aa) or (bb) and $R^5$ is any of the groups in (aa) or (bb); and if $CR^iR^{ii}$ is absent, then $R^3$, $R^4$ and $R^5$ are selected from (dd), (ee) or (ff):

(dd) $R^3$ and $R^4$ are hydrogen; and $R^5$ is a) hydrogen, provided that $R^5$ is not hydrogen when n is 1, X is $CH_2$, and Z is H;

b) $(C_{1-12})$alkyl; $(C_{2-12})$alkenyl; $(C_{2-12})$alkynyl; $(C_{3-12})$cycloalkyl; or $(C_{3-12})$cycloalkenyl; where the alkyl, alkenyl, alkynyl, cycloalkyl and cycloalkenyl groups are optionally mono- or independently plurisubstituted with $R^6$, and where the alkyl, alkenyl, alkynyl portions include linear or branched chains and may include cyclic portions;

$R^6$ is $(C_{1-6})$alkyl; $(C_{1-6})$alkoxy; cycloalkyl; carboxy; acetamido; cyano; nitro; halogen; hydroxy; hydroxy$(C_{1-6})$alkyl; hydroxymethyl; trifluoromethyl; trifluoromethoxy; sulfamoyl; sulfonamido; carbamoyl; aryl; heteroaryl; where the aryl and heteroaryl groups are optionally mono- or independently plurisubstituted with $R^7$; amino, where the amino group is optionally mono- or independently plurisubstituted with $R^8$; —$SOR^8$; —$SO_2R^8$; —$COR^8$; —$CO_2R^8$, —$CONHR^8$; —$CON(R^8)_2$; —$OR^8$; or —S—$R^8$;

$R^7$ is halogen; $(C_{1-10})$alkyl; $(C_{1-10})$alkoxy; $(C_{1-10})$alkylamino; $(C_{1-10})$dialkylamino; benzyl; benzyloxy; hydroxyl$(C_{1-6})$alkyl; hydroxymethyl; nitro; trifluoromethyl; trifluoromethoxy; trifluoromethylthio; N-hydroxyimino; cyano; carboxy; acetamido; hydroxy; sulfamoyl; sulfonamido; or carbamoyl;

$R^8$ is $(C_{1-10})$alkyl; $(C_{2-10})$alkenyl; $(C_{2-10})$alkynyl; $(C_{3-10})$cycloalkyl; $(C_{5-10})$cycloalkenyl; benzyl; phenethyl; aryl; or heteroaryl; where the alkyl, alkenyl, alkynyl, cycloalkyl, cycloalkenyl groups are optionally mono- or independently plurisubstituted with aryl or heteroaryl where the aryl and heteroaryl groups are optionally mono- or independently plurisubstituted with $R^7$; and where the aryl and heteroaryl groups are optionally mono- or independently plurisubstituted with $R^7$;

c) aryl optionally fused to a $(C_{3-10})$cycloalkyl; or heteroaryl optionally fused to a $(C_{3-10})$cycloalkyl; where the aryl and heteroaryl groups are optionally mono- or independently plurisubstituted with $R^7$;

d) indanyl; 1,2,3,4-tetrahydronaphthyl; $(CH_2)_j$adamantyl in which j is 0-3; or a [2.2.1] or [3.1.1] bicyclic carbocyclic moiety, including (4-pentylbicyclo[2.2.2]oct-1-yl)amine; where the indanyl, 1,2,3,4-tetrahydronaphthyl, $(CH_2)_j$ adamantyl, and [2.2.1] or [3.1.1] bicyclic carbocyclic moieties are optionally mono- or independently plurisubstituted with hydroxy, $(C_{1-8})$alkyl, $(C_{1-8})$alkoxy, $(C_{1-8})$alkanoyloxy, or $R^9R^{10}N$—CO—O—, where $R^9$ and $R^{10}$ are independently $(C_{1-8})$alkyl, or phenyl, where the alkyl and phenyl groups are optionally mono- or independently plurisubstituted with $(C_{1-8})$alkyl, $(C_{1-8})$alkoxy, halogen, or trifluoromethyl, or $R^9$ and $R^{10}$ together are $(C_{3-6})$alkylene;

e) $R^{11}(CH_2)_p$— where $R^{11}$ is 2-oxopyrrolidinyl; $(C_{1-6})$alkoxy; phenyl; phenoxy; $(C_{1-8})$cycloalkyl; [3.3.3] bicyclic carbocyclic moiety; pyridinyl; naphthyl; cyclohexenyl; or adamantyl; where the 2-oxopyrrolidinyl, $(C_{1-6})$alkoxy, phenyl, pyridinyl, and naphthyl groups are optionally mono- or independently di- or independently trisubstituted with $R^{12}$; where the phenoxy group is optionally mono- or independently disubstituted with $(C_{1-4})$alkyl, $(C_{1-4})$alkoxy, or halogen; and where the [3.3.3] bicyclic carbocyclic moiety is optionally mono-or independently plurisubstituted with $(C_{1-8})$alkyl; and p is 0 to 3;

$R^{12}$ is halogen; trifluoromethyl; cyano; nitro; $(C_{1-6})$alkyl; $(C_{1-6})$alkoxy; cycloalkyl; carboxy; acetamido; hydroxy; hydroxy$(C_{1-6})$alkyl; hydroxymethyl; trifluoromethoxy; sulfamoyl; carbamoyl; sulfonamido; alkylsufonyl; phenylsulfonyl; aryl; heteroaryl; where the aryl and heteroaryl groups are optionally mono- or independently plurisubstituted with $R^7$;

$(R^{13})_2CH(CH_2)_q$—, where $R^{13}$ is phenyl; in which the phenyl groups are independently optionally mono- or independently disubstituted with $R^{12}$; and q is 0 to 3;

g) a group of the formula:

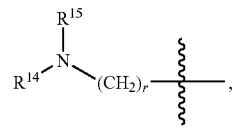

where $R^{14}$ and $R^{15}$ are independently hydrogen; $(C_{1-8})$alkyl; $(C_{1-6})$alkylcarbonyl; $(C_{3-12})$cycloalkyl ring; $(C_{3-12})$cycloalkenyl ring; benzyl; benzoyl; pyridine; pyrimidine; phenyl; phenylamino-carbonyl; alkylsulfonyl; or phenylsulfonyl; where the cycloalkyl ring is optionally substituted with hydroxy$(C_{1-6})$alkyl, and where the benzyl, benzoyl, pyridine, pyrimidine, phenyl, phenylaminocarbonyl, alkylsulfonyl, and phenylsulfonyl groups are optionally mono- or independently di-substituted with $R^{12}$; or $R^{14}$ and $R^{15}$ together form a $(C_{3-12})$cycloalkyl ring; and r is 2 to 6;

h) a group of the formula:

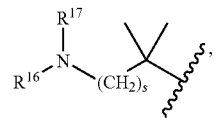

where $R^{16}$ and $R^{17}$ are each independently hydrogen; $(C_{1-8})$alkyl; $(C_{1-6})$alkylcarbonyl; di-$(C_{1-6})$alkylaminocarbonyl;

benzyl; benzoyl; pyridine; pyrimidine; phenyl; phenylaminocarbonyl; alkylsulfonyl; or phenylsulfonyl; where the benzyl, benzoyl, pyridine, pyrimidine, phenyl, phenylaminocarbonyl, alkylsulfonyl, and phenylsulfonyl groups are optionally mono- or independently di-substituted with $R^{12}$; or $R^{16}$ and $R^{17}$ together form a $(C_{3-12})$cycloalkyl ring; and s is 1 to 6;

i) a group of the formula:

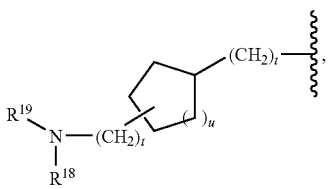

where $R^{18}$ and $R^{19}$ are independently hydrogen; $(C_{1-8})$alkyl; $(C_{1-6})$alkylcarbonyl; di-$(C_{1-6})$alkylaminocarbonyl; benzyl; benzothiazole; benzoyl; pyridine; pyrimidine; phenyl; phenylaminocarbonyl; alkylsulfonyl; or phenylsulfonyl; where the benzyl, benzoyl, benzothiazole, pyridine, pyrimidine, phenyl, phenylaminocarbonyl, alkylsulfonyl, and phenylsulfonyl groups are optionally mono- or independently di-substituted with $R^{12}$; or $R^{18}$ and $R^{19}$ together form a $(C_{3-12})$cycloalkyl ring; each t is independently 0 to 6; and u is 0 to 3;

j) a group of the formula:

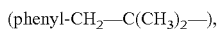

where the phenyl group is optionally mono- or independently plurisubstituted with $R^{12}$;

k) a group of the formula:

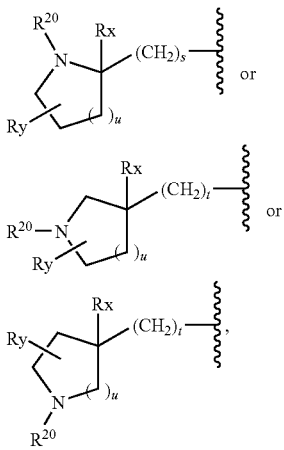

where $R^{20}$ is hydrogen; $(C_{1-8})$alkyl; $(C_{1-6})$alkylcarbonyl; di-$(C_{1-6})$alkylaminocarbonyl; $(C_{3-8})$cycloalkylcarbonyl; benzyl; benzoyl; $(C_{1-6})$alkyloxycarbonyl; arlkyloxycarbonyl; pyridine; pyrimidine; phenyl; phenyl substituted thiazole ring; phenylaminocarbonyl; alkylsulfonyl; or phenylsulfonyl; where the benzyl, benzoyl, pyridine, pyrimidine, phenyl, phenylaminocarbonyl, alkylsulfonyl, and phenylsulfonyl groups are optionally mono- or independently di-substituted with $R^{12}$; $R_x$ is hydrogen; $(C_{1-8})$alkyl; $(C_{3-12})$cycloalkyl; benzyl; phenyl; where the benzyl and phenyl, groups are optionally mono- or independently di-substituted on the ring with $R^{12}$; $R_y$ is absent or is halogen, $(C_{1-8})$alkyl, $(C_{1-8})$alkoxy, O-alkylcarboxylate, O-aralkylcarboxylate, N-alkylcarboxamido, N-aralkylcarboxamido; or phenyl;

s is 1 to 6; t is 0 to 6; and u is 0 to 3; or l) a group of the formula:

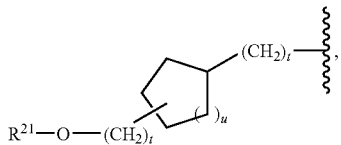

where $R^{21}$ is hydrogen; $(C_{1-8})$alkyl; benzyl; or phenyl; in which the benzyl and phenyl groups are optionally mono- or independently di-substituted on the ring with $R^{12}$; each t is independently 0 to 6; and u is 0 to 3; or (ee) $R^3$, $R^4$ and $R^5$ are independently hydrogen; alkyl; alkenyl; alkynyl; cycloalkyl; cycloalkylalkyl; bicycloalkyl; tricycloalkyl; alkylcycloalkyl; hydroxyalkyl; hydroxyalkylcycloalkyl; hydroxycycloalkyl; hydroxybicycloalkyl; hydroxytricycloalkyl; bicycloalkylalkyl; alkylbicycloalkyl; alkylthioalkyl; arylalkylthioalkyl; cycloalkenyl; aryl, aralkyl; heteroaryl; heteroarylalkyl; cycloheteroalkyl or cycloheteroalkylalkyl; all optionally mono- or independently plurisubstituted with halogen, alkyl, polyhaloalkyl, alkoxy, haloalkoxy, polyhaloalkoxy, alkoxycarbonyl, alkenyl, alkynyl, cycloalkyl, cycloalkylalkyl, polycycloalkyl, heteroarylamino, arylamino, cycloheteroalkyl, cycloheteroalkylalkyl, hydroxy, hydroxyalkyl, nitro, cyano, amino, substituted amino, alkylamino, dialkylamino, thiol, alkylthio, alkylcarbonyl, acyl, alkoxycarbonyl, aminocarbonyl, alkynylaminocarbonyl, alkylaminocarbonyl, alkenylaminocarbonyl, alkylcarbonyloxy, alkylcarbonylamino, arylcarbonylamino, alkylsulfonylamino, alkylaminocarbonyl-amino, alkoxycarbonylamino, alkylsulfonyl, aminosulfinyl, aminosulfonyl, alkylsulfinyl, sulfonamido or sulfonyl, provided that when n is 1, X is $CH_2$, the ring containing X is saturated, and Z, $R^3$ and $R^5$ are H, $R^4$ is not a side chain of a naturally occurring α-amino acid, and provided that when n is 1, X is $CH_2$, the ring containing X is saturated, and Z and $R^5$ are H, $R^3$ and $R^4$ are not both methyl; or $R^4$ and $R^5$ together form —$(CR^{22}R^{23})_m$— where m is 2 to 6, and $R^{22}$ and $R^{23}$ are independently hydrogen; hydroxyl; alkoxy; alkyl; alkenyl; alkynyl; cycloalkyl; halo; amino; substituted amino; cycloalkylalkyl; cycloalkenyl; aryl; arylalkyl; heteroaryl, heteroarylalkyl; cycloheteroalkyl; cycloheteroalkylalkyl; alkylcarbonylamino; arylcarbonylamino; alkoxycarbonyl-amino; aryloxycarbonyl-amino; alkoxycarbonyl; aryloxycarbonyl; or alkylaminocarbonylamino; provided that when n is 1, X is $CH_2$, the ring containing X is saturated, Z and $R^3$ are H, $R^4$ and $R^5$ together are not —$(CH_2)_2$— or —$(CH_2)_3$—; or $R^4$ and $R^5$ together with the atoms to which they are attached form a 5 to 7 membered ring containing a total of 2 to 4 heteroatoms selected from N, O, S, SO, or $SO_2$; or $R^4$ and $R^5$ together with the atoms to which they are attached form a 4 to 8 membered cycloheteroalkyl ring wherein the cycloheteroalkyl ring optionally has an aryl, heteroaryl or 3 to 7 membered cycloalkyl ring fused thereto; or (ff) $R^3$ is hydrogen; and $R^4$ and $R^5$ together with the atoms to which they are attached form a 4 to 8 member mono- or polycyclic heterocyclic ring system containing 1 to 3 heteroatoms selected from N, O, S, SO and SO$_2$, wherein the heterocyclic ring system is optionally mono- or independently plurisubstituted with any of the groups set forth in (dd) or (ee); provided that when n is 1, X is CH$_2$, the ring containing X is saturated, and Z and R$^3$ are H, R$^4$ and R$^5$ together are not —(CH$_2$)$_2$— or —(CH$_2$)$_3$—; and wherein the bond containing the wavy line signifies the point of attachment.

In some embodiments of compounds of formula I, R$^1$ and R$^2$ independently or together are the boronic acid protecting group formed from (+)-pinanediol; pinacol; 1,2-dicyclohexyl-ethanediol; 1,2-ethanediol; 2,2-diethanolamine; 1,3-propanediol; 2,3-butanediol, diisopropyl tartrate; 1,4-butanediol; diisopropylethanediol; (S,S,)-5,6-decanediol; 1,1,2-triphenyl-1,2-ethanediol; (2R,3R)-1,4-dimethyoxy-1,1,4,4-tetraphenyl-2,3-butanediol; methanol; ethanol; isopropanol; catechol; or 1-butanol. Thus, it will be understood by those of skill in the art that R$^1$ and R$^2$ represent a single protecting group attached to both boronic ester oxygens when diols such as (+)-pinanediol and pinacol are used, whereas R$^1$ and R$^2$ represent separate moieties on the boronic ester oxygens such as methyl or ethyl when the esters are formed from methanol and ethanol, respectively. In other embodiments of compounds of formula I, R$^1$ and R$^2$ independently or together are a group capable of being hydrolyzed to a hydroxyl group in an aqueous solution at physiological pH or in biological fluids and are formed from 1,2-dicyclohexylethanediol; 1,2-ethanediol; 1,3-propanediol; 2,3-butanediol, 1,4-butanediol; diisopropylethanediol; methanol; ethanol; isopropanol; or 1-butanol. For example, when R$^1$ and R$^2$ are each formed from methanol, the resulting R$^1$ and R$^2$ groups are methyl. When 2,3-butanediol is used, the resulting R$^1$ and R$^2$ groups are a single group and the resulting boronic ester has the following structure:

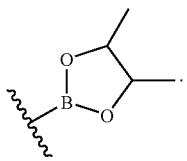 [SMILES: *B1OC(C)C(C)O1]

Compounds of formula I include those wherein if CR$^i$R$^{ii}$ is absent, then R$^3$, R$^4$ and R$^5$ are selected from (dd), (ee) or (ff):

(dd) R$^3$ and R$^4$ are hydrogen; and
R$^5$ is
a) (C$_{1-12}$)alkyl; (C$_{2-12}$)alkenyl; (C$_{2-12}$)alkynyl; (C$_{3-12}$)cycloalkyl; or (C$_{3-12}$)cycloalkenyl; where the alkyl, alkenyl, alkynyl, cycloalkyl and cycloalkenyl groups are optionally mono- or independently plurisubstituted with R$^6$, and where the alkyl, alkenyl, alkynyl portions include linear or branched chains and may include cyclic portions;
R$^6$ is (C$_{1-6}$)alkyl; (C$_{1-6}$)alkoxy; cycloalkyl; carboxy; acetamido; cyano; nitro; halogen; hydroxy; hydroxy(C$_{1-6}$)alkyl; hydroxymethyl; trifluoromethyl; trifluoromethoxy; sulfamoyl; sulfonamido; carbamoyl; aryl; heteroaryl; where the aryl and heteroaryl groups are optionally mono- or independently plurisubstituted with R$^7$; amino, where the amino group is optionally mono- or independently plurisubstituted with R$^8$; —SOR$^8$; —SO$_2$R$^8$; —COR$^S$; —CO$_2$R$^8$, —CONHR$^8$; —CON(R$^8$)$_2$; —OR$^8$; or —S—R$^8$;

R$^7$ is halogen; (C$_{1-10}$)alkyl; (C$_{1-10}$)alkoxy; (C$_{1-10}$)alkylamino; (C$_{1-10}$)dialkylamino; benzyl; benzyloxy; hydroxyl(C$_{1-6}$)alkyl; hydroxymethyl; nitro; trifluoromethyl; trifluoromethoxy; trifluoromethylthio; N-hydroxyimino; cyano; carboxy; acetamido; hydroxy; sulfamoyl; sulfonamido; or carbamoyl;

R$^8$ is (C$_{1-10}$)alkyl; (C$_{2-10}$)alkenyl; (C$_{2-10}$)alkynyl; (C$_{3-10}$)cycloalkyl; (C$_{5-10}$)cycloalkenyl; benzyl; phenethyl; aryl; or heteroaryl; where the alkyl, alkenyl, alkynyl, cycloalkyl, cycloalkenyl groups are optionally mono- or independently plurisubstituted with aryl or heteroaryl where the aryl and heteroaryl groups are optionally mono- or independently plurisubstituted with R$^7$; and where the aryl and heteroaryl groups are optionally mono- or independently plurisubstituted with R$^7$;

b) aryl optionally fused to a (C$_{3-10}$)cycloalkyl; or heteroaryl optionally fused to a (C$_{3-10}$)cycloalkyl; where the aryl and heteroaryl groups are optionally mono- or independently plurisubstituted with R$^7$;

c) indanyl; 1,2,3,4-tetrahydronaphthyl; (CH$_2$)$_j$adamantyl in which j is 0-3; or a [2.2.1] or [3.1.1] bicyclic carbocyclic moiety, including (4-pentylbicyclo[2.2.2]oct-1-yl)amine; where the indanyl, 1,2,3,4-tetrahydronaphthyl, (CH$_2$)$_j$ adamantyl, and [2.2.1] or [3.1.1] bicyclic carbocyclic moieties are optionally mono- or independently plurisubstituted with hydroxy, (C$_{1-8}$)alkyl, (C$_{1-8}$)alkoxy, (C$_{1-8}$)alkanoyloxy, or R$^9$R$^{10}$N—CO—O—, where R$^9$ and R$^{10}$ are independently (C$_{1-8}$)alkyl, or phenyl, where the alkyl and phenyl groups are optionally mono- or independently plurisubstituted with (C$_{1-8}$)alkyl, (C$_{1-8}$)alkoxy, halogen, or trifluoromethyl, or R$^9$ and R$^{10}$ together are (C$_{3-6}$)alkylene;

d) R$^{11}$(CH$_2$)$_p$— where R$^{11}$ is 2-oxopyrrolidinyl; (C$_{1-6}$)alkoxy; phenyl; phenoxy; (C$_{1-8}$)cycloalkyl; [3.3.3] bicyclic carbocyclic moiety; pyridinyl; naphthyl; cyclohexenyl; or adamantyl; where the 2-oxopyrrolidinyl, (C$_{1-6}$)alkoxy, phenyl, pyridinyl, and naphthyl groups are optionally mono- or independently di- or independently trisubstituted with R$^{12}$; where the phenoxy group is optionally mono- or independently disubstituted with (C$_{1-4}$)alkyl, (C$_{1-4}$)alkoxy, or halogen; and where the [3.3.3] bicyclic carbocyclic moiety is optionally mono-or independently plurisubstituted with (C$_{1-8}$)alkyl; and p is 0 to 3;

R$^{12}$ is halogen; trifluoromethyl; cyano; nitro; (C$_{1-6}$)alkyl; (C$_{1-6}$)alkoxy; cycloalkyl; carboxy; acetamido; hydroxy; hydroxy(C$_{1-6}$)alkyl; hydroxymethyl; trifluoromethoxy; sulfamoyl; carbamoyl; sulfonamido; alkylsufonyl; phenylsulfonyl; aryl; heteroaryl; where the aryl and heteroaryl groups are optionally mono- or independently plurisubstituted with R$^7$;

e) (R$^{13}$)$_2$CH(CH$_2$)$_q$—, where R$^{13}$ is phenyl; in which the phenyl groups are independently optionally mono- or independently disubstituted with R$^{12}$; and q is 0 to 3;

f) a group of the formula:

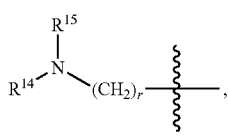

where $R^{14}$ and $R^{15}$ are independently hydrogen; $(C_{1-8})$alkyl; $(C_{1-6})$alkylcarbonyl; $(C_{3-12})$cycloalkyl ring; $(C_{3-12})$cycloalkenyl ring; benzyl; benzoyl; pyridine; pyrimidine; phenyl; phenylamino-carbonyl; alkylsulfonyl; or phenylsulfonyl; where the cycloalkyl ring is optionally substituted with hydroxy$(C_{1-6})$alkyl, and where the benzyl, benzoyl, pyridine, pyrimidine, phenyl, phenylaminocarbonyl, alkylsulfonyl, and phenylsulfonyl groups are optionally mono- or independently di-substituted with $R^{12}$; or $R^{14}$ and $R^{15}$ together form a $(C_{3-12})$cycloalkyl ring; and r is 2 to 6;

g) a group of the formula:

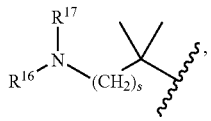

where $R^{16}$ and $R^{17}$ are each independently hydrogen; $(C_{1-8})$ alkyl; $(C_{1-6})$alkylcarbonyl; di-$(C_{1-6})$alkylaminocarbonyl; benzyl; benzoyl; pyridine; pyrimidine; phenyl; phenylaminocarbonyl; alkylsulfonyl; or phenylsulfonyl; where the benzyl, benzoyl, pyridine, pyrimidine, phenyl, phenylaminocarbonyl, alkylsulfonyl, and phenylsulfonyl groups are optionally mono- or independently di-substituted with $R^{12}$; or $R^{16}$ and $R^{17}$ together form a $(C_{3-12})$cycloalkyl ring; and s is 1 to 6;

h) a group of the formula:

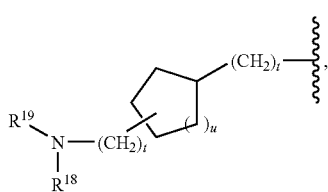

where $R^{18}$ and $R^{19}$ are independently hydrogen; $(C_{1-8})$alkyl; $(C_{1-6})$alkylcarbonyl; di-$(C_{1-6})$alkylaminocarbonyl; benzyl; benzothiazole; benzoyl; pyridine; pyrimidine; phenyl; phenylaminocarbonyl; alkylsulfonyl; or phenylsulfonyl; where the benzyl, benzoyl, benzothiazole, pyridine, pyrimidine, phenyl, phenylaminocarbonyl, alkylsulfonyl, and phenylsulfonyl groups are optionally mono- or independently di-substituted with $R^{12}$; or $R^{18}$ and $R^{19}$ together form a $(C_{3-12})$cycloalkyl ring; each t is independently 0 to 6; and u is 0 to 3;

i) a group of the formula:

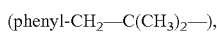

(phenyl-CH$_2$—C(CH$_3$)$_2$—), where the phenyl group is optionally mono- or independently plurisubstituted with $R^{12}$;

j) a group of the formula:

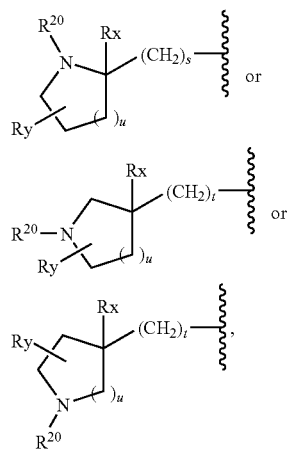

where $R^{20}$ is hydrogen; $(C_{1-8})$alkyl; $(C_{1-6})$alkylcarbonyl; di-$(C_{1-6})$alkylaminocarbonyl; $(C_{3-8})$cycloalkylcarbonyl; benzyl; benzoyl; $(C_{1-6})$alkyloxycarbonyl; arlkyloxycarbonyl, pyridine; pyrimidine; phenyl; phenyl substituted thiazole ring; phenylaminocarbonyl; alkylsulfonyl; or phenylsulfonyl; where the benzyl, benzoyl, pyridine, pyrimidine, phenyl, phenylaminocarbonyl, alkylsulfonyl, and phenylsulfonyl groups are optionally mono- or independently di-substituted with $R^{12}$; $R_x$ is hydrogen; $(C_{1-8})$alkyl; $(C_{3-12})$cycloalkyl; benzyl; phenyl; where the benzyl and phenyl, groups are optionally mono- or independently di-substituted on the ring with $R^{12}$; $R_y$ is absent or is halogen, $(C_{1-8})$alkyl, $(C_{1-8})$alkoxy, O-alkylcarboxylate, O-aralkylcarboxylate, N-alkylcarboxamido, N-aralkylcarboxamido; or phenyl;
s is 1 to 6; t is 0 to 6; and u is 0 to 3; or k) a group of the formula:

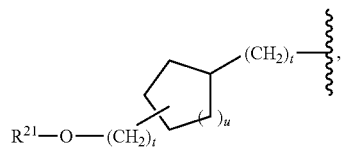

where $R^{21}$ is hydrogen; $(C_{1-8})$alkyl; benzyl; or phenyl; in which the benzyl and phenyl groups are optionally mono- or independently di-substituted on the ring with $R^{12}$; each t is independently 0 to 6; and u is 0 to 3; or (ee) $R^3$ and $R^4$ are independently hydrogen, alkyl; alkenyl; alkynyl; cycloalkyl; cycloalkylalkyl; bicycloalkyl; tricycloalkyl; alkylcycloalkyl; hydroxyalkyl; hydroxyalkylcycloalkyl; hydroxycycloalkyl; hydroxybicycloalkyl; hydroxytricycloalkyl; bicycloalkylalkyl; alkylbicycloalkyl; alkylthioalkyl; arylalkylthioalkyl; cycloalkenyl; aryl, aralkyl; heteroaryl; heteroarylalkyl; cycloheteroalkyl or cycloheteroalkylalkyl; all optionally mono- or independently plurisubstituted with halogen, alkyl, polyhaloalkyl, alkoxy, haloalkoxy, polyhaloalkoxy, alkoxycarbonyl, alkenyl, alkynyl, cycloalkyl, cycloalkylalkyl, polycycloalkyl, heteroarylamino, arylamino, cycloheteroalkyl, cycloheteroalkylalkyl, hydroxy, hydroxyalkyl, nitro, cyano, amino, substituted amino, alkylamino, dialkylamino, thiol, alkylthio, alkylcarbonyl, acyl, alkoxycarbonyl, aminocarbonyl, alkynylaminocarbonyl, alkylaminocarbonyl, alkenylaminocarbonyl, alkylcarbonyloxy, alkylcarbonylamino, arylcarbonylamino, alkylsulfonylamino, alkylaminocarbonyl-amino, alkoxycarbonylamino, alkylsulfonyl, aminosulfinyl, aminosulfonyl, alkylsulfinyl, sulfonamido or sulfonyl;

$R^5$ is alkyl; alkenyl; alkynyl; cycloalkyl; cycloalkylalkyl; bicycloalkyl; tricycloalkyl; alkylcycloalkyl; hydroxyalkyl; hydroxyalkylcycloalkyl; hydroxycycloalkyl; hydroxybicycloalkyl; hydroxytricycloalkyl; bicycloalkylalkyl; alkylbicycloalkyl; alkylthioalkyl; arylalkylthioalkyl; cycloalkenyl; aryl, aralkyl; heteroaryl; heteroarylalkyl; cycloheteroalkyl or cycloheteroalkylalkyl; all optionally mono- or independently plurisubstituted with halogen, alkyl, polyhaloalkyl, alkoxy, haloalkoxy, polyhaloalkoxy, alkoxycarbonyl, alkenyl, alkynyl, cycloalkyl, cycloalkylalkyl, polycycloalkyl, heteroarylamino, arylamino, cycloheteroalkyl, cycloheteroalkylalkyl, hydroxy, hydroxyalkyl, nitro, cyano, amino, substituted amino, alkylamino, dialkylamino, thiol, alkylthio, alkylcarbonyl, acyl, alkoxycarbonyl, aminocarbonyl, alkynylaminocarbonyl, alkylaminocarbonyl, alkenylaminocarbonyl, alkylcarbonyloxy, alkylcarbonylamino, arylcarbonylamino, alkylsulfonylamino, alkylaminocarbonyl-amino, alkoxycarbonylamino, alkylsulfonyl, aminosulfinyl, aminosulfonyl, alkylsulfinyl, sulfonamido or sulfonyl; or $R^4$ and $R^5$ together form —$(CR^{22}R^{23})_m$— wherein m is 2 to 6, and $R^{22}$ and $R^{23}$ are independently hydrogen; hydroxyl; alkoxy; alkyl; alkenyl; alkynyl; cycloalkyl; halo; amino; substituted amino; cycloalkylalkyl; cycloalkenyl; aryl; arylalkyl; heteroaryl, heteroarylalkyl; cycloheteroalkyl; cycloheteroalkylalkyl; alkylcarbonylamino; arylcarbonylamino; alkoxycarbonyl-amino; aryloxycarbonyl-amino; alkoxycarbonyl; aryloxycarbonyl; or alkylaminocarbonylamino; provided that when n is 1, X is CH$_2$, and Z and $R^3$ are H, $R^4$ and $R^5$ together are not —(CH$_2$)$_2$— or —(CH$_2$)$_3$—; or $R^4$ and $R^5$ together with the atoms to which they are attached form a 5 to 7 membered ring containing a total of 2 to 4 heteroatoms selected from N, O, S, SO, or SO$_2$; or $R^4$ and $R^5$ together with the atoms to which they are attached form a 4 to 8 membered cycloheteroalkyl ring wherein the cycloheteroalkyl ring optionally has an aryl, heteroaryl or 3 to 7 membered cycloalkyl ring fused thereto; or (ff) $R^3$ is hydrogen; and $R^4$ and $R^5$ together with the atoms to which they are attached form a 4 to 8 member mono- or polycyclic heterocyclic ring system containing 1 to 3 heteroatoms selected from N, O, S, SO and SO$_2$, wherein the heterocyclic ring system is optionally mono- or independently plurisubstituted with any of the groups set forth in (dd) or (ee); provided that when n is 1, X is CH$_2$, the ring containing X is saturated, and Z and $R^3$ are H, $R^4$ and $R^5$ together are not —(CH$_2$)$_2$— or —(CH$_2$)$_3$—.

Compounds of formula I also include those wherein X is CH$_2$; the ring containing X is saturated; CR$^i$R$^{ii}$ is absent, $R^1$, $R^2$, $R^3$ and $R^4$ are hydrogen; and $R^5$ is (C$_{1-12}$)alkyl; (C$_{2-12}$)alkenyl; (C$_{2-12}$)alkynyl; (C$_{3-12}$)cycloalkyl; or (C$_{3-12}$)cycloalkenyl; where the alkyl, alkenyl, alkynyl, cycloalkyl and cycloalkenyl groups are optionally mono- or independently plurisubstituted with $R^6$, and where the alkyl, alkenyl, alkynyl portions include linear or branched chains and may include cyclic portions. In some such embodiments, $R^5$ is a (C$_{1-12}$)alkyl or (C$_{3-12}$)cycloalkyl, including, but not limited to, methyl, ethyl, n-propyl, isopropyl, n-butyl, isobutyl, sec-butyl, tert-butyl, cyclopropyl, cyclobutyl, cyclopentyl, cyclohexyl, cyclohexylmethyl, 1-cyclohexylethyl, or adamantyl.

In some embodiments of compounds of formula I, X is CH$_2$; the ring containing X is saturated; CR$^i$R$^{ii}$ is absent, $R^1$, $R^2$, $R^3$ and $R^4$ are hydrogen; and $R^5$ is indanyl; 1,2,3,4-tetrahydronaphthyl; (CH$_2$); adamantyl in which j is 0-3; or a [2.2.1] or [3.1.1] bicyclic carbocyclic moiety, including (4-pentylbicyclo[2.2.2]-oct-1-yl)amine; where the indanyl, 1,2,3,4-tetrahydronaphthyl, (CH$_2$) adamantyl, and [2.2.1] or [3.1.1] bicyclic carbocyclic moieties are optionally mono- or independently plurisubstituted with hydroxy, (C$_{1-8}$)alkyl, (C$_{1-8}$)alkoxy, (C$_{1-8}$)alkanoyloxy, or R$^9$R$^{10}$N—CO—O—, where R$^9$ and R$^{10}$ are independently (C$_{1-8}$)alkyl, or phenyl, where the alkyl and phenyl groups are optionally mono- or independently plurisubstituted with (C$_{1-8}$)alkyl, (C$_{1-8}$)alkoxy, halogen, or trifluoromethyl, or R$^9$ and R$^{10}$ together are (C$_{3-6}$)alkylene.

In other embodiments of compounds of formula I, X is CH$_2$; the ring containing X is saturated; CR$^i$R$^{ii}$ is absent, $R^1$, $R^2$, $R^3$ and $R^4$ are hydrogen; and $R^5$ is R$^{11}$(CH$_2$)$_p$— where R$^{11}$ is 2-oxopyrrolidinyl; (C$_{1-6}$)alkoxy; phenyl; phenoxy; (C$_{1-8}$)cycloalkyl; [3.3.3] bicyclic carbocyclic moiety; pyridinyl; naphthyl; cyclohexenyl; or adamantyl; where the 2-oxopyrrolidinyl, (C$_{1-6}$)alkoxy, phenyl, pyridinyl, and naphthyl groups are optionally mono- or independently di- or independently trisubstituted with R$^{12}$; where the phenoxy group is optionally mono- or independently disubstituted with (C$_{1-4}$)alkyl, (C$_{1-4}$)alkoxy, or halogen; and where the [3.3.3] bicyclic carbocyclic moiety is optionally mono-or independently plurisubstituted with (C$_{1-8}$)alkyl; p is 0 to 3; and R$^{12}$ is halogen; trifluoromethyl; cyano; nitro; (C$_{1-6}$)alkyl; (C$_{1-6}$)alkoxy; cycloalkyl; carboxy; acetamido; hydroxy; hydroxy(C$_{1-6}$)alkyl; hydroxymethyl; trifluoromethoxy; sulfamoyl; carbamoyl; sulfonamido; alkylsufonyl; phenylsulfonyl; aryl; heteroaryl; where the aryl and heteroaryl groups are optionally mono- or independently plurisubstituted with R$^7$.

In certain embodiments of compounds of formula I, X is CH$_2$; the ring containing X is saturated; CR$^i$R$^{ii}$ is absent; $R^1$, $R^2$, $R^3$ and $R^4$ are hydrogen; and $R^5$ is (R$^{13}$)$_2$CH(CH$_2$)$_q$—, where R$^{13}$ is phenyl; in which the phenyl groups are independently optionally mono- or independently disubstituted with R$^{12}$; and q is 0 to 3.

In some embodiments of compounds of formula I, X is CH$_2$; the ring containing X is saturated; CR$^i$R$^{ii}$ is absent, $R^1$, $R^2$, $R^3$ and $R^4$ are hydrogen; and $R^5$ is a group of the formula:

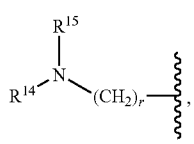

where R$^{14}$ and R$^{15}$ are independently hydrogen; (C$_{1-8}$)alkyl; (C$_{1-6}$)alkylcarbonyl; (C$_{3-12}$)cycloalkyl ring; (C$_{3-12}$)cycloalkenyl ring; benzyl; benzoyl; pyridine; pyrimidine; phenyl; phenylamino-carbonyl; alkylsulfonyl; or phenylsulfonyl; where the cycloalkyl ring is optionally substituted with hydroxy(C$_{1-6}$)alkyl, and where the benzyl, benzoyl, pyridine, pyrimidine, phenyl, phenylaminocarbonyl, alkylsulfonyl, and phenylsulfonyl groups are optionally mono- or independently di-substituted with R$^{12}$; or R$^{14}$ and R$^{15}$ together form a (C$_{3-12}$)cycloalkyl ring; and r is 2 to 6.

Compounds of formula I include those wherein X is $CH_2$; the ring containing X is saturated; $CR^iR^{ii}$ is absent, $R^1$, $R^2$, $R^3$ and $R^4$ are hydrogen; and $R^5$ is a group of the formula:

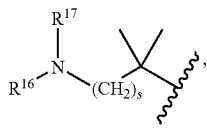

where $R^{16}$ and $R^{17}$ are each independently hydrogen; $(C_{1-8})$ alkyl; $(C_{1-6})$alkylcarbonyl; di-$(C_{1-6})$alkylaminocarbonyl; benzyl; benzoyl; pyridine; pyrimidine; phenyl; phenylaminocarbonyl; alkylsulfonyl; or phenylsulfonyl; where the benzyl, benzoyl, pyridine, pyrimidine, phenyl, phenylaminocarbonyl, alkylsulfonyl, and phenylsulfonyl groups are optionally mono- or independently di-substituted with $R^{12}$; or $R^{16}$ and $R^{17}$ together form a $(C_{3-12})$cycloalkyl ring; and s is 1 to 6.

Compounds of formula I wherein X is $CH_2$; the ring containing X is saturated; $CR^iR^{ii}$ is absent, $R^1$, $R^2$, $R^3$ and $R^4$ are hydrogen; and $R^5$ is a group of the formula:

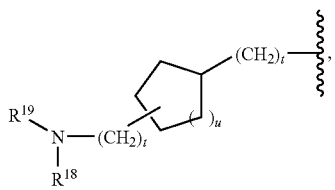

where $R^{18}$ and $R^{19}$ are independently hydrogen; $(C_{1-8})$alkyl; $(C_{1-6})$alkylcarbonyl; di-$(C_{1-6})$alkylaminocarbonyl; benzyl; benzothiazole; benzoyl; pyridine; pyrimidine; phenyl; phenylaminocarbonyl; alkylsulfonyl; or phenylsulfonyl; where the benzyl, benzoyl, benzothiazole, pyridine, pyrimidine, phenyl, phenylaminocarbonyl, alkylsulfonyl, and phenylsulfonyl groups are optionally mono- or independently di-substituted with $R^{12}$; or $R^{18}$ and $R^{19}$ together form a $(C_{3-12})$ cycloalkyl ring; each t is independently 0 to 6; and u is 0 to 3. In some such embodiments, $R^5$ has formula:

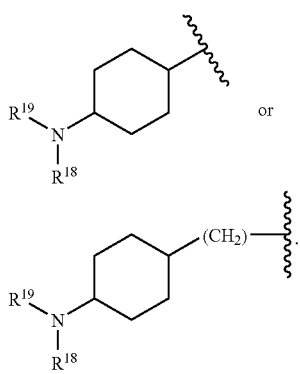

In some embodiments of compounds of formula I, X is $CH_2$; the ring containing X is saturated; $CR^iR^{ii}$ is absent, $R^1$, $R^2$, $R^3$ and $R^4$ are hydrogen; and $R^5$ is a group of the formula:

(phenyl-$CH_2$—$C(CH_3)_2$—)

where the phenyl group is optionally mono- or independently plurisubstituted with $R^{12}$.

Compounds of Formula I include those having the following structure, Formula IA:

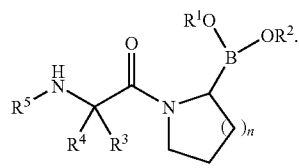

In some such embodiments, $R^5$ is alkyl; alkenyl; alkynyl; cycloalkyl; cycloalkylalkyl; bicycloalkyl; tricycloalkyl; alkylcycloalkyl; hydroxyalkyl; hydroxyalkylcycloalkyl; hydroxycycloalkyl; hydroxybicycloalkyl; hydroxytricycloalkyl; bicycloalkylalkyl; alkylbicycloalkyl; alkylthioalkyl; arylalkylthioalkyl; cycloalkenyl; aryl, aralkyl; heteroaryl; heteroarylalkyl; cycloheteroalkyl or cycloheteroalkylalkyl; all optionally mono- or independently plurisubstituted with halogen, alkyl, polyhaloalkyl, alkoxy, haloalkoxy, polyhaloalkoxy, alkoxycarbonyl, alkenyl, alkynyl, cycloalkyl, cycloalkylalkyl, polycycloalkyl, heteroarylamino, arylamino, cycloheteroalkyl, cycloheteroalkylalkyl, hydroxy, hydroxyalkyl, nitro, cyano, amino, substituted amino, alkylamino, dialkylamino, thiol, alkylthio, alkylcarbonyl, acyl, alkoxycarbonyl, aminocarbonyl, alkynylaminocarbonyl, alkylaminocarbonyl, alkenylaminocarbonyl, alkylcarbonyloxy, alkylcarbonylamino, arylcarbonylamino, alkylsulfonylamino, alkylaminocarbonyl-amino, alkoxycarbonylamino, alkylsulfonyl, aminosulfinyl, aminosulfonyl, alkylsulfinyl, sulfonamido or sulfonyl. In other such embodiments, $R^5$ is alkyl; alkenyl; cycloalkyl; cycloalkylalkyl; hydroxyalkyl; cycloalkenyl; aryl, aralkyl; heteroaryl; heteroarylalkyl; cycloheteroalkyl or cycloheteroalkylalkyl; all optionally mono- or independently plurisubstituted as described above (in, e.g., (cc)). In still other such embodiments, $R^5$ is alkyl, cycloalkyl or cycloheteroalkyl, optionally mono- or independently plurisubstituted as described above. In some embodiments of compounds of Formula IA, $R^3$ and $R^4$ are both hydrogen. In other embodiments, n is 1. In some embodiments of compounds of Formula IA where n is 1 and $R^1$, $R^2$, $R^3$, and $R^4$ are hydrogen, $R^5$ is not methyl.

Compounds of formula I include those wherein X is $CH_2$; the ring containing X is saturated; $CR^iR^{ii}$ is absent, $R^1$, $R^2$, $R^3$ and $R^4$ are hydrogen; and $R^5$ is a group of the formula:

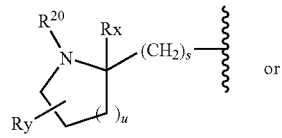 or

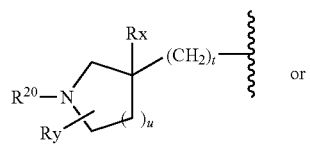 or

-continued

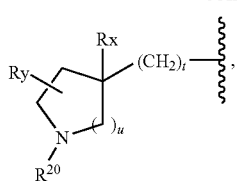

where $R^{20}$ is hydrogen; $(C_{1-8})$alkyl; $(C_{1-6})$alkylcarbonyl; di-$(C_{1-6})$alkylaminocarbonyl; $(C_{3-8})$cycloalkylcarbonyl; benzyl; benzoyl; $(C_{1-6})$alkyloxycarbonyl; arlkyloxycarbonyl, pyridine; pyrimidine; phenyl; phenyl substituted thiazole ring; phenylaminocarbonyl; alkylsulfonyl; or phenylsulfonyl; where the benzyl, benzoyl, pyridine, pyrimidine, phenyl, phenylaminocarbonyl, alkylsulfonyl, and phenylsulfonyl groups are optionally mono- or independently di-substituted with $R^{12}$; $R_x$ is hydrogen; $(C_{1-8})$alkyl; $(C_{3-12})$cycloalkyl; benzyl; phenyl; where the benzyl and phenyl, groups are optionally mono- or independently di-substituted on the ring with $R^{12}$; $R_y$ is absent or is halogen, $(C_{1-8})$alkyl, $(C_{1-8})$alkoxy, O-alkylcarboxylate, O-aralkylcarboxylate, N-alkylcarboxamido, N-aralkylcarboxamido; or phenyl;

s is 1 to 6; t is 0 to 6; and u is 0 to 3. In some such embodiments, $R^5$ has formula:

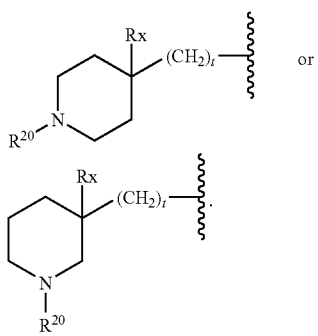

In other such embodiments, $R^5$ is

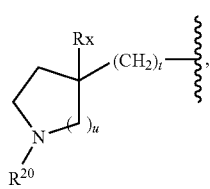

including for example, the following structures:

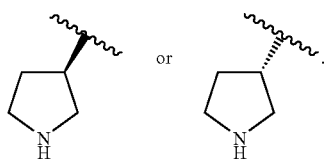 [SMILES: *[C@@H]1CCNC1 ; "or" ; *[C@H]1CCNC1 ; "."]

In still other such embodiments, the compound has the formula

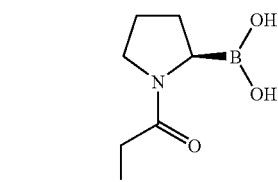

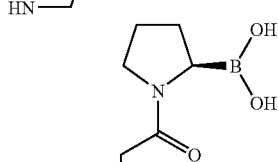

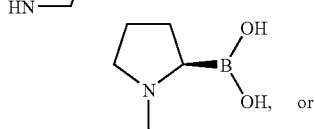

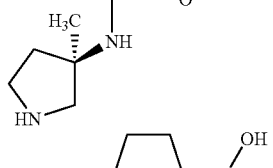

Compounds of formula I wherein X is $CH_2$; the ring containing X is saturated; $CR^iR^{ii}$ is absent, $R^1$, $R^2$, $R^3$ and $R^4$ are hydrogen; and $R^5$ is a group of the formula:

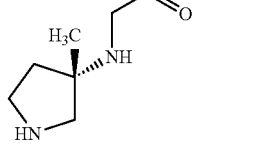
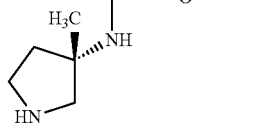

where $R^{21}$ is hydrogen; $(C_{1-8})$alkyl; benzyl; or phenyl; in which the benzyl and phenyl groups are optionally mono- or independently di-substituted on the ring with $R^{12}$; each t is independently 0 to 6; and u is 0 to 3. In some such embodiments, $R^5$ has formula:

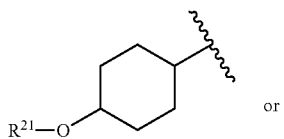

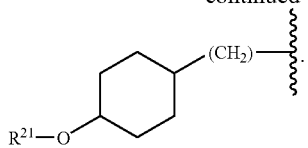

Compounds of formula I include those wherein $R^1$ and $R^2$ are hydrogen; n is 1; X together with an adjacent ring carbon and Z form a fused cyclopropyl; $CR^iR^{ii}$ is absent;

$R^3$, $R^4$ and $R^5$ are independently hydrogen; alkyl; alkenyl; alkynyl; cycloalkyl; cycloalkylalkyl; bicycloalkyl; tricycloalkyl; alkylcycloalkyl; hydroxyalkyl; hydroxyalkylcycloalkyl; hydroxycycloalkyl; hydroxybicycloalkyl; hydroxytricycloalkyl; bicycloalkylalkyl; alkylbicycloalkyl; alkylthioalkyl; arylalkylthioalkyl; cycloalkenyl; aryl, aralkyl; heteroaryl; heteroarylalkyl; cycloheteroalkyl or cycloheteroalkylalkyl; all optionally mono- or independently plurisubstituted with halogen, alkyl, polyhaloalkyl, alkoxy, haloalkoxy, polyhaloalkoxy, alkoxycarbonyl, alkenyl, alkynyl, cycloalkyl, cycloalkylalkyl, polycycloalkyl, heteroarylamino, arylamino, cycloheteroalkyl, cycloheteroalkylalkyl, hydroxy, hydroxyalkyl, nitro, cyano, amino, substituted amino, alkylamino, dialkylamino, thiol, alkylthio, alkylcarbonyl, acyl, alkoxycarbonyl, aminocarbonyl, alkynylaminocarbonyl, alkylaminocarbonyl, alkenylaminocarbonyl, alkylcarbonyloxy, alkylcarbonylamino, arylcarbonylamino, alkylsulfonylamino, alkylaminocarbonyl-amino, alkoxycarbonylamino, alkylsulfonyl, aminosulfinyl, aminosulfonyl, alkylsulfinyl, sulfonamido or sulfonyl; or

- $R^4$ and $R^5$ together form $-(CR^{22}R^{23})_m-$ where m is 2 to 6, and $R^{22}$ and $R^{23}$ are independently hydrogen; hydroxyl; alkoxy; alkyl; alkenyl; alkynyl; cycloalkyl; halo; amino; substituted amino; cycloalkylalkyl; cycloalkenyl; aryl; arylalkyl; heteroaryl, heteroarylalkyl; cycloheteroalkyl; cycloheteroalkylalkyl; alkylcarbonylamino; arylcarbonylamino; alkoxycarbonylamino; aryloxycarbonyl-amino; alkoxycarbonyl; aryloxycarbonyl; or alkylaminocarbonylamino; or
- $R^4$ and $R^5$ together with the atoms to which they are attached form a 5 to 7 membered ring containing a total of 2 to 4 heteroatoms selected from N, O, S, SO, or $SO_2$; or
- $R^4$ and $R^5$ together with the atoms to which they are attached form a 4 to 8 membered cycloheteroalkyl ring wherein the cycloheteroalkyl ring optionally has an aryl, heteroaryl or 3 to 7 membered cycloalkyl ring fused thereto.

In some embodiments of compounds of Formula I, $R^I$, $R^2$, $R^3$ and $R^4$ are hydrogen; n is 1; X is $CH_2$; $CR^iR^{ii}$ is absent; and $R^5$ is aryl or aralkyl.

In some embodiments, compounds of formula I have the formula:

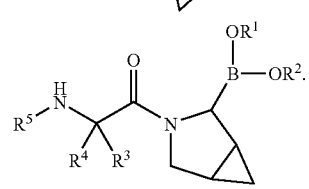

In other embodiments, compounds of formula I have the formula:

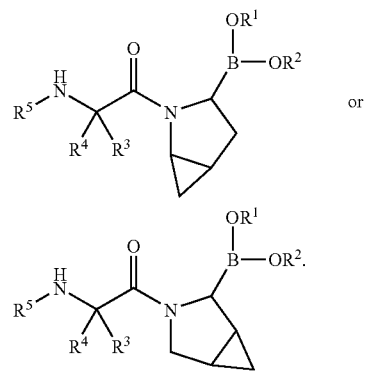

In still other embodiments, compounds of formula I have the formula:

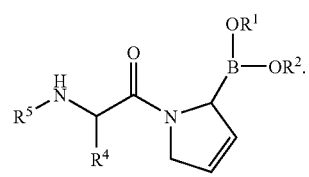

In still other embodiments, compounds of formula I have the formula:

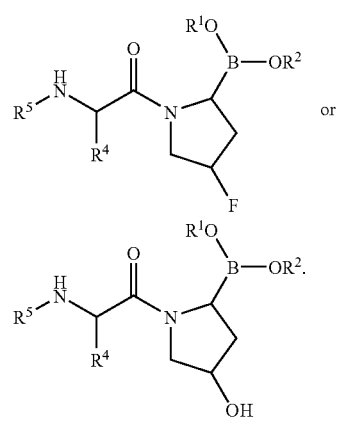

Compounds of formula I include those wherein, if $CR^iR^{ii}$ is present, $R^i$ and $R^3$ are hydrogen; $R^{ii}$ and $R^4$ together form a 4 to 8 membered cyclic, polycyclic or heterocyclic ring system containing 1 to 3 heteroatoms selected from N, O, S, SO and $SO_2$, and includes single rings, fused bicyclic and tricyclic rings, which are optionally mono- or independently plurisubstituted with any of the groups set forth in (aa) or (bb) and $R^5$ is any of the groups in (aa) or (bb); or if $CR^iR^{ii}$ is absent, then $R^3$ is hydrogen; and $R^4$ and $R^5$ together with the atoms to which they are attached form a 4 to 8 membered cyclic, polycyclic or heterocyclic ring system containing 1 to 3 heteroatoms selected from N, O, S, SO and $SO_2$, and includes single rings, fused bicyclic and tricyclic rings, which are optionally mono- or independently plurisubstituted with any of the groups set forth in (dd) or (ee); provided that when n is 1, X is $CH_2$, the ring containing X is saturated, and Z and $R^3$ are hydrogen, $R^4$ and $R^5$ together are not $-(CH_2)_2-$ or $-(CH_2)_3-$.

In some such embodiments, compounds of formula I have formula II:

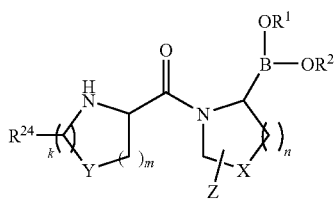

(II)

wherein:
Y is O S, CHR$^{25}$ or NR$^{26}$;
k is 0 to 3 and m is 0 to 3 when Y is CHR$^{25}$;
k is 2 to 3 and m is 1 to 3 when Y is O or NR$^{26}$;
each R$^{24}$ is independently:
a) hydrogen;
b) $(C_{1-12})$alkyl; $(C_{2-12})$alkenyl; $(C_{2-12})$alkynyl; $(C_{3-12})$cycloalkyl; or $(C_{3-12})$cycloalkenyl; where the alkyl, alkenyl, alkynyl, cycloalkyl and cycloalkenyl groups are optionally mono- or independently plurisubstituted with R$^{12}$, and where the alkyl, alkenyl, alkynyl portions include linear or branched chains and may include cyclic portions;
c) aryl; or heteroaryl; where the aryl and heteroaryl groups are optionally mono- or independently plurisubstituted with R$^{12}$;
d) R$^{11}$(CH$_2$)$_p$— where R$^{11}$ is 2-oxopyrrolidinyl; $(C_{1-6})$alkoxy; phenyl; phenoxy; $(C_{1-8})$cycloalkyl; [3.3.3] bicyclic carbocyclic moiety; pyridinyl; naphthyl; cyclohexenyl; $(C_{1-8})$alkylcarbonyl; $(C_{3-12})$cycloalkylcarbonyl; benzyl; benzoyl; pyrimidinyl; phenylaminocarbonyl; alkylsulfonyl; phenylsulfonyl; or adamantyl; where the cycloalkyl ring is optionally substituted with hydroxy$(C_{1-6})$alkyl; where the 2-oxopyrrolidinyl, $(C_{1-6})$alkoxy, phenyl, pyridinyl, benzyl, benzoyl, pyrimidinyl, phenylaminocarbonyl, alkylsulfonyl, phenylsulfonyl, and naphthyl groups are optionally mono- or independently di- or independently trisubstituted with R$^{12}$; where the phenoxy group is optionally mono- or independently disubstituted with $(C_{1-4})$alkyl, $(C_{1-4})$alkoxy, or halogen; and where the [3.3.3] bicyclic carbocyclic moiety is optionally mono-or independently plurisubstituted with $(C_{1-8})$alkyl; p is 0 to 3; and
R$^{12}$ is halogen; trifluoromethyl; cyano; nitro; $(C_{1-6})$alkyl; $(C_{1-6})$alkoxy; cycloalkyl; carboxy; acetamido; hydroxy; hydroxy$(C_{1-6})$alkyl; hydroxymethyl; trifluoromethoxy; sulfamoyl; carbamoyl; sulfonamido; alkylsufonyl; phenylsulfonyl; aryl; heteroaryl; where the aryl and heteroaryl groups are optionally mono- or independently plurisubstituted with R$^7$;
e) (R$^{13}$)$_2$CH(CH$_2$)$_q$—, where R$^{13}$ is phenyl; in which the phenyl groups are independently optionally mono- or independently disubstituted with R$^{12}$; and q is 0 to 3;
f) a group of the formula:

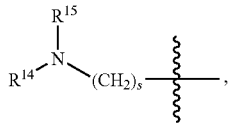

where R$^{14}$ and R$^{15}$ are independently hydrogen; $(C_{1-8})$alkyl; $(C_{1-6})$alkylcarbonyl; $(C_{3-12})$cycloalkyl ring; $(C_{3-12})$cycloalkenyl ring; benzyl; benzoyl; pyridine; pyrimidine; phenyl; phenylamino-carbonyl; alkylsulfonyl; or phenylsulfonyl; where the cycloalkyl ring is optionally substituted with hydroxy$(C_{1-6})$alkyl, and where the benzyl, benzoyl, pyridine, pyrimidine, phenyl, phenylaminocarbonyl, alkylsulfonyl, and phenylsulfonyl groups are optionally mono- or independently di-substituted with R$^{12}$; or R$^{14}$ and R$^{15}$ together form a $(C_{3-12})$cycloalkyl ring; and s is 1 to 6; or
g) a group of the formula:

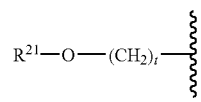

where R$^{21}$ is hydrogen; $(C_{1-8})$alkyl; benzyl; or phenyl; in which the benzyl and phenyl groups are optionally mono- or independently di-substituted on the ring with R$^{12}$; and t is 1 to 6;
R$^{25}$ is:
a) hydrogen;
b) $(C_{1-12})$alkyl; $(C_{2-12})$alkenyl; $(C_{2-12})$alkynyl; $(C_{3-12})$cycloalkyl; or $(C_{3-12})$cycloalkenyl; where the alkyl, alkenyl, alkynyl, cycloalkyl and cycloalkenyl groups are optionally mono- or independently plurisubstituted with R$^{12}$, and where the alkyl, alkenyl, alkynyl portions include linear or branched chains and may include cyclic portions;
c) aryl; or heteroaryl; where the aryl and heteroaryl groups are optionally mono- or independently plurisubstituted with R$^{12}$;
d) R$^{11}$(CH$_2$)$_p$— where R$^{11}$ is 2-oxopyrrolidinyl; $(C_{1-6})$alkoxy; phenyl; phenoxy; $(C_{1-8})$cycloalkyl; [3.3.3] bicyclic carbocyclic moiety; pyridinyl; naphthyl; cyclohexenyl; $(C_{1-8})$alkylcarbonyl; $(C_{3-12})$cycloalkylcarbonyl; benzyl; benzoyl; pyrimidinyl; phenylaminocarbonyl; alkylsulfonyl; phenylsulfonyl; or adamantyl; where the cycloalkyl ring is optionally substituted with hydroxy$(C_{1-6})$alkyl; where the 2-oxopyrrolidinyl, $(C_{1-6})$alkoxy, phenyl, pyridinyl, benzyl, benzoyl, pyrimidinyl, phenylaminocarbonyl, alkylsulfonyl, phenylsulfonyl, and naphthyl groups are optionally mono- or independently di- or independently trisubstituted with R$^{12}$; where the phenoxy group is optionally mono- or independently disubstituted with $(C_{1-4})$alkyl, $(C_{1-4})$alkoxy, or halogen; and where the [3.3.3] bicyclic carbocyclic moiety is optionally mono-or independently plurisubstituted with $(C_{1-8})$alkyl; p is 0 to 3; and
R$^{12}$ is halogen; trifluoromethyl; cyano; nitro; $(C_{1-6})$alkyl; $(C_{1-6})$alkoxy; cycloalkyl; carboxy; acetamido; hydroxy; hydroxy$(C_{1-6})$alkyl; hydroxymethyl; trifluoromethoxy; sulfamoyl; carbamoyl; sulfonamido; alkylsufonyl; phenylsulfonyl; aryl; heteroaryl; where the aryl and heteroaryl groups are optionally mono- or independently plurisubstituted with R$^7$;
e) (R$^{13}$)$_2$CH(CH$_2$)$_q$—, where R$^{13}$ is phenyl; in which the phenyl groups are independently optionally mono- or independently disubstituted with R$^{12}$; and q is 0 to 3;
f) a group of the formula:

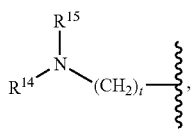

where $R^{14}$ and $R^{15}$ are independently hydrogen; $(C_{1-8})$alkyl; $(C_{1-6})$alkylcarbonyl; $(C_{3-12})$cycloalkyl ring; $(C_{3-12})$cycloalkenyl ring; benzyl; benzoyl; pyridine; pyrimidine; phenyl; phenylamino-carbonyl; alkylsulfonyl; or phenylsulfonyl; where the cycloalkyl ring is optionally substituted with hydroxy$(C_{1-6})$alkyl, and where the benzyl, benzoyl, pyridine, pyrimidine, phenyl, phenylaminocarbonyl, alkylsulfonyl, and phenylsulfonyl groups are optionally mono- or independently di-substituted with $R^{12}$; or $R^{14}$ and $R^{15}$ together form a $(C_{3-12})$cycloalkyl ring; and t is 0 to 6; or g) a group of the formula:

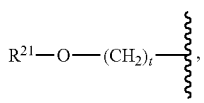

where $R^{21}$ is hydrogen; $(C_{1-8})$alkyl; benzyl; or phenyl; in which the benzyl and phenyl groups are optionally mono- or independently di-substituted on the ring with $R^{12}$; and t is 0 to 6; and $R^{26}$ is:

a) hydrogen;
b) $(C_{1-12})$alkyl; $(C_{2-12})$alkenyl; $(C_{2-12})$alkynyl; $(C_{3-12})$cycloalkyl; or $(C_{3-12})$cycloalkenyl; where the alkyl, alkenyl, alkynyl, cycloalkyl and cycloalkenyl groups are optionally mono- or independently plurisubstituted with $R^{12}$, and where the alkyl, alkenyl, alkynyl portions include linear or branched chains and may include cyclic portions;
c) aryl; or heteroaryl; where the aryl and heteroaryl groups are optionally mono- or independently plurisubstituted with $R^{12}$;
d) $R^{27}(CH_2)_p$—, where $R^{27}$ is 2-oxopyrrolidinyl; $(C_{1-6})$alkoxy; phenyl; phenoxy; $(C_{1-8})$cycloalkyl; [3.3.3] bicyclic carbocyclic moiety; pyridinyl; naphthyl; cyclohexenyl; $(C_{1-8})$alkylcarbonyl; $(C_{3-12})$cycloalkylcarbonyl; benzyl; benzoyl; pyrimidinyl; phenylaminocarbonyl; alkylsulfonyl; phenylsulfonyl; or adamantyl; where the cycloalkyl ring is optionally substituted with hydroxy$(C_{1-6})$alkyl; where the 2-oxopyrrolidinyl, $(C_{1-6})$alkoxy, phenyl, pyridinyl, benzyl, benzoyl, pyrimidinyl, phenylaminocarbonyl, alkylsulfonyl, phenylsulfonyl, and naphthyl groups are optionally mono- or independently di- or independently trisubstituted with $R^{12}$; where the phenoxy group is optionally mono- or independently disubstituted with $(C_{1-4})$alkyl, $(C_{1-4})$alkoxy, or halogen; and where the [3.3.3] bicyclic carbocyclic moiety is optionally mono-or independently plurisubstituted with $(C_{1-8})$alkyl; p is 0 to 3; and $R^{12}$ is halogen; trifluoromethyl; cyano; nitro; $(C_{1-6})$alkyl; $(C_{1-6})$alkoxy; cycloalkyl; carboxy; acetamido; hydroxy; hydroxy$(C_{1-6})$alkyl; hydroxymethyl; trifluoromethoxy; sulfamoyl; carbamoyl; sulfonamido; alkylsufonyl; phenylsulfonyl; aryl; heteroaryl; where the aryl and heteroaryl groups are optionally mono- or independently plurisubstituted with $R^7$;

e) $(R^{13})_2CH(CH_2)_q$—, where $R^{13}$ is phenyl, in which the phenyl groups are independently optionally mono- or independently disubstituted with $R^{12}$; and q is 0 to 3;

f) a group of the formula:

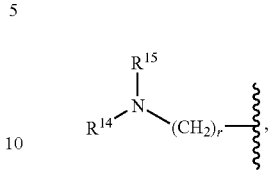

where $R^{14}$ and $R^{15}$ are independently hydrogen; $(C_{1-8})$alkyl; $(C_{1-6})$alkylcarbonyl; $(C_{3-12})$cycloalkyl ring; $(C_{3-12})$cycloalkenyl ring; benzyl; benzoyl; pyridine; pyrimidine; phenyl; phenylamino-carbonyl; alkylsulfonyl; or phenylsulfonyl; where the cycloalkyl ring is optionally substituted with hydroxy$(C_{1-6})$alkyl, and where the benzyl, benzoyl, pyridine, pyrimidine, phenyl, phenylaminocarbonyl, alkylsulfonyl, and phenylsulfonyl groups are optionally mono- or independently di-substituted with $R^{12}$; or $R^{14}$ and $R^{15}$ together form a $(C_{3-12})$cycloalkyl ring; and r is 0 or 2 to 6; or g) a group of the formula:

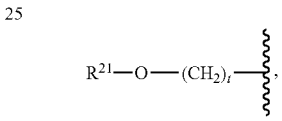

where $R^{21}$ is hydrogen; $(C_{1-8})$alkyl; benzyl; or phenyl; in which the benzyl and phenyl groups are optionally mono- or independently di-substituted on the ring with $R^{12}$; and t is 0 or 2 to 6.

In some embodiments of compounds of formula II, X is $CH_2$; the ring containing X is saturated; and $R^1$, $R^2$ and $R^{25}$ are hydrogen. In other embodiments of compounds of formula II, X is $CH_2$; the ring containing X is saturated; $R^1$, $R^2$ and $R^{25}$ are hydrogen; and $R^{24}$ is hydrogen, provided that if k, n, and m are each 1, and Y is $CHR^{25}$, Z is not H. In still other embodiments of compounds of formula II, X is $CH_2$; the ring containing X is saturated; $R^1$, $R^2$ and $R^{25}$ are hydrogen; and $R^{24}$ is $(C_{1-12})$alkyl; $(C_{2-12})$alkenyl; $(C_{2-12})$alkynyl; $(C_{3-12})$cycloalkyl; or $(C_{3-12})$cycloalkenyl; where the alkyl, alkenyl, alkynyl, cycloalkyl and cycloalkenyl groups are optionally mono- or independently plurisubstituted with $R^{12}$, and where the alkyl, alkenyl, alkynyl portions include linear or branched chains and may include cyclic portions. In some embodiments of compounds of formula II, X is $CH_2$; the ring containing X is saturated; $R^1$, $R^2$ and $R^{25}$ are hydrogen; and $R^{24}$ is phenyl optionally mono- or independently plurisubstituted with $R^{12}$.

Compounds of formula II include those wherein X is $CH_2$; the ring containing X is saturated; $R^1$, $R^2$ and $R^{25}$ are hydrogen; and $R^{24}$ is $R^{11}(CH_2)_p$— where $R^{11}$ is 2-oxopyrrolidinyl; $(C_{1-6})$alkoxy; phenyl; phenoxy; $(C_{1-8})$cycloalkyl; [3.3.3] bicyclic carbocyclic moiety; pyridinyl; naphthyl; cyclohexenyl; $(C_{1-8})$alkylcarbonyl; $(C_{3-12})$cycloalkylcarbonyl; benzyl; benzoyl; pyrimidinyl; phenylaminocarbonyl; alkylsulfonyl; phenylsulfonyl; or adamantyl; where the cycloalkyl ring is optionally substituted with hydroxy$(C_{1-6})$alkyl; where the 2-oxopyrrolidinyl, $(C_{1-6})$alkoxy, phenyl, pyridinyl, benzyl, benzoyl, pyrimidinyl, phenylaminocarbonyl, alkylsulfonyl, phenylsulfonyl, and naphthyl groups are optionally mono- or independently di- or independently trisubstituted with $R^{12}$; where the phenoxy group is optionally mono- or independently disubstituted with $(C_{1-4})$alkyl, $(C_{1-4})$alkoxy, or halogen; and where the [3.3.3] bicyclic carbocyclic moiety is optionally mono-or independently plurisubstituted with $(C_{1-8})$alkyl; p is 0 to 3; and $R^{12}$ is halogen; trifluoromethyl; cyano; nitro; $(C_{1-6})$alkyl; $(C_{1-6})$alkoxy; cycloalkyl; carboxy; acetamido; hydroxy; hydroxy$(C_{1-6})$alkyl; hydroxymethyl; trifluoromethoxy; sulfamoyl; carbamoyl; sulfonamido; alkylsufonyl; phenylsulfonyl; aryl; heteroaryl; where the aryl and heteroaryl groups are optionally mono- or independently plurisubstituted with $R^7$.

In certain embodiments of compounds of formula II, X is $CH_2$; the ring containing X is saturated; $R^1$, $R^2$ and $R^{25}$ are hydrogen; and $R^{24}$ is $(R^{13})_2CH(CH_2)_q$—, where $R^{13}$ is phenyl; in which the phenyl groups are independently optionally mono- or independently disubstituted with $R^{12}$; and q is 0 to 3.

In other embodiments of compounds of formula II, X is $CH_2$; the ring containing X is saturated; $R^1$, $R^2$ and $R^{25}$ are hydrogen; and $R^{24}$ is a group of the formula:

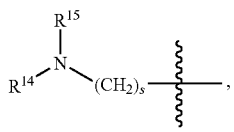

where $R^{14}$ and $R^{15}$ are independently hydrogen; $(C_{1-8})$alkyl; $(C_{1-6})$alkylcarbonyl; $(C_{3-12})$cycloalkyl ring; $(C_{3-12})$cycloalkenyl ring; benzyl; benzoyl; pyridine; pyrimidine; phenyl; phenylamino-carbonyl; alkylsulfonyl; or phenylsulfonyl; where the cycloalkyl ring is optionally substituted with hydroxy$(C_{1-6})$alkyl, and where the benzyl, benzoyl, pyridine, pyrimidine, phenyl, phenylaminocarbonyl, alkylsulfonyl, and phenylsulfonyl groups are optionally mono- or independently di-substituted with $R^{12}$; or $R^{14}$ and $R^{15}$ together form a $(C_{3-12})$cycloalkyl ring; and s is 1 to 6.

In some embodiments of compounds of formula II, X is $CH_2$; the ring containing X is saturated; $R^1$, $R^2$ and $R^{25}$ are hydrogen; and $R^{24}$ is a group of the formula:

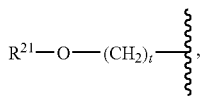

where $R^{21}$ is hydrogen; $(C_{1-8})$alkyl; benzyl; or phenyl; in which the benzyl and phenyl groups are optionally mono- or independently di-substituted on the ring with $R^{12}$; and t is 1 to 6.

Compounds of formula II include those wherein X is $CH_2$; the ring containing X is saturated; $R^1$, $R^2$ and $R^{24}$ are hydrogen. In some embodiments of compounds of formula II, X is $CH_2$; the ring containing X is saturated; $R^1$, $R^2$, $R^{24}$ are hydrogen; and $R^{25}$ is $(C_{1-12})$alkyl; $(C_{2-12})$alkenyl; $(C_{2-12})$alkynyl; $(C_{3-12})$cycloalkyl; or $(C_{3-12})$cycloalkenyl; where the alkyl, alkenyl, alkynyl, cycloalkyl and cycloalkenyl groups are optionally mono- or independently plurisubstituted with $R^{12}$, and where the alkyl, alkenyl, alkynyl portions include linear or branched chains and may include cyclic portions. In other embodiments of compounds of formula II, X is $CH_2$; the ring containing X is saturated; $R^1$, $R^2$, $R^{24}$ are hydrogen; and $R^{25}$ is phenyl optionally mono- or independently plurisubstituted with $R^{12}$.

Compounds of formula II include those wherein X is $CH_2$; the ring containing X is saturated; $R^1$, $R^2$, $R^{24}$ are hydrogen; and $R^{25}$ is $R^{11}(CH_2)_p$— where $R^{11}$ is 2-oxopyrrolidinyl, $(C_{1-6})$alkoxy, phenyl; phenoxy; $(C_{1-8})$cycloalkyl; [3.3.3] bicyclic carbocyclic moiety; pyridinyl; naphthyl; cyclohexenyl; or adamantyl; where the 2-oxopyrrolidinyl, $(C_{1-6})$alkoxy, phenyl, pyridinyl, and naphthyl groups are optionally mono- or independently di- or independently trisubstituted with $R^{12}$; where the phenoxy group is optionally mono- or independently disubstituted with $(C_{1-4})$alkyl, $(C_{1-4})$alkoxy, or halogen; and where the [3.3.3] bicyclic carbocyclic moiety is optionally mono-or independently plurisubstituted with $(C_{1-8})$alkyl; p is 0 to 3; and $R^{12}$ is halogen; trifluoromethyl; cyano; nitro; $(C_{1-6})$alkyl; $(C_{1-6})$alkoxy; cycloalkyl; carboxy; acetamido; hydroxy; hydroxy$(C_{1-6})$alkyl; hydroxymethyl; trifluoromethoxy; sulfamoyl; carbamoyl; sulfonamido; alkylsufonyl; phenylsulfonyl; aryl; heteroaryl; where the aryl and heteroaryl groups are optionally mono- or independently plurisubstituted with $R^7$.

In other embodiments of compounds of formula II, X is $CH_2$; the ring containing X is saturated; $R^1$, $R^2$, $R^{24}$ are hydrogen; and $R^{25}$ is $(R^{13})_2CH(CH_2)_q$—, where $R^{13}$ is phenyl; in which the phenyl groups are independently optionally mono- or independently disubstituted with $R^{12}$; and q is 0 to 3.

Compounds of formula II include those wherein X is $CH_2$; the ring containing X is saturated; $R^1$, $R^2$, $R^{24}$ are hydrogen; and $R^{25}$ is a group of the formula:

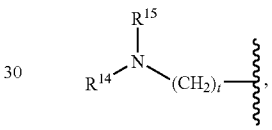

where $R^{14}$ and $R^{15}$ are independently hydrogen; $(C_{1-8})$alkyl; $(C_{1-6})$alkylcarbonyl; $(C_{3-12})$cycloalkyl ring; $(C_{3-12})$cycloalkenyl ring; benzyl; benzoyl; pyridine; pyrimidine; phenyl; phenylamino-carbonyl; alkylsulfonyl; or phenylsulfonyl; where the cycloalkyl ring is optionally substituted with hydroxy$(C_{1-6})$alkyl, and where the benzyl, benzoyl, pyridine, pyrimidine, phenyl, phenylaminocarbonyl, alkylsulfonyl, and phenylsulfonyl groups are optionally mono- or independently di-substituted with $R^{12}$; or $R^{14}$ and $R^{15}$ together form a $(C_{3-12})$cycloalkyl ring; and t is 0 to 6.

In some embodiments of compounds of formula II, X is $CH_2$; the ring containing X is saturated; $R^1$, $R^2$, $R^{24}$ are hydrogen; and $R^{25}$ is a group of the formula:

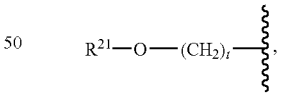

where $R^{21}$ is hydrogen; $(C_{1-8})$alkyl; benzyl; or phenyl; in which the benzyl and phenyl groups are optionally mono- or independently di-substituted on the ring with $R^{12}$; and t is 0 to 6. In other embodiments of compounds of formula II, X is $CH_2$; the ring containing X is saturated; $R^1$, $R^2$, $R^{24}$ and $R^{26}$ are hydrogen. In still other embodiments of compounds of formula II, X is $CH_2$; the ring containing X is saturated; $R^1$, $R^2$, $R^{24}$ are hydrogen; and $R^{26}$ is $(C_{1-12})$alkyl; $(C_{2-12})$alkenyl; $(C_{2-12})$alkynyl; $(C_{3-12})$cycloalkyl; or $(C_{3-12})$cycloalkenyl; where the alkyl, alkenyl, alkynyl, cycloalkyl and cycloalkenyl groups are optionally mono- or independently plurisubstituted with $R^{12}$, and where the alkyl, alkenyl, alkynyl portions include linear or branched chains and may include cyclic portions. Compounds of formula II include those wherein X is CH$_2$; the ring containing X is saturated; R$^1$, R$^2$, R$^{24}$ are hydrogen; and R$^{26}$ is phenyl optionally mono- or independently plurisubstituted with R$^{12}$.

Compounds of formula II wherein X is CH$_2$; the ring containing X is saturated; R$^1$, R$^2$, R$^{24}$ are hydrogen; and R$^{26}$ is R$^{27}$(CH$_2$)$_p$—, where R$^{27}$ is 2-oxopyrrolidinyl; (C$_{1-6}$)alkoxy; phenyl; phenoxy; (C$_{1-8}$)cycloalkyl; [3.3.3] bicyclic carbocyclic moiety; pyridinyl; naphthyl; cyclohexenyl; (C$_{1-8}$)alkylcarbonyl; (C$_{3-12}$)cycloalkylcarbonyl; benzyl; benzoyl; pyrimidinyl; phenylaminocarbonyl; alkylsulfonyl; phenylsulfonyl; or adamantyl; where the cycloalkyl ring is optionally substituted with hydroxy(C$_{1-6}$)alkyl; where the 2-oxopyrrolidinyl, (C$_{1-6}$)alkoxy, phenyl, pyridinyl, benzyl, benzoyl, pyrimidinyl, phenylaminocarbonyl, alkylsulfonyl, phenylsulfonyl, and naphthyl groups are optionally mono- or independently di- or independently trisubstituted with R$^{12}$; where the phenoxy group is optionally mono- or independently disubstituted with (C$_{1-4}$)alkyl, (C$_{1-4}$)alkoxy, or halogen; and where the [3.3.3] bicyclic carbocyclic moiety is optionally mono- or independently plurisubstituted with (C$_{1-8}$)alkyl; p is 0 to 3; and R$^{12}$ is halogen; trifluoromethyl; cyano; nitro; (C$_{1-6}$)alkyl; (C$_{1-6}$)alkoxy; cycloalkyl; carboxy; acetamido; hydroxy; hydroxy(C$_{1-6}$)alkyl; hydroxymethyl; trifluoromethoxy; sulfamoyl; carbamoyl; sulfonamido; alkylsufonyl; phenylsulfonyl; aryl; heteroaryl; where the aryl and heteroaryl groups are optionally mono- or independently plurisubstituted with R$^7$; and p is 0 to 3.

Compounds of formula II include those wherein X is CH$_2$; the ring containing X is saturated; R$^1$, R$^2$, R$^{24}$ are hydrogen; and R$^{26}$ is (R$^{13}$)$_2$CH(CH$_2$)$_q$—; where R$^{13}$ is phenyl, in which the phenyl groups are independently optionally mono- or independently disubstituted with R$^{12}$; and q is 0 to 3.

In some embodiments of compounds of formula II, X is CH$_2$; the ring containing X is saturated; R$^1$, R$^2$, R$^{24}$ are hydrogen; and R$^{26}$ is a group of the formula:

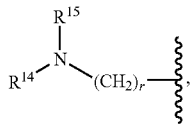

where R$^{14}$ and R$^{15}$ are independently hydrogen; (C$_{1-8}$)alkyl; (C$_{1-6}$)alkylcarbonyl; (C$_{3-12}$)cycloalkyl ring; (C$_{3-12}$)cycloalkenyl ring; benzyl; benzoyl; pyridine; pyrimidine; phenyl; phenylamino-carbonyl; alkylsulfonyl; or phenylsulfonyl; where the cycloalkyl ring is optionally substituted with hydroxy(C$_{1-6}$)alkyl, and where the benzyl, benzoyl, pyridine, pyrimidine, phenyl, phenylaminocarbonyl, alkylsulfonyl, and phenylsulfonyl groups are optionally mono- or independently di-substituted with R$^{12}$; or R$^{14}$ and R$^{15}$ together form a (C$_{3-12}$)cycloalkyl ring; and r is 0 or 2 to 6.

In other embodiments of compounds of formula II, X is CH$_2$; the ring containing X is saturated; R$^1$, R$^2$, R$^{24}$ are hydrogen; and R$^{26}$ is a group of the formula:

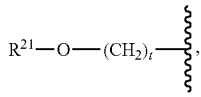

where R$^{21}$ is hydrogen; (C$_{1-8}$)alkyl; benzyl; or phenyl; in which the benzyl and phenyl groups are optionally mono- or independently di-substituted on the ring with R$^{12}$; and t is 0 or 2 to 6.

Compounds of formula II include those that have the formula:

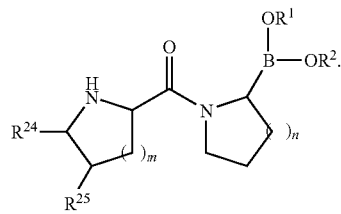

In some such embodiments, R$^{25}$ is phenyl optionally mono- or independently plurisubstituted with R$^{12}$.

In other embodiments of compounds of formula II, the compound has the formula:

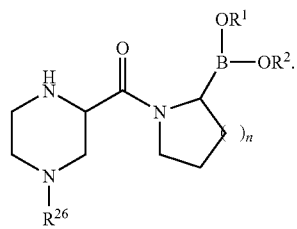

Compounds of formula II also include those that have the formula:

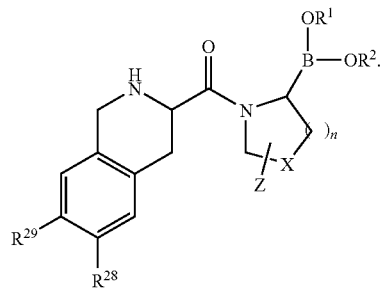

wherein:
R$^{28}$ and R$^{29}$ are each independently hydrogen, hydroxy, alkyl, alkoxy, aryloxy, or halogen.

In some embodiments of compounds of formula I wherein CR$^i$R$^{ii}$ is present, the compound has formula III:

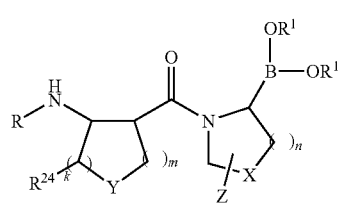

wherein:
Y is O, S, CHR$^{25}$ or NR$^{26}$;
k is 0 to 3 and m is 0 to 3 when Y is CHR$^{25}$;
k is 1 to 3 and m is 0 to 3 when Y is NR$^{26}$;
k is 1 to 3 and m is 0 to 3 when Y is O;

R is a) hydrogen;

b) $(C_{1-12})$alkyl; $(C_{2-12})$alkenyl; $(C_{2-12})$alkynyl; $(C_{3-12})$cycloalkyl; or $(C_{3-12})$cycloalkenyl; where the alkyl, alkenyl, alkynyl, cycloalkyl and cycloalkenyl groups are optionally mono- or independently plurisubstituted with $R^6$, and where the alkyl, alkenyl, alkynyl portions include linear or branched chains and may include cyclic portions;

$R^6$ is $(C_{1-6})$alkyl; $(C_{1-6})$alkoxy; cycloalkyl; carboxy; acetamido; cyano; nitro; halogen; hydroxy; hydroxy$(C_{1-6})$alkyl; hydroxymethyl; trifluoromethyl; trifluoromethoxy; sulfamoyl; sulfonamido; carbamoyl; aryl; heteroaryl; where the aryl and heteroaryl groups are optionally mono- or independently plurisubstituted with $R^7$; amino, where the amino group is optionally mono- or independently plurisubstituted with $R^8$; —$SOR^8$; —$SO_2R^8$; —$COR^8$; —$CO_2R^8$, —$CONHR^8$; —$CON(R^8)_2$; —$OR^8$; or —$S$—$R^8$;

$R^7$ is halogen; $(C_{1-10})$alkyl; $(C_{1-10})$alkoxy; $(C_{1-10})$alkylamino; $(C_{1-10})$ dialkylamino; benzyl; benzyloxy; hydroxyl$(C_{1-6})$alkyl; hydroxymethyl; nitro; trifluoromethyl; trifluoromethoxy; trifluoromethylthio; N-hydroxyimino; cyano; carboxy; acetamido; hydroxy; sulfamoyl; sulfonamido; or carbamoyl;

$R^8$ is $(C_{1-10})$alkyl; $(C_{2-10})$alkenyl; $(C_{2-10})$alkynyl; $(C_{3-10})$cycloalkyl; $(C_{5-10})$cycloalkenyl; benzyl; phenethyl; aryl; or heteroaryl; where the alkyl, alkenyl, alkynyl, cycloalkyl, cycloalkenyl groups are optionally mono- or independently plurisubstituted with aryl or heteroaryl where the aryl and heteroaryl groups are optionally mono- or independently plurisubstituted with $R^7$; and where the aryl and heteroaryl groups are optionally mono- or independently plurisubstituted with $R^7$;

c) aryl optionally fused to a $(C_{3-10})$cycloalkyl; or heteroaryl optionally fused to a $(C_{3-10})$cycloalkyl; where the aryl and heteroaryl groups are optionally mono- or independently plurisubstituted with $R^7$;

d) indanyl; 1,2,3,4-tetrahydronaphthyl; $(CH_2)_j$adamantyl in which j is 0-3; or a [2.2.1] or [3.1.1] bicyclic carbocyclic moiety, including (4-pentylbicyclo[2.2.2]oct-1-yl) amine; where the indanyl, 1,2,3,4-tetrahydronaphthyl, $(CH_2)_j$ adamantyl, and [2.2.1] or [3.1.1] bicyclic carbocyclic moieties are optionally mono- or independently plurisubstituted with hydroxy, $(C_{1-8})$alkyl, $(C_{1-8})$alkoxy, $(C_{1-8})$alkanoyloxy, or $R^9R^{10}N$—CO—O—, where $R^9$ and $R^{10}$ are independently $(C_{1-8})$alkyl, or phenyl, where the alkyl and phenyl groups are optionally mono- or independently plurisubstituted with $(C_{1-8})$alkyl, $(C_{1-8})$alkoxy, halogen, or trifluoromethyl, or $R^9$ and $R^{10}$ together are $(C_{3-6})$alkylene;

e) $R^{11}(CH_2)_p$— where $R^{11}$ is 2-oxopyrrolidinyl; $(C_{1-6})$alkoxy; phenyl; phenoxy; $(C_{1-8})$cycloalkyl; [3.3.3] bicyclic carbocyclic moiety; pyridinyl; naphthyl; cyclohexenyl; or adamantyl; where the 2-oxopyrrolidinyl, $(C_{1-6})$alkoxy, phenyl, pyridinyl, and naphthyl groups are optionally mono- or independently di- or independently trisubstituted with $R^{12}$; where the phenoxy group is optionally mono- or independently disubstituted with $(C_{1-4})$alkyl, $(C_{1-4})$alkoxy, or halogen; and where the [3.3.3] bicyclic carbocyclic moiety is optionally mono- or independently plurisubstituted with $(C_{1-8})$alkyl; and p is 0 to 3;

$R^{12}$ is halogen; trifluoromethyl; cyano; nitro; $(C_{1-6})$alkyl; $(C_{1-6})$alkoxy; cycloalkyl; carboxy; acetamido; hydroxy; hydroxy$(C_{1-6})$alkyl; hydroxymethyl; trifluoromethoxy; sulfamoyl; carbamoyl; sulfonamido; alkylsulfonyl; phenyl sulfonyl; aryl; heteroaryl; where the aryl and heteroaryl groups are optionally mono- or independently plurisubstituted with $R^7$;

f) $(R^{13})_2CH(CH_2)_q$—, where $R^{13}$ is phenyl; in which the phenyl groups are independently optionally mono- or independently disubstituted with $R^{12}$; and q is 0 to 3;

g) a group of the formula:

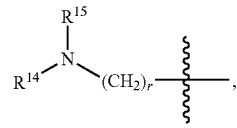

where $R^{14}$ and $R^{15}$ are independently hydrogen; $(C_{1-8})$alkyl; $(C_{1-6})$alkylcarbonyl; $(C_{3-12})$cycloalkyl ring; $(C_{3-12})$cycloalkenyl ring; benzyl; benzoyl; pyridine; pyrimidine; phenyl; phenylamino-carbonyl; alkylsulfonyl; or phenylsulfonyl; where the cycloalkyl ring is optionally substituted with hydroxy$(C_{1-6})$alkyl, and where the benzyl, benzoyl, pyridine, pyrimidine, phenyl, phenylaminocarbonyl, alkylsulfonyl, and phenylsulfonyl groups are optionally mono- or independently di-substituted with $R^{12}$; or $R^{14}$ and $R^{15}$ together form a $(C_{3-12})$cycloalkyl ring; and r is 2 to 6;

h) a group of the formula:

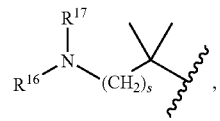

where $R^{16}$ and $R^{17}$ are each independently hydrogen; $(C_{1-8})$alkyl; $(C_{1-6})$alkylcarbonyl; di-$(C_{1-6})$alkylaminocarbonyl; benzyl; benzoyl; pyridine; pyrimidine; phenyl; phenylaminocarbonyl; alkylsulfonyl; or phenylsulfonyl; where the benzyl, benzoyl, pyridine, pyrimidine, phenyl, phenylaminocarbonyl, alkylsulfonyl, and phenylsulfonyl groups are optionally mono- or independently di-substituted with $R^{12}$; or $R^{16}$ and $R^{17}$ together form a $(C_{3-12})$cycloalkyl ring; and s is 1 to 6;

i) a group of the formula:

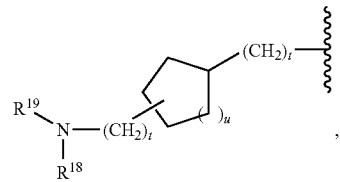

where $R^{18}$ and $R^{19}$ are independently hydrogen; $(C_{1-8})$alkyl; $(C_{1-6})$alkylcarbonyl; di-$(C_{1-6})$alkylaminocarbonyl; benzyl; benzothiazole; benzoyl; pyridine; pyrimidine; phenyl; phenylaminocarbonyl; alkylsulfonyl; or phenylsulfonyl; where the benzyl, benzoyl, benzothiazole, pyridine, pyrimidine, phenyl, phenylaminocarbonyl, alkylsulfonyl, and phenylsulfonyl groups are optionally mono- or independently di-substituted with $R^{12}$; or $R^{18}$ and $R^{19}$ together form a $(C_{3-12})$cycloalkyl ring; each t is independently 0 to 6; and u is 0 to 3;

j) a group of the formula:

(phenyl-CH$_2$—C(CH$_3$)$_2$—), where the phenyl group is optionally mono- or independently plurisubstituted with R$^{12}$;

k) a group of the formula:

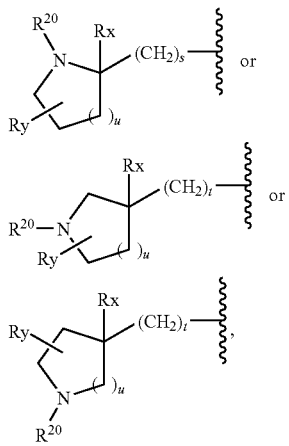

where R$^{20}$ is hydrogen; (C$_{1-8}$)alkyl; (C$_{1-6}$)alkylcarbonyl; di-(C$_{1-6}$)alkylaminocarbonyl; (C$_{3-8}$)cycloalkylcarbonyl; benzyl; benzoyl; (C$_{1-6}$)alkyloxycarbonyl; arlkyloxycarbonyl; pyridine; pyrimidine; phenyl; phenyl substituted thiazole ring; phenylaminocarbonyl; alkylsulfonyl; or phenylsulfonyl; where the benzyl, benzoyl, pyridine, pyrimidine, phenyl, phenylaminocarbonyl, alkylsulfonyl, and phenylsulfonyl groups are optionally mono- or independently di-substituted with R$^{12}$; R$_x$ is hydrogen; (C$_{1-8}$)alkyl; (C$_{3-12}$)cycloalkyl; benzyl; phenyl; where the benzyl and phenyl, groups are optionally mono- or independently di-substituted on the ring with R$^{12}$; R$_y$ is absent or is halogen, (C$_{1-8}$)alkyl, (C$_{1-8}$)alkoxy, O-alkylcarboxylate, O-aralkylcarboxylate, N-alkylcarboxamido, N-aralkylcarboxamido; or phenyl;
s is 1 to 6; t is 0 to 6; and u is 0 to 3; or l) a group of the formula:

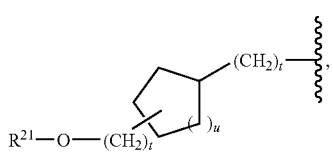

where R$^{21}$ is hydrogen; (C$_{1-8}$)alkyl; benzyl; or phenyl; in which the benzyl and phenyl groups are optionally mono- or independently di-substituted on the ring with R$^{12}$; each t is independently 0 to 6; and u is 0 to 3;

each R$^{24}$ is independently:
a) hydrogen;
b) (C$_{1-12}$)alkyl; (C$_{2-12}$)alkenyl; (C$_{2-12}$)alkynyl; (C$_{3-12}$)cycloalkyl; or (C$_{3-12}$)cycloalkenyl; where the alkyl, alkenyl, alkynyl, cycloalkyl and cycloalkenyl groups are optionally mono- or independently plurisubstituted with R$^{12}$, and where the alkyl, alkenyl, alkynyl portions include linear or branched chains and may include cyclic portions;
c) aryl; or heteroaryl; where the aryl and heteroaryl groups are optionally mono- or independently plurisubstituted with R$^{12}$;

d) R$^{11}$(CH$_2$)$_p$— where R$^{11}$ is 2-oxopyrrolidinyl; (C$_{1-6}$)alkoxy; phenyl; phenoxy; (C$_{1-8}$)cycloalkyl; [3.3.3] bicyclic carbocyclic moiety; pyridinyl; naphthyl; cyclohexenyl; (C$_{1-8}$)alkylcarbonyl; (C$_{3-12}$)cycloalkylcarbonyl; benzyl; benzoyl; pyrimidinyl; phenylaminocarbonyl; alkylsulfonyl; phenylsulfonyl; or adamantyl; where the cycloalkyl ring is optionally substituted with hydroxy (C$_{1-6}$)alkyl; where the 2-oxopyrrolidinyl, (C$_{1-6}$)alkoxy, phenyl, pyridinyl, benzyl, benzoyl, pyrimidinyl, phenylaminocarbonyl, alkylsulfonyl, phenylsulfonyl, and naphthyl groups are optionally mono- or independently di- or independently trisubstituted with R$^{12}$; where the phenoxy group is optionally mono- or independently disubstituted with (C$_{1-4}$)alkyl, (C$_{1-4}$)alkoxy, or halogen; and where the [3.3.3] bicyclic carbocyclic moiety is optionally mono-or independently plurisubstituted with (C$_{1-8}$)alkyl; p is 0 to 3; and
R$^{12}$ is halogen; trifluoromethyl; cyano; nitro; (C$_{1-6}$)alkyl; (C$_{1-6}$)alkoxy; cycloalkyl; carboxy; acetamido; hydroxy; hydroxy(C$_{1-6}$)alkyl; hydroxymethyl; trifluoromethoxy; sulfamoyl; carbamoyl; sulfonamido; alkylsufonyl; phenylsulfonyl; aryl; heteroaryl; where the aryl and heteroaryl groups are optionally mono- or independently plurisubstituted with R$^7$;
e) (R$^{13}$)$_2$CH(CH$_2$)$_q$—, where R$^{13}$ is phenyl; in which the phenyl groups are independently optionally mono- or independently disubstituted with R$^{12}$; and q is 0 to 3;
f) a group of the formula:

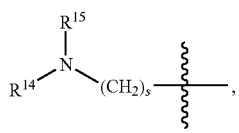

where R$^{14}$ and R$^{15}$ are independently hydrogen; (C$_{1-8}$)alkyl; (C$_{1-6}$)alkylcarbonyl; (C$_{3-12}$)cycloalkyl ring; (C$_{3-12}$)cycloalkenyl ring; benzyl; benzoyl; pyridine; pyrimidine; phenyl; phenylamino-carbonyl; alkylsulfonyl; or phenylsulfonyl; where the cycloalkyl ring is optionally substituted with hydroxy(C$_{1-6}$)alkyl, and where the benzyl, benzoyl, pyridine, pyrimidine, phenyl, phenylaminocarbonyl, alkylsulfonyl, and phenylsulfonyl groups are optionally mono- or independently di-substituted with R$^{12}$; or R$^{14}$ and R$^{15}$ together form a (C$_{3-12}$)cycloalkyl ring; and s is 0 to 6; or
g) a group of the formula:

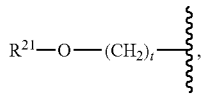

where R$^{21}$ is hydrogen; (C$_{1-8}$)alkyl; benzyl; or phenyl; in which the benzyl and phenyl groups are optionally mono- or independently di-substituted on the ring with R$^{12}$; and t is 0 to 6;

R$^{25}$ is:
a) hydrogen;
b) (C$_{1-12}$)alkyl; (C$_{2-12}$)alkenyl; (C$_{2-12}$)alkynyl; (C$_{3-12}$)cycloalkyl; or (C$_{3-12}$)cycloalkenyl; where the alkyl, alkenyl, alkynyl, cycloalkyl and cycloalkenyl groups are optionally mono- or independently plurisubstituted with R$^{12}$, and where the alkyl, alkenyl, alkynyl portions include linear or branched chains and may include cyclic portions;
c) aryl; or heteroaryl; where the aryl and heteroaryl groups are optionally mono- or independently plurisubstituted with R$^{12}$;

d) $R^{11}(CH_2)_p$— where $R^{11}$ is 2-oxopyrrolidinyl; $(C_{1-6})$alkoxy; phenyl; phenoxy; $(C_{1-8})$cycloalkyl; [3.3.3] bicyclic carbocyclic moiety; pyridinyl; naphthyl; cyclohexenyl; $(C_{1-8})$alkylcarbonyl; $(C_{3-12})$cycloalkylcarbonyl; benzyl; benzoyl; pyrimidinyl; phenylaminocarbonyl; alkylsulfonyl; phenylsulfonyl; or adamantyl; where the cycloalkyl ring is optionally substituted with hydroxy$(C_{1-6})$alkyl; where the 2-oxopyrrolidinyl, $(C_{1-6})$alkoxy, phenyl, pyridinyl, benzyl, benzoyl, pyrimidinyl, phenylaminocarbonyl, alkylsulfonyl, phenylsulfonyl, and naphthyl groups are optionally mono- or independently di- or independently trisubstituted with $R^{12}$; where the phenoxy group is optionally mono- or independently disubstituted with $(C_{1-4})$alkyl, $(C_{1-4})$alkoxy, or halogen; and where the [3.3.3] bicyclic carbocyclic moiety is optionally mono-or independently plurisubstituted with $(C_{1-8})$alkyl; p is 0 to 3; and $R^{12}$ is halogen; trifluoromethyl; cyano; nitro; $(C_{1-6})$alkyl; $(C_{1-6})$alkoxy; cycloalkyl; carboxy; acetamido; hydroxy; hydroxy$(C_{1-6})$alkyl; hydroxymethyl; trifluoromethoxy; sulfamoyl; carbamoyl; sulfonamido; alkylsufonyl; phenylsulfonyl; aryl; heteroaryl; where the aryl and heteroaryl groups are optionally mono- or independently plurisubstituted with $R^2$;

e) $(R^{13})_2CH(CH_2)_q$—, where $R^{13}$ is phenyl; in which the phenyl groups are independently optionally mono- or independently disubstituted with $R^{12}$; and q is 0 to 3;

f) a group of the formula:

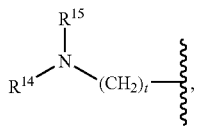

where $R^{14}$ and $R^{15}$ are independently hydrogen; $(C_{1-8})$alkyl; $(C_{1-6})$alkylcarbonyl; $(C_{3-12})$cycloalkyl ring; $(C_{3-12})$cycloalkenyl ring; benzyl; benzoyl; pyridine; pyrimidine; phenyl; phenylamino-carbonyl; alkylsulfonyl; or phenylsulfonyl; where the cycloalkyl ring is optionally substituted with hydroxy$(C_{1-6})$alkyl, and where the benzyl, benzoyl, pyridine, pyrimidine, phenyl, phenylaminocarbonyl, alkylsulfonyl, and phenylsulfonyl groups are optionally mono- or independently di-substituted with $R^{12}$; or $R^{14}$ and $R^{15}$ together form a $(C_{3-12})$cycloalkyl ring; and t is 0 to 6; or g) a group of the formula:

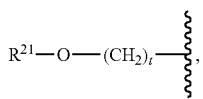

where $R^{21}$ is hydrogen; $(C_{1-8})$alkyl; benzyl; or phenyl; in which the benzyl and phenyl groups are optionally mono- or independently di-substituted on the ring with $R^{12}$; and t is 0 to 6; and R26 is:
a) hydrogen;
b) $(C_{1-12})$alkyl; $(C_{2-12})$alkenyl; $(C_{2-12})$alkynyl; $(C_{3-12})$cycloalkyl; or $(C_{3-12})$cycloalkenyl; where the alkyl, alkenyl, alkynyl, cycloalkyl and cycloalkenyl groups are optionally mono- or independently plurisubstituted with $R^{12}$, and where the alkyl, alkenyl, alkynyl portions include linear or branched chains and may include cyclic portions;

c) aryl; or heteroaryl; where the aryl and heteroaryl groups are optionally mono- or independently plurisubstituted with $R^{12}$;

d) $R^{27}(CH_2)_p$—, where $R^{27}$ is 2-oxopyrrolidinyl; $(C_{1-6})$alkoxy; phenyl; phenoxy; $(C_{1-8})$cycloalkyl; [3.3.3] bicyclic carbocyclic moiety; pyridinyl; naphthyl; cyclohexenyl; $(C_{1-8})$alkylcarbonyl; $(C_{3-12})$cycloalkylcarbonyl; benzyl; benzoyl; pyrimidinyl; phenylaminocarbonyl; alkylsulfonyl; phenylsulfonyl; or adamantyl; where the cycloalkyl ring is optionally substituted with hydroxy$(C_{1-6})$alkyl; where the 2-oxopyrrolidinyl, $(C_{1-6})$alkoxy, phenyl, pyridinyl, benzyl, benzoyl, pyrimidinyl, phenylaminocarbonyl, alkylsulfonyl, phenylsulfonyl, and naphthyl groups are optionally mono- or independently di- or independently trisubstituted with $R^{12}$; where the phenoxy group is optionally mono- or independently disubstituted with $(C_{1-4})$alkyl, $(C_{1-4})$alkoxy, or halogen; and where the [3.3.3] bicyclic carbocyclic moiety is optionally mono-or independently plurisubstituted with $(C_{1-8})$alkyl; p is 0 to 3; and $R^{12}$ is halogen; trifluoromethyl; cyano; nitro; $(C_{1-6})$alkyl; $(C_{1-6})$alkoxy; cycloalkyl; carboxy; acetamido; hydroxy; hydroxy$(C_{1-6})$alkyl; hydroxymethyl; trifluoromethoxy; sulfamoyl; carbamoyl; sulfonamido; alkylsufonyl; phenylsulfonyl; aryl; heteroaryl; where the aryl and heteroaryl groups are optionally mono- or independently plurisubstituted with $R^7$;

e) $(R^{13})_2CH(CH_2)_q$—, where $R^{13}$ is phenyl, in which the phenyl groups are independently optionally mono- or independently disubstituted with $R^{12}$; and q is 0 to 3;

f) a group of the formula:

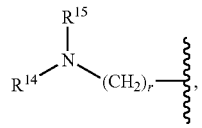

where $R^{14}$ and $R^{15}$ are independently hydrogen; $(C_{1-8})$alkyl; $(C_{1-6})$alkylcarbonyl; $(C_{3-12})$cycloalkyl ring; $(C_{3-12})$cycloalkenyl ring; benzyl; benzoyl; pyridine; pyrimidine; phenyl; phenylamino-carbonyl; cycloalkenyl ring; benzyl; benzoyl; pyridine; pyrimidine; phenyl; phenylamino-carbonyl; alkylsulfonyl; or phenylsulfonyl; where the cycloalkyl ring is optionally substituted with hydroxy$(C_{1-6})$alkyl, and where the benzyl, benzoyl, pyridine, pyrimidine, phenyl, phenylaminocarbonyl, alkylsulfonyl, and phenylsulfonyl groups are optionally mono- or independently di-substituted with $R^{12}$; or $R^{14}$ and $R^{15}$ together form a $(C_{3-12})$cycloalkyl ring; and r is 0 or 2 to 6; or g) a group of the formula:

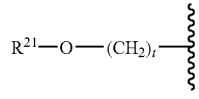

where $R^{21}$ is hydrogen; $(C_{1-8})$alkyl; benzyl; or phenyl; in which the benzyl and phenyl groups are optionally mono- or independently di-substituted on the ring with $R^{12}$; and t is 0 or 2 to 6.

Compounds of formula III include those wherein X is $CH_2$; the ring containing X is saturated; and $R^1$, $R^2$ and $R^{25}$ are hydrogen; those wherein X is $CH_2$; the ring containing X is saturated; $R^1$, $R^2$ and $R^{25}$ are hydrogen; and $R^{24}$ is hydrogen; and those wherein X is $CH_2$; the ring containing X is saturated; $R^1$, $R^2$ and $R^{25}$ are hydrogen; and $R^{24}$ is $(C_{1-12})$alkyl; $(C_{2-12})$alkenyl; $(C_{2-12})$alkynyl; $(C_{3-12})$cycloalkyl; or $(C_{3-12})$cycloalkenyl; where the alkyl, alkenyl, alkynyl, cycloalkyl and cycloalkenyl groups are optionally mono- or independently plurisubstituted with $R^{12}$, and where the alkyl, alkenyl, alkynyl portions include linear or branched chains and may include cyclic portions.

In some embodiments of compounds of formula III, X is $CH_2$; the ring containing X is saturated; $R^1$, $R^2$ and $R^{25}$ are hydrogen; and $R^{24}$ is phenyl optionally mono- or independently plurisubstituted with $R^{12}$. In other embodiments, X is $CH_2$; the ring containing X is saturated; $R^1$, $R^2$ and $R^{25}$ are hydrogen; and $R^{24}$ is $R^{11}(CH_2)_p$— where $R^{11}$ is 2-oxopyrrolidinyl, $(C_{1-6})$alkoxy, phenyl; phenoxy; $(C_{1-8})$cycloalkyl; [3.3.3] bicyclic carbocyclic moiety; pyridinyl; naphthyl; cyclohexenyl; or adamantyl; where the 2-oxopyrrolidinyl, $(C_{1-6})$alkoxy, phenyl, pyridinyl, and naphthyl groups are optionally mono- or independently di- or independently trisubstituted with $R^{12}$; where the phenoxy group is optionally mono- or independently disubstituted with $(C_{1-4})$alkyl, $(C_{1-4})$alkoxy, or halogen; and where the [3.3.3] bicyclic carbocyclic moiety is optionally mono-or independently plurisubstituted with $(C_{1-8})$alkyl; p is 0 to 3; and $R^{12}$ is halogen; trifluoromethyl; cyano; nitro; $(C_{1-6})$alkyl; $(C_{1-6})$alkoxy; cycloalkyl; carboxy; acetamido; hydroxy; hydroxy$(C_{1-6})$alkyl; hydroxymethyl; trifluoromethoxy; sulfamoyl; carbamoyl; sulfonamido; alkylsufonyl; phenylsulfonyl; aryl; heteroaryl; where the aryl and heteroaryl groups are optionally mono- or independently plurisubstituted with $R^7$. In still other embodiments, X is $CH_2$; the ring containing X is saturated; $R^1$, $R^2$ and $R^{25}$ are hydrogen; and $R^{24}$ is $(R^{13})_2CH(CH_2)_q$—, where $R^{13}$ is phenyl; in which the phenyl groups are independently optionally mono- or independently disubstituted with $R^{12}$; and q is 0 to 3.

Compounds of formula III include those wherein X is $CH_2$; the ring containing X is saturated; $R^1$, $R^2$ and $R^{25}$ are hydrogen; and $R^{24}$ is a group of the formula:

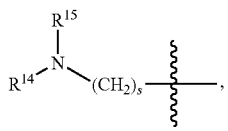

where $R^{14}$ and $R^{15}$ are independently hydrogen; $(C_{1-8})$alkyl; $(C_{1-6})$alkylcarbonyl; $(C_{3-12})$cycloalkyl ring; $(C_{3-12})$cycloalkenyl ring; benzyl; benzoyl; pyridine; pyrimidine; phenyl; phenylamino-carbonyl; alkylsulfonyl; or phenylsulfonyl; where the cycloalkyl ring is optionally substituted with hydroxy$(C_{1-6})$alkyl, and where the benzyl, benzoyl, pyridine, pyrimidine, phenyl, phenylaminocarbonyl, alkylsulfonyl, and phenylsulfonyl groups are optionally mono- or independently di-substituted with $R^{12}$; or $R^{14}$ and $R^{15}$ together form a $(C_{3-12})$cycloalkyl ring; and s is 1 to 6.

Compounds of formula III also include those wherein X is $CH_2$; the ring containing X is saturated; $R^1$, $R^2$ and $R^{25}$ are hydrogen; and $R^{24}$ is a group of the formula:

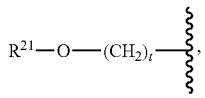

where $R^{21}$ is hydrogen; $(C_{1-8})$alkyl; benzyl; or phenyl; in which the benzyl and phenyl groups are optionally mono- or independently di-substituted on the ring with $R^{12}$; and t is 0 to 6.

In some embodiments of compounds of formula III, X is $CH_2$; the ring containing X is saturated; $R^1$, $R^2$ and $R^{24}$ are hydrogen. In other embodiments, X is $CH_2$; the ring containing X is saturated; $R^1$, $R^2$, $R^{24}$ are hydrogen; and $R^{25}$ is $(C_{1-12})$alkyl; $(C_{2-12})$alkenyl; $(C_{2-12})$alkynyl; $(C_{3-12})$cycloalkyl; or $(C_{3-12})$cycloalkenyl; where the alkyl, alkenyl, alkynyl, cycloalkyl and cycloalkenyl groups are optionally mono- or independently plurisubstituted with $R^{12}$, and where the alkyl, alkenyl, alkynyl portions include linear or branched chains and may include cyclic portions. In still other embodiments, X is $CH_2$; the ring containing X is saturated; $R^1$, $R^2$, $R^{24}$ are hydrogen; and $R^{25}$ is phenyl optionally mono- or independently plurisubstituted with $R^{12}$.

In some embodiments of compounds of formula III, X is $CH_2$; the ring containing X is saturated; $R^1$, $R^2$, $R^{24}$ are hydrogen; and $R^{25}$ is $R''(CH_2)_p$— where $R^{11}$ is 2-oxopyrrolidinyl, $(C_{1-6})$alkoxy, phenyl; phenoxy; $(C_{1-8})$cycloalkyl; [3.3.3] bicyclic carbocyclic moiety; pyridinyl; naphthyl; cyclohexenyl; or adamantyl; where the 2-oxopyrrolidinyl, $(C_{1-6})$alkoxy, phenyl, pyridinyl, and naphthyl groups are optionally mono- or independently di- or independently trisubstituted with $R^{12}$; where the phenoxy group is optionally mono- or independently disubstituted with $(C_{1-4})$alkyl, $(C_{1-4})$alkoxy, or halogen; and where the [3.3.3] bicyclic carbocyclic moiety is optionally mono-or independently plurisubstituted with $(C_{1-8})$alkyl; p is 0 to 3; and $R^{12}$ is halogen; trifluoromethyl; cyano; nitro; $(C_{1-6})$alkyl; $(C_{1-6})$alkoxy; cycloalkyl; carboxy; acetamido; hydroxy; hydroxy$(C_{1-6})$alkyl; hydroxymethyl; trifluoromethoxy; sulfamoyl; carbamoyl; sulfonamido; alkylsufonyl; phenylsulfonyl; aryl; heteroaryl; where the aryl and heteroaryl groups are optionally mono- or independently plurisubstituted with $R^7$.

In other embodiments of compounds of formula III, X is $CH_2$; the ring containing X is saturated; $R^1$, $R^2$, $R^{24}$ are hydrogen; and $R^{25}$ is $(R^{13})_2CH(CH_2)_q$—, where $R^{13}$ is phenyl; in which the phenyl groups are independently optionally mono- or independently disubstituted with $R^{12}$; and q is 0 to 3. In still other embodiments, X is $CH_2$; the ring containing X is saturated; $R^1$, $R^2$, $R^{24}$ are hydrogen; and $R^{25}$ is a group of the formula:

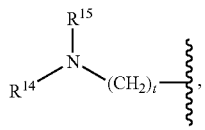

where $R^{14}$ and $R^{15}$ are independently hydrogen; $(C_{1-8})$alkyl; $(C_{1-6})$alkylcarbonyl; $(C_{3-12})$cycloalkyl ring; $(C_{3-12})$cycloalkenyl ring; benzyl; benzoyl; pyridine; pyrimidine; phenyl; phenylamino-carbonyl; alkylsulfonyl; or phenylsulfonyl; where the cycloalkyl ring is optionally substituted with hydroxy$(C_{1-6})$alkyl, and where the benzyl, benzoyl, pyridine, pyrimidine, phenyl, phenylaminocarbonyl, alkylsulfonyl, and phenylsulfonyl groups are optionally mono- or independently di-substituted with $R^{12}$; or $R^{14}$ and $R^{15}$ together form a $(C_{3-12})$cycloalkyl ring; and t is 0 to 6.

In certain embodiments of compounds of formula III, X is $CH_2$; the ring containing X is saturated; $R^1$, $R^2$, $R^{24}$ are hydrogen; and $R^{25}$ is a group of the formula:

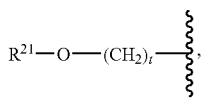

where $R^{21}$ is hydrogen; $(C_{1-8})$alkyl; benzyl; or phenyl; in which the benzyl and phenyl groups are optionally mono- or independently di-substituted on the ring with $R^{12}$; and t is 0 to 6.

In some embodiments of compounds of formula III, X is $CH_2$; the ring containing X is saturated; $R^1$, $R^2$, $R^{24}$ and $R^{26}$ are hydrogen. In other embodiments, X is $CH_2$; the ring containing X is saturated; $R^1$, $R^2$, $R^{24}$ are hydrogen; and $R^{26}$ is $(C_{1-12})$alkyl; $(C_{2-12})$alkenyl; $(C_{2-12})$alkynyl; $(C_{3-12})$cycloalkyl; or $(C_{3-12})$cycloalkenyl; where the alkyl, alkenyl, alkynyl, cycloalkyl and cycloalkenyl groups are optionally mono- or independently plurisubstituted with $R^{12}$, and where the alkyl, alkenyl, alkynyl portions include linear or branched chains and may include cyclic portions. In yet other embodiments, X is $CH_2$; the ring containing X is saturated; $R^1$, $R^2$, $R^{24}$ are hydrogen; and $R^{26}$ is phenyl optionally mono- or independently plurisubstituted with $R^{12}$.

Compounds of formula III include those wherein X is $CH_2$; the ring containing X is saturated; $R^1$, $R^2$, $R^{24}$ are hydrogen; and $R^{26}$ is $R^{27}(CH_2)_p$—, where $R^{27}$ is 2-oxopyrrolidinyl; $(C_{1-6})$alkoxy; phenyl; phenoxy; $(C_{1-8})$cycloalkyl; [3.3.3] bicyclic carbocyclic moiety; pyridinyl; naphthyl; cyclohexenyl; $(C_{1-8})$alkylcarbonyl; $(C_{3-12})$cycloalkylcarbonyl; benzyl; benzoyl; pyrimidinyl; phenylaminocarbonyl; alkylsulfonyl; phenylsulfonyl; or adamantyl; where the cycloalkyl ring is optionally substituted with hydroxy$(C_{1-6})$alkyl; where the 2-oxopyrrolidinyl, $(C_{1-6})$alkoxy, phenyl, pyridinyl, benzyl, benzoyl, pyrimidinyl, phenylaminocarbonyl, alkylsulfonyl, phenylsulfonyl, and naphthyl groups are optionally mono- or independently di- or independently trisubstituted with $R^{12}$; where the phenoxy group is optionally mono- or independently disubstituted with $(C_{1-4})$alkyl, $(C_{1-4})$alkoxy, or halogen; and where the [3.3.3] bicyclic carbocyclic moiety is optionally mono-or independently plurisubstituted with $(C_{1-8})$alkyl; p is 0 to 3; and $R^{12}$ is halogen; trifluoromethyl; cyano; nitro; $(C_{1-6})$alkyl; $(C_{1-6})$alkoxy; cycloalkyl; carboxy; acetamido; hydroxy; hydroxy$(C_{1-6})$alkyl; hydroxymethyl; trifluoromethoxy; sulfamoyl; carbamoyl; sulfonamido; alkylsufonyl; phenylsulfonyl; aryl; heteroaryl; where the aryl and heteroaryl groups are optionally mono- or independently plurisubstituted with $R^7$; and p is 0 to 3. In some embodiments of compounds of formula III, X is $CH_2$; the ring containing X is saturated; $R^1$, $R^2$, $R^{24}$ are hydrogen; and $R^{26}$ is $(R^{13})_2CH(CH_2)_q$—; where $R^{13}$ is phenyl, in which the phenyl groups are independently optionally mono- or independently disubstituted with $R^{12}$; and q is 0 to 3.

Compounds of formula III include those wherein X is $CH_2$; the ring containing X is saturated; $R^1$, $R^2$, $R^{24}$ are hydrogen; and $R^{26}$ is a group of the formula:

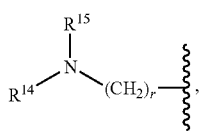

where $R^{14}$ and $R^{15}$ are independently hydrogen; $(C_{1-8})$alkyl; $(C_{1-6})$alkylcarbonyl; $(C_{3-12})$cycloalkyl ring; $(C_{3-12})$cycloalkenyl ring; benzyl; benzoyl; pyridine; pyrimidine; phenyl; phenylamino-carbonyl; alkylsulfonyl; or phenylsulfonyl; where the cycloalkyl ring is optionally substituted with hydroxy$(C_{1-6})$alkyl, and where the benzyl, benzoyl, pyridine, pyrimidine, phenyl, phenylaminocarbonyl, alkylsulfonyl, and phenylsulfonyl groups are optionally mono- or independently di-substituted with $R^{12}$; or $R^{14}$ and $R^{15}$ together form a $(C_{3-12})$cycloalkyl ring; and r is 0 or 2 to 6.

Compounds of formula III also include those wherein X is $CH_2$; the ring containing X is saturated; $R^1$, $R^2$, $R^{24}$ are hydrogen; and $R^{26}$ is a group of the formula:

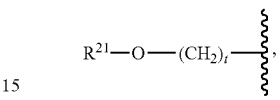

where $R^{21}$ is hydrogen; $(C_{1-8})$alkyl; benzyl; or phenyl; in which the benzyl and phenyl groups are optionally mono- or independently di-substituted on the ring with $R^{12}$; and t is 0 or 2 to 6.

In some embodiments of compounds of formula I, $CR^iR^{ii}$ is present. In other embodiments of compounds of formula I where $CR^iR^{ii}$ is present, the compound has formula IVA or IVB:

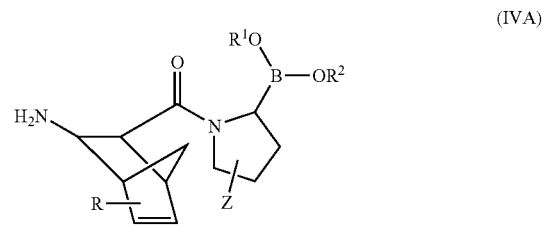

(IVA)

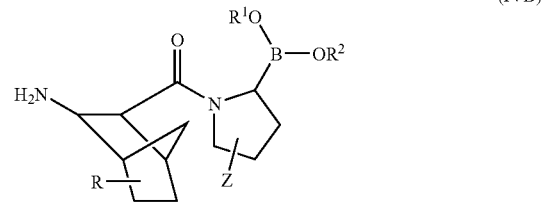

(IVB)

wherein
R is
a) hydrogen;
b) $(C_{1-12})$alkyl; $(C_{2-12})$alkenyl; $(C_{2-12})$alkynyl; $(C_{3-12})$cycloalkyl; or $(C_{3-12})$cycloalkenyl; where the alkyl, alkenyl, alkynyl, cycloalkyl and cycloalkenyl groups are optionally mono- or independently plurisubstituted with $R^{12}$, and where the alkyl, alkenyl, alkynyl portions include linear or branched chains and may include cyclic portions;
c) aryl; or heteroaryl; where the aryl and heteroaryl groups are optionally mono- or independently plurisubstituted with $R^{12}$;
d) $R^{11}(CH_2)_p$— where $R^{11}$ is 2-oxopyrrolidinyl; $(C_{1-6})$alkoxy; phenyl; phenoxy; $(C_{1-8})$cycloalkyl; [3.3.3] bicyclic carbocyclic moiety; pyridinyl; naphthyl; cyclohexenyl; or adamantyl; where the 2-oxopyrrolidinyl, $(C_{1-6})$alkoxy, phenyl, pyridinyl, and naphthyl groups are optionally mono- or independently di- or independently trisubstituted with $R^{12}$; where the phenoxy group is optionally mono- or independently disubstituted with $(C_{1-4})$alkyl, $(C_{1-4})$alkoxy, or halogen; and where the [3.3.3] bicyclic carbocyclic moiety is optionally mono-or independently plurisubstituted with $(C_{1-8})$alkyl; p is 0 to 3; and $R^{12}$ is halogen; trifluoromethyl; cyano; nitro; $(C_{1-6})$alkyl; $(C_{1-6})$alkoxy; cycloalkyl; carboxy; acetamido; hydroxy; hydroxy$(C_{1-6})$alkyl; hydroxymethyl; trifluoromethoxy; sulfamoyl; carbamoyl; sulfonamido; alkylsufonyl; phenylsulfonyl; aryl; heteroaryl; where the aryl and heteroaryl groups are optionally mono- or independently plurisubstituted with $R^7$;

e) $(R^{13})_2CH(CH_2)_q-$, where $R^{13}$ is phenyl; in which the phenyl groups are independently optionally mono- or independently disubstituted with $R^{12}$; and q is 0 to 3;

f) a group of the formula:

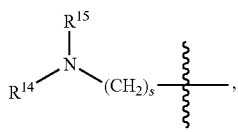

where $R^{14}$ and $R^{15}$ are independently hydrogen; $(C_{1-8})$alkyl; $(C_{1-6})$alkylcarbonyl; $(C_{3-12})$cycloalkyl ring; $(C_{3-12})$cycloalkenyl ring; benzyl; benzoyl; pyridine; pyrimidine; phenyl; phenylamino-carbonyl; alkylsulfonyl; or phenylsulfonyl; where the cycloalkyl ring is optionally substituted with hydroxy$(C_{1-6})$alkyl, and where the benzyl, benzoyl, pyridine, pyrimidine, phenyl, phenylaminocarbonyl, alkylsulfonyl, and phenylsulfonyl groups are optionally mono- or independently di-substituted with $R^{12}$; or $R^{14}$ and $R^{15}$ together form a $(C_{3-12})$cycloalkyl ring; and s is 0 to 6; or g) a group of the formula:

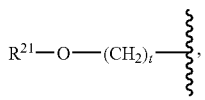

where $R^{21}$ is hydrogen; $(C_{1-8})$alkyl; benzyl; or phenyl; in which the benzyl and phenyl groups are optionally mono- or independently di-substituted on the ring with $R^{12}$; and t is 0 to 6;

It has further been discovered that certain boronic acid compounds of the invention can exist as either linear or cyclic isomers. Typically, such compounds form an equilibrium mixture in aqueous solution. As shown in FIG. 1, the concentration of the two isomers of such compounds is typically pH dependent. Thus, it is expected that such inventive compounds will exist as a mixture of linear and cyclic isomers in vivo. Moreover, the cyclic forms of inventive compounds may serve as novel, orally available prodrugs. Hence, in this aspect of the invention, there are provided compounds that have the formula VA, VB, or a mixture thereof:

VA

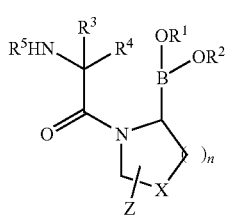

-continued

VB

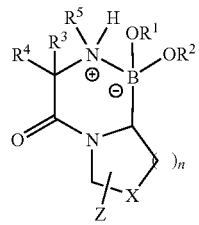

including all enantiomers, diastereoisomers, solvates, hydrates and pharmaceutically acceptable salts thereof, wherein:

n is 1 to 3;

X is $CH_2$; S; O; $CF_2$ or $C(CH_3)_2$;

Z is H; halogen; hydroxyl; $(C_{1-6})$alkoxy; $(C_{1-12})$alkyl; $(C_{3-12})$cycloalkyl; phenyl; or heteroaryl; where the phenyl and heteroaryl groups are optionally mono- or independently plurisubstituted with $R^7$;

optionally, X together with an adjacent ring carbon and Z form a fused cyclopropyl; and optionally, one of the bonds in the ring containing X is a double bond;

$R^1$ and $R^2$ independently or together are hydrogen; a boronic acid protecting group; or a group capable of being hydrolyzed to a hydroxyl group in an aqueous solution at physiological pH or in biological fluids;

$R^3$, $R^4$ and $R^5$ are selected from (dd) or (ee):

(dd) $R^3$ and $R^4$ are hydrogen; and
  $R^5$ is
    a) hydrogen, provided that $R^5$ is not hydrogen when n is 1, X is $CH_2$, and Z is H;
    b) $(C_{1-12})$alkyl; $(C_{2-12})$alkenyl; $(C_{2-12})$alkynyl; $(C_{3-12})$ cycloalkyl; or $(C_{3-12})$cycloalkenyl; where the alkyl, alkenyl, alkynyl, cycloalkyl and cycloalkenyl groups are optionally mono- or independently plurisubstituted with $R^6$, and where the alkyl, alkenyl, alkynyl portions include linear or branched chains and may include cyclic portions;
  $R^6$ is $(C_{1-6})$alkyl; $(C_{1-6})$alkoxy; cycloalkyl; carboxy; acetamido; cyano; nitro; halogen; hydroxy; hydroxy$(C_{1-6})$alkyl; hydroxymethyl; trifluoromethyl; trifluoromethoxy; sulfamoyl; sulfonamido; carbamoyl; aryl; heteroaryl; where the aryl and heteroaryl groups are optionally mono- or independently plurisubstituted with $R^7$; amino, where the amino group is optionally mono- or independently plurisubstituted with $R^8$; —$SOR^8$; —$SO_2R^8$; —$COR^8$; —$CO_2R^8$, —$CONHR^8$; —$CON(R^8)_2$; —$OR^8$; or —S—$R^8$;
  $R^7$ is halogen; $(C_{1-10})$alkyl; $(C_{1-10})$alkoxy; $(C_{1-10})$alkylamino; $(C_{1-10})$dialkylamino; benzyl; benzyloxy; hydroxyl$(C_{1-6})$alkyl; hydroxymethyl; nitro; trifluoromethyl; trifluoromethoxy; trifluoromethylthio; N-hydroxyimino; cyano; carboxy; acetamido; hydroxy; sulfamoyl; sulfonamido; or carbamoyl;
  $R^8$ is $(C_{1-10})$alkyl; $(C_{2-10})$alkenyl; $(C_{2-10})$alkynyl; $(C_{3-10})$cycloalkyl; $(C_{5-10})$cycloalkenyl; benzyl; phenethyl; aryl; or heteroaryl; where the alkyl, alkenyl, alkynyl, cycloalkyl, cycloalkenyl groups are optionally mono- or independently plurisubstituted with aryl or heteroaryl where the aryl and heteroaryl groups are optionally mono- or independently plurisubstituted with $R^7$; and where the aryl and heteroaryl groups are optionally mono- or independently plurisubstituted with $R^7$;

c) aryl optionally fused to a $(C_{3-10})$cycloalkyl; or heteroaryl optionally fused to a $(C_{3-10})$cycloalkyl; where the aryl and heteroaryl groups are optionally mono- or independently plurisubstituted with $R^7$;

d) indanyl; 1,2,3,4-tetrahydronaphthyl; $(CH_2)_j$adamantyl in which j is 0-3; or a [2.2.1] or [3.1.1] bicyclic carbocyclic moiety, including (4-pentylbicyclo[2.2.2]oct-1-yl)amine; where the indanyl, 1,2,3,4-tetrahydronaphthyl, $(CH_2)_j$ adamantyl, and [2.2.1] or [3.1.1] bicyclic carbocyclic moieties are optionally mono- or independently plurisubstituted with hydroxy, $(C_{1-8})$alkyl, $(C_{1-8})$alkoxy, $(C_{1-8})$alkanoyloxy, or $R^9R^{10}N$—CO—O—, where $R^9$ and $R^{10}$ are independently $(C_{1-8})$alkyl, or phenyl, where the alkyl and phenyl groups are optionally mono- or independently plurisubstituted with $(C_{1-8})$alkyl, $(C_{1-8})$alkoxy, halogen, or trifluoromethyl, or $R^9$ and $R^{10}$ together are $(C_{3-6})$alkylene;

e) $R^{11}(CH_2)_p$— where $R^{11}$ is 2-oxopyrrolidinyl; $(C_{1-6})$alkoxy; phenyl; phenoxy; $(C_{1-8})$cycloalkyl; [3.3.3] bicyclic carbocyclic moiety; pyridinyl; naphthyl; cyclohexenyl; or adamantyl; where the 2-oxopyrrolidinyl, $(C_{1-6})$alkoxy, phenyl, pyridinyl, and naphthyl groups are optionally mono- or independently di- or independently trisubstituted with $R^{12}$; where the phenoxy group is optionally mono- or independently disubstituted with $(C_{1-4})$alkyl, $(C_{1-4})$alkoxy, or halogen; and where the [3.3.3] bicyclic carbocyclic moiety is optionally mono-or independently plurisubstituted with $(C_{1-8})$alkyl; and p is 0 to 3;

$R^{12}$ is halogen; trifluoromethyl; cyano; nitro; $(C_{1-6})$alkyl; $(C_{1-6})$alkoxy; cycloalkyl; carboxy; acetamido; hydroxy; hydroxy$(C_{1-6})$alkyl; hydroxymethyl; trifluoromethoxy; sulfamoyl; carbamoyl; sulfonamido; alkylsufonyl; phenylsulfonyl; aryl; heteroaryl; where the aryl and heteroaryl groups are optionally mono- or independently plurisubstituted with $R^7$;

f) $(R^{13})_2CH(CH_2)_q$—, where $R^{13}$ is phenyl; in which the phenyl groups are independently optionally mono- or independently disubstituted with $R^{12}$; and q is 0 to 3;

g) a group of the formula:

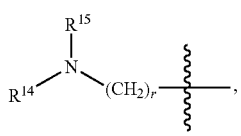

where $R^{14}$ and $R^{15}$ are independently hydrogen; $(C_{1-8})$alkyl; $(C_{1-6})$alkylcarbonyl; $(C_{3-12})$cycloalkyl ring; $(C_{3-12})$cycloalkenyl ring; benzyl; benzoyl; pyridine; pyrimidine; phenyl; phenylamino-carbonyl; alkylsulfonyl; or phenylsulfonyl; where the cycloalkyl ring is optionally substituted with hydroxy$(C_{1-6})$alkyl, and where the benzyl, benzoyl, pyridine, pyrimidine, phenyl, phenylaminocarbonyl, alkylsulfonyl, and phenylsulfonyl groups are optionally mono- or independently di-substituted with $R^{12}$; or $R^{14}$ and $R^{15}$ together form a $(C_{3-12})$cycloalkyl ring; and r is 2 to 6;

h) a group of the formula:

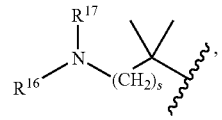

where $R^{16}$ and $R^{17}$ are each independently hydrogen; $(C_{1-8})$alkyl; $(C_{1-6})$alkylcarbonyl; di-$(C_{1-6})$alkylaminocarbonyl; benzyl; benzoyl; pyridine; pyrimidine; phenyl; phenylaminocarbonyl; alkylsulfonyl; or phenylsulfonyl; where the benzyl, benzoyl, pyridine, pyrimidine, phenyl, phenylaminocarbonyl, alkylsulfonyl, and phenylsulfonyl groups are optionally mono- or independently di-substituted with $R^{12}$; or $R^{16}$ and $R^{17}$ together form a $(C_{3-12})$cycloalkyl ring; and s is 1 to 6;

i) a group of the formula:

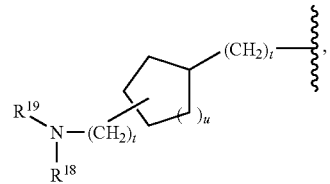

where $R^{18}$ and $R^{19}$ are independently hydrogen; $(C_{1-8})$alkyl; $(C_{1-6})$alkylcarbonyl; di-$(C_{1-6})$alkylaminocarbonyl; benzyl; benzothiazole; benzoyl; pyridine; pyrimidine; phenyl; phenylaminocarbonyl; alkylsulfonyl; or phenylsulfonyl; where the benzyl, benzoyl, benzothiazole, pyridine, pyrimidine, phenyl, phenylaminocarbonyl, alkylsulfonyl, and phenylsulfonyl groups are optionally mono- or independently di-substituted with $R^{12}$; or $R^{18}$ and $R^{19}$ together form a $(C_{3-12})$cycloalkyl ring; each t is independently 0 to 6; and u is 0 to 3;

j) a group of the formula:

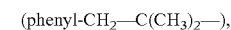

(phenyl-$CH_2$—C($CH_3$)$_2$—), where the phenyl group is optionally mono- or independently plurisubstituted with $R^{12}$;

k) a group of the formula:

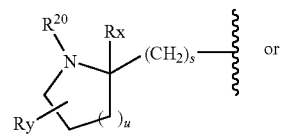

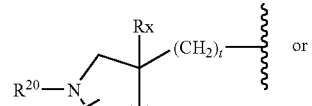

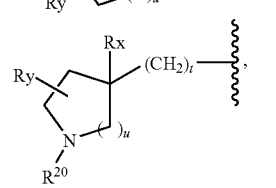

where $R^{20}$ is hydrogen; $(C_{1-8})$alkyl; $(C_{1-6})$alkylcarbonyl; di-$(C_{1-6})$alkylaminocarbonyl; $(C_{3-8})$cycloalkylcarbonyl; benzyl; benzoyl; $(C_{1-6})$alkyloxycarbonyl; arlkyloxycarbonyl, pyridine; pyrimidine; phenyl; phenyl substituted thiazole ring; phenylaminocarbonyl; alkylsulfonyl; or phenylsulfonyl; where the benzyl, benzoyl, pyridine, pyrimidine, phenyl, phenylaminocarbonyl, alkylsulfonyl, and phenylsulfonyl groups are optionally mono- or independently di-substituted with $R^{12}$; $R_x$ is hydrogen; $(C_{1-8})$alkyl; $(C_{3-12})$cycloalkyl; benzyl; phenyl; where the benzyl and phenyl, groups are optionally mono- or independently di-substituted on the ring with $R^{12}$; $R_y$ is absent or is halogen, $(C_{1-8})$alkyl, $(C_{1-8})$alkoxy, O-alkylcarboxylate, O-aralkylcarboxylate, N-alkylcarboxamido, N-aralkylcarboxamido; or phenyl;

s is 1 to 6; t is 0 to 6; and u is 0 to 3; or l) a group of the formula:

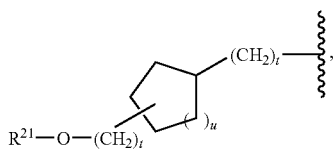

where $R^{21}$ is hydrogen; $(C_{1-8})$alkyl; benzyl; or phenyl; in which the benzyl and phenyl groups are optionally mono- or independently di-substituted on the ring with $R^{12}$; each t is independently 0 to 6; and u is 0 to 3; or (ee) $R^3$, $R^4$ and $R^5$ are independently hydrogen; alkyl; alkenyl; alkynyl; cycloalkyl; cycloalkylalkyl; bicycloalkyl; tricycloalkyl; alkylcycloalkyl; hydroxyalkyl; hydroxyalkylcycloalkyl; hydroxycycloalkyl; hydroxybicycloalkyl; hydroxytricycloalkyl; bicycloalkylalkyl; alkylbicycloalkyl; alkylthioalkyl; arylalkylthioalkyl; cycloalkenyl; aryl, aralkyl; heteroaryl; heteroarylalkyl; cycloheteroalkyl or cycloheteroalkylalkyl; all optionally mono- or independently plurisubstituted with halogen, alkyl, polyhaloalkyl, alkoxy, haloalkoxy, polyhaloalkoxy, alkoxycarbonyl, alkenyl, alkynyl, cycloalkyl, cycloalkylalkyl, polycycloalkyl, heteroarylamino, arylamino, cycloheteroalkyl, cycloheteroalkylalkyl, hydroxy, hydroxyalkyl, nitro, cyano, amino, substituted amino, alkylamino, dialkylamino, thiol, alkylthio, alkylcarbonyl, acyl, alkoxycarbonyl, aminocarbonyl, alkynylaminocarbonyl, alkylaminocarbonyl, alkenylaminocarbonyl, alkylcarbonyloxy, alkylcarbonylamino, arylcarbonylamino, alkylsulfonylamino, alkylaminocarbonyl-amino, alkoxycarbonylamino, alkylsulfonyl, aminosulfinyl, aminosulfonyl, alkylsulfinyl, sulfonamido or sulfonyl; provided that when n is 1, X is $CH_2$, the ring containing X is saturated, and Z, $R^3$ and $R^5$ are H, $R^4$ is not a side chain of a naturally occurring α-amino acid; and provided that when n is 1, X is $CH_2$, the ring containing X is saturated, and Z and $R^5$ are H, $R^3$ and $R^4$ are not both methyl; and wherein the bond containing the wavy line signifies the point of attachment.

In some embodiments of compounds of formula VA and VB, $R^1$ and $R^2$ independently or together are the boronic acid protecting group formed from (+)-pinanediol; pinacol; 1,2-dicyclohexyl-ethanediol; 1,2-ethanediol; 2,2-diethanolamine; 1,3-propanediol; 2,3-butanediol, diisopropyl tartrate; 1,4-butanediol; diisopropylethanediol; (S,S,)-5,6-decanediol; 1,1,2-triphenyl-1,2-ethanediol; (2R,3R)-1,4-dimethyoxy-1,1,4,4-tetraphenyl-2,3-butanediol; methanol; ethanol; isopropanol; catechol; or 1-butanol. In other embodiments, $R^1$ and $R^2$ independently or together are a group capable of being hydrolyzed to a hydroxyl group in an aqueous solution at physiological pH or in biological fluids formed from 1,2-dicyclohexylethanediol; 1,2-ethanediol; 1,3-propanediol; 2,3-butanediol, 1,4-butanediol; diisopropylethanediol; methanol; ethanol; isopropanol; or 1-butanol.

In some embodiments of compounds of formula VA or VB, $R^3$ and $R^4$ are independently hydrogen, alkyl; alkenyl; alkynyl; cycloalkyl; cycloalkylalkyl; bicycloalkyl; tricycloalkyl; alkylcycloalkyl; hydroxyalkyl; hydroxyalkylcycloalkyl; hydroxycycloalkyl; hydroxybicycloalkyl; hydroxytricycloalkyl; bicycloalkylalkyl; alkylbicycloalkyl; alkylthioalkyl; arylalkylthioalkyl; cycloalkenyl; aryl, aralkyl; heteroaryl; heteroarylalkyl; cycloheteroalkyl or cycloheteroalkylalkyl; all optionally mono- or independently plurisubstituted with halogen, alkyl, polyhaloalkyl, alkoxy, haloalkoxy, polyhaloalkoxy, alkoxycarbonyl, alkenyl, alkynyl, cycloalkyl, cycloalkylalkyl, polycycloalkyl, heteroarylamino, arylamino, cycloheteroalkyl, cycloheteroalkylalkyl, hydroxy, hydroxyalkyl, nitro, cyano, amino, substituted amino, alkylamino, dialkylamino, thiol, alkylthio, alkylcarbonyl, acyl, alkoxycarbonyl, aminocarbonyl, alkynylaminocarbonyl, alkylaminocarbonyl, alkenylaminocarbonyl, alkylcarbonyloxy, alkylcarbonylamino, arylcarbonylamino, alkylsulfonylamino, alkylaminocarbonyl-amino, alkoxycarbonylamino, alkylsulfonyl, aminosulfinyl, aminosulfonyl, alkylsulfinyl, sulfonamido or sulfonyl; and $R^5$ is alkyl; alkenyl; alkynyl; cycloalkyl; cycloalkylalkyl; bicycloalkyl; tricycloalkyl; alkylcycloalkyl; hydroxyalkyl; hydroxyalkylcycloalkyl; hydroxycycloalkyl; hydroxybicycloalkyl; hydroxytricycloalkyl; bicycloalkylalkyl; alkylbicycloalkyl; alkylthioalkyl; arylalkylthioalkyl; cycloalkenyl; aryl, aralkyl; heteroaryl; heteroarylalkyl; cycloheteroalkyl or cycloheteroalkylalkyl; all optionally mono- or independently plurisubstituted with halogen, alkyl, polyhaloalkyl, alkoxy, haloalkoxy, polyhaloalkoxy, alkoxycarbonyl, alkenyl, alkynyl, cycloalkyl, cycloalkylalkyl, polycycloalkyl, heteroarylamino, arylamino, cycloheteroalkyl, cycloheteroalkylalkyl, hydroxy, hydroxyalkyl, nitro, cyano, amino, substituted amino, alkylamino, dialkylamino, thiol, alkylthio, alkylcarbonyl, acyl, alkoxycarbonyl, aminocarbonyl, alkynylamino-carbonyl, alkylaminocarbonyl, alkenylaminocarbonyl, alkylcarbonyloxy, alkylcarbonylamino, arylcarbonylamino, alkylsulfonylamino, alkylaminocarbonyl-amino, alkoxycarbonylamino, alkylsulfonyl, aminosulfinyl, aminosulfonyl, alkylsulfinyl, sulfonamido or sulfonyl.

In still other embodiments of compounds of formula VA or VB, X is $CH_2$; the ring containing X is saturated; $R^1$, $R^2$, $R^3$ and $R^4$ are hydrogen; and $R^5$ is $(C_{1-12})$alkyl; $(C_{2-12})$alkenyl; $(C_{2-12})$alkynyl; $(C_{3-12})$cycloalkyl; or $(C_{3-12})$cycloalkenyl; where the alkyl, alkenyl, alkynyl, cycloalkyl and cycloalkenyl groups are optionally mono- or independently plurisubstituted with $R^6$, and where the alkyl, alkenyl, alkynyl portions include linear or branched chains and may include cyclic portions. In some such embodiments, $R^5$ is $(C_{3-12})$ cycloalkyl such as cyclopentyl.

In some embodiments of compounds of formula VA or VB, X is $CH_2$; the ring containing X is saturated; $R^1$, $R^2$, $R^3$ and $R^4$ are hydrogen; and $R^5$ is indanyl; 1,2,3,4-tetrahydronaphthyl; $(CH_2)_j$ adamantyl in which j is 0-3; or a [2.2.1] or [3.1.1] bicyclic carbocyclic moiety, including (4-pentylbicyclo[2.2.2]-oct-1-yl)amine; where the indanyl, 1,2,3,4-tetrahydronaphthyl, $(CH_2)_j$ adamantyl, and [2.2.1] or [3.1.1] bicyclic carbocyclic moieties are optionally mono- or independently plurisubstituted with hydroxy, $(C_{1-8})$alkyl, $(C_{1-8})$alkoxy, $(C_{1-8})$alkanoyloxy, or $R^9R^{10}N$—CO—O—, where $R^9$ and $R^{10}$ are independently $(C_{1-8})$alkyl, or phenyl, where the alkyl and phenyl groups are optionally mono- or independently plurisubstituted with $(C_{1-8})$alkyl, $(C_{1-8})$alkoxy, halogen, or trifluoromethyl, or $R^9$ and $R^{10}$ together are $(C_{3-6})$alkylene.

Compounds of formula VA or VB include those wherein X is $CH_2$; the ring containing X is saturated; $R^1$, $R^2$, $R^3$ and $R^4$ are hydrogen; and $R^5$ is $R^{11}(CH_2)_p$— where $R^{11}$ is 2-oxopyrrolidinyl; $(C_{1-6})$alkoxy; phenyl; phenoxy; $(C_{1-8})$cycloalkyl; [3.3.3] bicyclic carbocyclic moiety; pyridinyl; naphthyl; cyclohexenyl; or adamantyl; where the 2-oxopyrrolidinyl, $(C_{1-6})$alkoxy, phenyl, pyridinyl, and naphthyl groups are optionally mono- or independently di- or independently trisubstituted with $R^{12}$; where the phenoxy group is optionally mono- or independently disubstituted with $(C_{1-4})$alkyl, $(C_{1-4})$alkoxy, or halogen; and where the [3.3.3] bicyclic carbocyclic moiety is optionally mono-or independently plurisubstituted with $(C_{1-8})$alkyl; p is 0 to 3; and $R^{12}$ is halogen; trifluoromethyl; cyano; nitro; $(C_{1-6})$alkyl; $(C_{1-6})$alkoxy; cycloalkyl; carboxy; acetamido; hydroxy; hydroxy$(C_{1-6})$alkyl; hydroxymethyl; trifluoromethoxy; sulfamoyl; carbamoyl; sulfonamido; alkylsufonyl; phenylsulfonyl; aryl; heteroaryl; where the aryl and heteroaryl groups are optionally mono- or independently plurisubstituted with $R^7$.

Compounds of VA or VB further include those wherein X is $CH_2$; the ring containing X is saturated; $R^1$, $R^2$, $R^3$ and $R^4$ are hydrogen; and $R^5$ is $(R^{13})_2CH(CH_2)_q$—, where $R^{13}$ is phenyl; in which the phenyl groups are independently optionally mono- or independently disubstituted with $R^{12}$; and q is 0 to 3.

In some embodiments of compounds of formula VA or VB, X is $CH_2$; the ring containing X is saturated; $R^1$, $R^2$, $R^3$ and $R^4$ are hydrogen; and $R^5$ is a group of the formula:

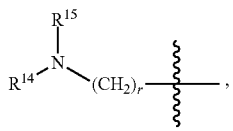

where $R^{14}$ and $R^{15}$ are independently hydrogen; $(C_{1-8})$alkyl; $(C_{1-6})$alkylcarbonyl; $(C_{3-12})$cycloalkyl ring; $(C_{3-12})$cycloalkenyl ring; benzyl; benzoyl; pyridine; pyrimidine; phenyl; phenylamino-carbonyl; alkylsulfonyl; or phenylsulfonyl; where the cycloalkyl ring is optionally substituted with hydroxy$(C_{1-6})$alkyl, and where the benzyl, benzoyl, pyridine, pyrimidine, phenyl, phenylaminocarbonyl, alkylsulfonyl, and phenylsulfonyl groups are optionally mono- or independently di-substituted with $R^{12}$; or $R^{14}$ and $R^{15}$ together form a $(C_{3-12})$cycloalkyl ring; and r is 2 to 6.

In other embodiments of compounds of formula VA or VB, X is $CH_2$; the ring containing X is saturated; $R^1$, $R^2$, $R^3$ and $R^4$ are hydrogen; and $R^5$ is a group of the formula:

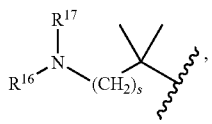

where $R^{16}$ and $R^{17}$ are each independently hydrogen; $(C_{1-8})$alkyl; $(C_{1-6})$alkylcarbonyl; di-$(C_{1-6})$alkylaminocarbonyl; benzyl; benzoyl; pyridine; pyrimidine; phenyl; phenylaminocarbonyl; alkylsulfonyl; or phenylsulfonyl; where the benzyl, benzoyl, pyridine, pyrimidine, phenyl, phenylaminocarbonyl, alkylsulfonyl, and phenylsulfonyl groups are optionally mono- or independently di-substituted with $R^{12}$; or $R^{16}$ and $R^{17}$ together form a $(C_{3-12})$cycloalkyl ring; and s is 1 to 6.

In certain embodiments of compounds of formula VA or VB, X is $CH_2$; the ring containing X is saturated; $R^1$, $R^2$, $R^3$ and $R^4$ are hydrogen; and $R^5$ is a group of the formula:

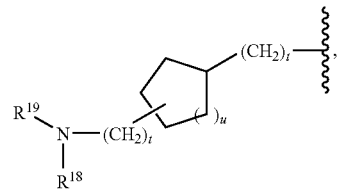

where $R^{18}$ and $R^{19}$ are independently hydrogen; $(C_{1-8})$alkyl; $(C_{1-6})$alkylcarbonyl; di-$(C_{1-6})$alkylaminocarbonyl; benzyl; benzothiazole; benzoyl; pyridine; pyrimidine; phenyl; phenylaminocarbonyl; alkylsulfonyl; or phenylsulfonyl; where the benzyl, benzoyl, benzothiazole, pyridine, pyrimidine, phenyl, phenylaminocarbonyl, alkylsulfonyl, and phenylsulfonyl groups are optionally mono- or independently di-substituted with $R^{12}$; or $R^{18}$ and $R^{19}$ together form a $(C_{3-12})$cycloalkyl ring; each t is independently 0 to 6; and u is 0 to 3. In some such embodiments, $R^5$ has formula:

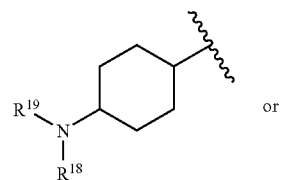

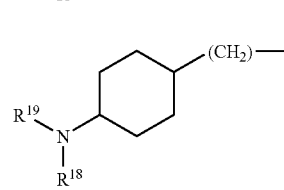

Compounds of formula VA or VB further include those wherein X is $CH_2$; the ring containing X is saturated; $R^1$, $R^2$, $R^3$ and $R^4$ are hydrogen; and $R^5$ is a group of the formula:

(phenyl-$CH_2$—$C(CH_3)_2$—), where the phenyl group is optionally mono- or independently plurisubstituted with $R^{12}$.

In some embodiments of compounds of formula VA or VB, X is $CH_2$; the ring containing X is saturated; $R^1$, $R^2$, $R^3$ and $R^4$ are hydrogen; and $R^5$ is a group of the formula:

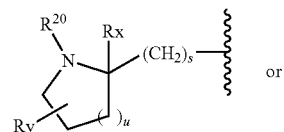

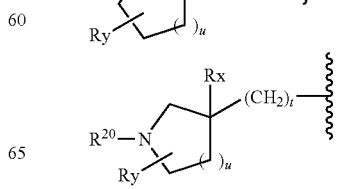

-continued

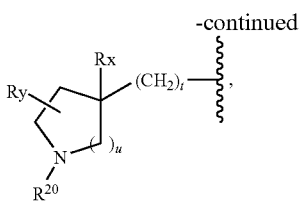

where $R^{20}$ is hydrogen; $(C_{1-8})$alkyl; $(C_{1-6})$alkylcarbonyl; di-$(C_{1-6})$alkylaminocarbonyl; $(C_{3-8})$cycloalkylcarbonyl; benzyl; benzoyl; $(C_{1-6})$alkyloxycarbonyl; arlkyloxycarbonyl; pyridine; pyrimidine; phenyl; phenyl substituted thiazole ring; phenylaminocarbonyl; alkylsulfonyl; or phenylsulfonyl; where the benzyl, benzoyl, pyridine, pyrimidine, phenyl, phenylaminocarbonyl, alkylsulfonyl, and phenylsulfonyl groups are optionally mono- or independently di-substituted with $R^{12}$; $R_x$ is hydrogen; $(C_{1-8})$alkyl; $(C_{3-12})$cycloalkyl; benzyl; phenyl; where the benzyl and phenyl, groups are optionally mono- or independently di-substituted on the ring with $R^{12}$; $R_y$ is absent or is halogen, $(C_{1-8})$alkyl, $(C_{1-8})$alkoxy, O-alkylcarboxylate, O-aralkylcarboxylate, N-alkylcarboxamido, N-aralkylcarboxamido; or phenyl;

s is 1 to 6; t is 0 to 6; and u is 0 to 3; or

In some such embodiments, $R^5$ has formula:

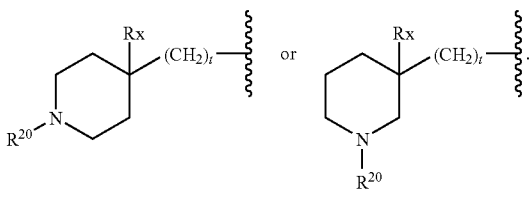

In other embodiments of compounds of formula VA or VB, X is $CH_2$; the ring containing X is saturated; $R^1$, $R^2$, $R^3$ and $R^4$ are hydrogen; and $R^5$ is a group of the formula:

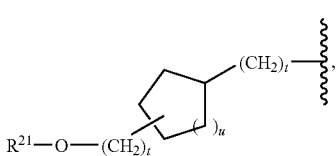

where $R^{21}$ is hydrogen; $(C_{1-8})$alkyl; benzyl; or phenyl; in which the benzyl and phenyl groups are optionally mono- or independently di-substituted on the ring with $R^{12}$; each t is independently 0 to 6; and u is 0 to 3. In some such embodiments, $R^5$ has formula:

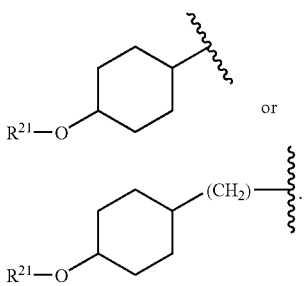

Compounds of formula VA or VB further include those wherein $R^1$ and $R^2$ are hydrogen; n is 1; X together with an adjacent ring carbon and Z form a fused cyclopropyl;

$R^3$, $R^4$ and $R^5$ are independently hydrogen; alkyl; alkenyl; alkynyl; cycloalkyl; cycloalkylalkyl; bicycloalkyl; tricycloalkyl; alkylcycloalkyl; hydroxyalkyl; hydroxyalkylcycloalkyl; hydroxycycloalkyl; hydroxybicycloalkyl; hydroxytricycloalkyl; bicycloalkylalkyl; alkylbicycloalkyl; alkylthioalkyl; arylalkylthioalkyl; cycloalkenyl; aryl, aralkyl; heteroaryl; heteroarylalkyl; cycloheteroalkyl or cycloheteroalkylalkyl; all optionally mono- or independently plurisubstituted with halogen, alkyl, polyhaloalkyl, alkoxy, haloalkoxy, polyhaloalkoxy, alkoxycarbonyl, alkenyl, alkynyl, cycloalkyl, cycloalkylalkyl, polycycloalkyl, heteroarylamino, arylamino, cycloheteroalkyl, cycloheteroalkylalkyl, hydroxy, hydroxyalkyl, nitro, cyano, amino, substituted amino, alkylamino, dialkylamino, thiol, alkylthio, alkylcarbonyl, acyl, alkoxycarbonyl, aminocarbonyl, alkynylaminocarbonyl, alkylaminocarbonyl, alkenylaminocarbonyl, alkylcarbonyloxy, alkylcarbonylamino, arylcarbonylamino, alkylsulfonylamino, alkylaminocarbonyl-amino, alkoxycarbonylamino, alkylsulfonyl, aminosulfinyl, aminosulfonyl, alkylsulfinyl, sulfonamido or sulfonyl.

In certain embodiments of compounds of formula VA or VB, the compounds have the formula:

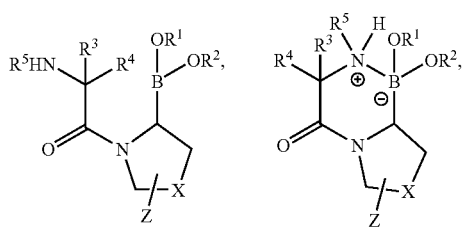

or a mixture thereof.

Compounds of formula VA or VB include those having the formula:

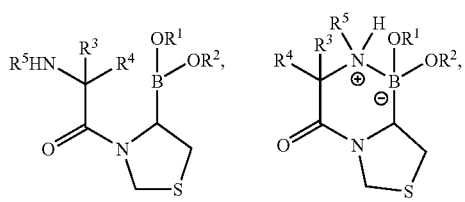

or a mixture thereof.

In other embodiments, compounds of formula VA or VB include those having the formula:

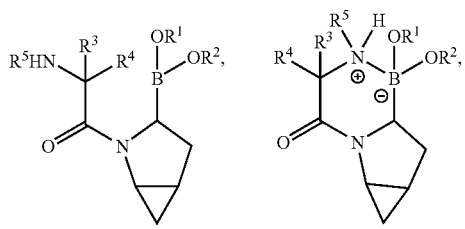

or a mixture thereof; or the formula:

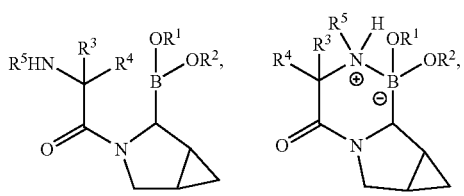

or a mixture thereof.

Compounds of formula VA or VB further include those having the formula:

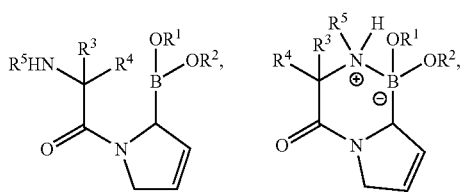

or a mixture thereof.

In still other embodiments, compounds of formula VA or VB have the formula:

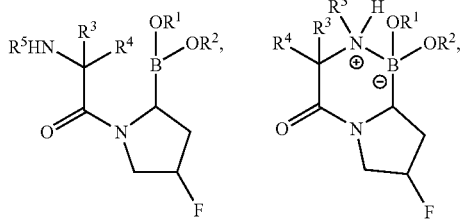

or a mixture thereof.

In yet other embodiments, compounds of formula VA or VB have the formula:

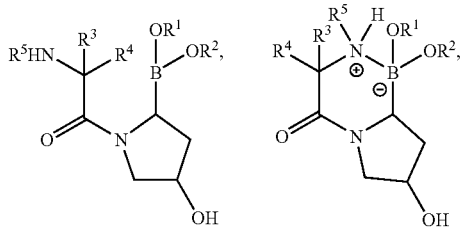

or a mixture thereof.

In still another aspect, the invention provides boronic acid inhibitors of dipeptidyl peptidase-IV having an inhibition constant of 10 micromolar or less for dipeptidyl peptidase-IV. Such inhibitors comprises a boroproline (including boropyrrolidines, boropiperidines, and boroazepanes) attached to an amino acid through an amide bond. The amino acid can be a beta-amino acid (including cyclic forms such as , an N-cycloalkyl-alpha-amino acid, an N-heterocyclyl-alpha amino acid, a cyclic alpha-amino acid having at least one substituent on the alpha-amino acid ring or having a ring other than pyrrolidine, or N-substituted glycine. In some embodiments, the boronic acid inhibitor is of Formula I:

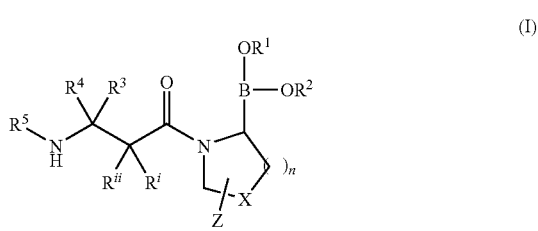

including all enantiomers, diastereoisomers, solvates, hydrates and pharmaceutically acceptable salts thereof, wherein:

n is 1 to 2;

X is $CH_2$; S; O; $CF_2$ or $C(CH_3)_2$;

Z is H; halogen; hydroxyl; $(C_{1-6})$alkoxy; $(C_{1-12})$alkyl; $(C_{3-12})$cycloalkyl; phenyl; or heteroaryl; where the phenyl and heteroaryl groups are optionally mono- or independently plurisubstituted with $R^7$;

optionally, X together with an adjacent ring carbon and Z form a fused cyclopropyl; and optionally, one of the bonds in the ring containing X is a double bond;

$R^1$ and $R^2$ independently or together are hydrogen; a boronic acid protecting group; or a group capable of being hydrolyzed to a hydroxyl group in an aqueous solution at physiological pH or in biological fluids;

$CR^iR^{ii}$ may be present or absent, wherein if $CR^iR^{ii}$ is present, then $R^i$, $R^{ii}$, $R^3$, $R^4$ and $R^5$ are selected from (aa), (bb) or (cc):

(aa) $R^i$, $R^{ii}$, $R^3$ and $R^4$ are hydrogen; and
$R^5$ is
a) hydrogen;
b) $(C_{1-12})$alkyl; $(C_{2-12})$alkenyl; $(C_{2-12})$alkynyl; $(C_{3-12})$cycloalkyl; or $(C_{3-12})$cycloalkenyl; where the alkyl, alkenyl, alkynyl, cycloalkyl and cycloalkenyl groups are optionally mono- or independently plurisubstituted with $R^6$, and where the alkyl, alkenyl, alkynyl portions include linear or branched chains and may include cyclic portions;

$R^6$ is $(C_{1-6})$alkyl; $(C_{1-6})$alkoxy; cycloalkyl; carboxy; acetamido; cyano; nitro; halogen; hydroxy; hydroxy$(C_{1-6})$alkyl; hydroxymethyl; trifluoromethyl; trifluoromethoxy; sulfamoyl; sulfonamido; carbamoyl; aryl; heteroaryl; where the aryl and heteroaryl groups are optionally mono- or independently plurisubstituted with $R^7$; amino, where the amino group is optionally mono- or independently plurisubstituted with $R^8$; $—SOR^B$; $—SO_2R^8$; $—COR^8$; $—CO_2R^8$, $—CONHR^8$; $—CON(R^8)_2$; $—OR^8$; or $—S—R^8$;

$R^7$ is halogen; $(C_{1-10})$alkyl; $(C_{1-10})$alkoxy; $(C_{1-10})$alkylamino; $(C_{1-10})$dialkylamino; benzyl; benzyloxy; hydroxyl$(C_{1-6})$alkyl; hydroxymethyl; nitro; trifluoromethyl; trifluoromethoxy; trifluoromethylthio; N-hydroxyimino; cyano; carboxy; acetamido; hydroxy; sulfamoyl; sulfonamido; or carbamoyl;

$R^8$ is $(C_{1-10})$alkyl; $(C_{2-10})$alkenyl; $(C_{2-10})$alkynyl; $(C_{3-10})$cycloalkyl; $(C_{5-10})$cycloalkenyl; benzyl; phenethyl; aryl; or heteroaryl; where the alkyl, alkenyl, alkynyl, cycloalkyl, cycloalkenyl groups are optionally mono- or independently plurisubstituted with aryl or heteroaryl where the aryl and heteroaryl groups are optionally mono- or independently plurisubstituted with $R^7$; and where the aryl and heteroaryl groups are optionally mono- or independently plurisubstituted with $R^7$;

c) aryl optionally fused to a $(C_{3-10})$cycloalkyl; or heteroaryl optionally fused to a $(C_{3-10})$cycloalkyl; where the aryl and heteroaryl groups are optionally mono- or independently plurisubstituted with $R^7$;

d) indanyl; 1,2,3,4-tetrahydronaphthyl; $(CH_2)_j$adamantyl in which j is 0-3; or a [2.2.1] or [3.1.1] bicyclic carbocyclic moiety, including (4-pentylbicyclo[2.2.2]oct-1-yl)amine; where the indanyl, 1,2,3,4-tetrahydronaphthyl, $(CH_2)_j$ adamantyl, and [2.2.1] or [3.1.1] bicyclic carbocyclic moieties are optionally mono- or independently plurisubstituted with hydroxy, $(C_{1-8})$alkoxy, $(C_{1-8})$alkanoyloxy, or $R^9R^{10}N$—CO—O—, where $R^9$ and $R^{10}$ are independently $(C_{1-8})$alkyl, or phenyl, where the alkyl and phenyl groups are optionally mono- or independently plurisubstituted with $(C_{1-8})$alkyl, $(C_{1-8})$alkoxy, halogen, or trifluoromethyl, or $R^9$ and $R^{10}$ together are $(C_{3-6})$alkylene;

e) $R^{11}(CH2)_p$— where $R^{11}$ is 2-oxopyrrolidinyl; $(C_{1-6})$alkoxy; phenyl; phenoxy; $(C_{1-8})$cycloalkyl; [3.3.3] bicyclic carbocyclic moiety; pyridinyl; naphthyl; cyclohexenyl; or adamantyl; where the 2-oxopyrrolidinyl, $(C_{1-6})$alkoxy, phenyl, pyridinyl, and naphthyl groups are optionally mono- or independently di- or independently trisubstituted with $R^{12}$; where the phenoxy group is optionally mono- or independently disubstituted with $(C_{1-4})$alkyl, $(C_{1-4}$alkoxy, or halogen; and where the [3.3.3] bicyclic carbocyclic moiety is optionally mono-or independently plurisubstituted with $(C_{1-8})$alkyl; and p is 0 to 3;

$R^{12}$ is halogen; trifluoromethyl; cyano; nitro; $(C_{1-6})$ alkyl; $(C_{1-6})$alkoxy; cycloalkyl; carboxy; acetamido; hydroxy; hydroxy$(C_{1-6})$alkyl; hydroxymethyl; trifluoromethoxy; sulfamoyl; carbamoyl; sulfonamido; alkylsufonyl; phenylsulfonyl; aryl; heteroaryl; where the aryl and heteroaryl groups are optionally mono- or independently plurisubstituted with $R^7$;

f) $(R^{13})_2CH(CH_2)_q$—, where $R^{13}$ is phenyl; in which the phenyl groups are independently optionally mono- or independently disubstituted with $R^{12}$; and q is 0 to 3;

g) a group of the formula:

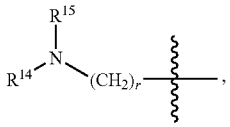

where $R^{14}$ and $R^{15}$ are independently hydrogen; $(C_{1-8})$alkyl; $(C_{1-6})$alkylcarbonyl; $(C_{3-12})$cycloalkyl ring; $(C_{3-12})$cycloalkenyl ring; benzyl; benzoyl; pyridine; pyrimidine; phenyl; phenylamino-carbonyl; alkylsulfonyl; or phenylsulfonyl; where the cycloalkyl ring is optionally substituted with hydroxy$(C_{1-6})$alkyl, and where the benzyl, benzoyl, pyridine, pyrimidine, phenyl, phenylaminocarbonyl, alkylsulfonyl, and phenylsulfonyl groups are optionally mono- or independently di-substituted with $R^{12}$; or $R^{14}$ and $R^{15}$ together form a $(C_{3-12})$cycloalkyl ring; and r is 2 to 6;

h) a group of the formula:

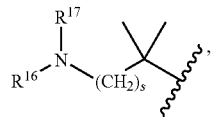

where $R^{16}$ and $R^{17}$ are each independently hydrogen; $(C_{1-8})$ alkyl; $(C_{1-6})$alkylcarbonyl; di-$(C_{1-6})$alkylaminocarbonyl; benzyl; benzoyl; pyridine; pyrimidine; phenyl; phenylaminocarbonyl; alkylsulfonyl; or phenylsulfonyl; where the benzyl, benzoyl, pyridine, pyrimidine, phenyl, phenylaminocarbonyl, alkylsulfonyl, and phenylsulfonyl groups are optionally mono- or independently di-substituted with $R^{12}$; or $R^{16}$ and $R^{17}$ together form a $(C_{3-12})$cycloalkyl ring; and s is 1 to 6;

i) a group of the formula:

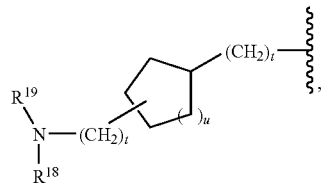

where $R^{18}$ and $R^{19}$ are independently hydrogen; $(C_{1-8})$alkyl; $(C_{1-6})$alkylcarbonyl; di-$(C_{1-6})$alkylaminocarbonyl; benzyl; benzothiazole; benzoyl; pyridine; pyrimidine; phenyl; phenylaminocarbonyl; alkylsulfonyl; or phenylsulfonyl; where the benzyl, benzoyl, benzothiazole, pyridine, pyrimidine, phenyl, phenylaminocarbonyl, alkylsulfonyl, and phenylsulfonyl groups are optionally mono- or independently di-substituted with $R^{12}$; or $R^{18}$ and $R^{19}$ together form a $(C_{3-12})$ cycloalkyl ring; each t is independently 0 to 6; and u is 0 to 3;

j) a group of the formula:

(phenyl-$CH_2$-C($CH_3$)$_2$-), where the phenyl group is optionally mono- or independently plurisubstituted with $R^{12}$;

k) a group f:

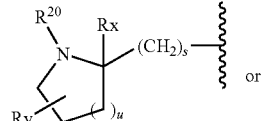

or

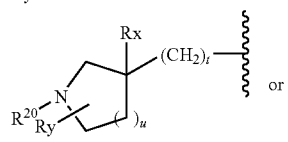

or

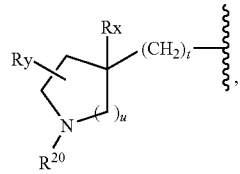

where $R^{20}$ is hydrogen; $(C_{1-8})$alkyl; $(C_{1-6})$alkylcarbonyl; di-$(C_{1-6})$alkylaminocarbonyl; $(C_{3-8})$cycloalkylcarbonyl; benzyl; benzoyl; $(C_{1-6})$alkyloxycarbonyl; arlkyloxycarbonyl, pyridine; pyrimidine; phenyl; phenyl substituted thiazole ring; phenylaminocarbonyl; alkylsulfonyl; or phenylsulfonyl; where the benzyl, benzoyl, pyridine, pyrimidine, phenyl, phenylaminocarbonyl, alkylsulfonyl, and phenylsulfonyl groups are optionally mono- or independently di-substituted with $R^{12}$; $R_x$ is hydrogen; $(C_{1-8})$alkyl; $(C_{3-12})$cycloalkyl; benzyl; phenyl; where the benzyl and phenyl, groups are optionally mono- or independently di-substituted on the ring with $R^{12}$; $R_y$ is absent or is halogen, $(C_{1-8})$alkyl, $(C_{1-8})$alkoxy, O-alkylcarboxylate, O-aralkylcarboxylate, N-alkylcarboxamido, N-aralkylcarboxamido; or phenyl;

s is 1 to 6; t is 0 to 6; and u is 0 to 3; or l) a group of the formula:

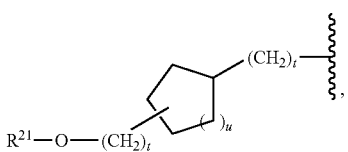

where $R^{21}$ is hydrogen; $(C_{1-8})$alkyl; benzyl; or phenyl; in which the benzyl and phenyl groups are optionally mono- or independently di-substituted on the ring with $R^{12}$; each t is independently 0 to 6; and u is 0 to 3;

(bb) $R^i$, $R^{ii}$, $R^3$, $R^4$ and $R^5$ are independently hydrogen; alkyl; alkenyl; alkynyl; cycloalkyl; cycloalkylalkyl; bicycloalkyl; tricycloalkyl; alkylcycloalkyl; hydroxyalkyl; hydroxyalkylcycloalkyl; hydroxycycloalkyl; hydroxybicycloalkyl; hydroxytricycloalkyl; bicycloalkylalkyl; alkylbicycloalkyl; alkylthioalkyl; arylalkylthioalkyl; cycloalkenyl; aryl; aralkyl; heteroaryl; heteroarylalkyl; cycloheteroalkyl or cycloheteroalkylalkyl; all optionally mono- or independently plurisubstituted with halogen, alkyl, polyhaloalkyl, alkoxy, haloalkoxy, polyhaloalkoxy, alkoxycarbonyl, alkenyl, alkynyl, cycloalkyl, cycloalkylalkyl, polycycloalkyl, heteroarylamino, arylamino, cycloheteroalkyl, cycloheteroalkylalkyl, hydroxy, hydroxyalkyl, nitro, cyano, amino, substituted amino, alkylamino, dialkylamino, thiol, alkylthio, alkylcarbonyl, acyl, alkoxycarbonyl, aminocarbonyl, alkynylamino-carbonyl, alkylaminocarbonyl, alkenylaminocarbonyl, alkylcarbonyloxy, alkylcarbonylamino, arylcarbonylamino, alkylsulfonylamino, alkylaminocarbonyl-amino, alkoxycarbonylamino, alkylsulfonyl, aminosulfinyl, aminosulfonyl, alkylsulfinyl, sulfonamido or sulfonyl; or $R^i$ together with $R^3$ or $R^4$, or $R^{ii}$ together with $R^3$ or $R^4$, and the atoms to which they are attached form a 4 to 8 membered cyclic, polycyclic or heterocyclic ring system containing 1 to 3 heteroatoms selected from N, O, S, SO or $SO_2$; and includes single rings, fused bicyclic and tricyclic rings, which are optionally mono- or independently plurisubstituted with any of the groups set forth in (aa); or $R^4$ and $R^5$ together form —$(CR^{22}R^{23})_m$— where m is 2 to 6, and $R^{22}$ and $R^{23}$ are independently hydrogen; hydroxyl; alkoxy; alkyl; alkenyl; alkynyl; cycloalkyl; halo; amino; substituted amino; cycloalkylalkyl; cycloalkenyl; aryl; arylalkyl; heteroaryl, heteroarylalkyl; cycloheteroalkyl; cycloheteroalkylalkyl; alkylcarbonylamino; arylcarbonylamino; alkoxycarbonyl-amino; aryloxycarbonyl-amino; alkoxycarbonyl; aryloxycarbonyl; or alkylaminocarbonylamino; or $R^4$ and $R^5$ together with the atoms to which they are attached form a 5 to 7 membered ring containing a total of 2 to 4 heteroatoms selected from N, O, S, SO, or $SO_2$; or $R^4$ and $R^5$ together with the atoms to which they are attached form a 4 to 8 membered cycloheteroalkyl ring wherein the cycloheteroalkyl ring optionally has an aryl, heteroaryl or 3 to 7 membered cycloalkyl ring fused thereto; or (cc) $R^i$ and $R^3$ are hydrogen; and $R^{ii}$ and $R^4$ together form a 4 to 8 membered cyclic, polycyclic or heterocyclic ring system containing 1 to 3 heteroatoms selected from N, O, S, SO and $SO_2$, and includes single rings, fused bicyclic and tricyclic rings, which are optionally mono- or independently plurisubstituted with any of the groups set forth in (aa) or (bb) and $R^5$ is any of the groups in (aa) or (bb); and if $CR^iR^{ii}$ is absent, then $R^3$, $R^4$ and $R^5$ are selected from (dd), (ee) or (ff):

(dd) $R^3$ and $R^4$ are hydrogen; and $R^5$ is a) $(C_{1-12})$alkyl; $(C_{2-12})$alkenyl; $(C_{2-12})$alkynyl; $(C_{3-12})$cycloalkyl; or $(C_{3-12})$cycloalkenyl; where the alkyl, alkenyl, alkynyl, cycloalkyl and cycloalkenyl groups are optionally mono- or independently plurisubstituted with $R^6$, and where the alkyl, alkenyl, alkynyl portions include linear or branched chains and may include cyclic portions;

$R^6$ is $(C_{1-6})$alkyl; $(C_{1-6})$alkoxy; cycloalkyl; carboxy; acetamido; cyano; nitro; halogen; hydroxy; hydroxy$(C_{1-6})$alkyl; hydroxymethyl; trifluoromethyl; trifluoromethoxy; sulfamoyl; sulfonamido; carbamoyl; aryl; heteroaryl; where the aryl and heteroaryl groups are optionally mono- or independently plurisubstituted with $R^7$; amino, where the amino group is optionally mono- or independently plurisubstituted with $R^8$; —$SOR^8$; —$SO_2R^8$; —$COR^S$; —$CO_2R^8$, —$CONHR^8$; —$CON(R^8)_2$; —$OR^8$; or —S—$R^8$;

$R^7$ is halogen; $(C_{1-10})$alkyl; $(C_{1-10})$alkoxy; $(C_{1-10})$alkylamino; $(C_{1-10})$dialkylamino; benzyl; benzyloxy; hydroxyl$(C_{1-6})$alkyl; hydroxymethyl; nitro; trifluoromethyl; trifluoromethoxy; trifluoromethylthio; N-hydroxyimino; cyano; carboxy; acetamido; hydroxy; sulfamoyl; sulfonamido; or carbamoyl;

$R^8$ is $(C_{1-10})$alkyl; $(C_{2-10})$alkenyl; $(C_{2-10})$alkynyl; $(C_{3-10})$cycloalkyl; $(C_{5-10})$cycloalkenyl; benzyl; phenethyl; aryl; or heteroaryl; where the alkyl, alkenyl, alkynyl, cycloalkyl, cycloalkenyl groups are optionally mono- or independently plurisubstituted with aryl or heteroaryl where the aryl and heteroaryl groups are optionally mono- or independently plurisubstituted with $R^7$; and where the aryl and heteroaryl groups are optionally mono- or independently plurisubstituted with $R^7$;

b) aryl optionally fused to a $(C_{3-10})$cycloalkyl; or heteroaryl optionally fused to a $(C_{3-10})$cycloalkyl; where the aryl and heteroaryl groups are optionally mono- or independently plurisubstituted with $R^7$;

c) indanyl; 1,2,3,4-tetrahydronaphthyl; $(CH_2)_j$adamantyl in which j is 0-3; or a [2.2.1] or [3.1.1] bicyclic carbocyclic moiety, including (4-pentylbicyclo[2.2.2]oct-1-yl)amine; where the indanyl, 1,2,3,4-tetrahydronaphthyl, $(CH_2)_j$ adamantyl, and [2.2.1] or [3.1.1] bicyclic carbocyclic moieties are optionally mono- or independently plurisubstituted ith hydroxy, $(C_{1-8})$alkyl, $(C_{1-8})$alkoxy, $(C_{1-8})$alkanoyloxy, or $R^9R^{10}N$—CO—O—, where $R^9$ and $R^{10}$ are independently $(C_{1-8})$alkyl, or phenyl, where the alkyl and phenyl groups are optionally mono- or independently plurisubstituted with $(C_{1-8})$alkyl, $(C_{1-8})$alkoxy, halogen, or trifluoromethyl, or $R^9$ and $R^{10}$ together are $(C_{3-6})$alkylene;

d) $R^{11}(CH_2)_p$— where $R^{11}$ is 2-oxopyrrolidinyl; $(C_{1-6})$alkoxy; phenyl; phenoxy; $(C_{1-8})$cycloalkyl; [3.3.3] bicyclic carbocyclic moiety; pyridinyl; naphthyl; cyclohexenyl; or adamantyl; where the 2-oxopyrrolidinyl, $(C_{1-6})$alkoxy, phenyl, pyridinyl, and naphthyl groups are optionally mono- or independently di- or independently trisubstituted with $R^{12}$; where the phenoxy group is optionally mono- or independently disubstituted with $(C_{1-4})$alkyl, $(C_{1-4})$alkoxy, or halogen; and where the [3.3.3] bicyclic carbocyclic moiety is optionally mono- or independently plurisubstituted with $(C_{1-8})$alkyl; and p is 0 to 3;

$R^{12}$ is halogen; trifluoromethyl; cyano; nitro; $(C_{1-6})$alkyl; $(C_{1-6})$alkoxy; cycloalkyl; carboxy; acetamido; hydroxy; hydroxy$(C_{1-6})$alkyl; hydroxymethyl; trifluoromethoxy; sulfamoyl; carbamoyl; sulfonamido; alkylsufonyl; phenylsulfonyl; aryl; heteroaryl; where the aryl and heteroaryl groups are optionally mono- or independently plurisubstituted with $R^7$;

e) $(R^{13})_2CH(CH_2)_q$—, where $R^{13}$ is phenyl; in which the phenyl groups are independently optionally mono- or independently disubstituted with $R^{12}$; and q is 0 to 3;

f) a group of the formula:

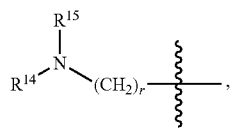

where $R^{14}$ and $R^{15}$ are independently hydrogen; $(C_{1-8})$alkyl; $(C_{1-6})$alkylcarbonyl; $(C_{3-12})$cycloalkyl ring; $(C_{3-12})$cycloalkenyl ring; benzyl; benzoyl; pyridine; pyrimidine; phenyl; phenylamino-carbonyl; alkylsulfonyl; or phenylsulfonyl; where the cycloalkyl ring is optionally substituted with hydroxy$(C_{1-6})$alkyl, and where the benzyl, benzoyl, pyridine, pyrimidine, phenyl, phenylaminocarbonyl, alkylsulfonyl, and phenylsulfonyl groups are optionally mono- or independently di-substituted with $R^{12}$; or $R^{14}$ and $R^{15}$ together form a $(C_{3-12})$cycloalkyl ring; and r is 2 to 6;

g) a group of the formula:

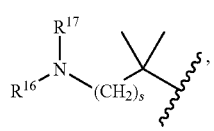

where $R^{16}$ and $R^{17}$ are each independently hydrogen; $(C_{1-8})$alkyl; $(C_{1-6})$alkylcarbonyl; di-$(C_{1-6})$alkylaminocarbonyl; benzyl; benzoyl; pyridine; pyrimidine; phenyl; phenylaminocarbonyl; alkylsulfonyl; or phenylsulfonyl; where the benzyl, benzoyl, pyridine, pyrimidine, phenyl, phenylaminocarbonyl, alkylsulfonyl, and phenylsulfonyl groups are optionally mono- or independently di-substituted with $R^{12}$; or $R^{16}$ and $R^{17}$ together form a $(C_{3-12})$cycloalkyl ring; and s is 1 to 6;

h) a group of the formula:

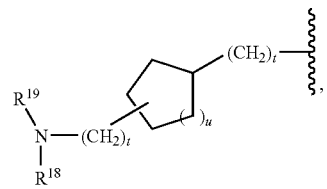

where $R^{18}$ and $R^{19}$ are independently hydrogen; $(C_{1-8})$alkyl; $(C_{1-6})$alkylcarbonyl; di-$(C_{1-6})$alkylaminocarbonyl; benzyl; benzothiazole; benzoyl; pyridine; pyrimidine; phenyl; phenylaminocarbonyl; alkylsulfonyl; or phenylsulfonyl; where the benzyl, benzoyl, benzothiazole, pyridine, pyrimidine, phenyl, phenylaminocarbonyl, alkylsulfonyl, and phenylsulfonyl groups are optionally mono- or independently di-substituted with $R^{12}$; or $R^{18}$ and $R^{19}$ together form a $(C_{3-12})$cycloalkyl ring; each t is independently 0 to 6; and u is 0 to 3;

i) a group of the formula:

(phenyl-CH$_2$—C(CH$_3$)$_2$—), where the phenyl group is optionally mono- or independently plurisubstituted with $R^{12}$;

j) a group of the formula:

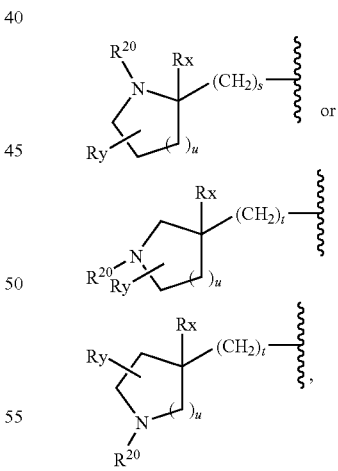

where $R^{20}$ is hydrogen; $(C_{1-8})$alkyl; $(C_{1-6})$alkylcarbonyl; di-$(C_{1-6})$alkylaminocarbonyl; $(C_{3-8})$cycloalkylcarbonyl; benzyl; benzoyl; $(C_{1-6})$alkyloxycarbonyl; arlkyloxycarbonyl, pyridine; pyrimidine; phenyl; phenyl substituted thiazole ring; phenylaminocarbonyl; alkylsulfonyl; or phenylsulfonyl; where the benzyl, benzoyl, pyridine, pyrimidine, phenyl, phenylaminocarbonyl, alkylsulfonyl, and phenylsulfonyl groups are optionally mono- or independently di-substituted with $R^{12}$; $R_x$ is hydrogen; $(C_{1-8})$alkyl; $(C_{3-12})$cycloalkyl; benzyl; phenyl; where the benzyl and phenyl, groups are optionally mono- or independently di-substituted on the ring with $R^{12}$; $R_y$ is absent or is halogen, $(C_{1-8})$alkyl, $(C_{1-8})$alkoxy, O-alkylcarboxylate, O-aralkylcarboxylate, N-alkylcarboxamido, N-aralkylcarboxamido; or phenyl;

s is 1 to 6; t is 0 to 6; and u is 0 to 3; or k) a group of the formula:

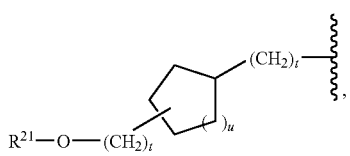

where $R^{21}$ is hydrogen; $(C_{1-8})$alkyl; benzyl; or phenyl; in which the benzyl and phenyl groups are optionally mono- or independently di-substituted on the ring with $R^{12}$; each t is independently 0 to 6; and u is 0 to 3; or (ee) $R^3$ and $R^4$ are independently hydrogen, alkyl; alkenyl; alkynyl; cycloalkyl; cycloalkylalkyl; bicycloalkyl; tricycloalkyl; alkylcycloalkyl; hydroxyalkyl; hydroxyalkylcycloalkyl; hydroxycycloalkyl; hydroxybicycloalkyl; hydroxytricycloalkyl; bicycloalkylalkyl; alkylbicycloalkyl; alkylthioalkyl; arylalkylthioalkyl; cycloalkenyl; aryl, aralkyl; heteroaryl; heteroarylalkyl; cycloheteroalkyl or cycloheteroalkylalkyl; all optionally mono- or independently plurisubstituted with halogen, alkyl, polyhaloalkyl, alkoxy, haloalkoxy, polyhaloalkoxy, alkoxycarbonyl, alkenyl, alkynyl, cycloalkyl, cycloalkylalkyl, polycycloalkyl, heteroarylamino, arylamino, cycloheteroalkyl, cycloheteroalkylalkyl, hydroxy, hydroxyalkyl, nitro, cyano, amino, substituted amino, alkylamino, dialkylamino, thiol, alkylthio, alkylcarbonyl, acyl, alkoxycarbonyl, aminocarbonyl, alkynylaminocarbonyl, alkylaminocarbonyl, alkenylaminocarbonyl, alkylcarbonyloxy, alkylcarbonylamino, arylcarbonylamino, alkylsulfonylamino, alkylaminocarbonyl-amino, alkoxycarbonylamino, alkylsulfonyl, aminosulfinyl, aminosulfonyl, alkylsulfinyl, sulfonamido or sulfonyl;

$R^5$ is alkyl; alkenyl; alkynyl; cycloalkyl; cycloalkylalkyl; bicycloalkyl; tricycloalkyl; alkylcycloalkyl; hydroxyalkyl; hydroxyalkylcycloalkyl; hydroxycycloalkyl; hydroxybicycloalkyl; hydroxytricycloalkyl; bicycloalkylalkyl; alkylbicycloalkyl; alkylthioalkyl; arylalkylthioalkyl; cycloalkenyl; aryl, aralkyl; heteroaryl; heteroarylalkyl; cycloheteroalkyl or cycloheteroalkylalkyl; all optionally mono- or independently plurisubstituted with halogen, alkyl, polyhaloalkyl, alkoxy, haloalkoxy, polyhaloalkoxy, alkoxycarbonyl, alkenyl, alkynyl, cycloalkyl, cycloalkylalkyl, polycycloalkyl, heteroarylamino, arylamino, cycloheteroalkyl, cycloheteroalkylalkyl, hydroxy, hydroxyalkyl, nitro, cyano, amino, substituted amino, alkylamino, dialkylamino, thiol, alkylthio, alkylcarbonyl, acyl, alkoxycarbonyl, aminocarbonyl, alkynylaminocarbonyl, alkylaminocarbonyl, alkenylaminocarbonyl, alkylcarbonyloxy, alkylcarbonylamino, arylcarbonylamino, alkylsulfonylamino, alkylaminocarbonyl-amino, alkoxycarbonylamino, alkylsulfonyl, aminosulfinyl, aminosulfonyl, alkylsulfinyl, sulfonamido or sulfonyl; or $R^4$ and $R^5$ together form —$(CR^{22}R^{23})_m$— wherein m is 2 to 6, and $R^{22}$ and $R^{23}$ are independently hydrogen; hydroxyl; alkoxy; alkyl; alkenyl; alkynyl; cycloalkyl; halo; amino; substituted amino; cycloalkylalkyl; cycloalkenyl; aryl; arylalkyl; heteroaryl, heteroarylalkyl; cycloheteroalkyl; cycloheteroalkylalkyl; alkylcarbonylamino; arylcarbonylamino; alkoxycarbonylamino; aryloxycarbonyl-amino; alkoxycarbonylamino; aryloxycarbonyl; or alkylaminocarbonylamino; provided that when n is 1, X is $CH_2$, and Z and $R^3$ are H, $R^4$ and $R^5$ together are not —$(CH_2)_2$— or —$(CH_2)_3$—; or $R^4$ and $R^5$ together with the atoms to which they are attached form a 5 to 7 membered ring containing a total of 2 to 4 heteroatoms selected from N, O, S, SO, or $SO_2$; or $R^4$ and $R^5$ together with the atoms to which they are attached form a 4 to 8 membered cycloheteroalkyl ring wherein the cycloheteroalkyl ring optionally has an aryl, heteroaryl or 3 to 7 membered cycloalkyl ring fused thereto; or (ff) $R^3$ is hydrogen; and $R^4$ and $R^5$ together with the atoms to which they are attached form a 4 to 8 member mono- or polycyclic heterocyclic ring system containing 1 to 3 heteroatoms selected from N, O, S, SO and $SO_2$, wherein the heterocyclic ring system is optionally mono- or independently plurisubstituted with any of the groups set forth in (dd) or (ee); provided that when n is 1, X is $CH_2$, the ring containing X is saturated, and Z and $R^3$ are H, $R^4$ and $R^5$ together are not —$(CH_2)_2$— or —$(CH_2)_3$—; and wherein a bond containing a wavy line signifies a point of attachment.

The invention also relates to methods for preparing the above-described compounds. As shown below and as described in the EXAMPLES, the compounds of formula I and II are prepared by reacting a cyclic amine (e.g., pyrrolidine or piperidine), suitably protected with a standard protecting group such as Boc-, Fmoc-, CBz- or the like, with sec-BuLi/TMEDA followed by $B(OCH_3)_3$, to provide the methyl boronic ester derivative. Acid hydrolysis of the methyl esters with 2N HCl provides the boronic acid intermediate 1. Reaction of 1 with (+) pinanediol, deprotection of the amino protecting group, and recrystallization provides the pinanediol ester 2 as an isomerically pure salt.

Intermediate 2 is useful for the synthesis of both series A and series B compounds. For example, N-acylation of 2 with chloroacetyl chloride provides the α-chloro amide 3. Treatment of 3 with $Na_2CO_3$ and cyclopentylamine, and hydrolysis of the pinanediol boronic ester, provides a compound of formula I, 4. Alternatively, coupling of intermediate 2 with N-Boc-5-phenyl-Pro using EDAC/HOBT provides amide 5. Deprotection of the amino group and hydrolysis of the boronic esters, provides a compound of formula II, 6.

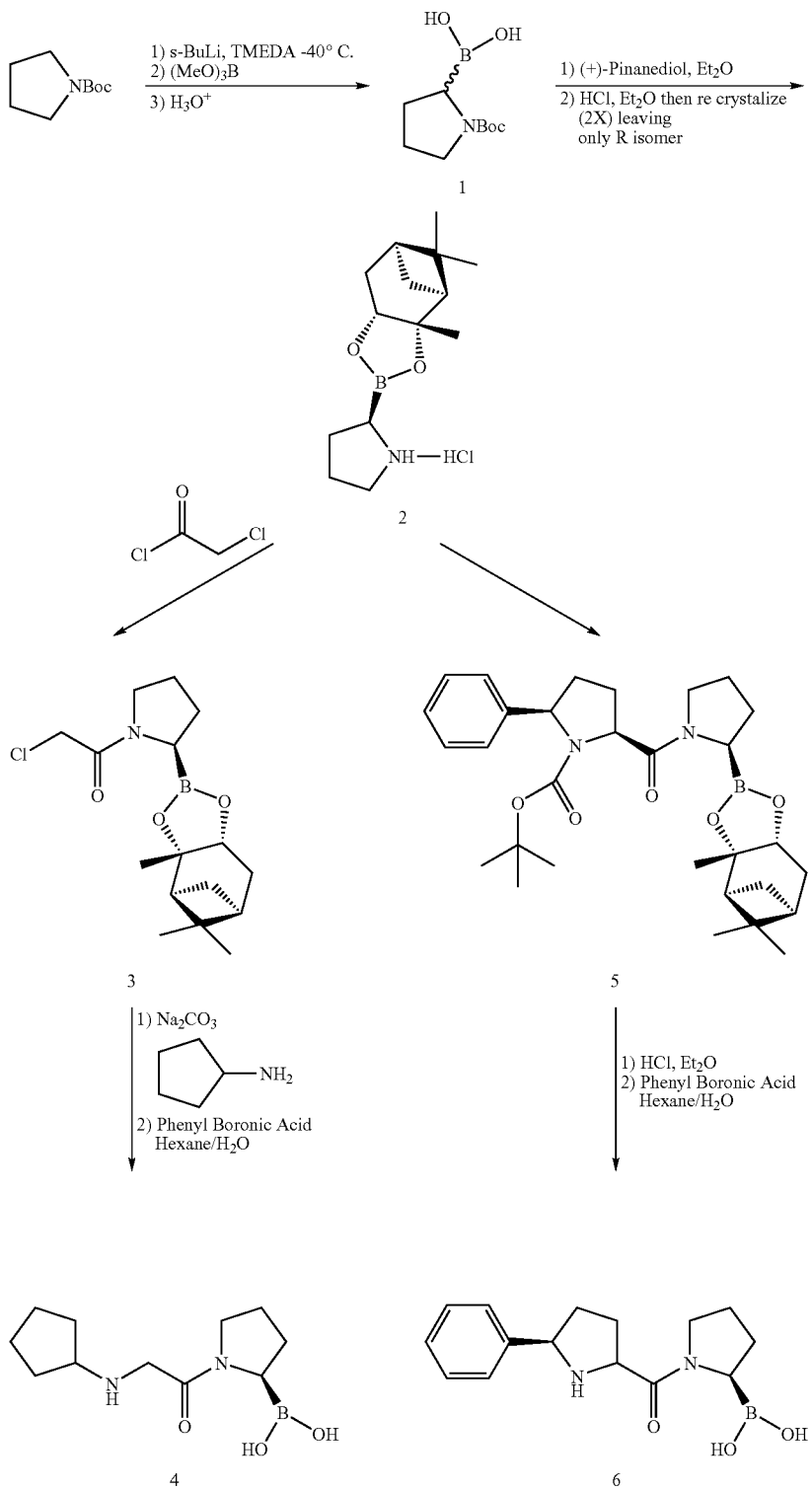

This synthetic scheme is adaptable for the preparation of all the compounds of the invention, by reacting the appropriate cyclic amine (pyrrollidine, piperidine, and other cyclic amines) with sec-BuLi/B(OCH$_3$)$_3$, and coupling the boronic ester intermediate with the desired acid chloride or acid via routes A or B, respectively. The appropriate cyclic amine may either be commercially available or is easily synthesized through known procedures, for example, those procedures disclosed in U.S. Pat. Nos. 6,617,340; 6,432,969; 6,380,398; 6,172,081; 6,166,063; 6,124,305; 6,110,949; 6,107,317; 6,011,155; and 6,395,767, which are hereby incorporated by reference in their entirety.

Thus, another aspect of the invention provides a process for preparing the compounds of formula I:

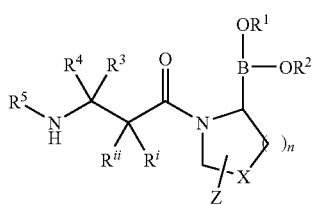

by coupling a reactive compound of formula:

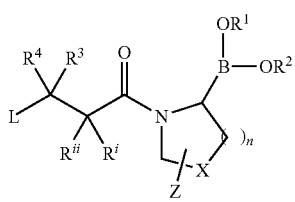

with an amine of formula: $R^5$—$NH_2$; optionally deprotecting the boronic acid ester; and recovering the resultant compound as a free acid or as an acid addition salt; wherein L is a leaving group. $R^1$, $R^2$, $R^3$, $R^4$, $R^i$, $R^{ii}$, n, X, and Z are as defined herein. Preferred embodiments are those where $R^3$ and $R^4$ are hydrogen, L is halogen, including but not limited to Cl, and $R^5$—$NH_2$ is cyclopentylamine.

Still another aspect of the invention provides a process for preparing the compounds of formula II:

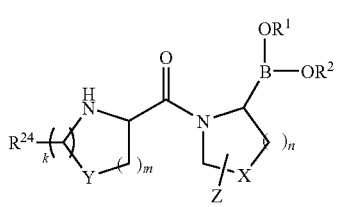

by coupling a 2-boroheterocycle having the formula:

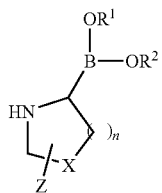

with the corresponding N-protected cyclic amino acid; optionally deprotecting the boronic acid ester; and recovering the resultant compound as a free acid or as an acid addition salt. $R^1$ and $R^2$ are not hydrogen, and n, X, and Z are as defined herein. Typically the 2-boroheterocycle is a 2-boropyrrolidino or 2-boropiperidino. In some such embodiments, the N-protected cyclic amino acid is N-Boc-4-phenyl-boroPro-OH.

The compounds of the invention may be prepared in the form of pharmaceutically acceptable salts, especially acid-addition salts, including salts of organic acids and mineral acids. Examples of such salts include salts of organic acids such as formic acid, fumaric acid, acetic acid, propionic acid, glycolic acid, lactic acid, pyruvic acid, oxalic acid, succinic acid, malic acid, tartaric acid, citric acid, benzoic acid, salicylic acid and the like. Suitable inorganic acid-addition salts include salts of hydrochloric, hydrobromic, sulphuric and phosphoric acids and the like. Further examples of pharmaceutically acceptable inorganic or organic acid addition salts include the pharmaceutically acceptable salts listed in Journal of Pharmaceutical Science, 66, 2 (1977) which are known to the skilled artisan.

The acid addition salts may be obtained as the direct products of compound synthesis. In the alternative, the free base may be dissolved in a suitable solvent containing the appropriate acid, and the salt isolated by evaporating the solvent or otherwise separating the salt and solvent.

The compounds of this invention may form solvates with standard low molecular weight solvents, including water to yield hydrates, using methods known to the skilled artisan.

It is to be understood that the invention extends to all of the stereoisomeric forms of the claimed compounds, including enantiomers and diastereomers, as well as the racemates.

Methods/Uses

Another aspect of the invention provides methods and uses for the compounds of the invention. In one approach, the invention compounds can be administered to an individual suffering from a disease or condition mediated by a post-proline/alanine cleaving amino-dipeptidase. In this embodiment, the individual is administered an amount of the invention compound effective in reducing the activity of the post-proline/alanine cleaving amino-dipeptidase and, thereby, reducing or alleviating symptoms of the disease or condition. In some embodiments, the administered compound reduces the activtity of DPP-IV. In some embodiments, the disease or condition is selected from the group consisting of diabetes, diabetec complications, hyperglycemia, Syndrome X, hyperinsulinemia, obesity, atherosclerosis and related diseases. The invention compounds to be administered may be one or more of the inventive bronic acid compounds, which may be formulated in any manner as described here, including combination with "other type(s) of therapeutic agents" identified further below.

Other exemplary embodiments of the invention methods are represented by:

Methods for inhibiting DPP-IV comprising administering to a mammal in need of such treatment a therapeutically effective amount of a compound of the invention, or a pharmaceutically acceptable acid addition salt thereof;

Methods for treating conditions mediated by DPP-IV comprising administering to a mammal in need of such treatment a therapeutically effective amount of a compound of the invention, or a pharmaceutically acceptable acid addition salt thereof;

Methods for treating controlling, or preventing diabetes comprising administering to a patient of an effective amount of a compound of the invention;

Methods for treating, controlling, or preventing insulin dependent (Type I) and/or non-insulin dependent (Type 2) diabetes mellitus in a mammalian patient in need of such treatment, comprising administering to the patient a therapeutically effective amount of a compound of the invention;

Methods for treating, controlling or preventing hyperglycemia in a mammalian patient in need of such treatment, comprising administering to the patient a therapeutically effective amount of a compound of the invention;

Methods for treating, controlling or preventing obesity in a mammalian patient in need of such treatment, comprising administering to the patient a therapeutically effective amount of a compound of the invention;

Methods for treating to enhance islet neogenesis, b-cell survival, and insulin biosynthesis in a mammalian patient in need of such treatment, comprising administering to the patient a therapeutically effective amount of a compound of the invention;

Methods for treating, controlling or preventing insulin resistance in a mammalian patient in need of such treatment, comprising administering to the patient a therapeutically effective amount of a compound of the invention;

Methods for treating, controlling or preventing one or more lipid disorders selected from the group consisting of dyslipidemia, hyperlipidemia, hypertriglyceridemia, hypercholesterolemia, low HDL, and high LDL in a mammalian patient in need of such treatment, comprising administering to the patient a therapeutically effective amount of a compound of the invention;

Methods for treating, controlling or preventing atherosclerosis in a mammalian patient in need of such treatment, comprising administering to the patient a therapeutically effective amount of a compound of the invention;

Methods for treating or controlling growth hormone deficiency in a mammalian patient in need of such treatment, comprising administering to the patient a therapeutically effective amount of a compound of the invention;

Methods for modulating the immune response in a mammalian patient in need of such treatment, comprising administering to the patient a therapeutically effective amount of a compound of the invention;

Methods for treating, or controlling HIV infection in a mammalian patient in need of such treatment, comprising administering to the patient a therapeutically effective amount of a compound of the invention;

Methods for treating, controlling or preventing in a mammalian patient in need of such treatment one or more disorders selected from the group consisting of neutropenia, anemia, neuronal disorders, tumor growth and metastasis, benign prostatic hypertrophy, gingivitis, hypertension and osteoporosis, comprising administering to the patient a therapeutically effective amount of a compound of the invention;

Methods for reducing sperm motility in a male in a mammalian patient in need of such treatment, comprising administering to the patient a therapeutically effective amount of a compound of the invention;

Methods for treating, controlling or preventing in a mammalian patient in need of such treatment one or more conditions selected from the group consisting of (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) irritable bowel syndrome, (15) inflammatory bowel disease, including Crohn's disease and ulcerative colitis, (16) rheumatoid arthritis, (17) other inflammatory conditions, (18) pancreatitis, (19) abdominal obesity, (20) neurodegenerative disease, (21) multiple sclerosis, (22) retinopathy, (23) nephropathy, (24) neuropathy, (25) Syndrome X, (26) ovarian hyperandrogenism, (27) allograft rejection in transplantation, and other conditions where insulin resistance is a component, comprising administering to the patient a therapeutically effective amount of a compound of the invention;

Methods for treating, controlling or preventing in a mammalian patient in need of such treatment one or more conditions selected from the group consisting of (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) irritable bowel syndrome, (15) inflammatory bowel disease, including Crohn's disease and ulcerative colitis, (16) rheumatoid arthritis, (17) other inflammatory conditions, (18) pancreatitis, (19) abdominal obesity, (20) neurodegenerative disease, (21) multiple sclerosis, (22) retinopathy, (23) nephropathy, (24) neuropathy, (25) Syndrome X, (26) ovarian hyperandrogenism, (27) allograft rejection in transplantation, (28) Type II diabetes, (29) growth hormone deficiency, (30) neutropenia, (31) anemia, (32) neuronal disorders, (33) tumor growth and metastasis, (34) benign prostatic hypertrophy, (35) gingivitis, (36) hypertension, (37) osteoporosis, and other conditions that may be treated by inhibition of dipeptidyl peptidase-IV, comprising administering to the patient of a therapeutically effective amount of a first compound of the invention, or a pharmaceutically acceptable salt thereof, and one or more other compounds selected from the group consisting of a) Other dipeptidyl peptidase-IV inhibitors;

b) Insulin sensitizers selected from the group consisting of (i) PPAR agonists, (ii) biguanides, and (iii) protein phosphatase-1B inhibitors;

c) Insulin or insulin mimetics;

d) Sulfonylureas or other insulin secretagogues;

e) α-glucosidase inhibitors;

f) glucagons receptor agonists;

g) GLP-1, GLP-1 mimetics, and GLP-1 receptor agonists;

h) GLP-2, GLP-2 mimetics, and GLP-2 receptor agonists;

i) GIP, GIP mimetics, and GIP receptor agonists;

j) PACAP, PACAP mimetics, and PACAP receptor 3 agonists;

k) Cholesterol lowering agents selected from the group consisting of (i) HMG-CoA reductase inhibitors, (ii) sequestrants, (iii) nicotinyl alcohol, nicotinic acid or a salt thereof, (iv) PPARα agonists, (v) PPARα/γ dual agonists, (vi) inhibitors of cholesterol absorption, (vii) acyl CoA:cholesterol acyltransferase inhibitors, and (viii) anti-oxidants;

l) PPAR agonists;

m) Anti-obesity compounds;

n) An ileal bile acid transporter inhibitor;

o) Anti-inflammatory agents;

p) G-CSF, G-CSF mimetics, and G-CSF receptor agonists; and q) EPO, EPO mimetics, and EPO receptor agonists.

Methods for the treatment, control, or prevention of one or more conditions selected from the group consisting of hypercholesterolemia, atherosclerosis, low HDL levels, high LDL levels, hyperlipidemia, hypertriglyceridemia, and dyslipidemia, comprising administering to a mammalian patient in need of such treatment a therapeutically effective amount of a compound of the invention and an HMG-CoA reductase inhibitor;

Methods wherein the HMC-CoA reductase inhibitor is a statin;

Methods wherein the statin is selected from the group consisting of lovastatin, simvastatin, pravastatin, fluvastatin, atorvastatin, itavastatin, ZD-4522 and rivastatin;

Methods for treating, controlling or preventing atherosclerosis, comprising administering to a mammalian patient in need of such treatment a therapeutically effective amount of a compound of the invention and an HMG-CoA reductase inhibitor;

Methods for treating, controlling or preventing obesity, comprising administering to a mammalian patient in need of such treatment a therapeutically effective amount of a compound of the invention and an anti-obesity agent;

Methods wherein the anti-obesity agent is a beta-3 adrenergic agonist, a lipase inhibitor, a serotonin (and dopamine) reuptake inhibitor, a thyroid receptor beta compound, an anorectic agent, and/or a fatty acid oxidation upregulator;

Methods wherein the anti-obesity agent is orlistat, ATL-962, AJ9677, L750355, CP331648, sibutramine, topiramate, axokine, dexamphetamine, phentermine, phenylpropanolamine, famoxin, and/or mazindol;

Methods for the treatment, control, or prevention of neutropenia comprising administering to a mammalian patient in need of such treatment a therapeutically effective amount of a compound of the invention and a neutrophilic agent;

Methods for the treatment, control, or prevention of neutropenia wherein the neutrophilic agent is G-CSF, a G-CSF mimetic, or a G-CSF receptor agonist;

Methods for the treatment, control, or prevention of neutropenia wherein the neutrophilic agent is pegfilgrastim, filgrastim, lenograstim, or nartograstim;

Methods for the treatment, control, or prevention of anemia, comprising administering to a mammalian patient in need of such treatment a therapeutically effective amount of a compound of the invention and a erythropoietin agonist;

Methods for the treatment, control, or prevention of anemia wherein the erythropoietin agonist is EPO, an EPO mimetic, or an EPO receptor agonist;

Methods for the treatment, control, or prevention of anemia wherein the erythropoietin agonist is epoetin alfa, or darbepoetin alfa;

Methods for treating diabetes, insulin resistance, hyperglycemia, hyperisulinemia, or elevated blood levels of free fatty acids or glycerol, obesity, Syndrome X, dysmetabolic syndrome, diabetic complications, hypertriglyceridemia, hyperinsulinemia, atherosclerosis, impaired glucose homeostasis, impaired glucose tolerance, infertility, polycystic ovary syndrome, growth disorders, frailty, arthritis, allograft rejection in transplantation, autoimmune diseases, AIDS, intestinal diseases, inflammatory bowel syndrome, nervosa, osteoporosis, or an immunomodulatory disease or a chronic inflammatory bowel disease, comprising administering to a mammalian species in need of treatment a therapeutically effective amount of a compound of the invention;

Methods for treating type II diabetes and/or obesity;

A variety of uses of the invention compounds are possible along the lines of the various methods of the treating an individual such as a mammal described above. Exemplary uses of the invention methods are represented by:

Use of a compound of the invention for the manufacture of a medicament for treating a condition that may be regulated or normalized via inhibition of DPP-IV;

Use of a compound of the invention for the manufacture of a medicament for treatment of metabolic disorders;

Use of a compound of the invention for the manufacture of a medicament for blood glucose lowering;

Use of a compound of the invention for the manufacture of a medicament for treatment of type II diabetes;

Use of a compound of the invention for the manufacture of a medicament for the treatment of impaired glucose tolerance (IGT);

Use of a compound of the invention for the manufacture of a medicament for the treatment of impaired fasting glucose (IFG);

Use of a compound of the invention for the manufacture of a medicament for prevention of hyperglycemia;

Use of a compound of the invention for the manufacture of a medicament for delaying the progression of impaired glucose tolerance (IGT) to type II diabetes;

Use of a compound of the invention for the manufacture of a medicament for delaying the progression of non-insulin requiring type II diabetes to insulin requiring type II diabetes;

Use of a compound of the invention for the manufacture of a medicament for increasing the number and/or the size of beta cells in a mammalian subject;

Use of a compound of the invention for the manufacture of a medicament for treatment of beta cell degeneration, in particular apoptosis of beta cells.

Use of a compound of the invention for the manufacture of a medicament for the treatment of disorders of food intake;

Use of a compound of the invention for the manufacture of a medicament for the treatment of obesity;

Use of a compound of the invention for the manufacture of a medicament for appetite regulation or induction of satiety;

Use of a compound of the invention for the manufacture of a medicament for the treatment of dyslipidemia;

Use of a compound of the invention for the manufacture of a medicament for treatment of functional dyspepsia, in particular irritable bowel syndrome; and Methods for treating the conditions mentioned above by administering to a subject in need thereof an effective amount of a compound of the invention.

Combination Treatments

The compounds of the invention may be used in combination with one or more other types of antidiabetic agents (employed to treat diabetes and related diseases) and/or one or more other types of therapeutic agents which may be administered orally in the same dosage form, in a separate oral dosage form or by injection.

The other type of antidiabetic agent which may be optionally employed in combination with the DPP-IV inhibitors of the invention may be 1,2,3 or more antidiabetic agents or antihyperglycemic agents including insulin secretagogues or insulin sensitizers, or other antidiabetic agents preferably having a mechanism of action different from DPP-IV inhibition and may include biguanides, sulfonyl ureas, glucosidase inhibitors, PPAR γ agonists, such as thiazolidinediones, SGLT2 inhibitors, PPAR α/γ dual agonists, aP2 inhibitors, glycogen phosphorylase inhibitors, advanced glycosylation end (AGE) products inhibitors, and/or meglitinides, as well as insulin, and/or glucagon-like peptide-1 (GLP-1) or mimetics thereof.

The use of the compounds of the invention in combination with 1, 2, 3 or more other antidiabetic agents may produce antihyperglycemic results greater than that possible from each of these medicaments alone and greater than the combined additive antihyperglycemic effects produced by these medicaments.

The other antidiabetic agent may be an oral antihyperglycemic agent preferably a biguanide such as metformin or phenformin or salts thereof, preferably metformin HCl.

Where the other antidiabetic agent is a biguanide, the compounds of the invention will be employed in a weight ratio to biguanide within the range from about 0.01:1 to about 100:1, preferably from about 0.1:1 to about 5:1.

Preferably, the other antidiabetic agent can be a sulfonyl urea such as glyburide (also known as glibenclamide), glimepiride (disclosed in U.S. Pat. No. 4,379,785), glipizide, gliclazide or chlorpropamide, other known sulfonylureas or other antihyperglycemic agents which act on the ATP-dependent channel of the γ-cells, with glyburide and glipizide being preferred, which may be administered in the same or in separate oral dosage forms.

The compounds of the invention will be employed in a weight ratio to the sulfonyl urea in the range from about 0.01:1 to about 100:1, preferably from about 0.05:1 to about 5:1.

The oral antidiabetic agent may also be a glucosidase inhibitor such as acarbose (disclosed in U.S. Pat. No. 4,904,769) or miglitol (disclosed in U.S. Pat. No. 4,639,436), which may be administered in the same or in a separate oral dosage forms.

The compounds of the invention will be employed in a weight ratio to the glucosidase inhibitor within the range from about 0.01:1 to about 100:1, preferably from about 0.2:1 to about 50:1.

The compounds of the invention may be employed in combination with a PPAR γ agonist such as a thiazolidinedione oral anti-diabetic agent or other insulin sensitizers (which has an insulin sensitivity effect in NIDDM patients) such as troglitazone (Warner-Lambert's Rezulin®, disclosed in U.S. Pat. No. 4,572,912), rosiglitazone (en), pioglitazone (Takeda), Mitsubishi MCC-555 (disclosed in U.S. Pat. No. 5,594,016), Glaxo-Wellcome's GL-262570, englitazone (CP-68722, Pfizer) or darglitazone (CP-86325, Pfizer), isaglitazone (MIT/J&J), JTT-501 (JPNT/P&U), L-895645 (Merck), R-119702 (Sankyo/WL), NN-2344 (Dr. Reddy/NN), or YM-440 (Yamanouchi), preferably rosiglitazone and pioglitazone.

The compounds of the invention will be employed in a weight ratio to the thiazolidinedione in an amount within the range from about 0.01:1 to about 100:1, preferably from about 0.1:1 to about 10:1.

The sulfonyl urea and thiazolidinedione in amounts of less than about 150 mg oral antidiabetic agent may be incorporated in a single tablet with the compounds of the invention.

The compounds of the invention may also be employed in combination with a antihyperglycemic agent such as insulin or with glucagon-like peptide-1 (GLP-1) such as GLP-1(1-36) amide, GLP-1(7-36) amide, GLP-1(7-36) (as disclosed in U.S. Pat. No. 5,614,492 to Habener, disclosure of which is incorporated herein by reference), or a GLP-1 mimic such as AC2993 or Exendin-4 (Amylin) and LY-315902 or LY-307167 (Lilly) and NN2211 (Novo-Nordisk), which may be administered via injection, intranasal, or by transdermal or buccal devices.

Where present, metformin, the sulfonyl ureas, such as glyburide, glimepiride, glipyride, glipizide, chlorpropamide and gliclazide and the glucosidase inhibitors acarbose or miglitol or insulin (injectable, pulmonary, buccal, or oral) may be employed in formulations as described above and in amounts and dosing as indicated in the PHYSICIAN'S DESK REFERENCE (PDR).

Where present, metformin or salt thereof may be employed in amounts within the range from about 500 to about 2000 mg per day which may be administered in single or divided doses one to four times daily.

Where present, the thiazolidinedione anti-diabetic agent may be employed in amounts within the range from about 0.01 to about 2000 mg/day which may be administered in single or divided doses one to four times per day.

Where present insulin may be employed in formulations, amounts and dosing as indicated by the PHYSICIAN'S DESK REFERENCE.

Where present GLP-1 peptides may be administered in oral buccal formulations, by nasal administration (for example inhalation spray) or parenterally as described in U.S. Pat. No. 5,346,701 (TheraTech), U.S. Pat. Nos. 5,614,492 and 5,631,224 which are incorporated herein by reference.

The other antidiabetic agent may also be a PPAR α/γ dual agonist such as AR-H039242 (Astra/Zeneca), GW-409544 (Glaxo-Wellcome), KRP297 (Kyorin Merck), as well as those disclosed by Murakami et al., "A Novel Insulin Sensitizer Acts As a Coligand for Peroxisome Proliferation—Activated Receptor Alpha (PPAR alpha) and PPAR gamma. Effect on PPAR alpha Activation on Abnormal Lipid Metabolism in Liver of Zucker Fatty Rats," *Diabetes* 47: 1841-47 (1998), and in U.S. application Ser. No. 09/664,598, filed Sep. 18, 2000, the disclosure of which is incorporated herein by reference, employing dosages as set out therein, which compounds designated as preferred are preferred for use herein.

The other antidiabetic agent may be an SGLT2 inhibitor, as disclosed in U.S. application Ser. No. 09/679,027, filed Oct. 4, 2000, which is incorporated herein by reference, employing dosages as set out herein. Preferred are the compounds designated as preferred in the above application.

The other antidiabetic agent, which may be employed in combination with the DPP-IV inhibitors in accordance with the present invention, can be an aP2 inhibitor, Ser. No. 09/519,079, filed Mar. 6, 2000, which are each incorporated herein by reference, employing dosages as set out herein. Preferred antidiabetic agents to be used in combination with the invention compounds are those indicated as preferred in the above cited patents.

The other antidiabetic agent that may employed with the DPP-IV inhibitors of the invention can be a glycogen phosphorylase inhibitor as disclosed, for instance, in WO 96/39384, WO 96/39385, WO 99/26659, WO 99/43663, WO 2000/47206, EP 978279, EP 1041068, and U.S. Pat. Nos. 5,952,322 and 5,998,463.

The meglitinide which may optionally be employed in combination with the compound of the invention may be repaglinide, nateglinide (Novartis) or KAD1229(PF/Kissei), with repaglinide being preferred.

The DPP-IV inhibitors of the invention will be employed in a weight ratio to the meglitinide, PPAR γ agonist, PPAR α/γ dual agonist, SGLT2 inhibitor, aP2 inhibitor, or glycogen phosphorylase inhibitor within the range from about 0.01:1 to about 100:1, preferably from about 0.1:1 to about 10:1.

The hypolipidemic agent or lipid-modulating agent which may be optionally employed in combination with the compounds of the invention may include 1,2,3 or more MTP inhibitors, HMG CoA reductase inhibitors, squalene synthetase inhibitors, fibric acid derivatives, ACAT inhibitors, lipoxygenase inhibitors, cholesterol absorption inhibitors, ileal Na+/bile acid cotransporter inhibitors, upregulators of LDL receptor activity, ATP citrate lyase inhibitors, cholesteryl ester transfer protein inhibitors, bile acid sequestrants, and/or nicotinic acid and derivatives thereof.

MTP inhibitors employed herein include MTP inhibitors disclosed in U.S. Pat. Nos. 5,595,872, 5,739,135, 5,712,279, 5,760,246, 5,827,875, 5,885,983 and 5,962,440. MTP inhibitors preferred herein are those identified as being preferred in the above referenced patents.

Most preferred MTP inhibitors, in accordance with the present invention, are implitapide (Bayer) and those set out in U.S. Pat. Nos. 5,739,135, 5,712,279, and 5,760,246. A particularly preferred MTP inhibitor in this context is 9-[4-[4-[[2-(2,2,2-Trifluoroethoxy)-benzoyl]amino]-1-piperidinyl] butyl]-N-(2,2,2-trifluoroethyl)-9H-fluorene-9-carboxamide.

The hypolipidemic agent may be an HMG CoA reductase inhibitor which includes, but is not limited to, mevastatin and related compounds as disclosed in U.S. Pat. No. 3,983,140, lovastatin (mevinolin) and related compounds disclosed in U.S. Pat. No. 4,231,938, pravastatin and related compounds such as disclosed in U.S. Pat. No. 4,346,227, simvastatin and related compounds as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354,772, cerivastatin disclosed in U.S. Pat. Nos. 5,006,530 and 5,177,080, atorvastatin disclosed in U.S. Pat. Nos. 4,681,893, 5,273,995, 5,385,929 and 5,686,104, atavastatin (Nissan/Sankyo nisvastatin (NK-104)), disclosed in U.S. Pat. No. 5,011,930, and Shionogi-Astra/Zeneca visastatin (ZD-4522), disclosed in U.S. Pat. No. 5,260,440.

The squalene synthetase inhibitors suitable for use herein include, but are not limited to, α-phosphono-sulfonates disclosed in U.S. Pat. No. 5,712,396, those disclosed by Biller et al, J. Med. Chem., 1988, Vol. 11, No. 10, pp 1869-1871, including isoprenoid (phosphinyl-methyl)phosphonates as well as other known squalene synthetase inhibitors, for example, as disclosed in U.S. Pat. Nos. 4,871,721 and 4,924,024 and in Biller, S. A., Neuenschwander, K., Ponpipom, M. M., and Poulter, C. D., Current Pharmaceutical Design, 2, 1-40 (1996).

In addition, other squalene synthetase inhibitors suitable for use herein include the terpenoid pyrophosphates disclosed by P. Ortiz de Montellano et al, J. Med. Chem., 1977, 20, 243-249, the farnesyl diphosphate analog A and presqualene pyrophosphate (PSQ-PP) analogs as disclosed by Corey and Volante, J. Am. Chem. Soc., 1976, 98, 1291-1293, phosphinylphosphonates reported by McClard, R. W. et al, J.A.C.S., 1987, 10, 5544 and cyclopropanes reported by Capson, T. L., PhD dissertation, June, 1987, Dept. Med. Chem. U of Utah, Abstracts Table of Contents, pp 16, 17, 40-43. 48-51, Summary.

Other hypolipidemic agents suitable for use herein include, but are not limited to, fibric acid derivatives, such as fenofibrate, gemfibrozil, clofibrate, bezafibrate, ciprofibrate, clinofibrate, and the like, probucol, and related compounds as disclosed in U.S. Pat. No. 3,674,836, probucol and gemfibrozil being preferred, bile acid sequestrants such as cholestyramine, colestipol and DEAE-Sephadex (Secholex®, Policexide®), as well as lipostabil (Rhone-Poulenc), Eisai E-5050 (an N-substituted ethanolamine derivative), imanixil (HOE-402), tetrahydrolipstatin (THL), istigmastanylphos-phorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid, acipimox, acifran, neomycin, p-aminosalicylic acid, aspirin, poly(diallylmethylamine) derivatives such as disclosed in U.S. Pat. No. 4,759,923, quaternary amine poly(diallyldimethylammonium chloride) and ionenes such as disclosed in U.S. Pat. No. 4,027,009, and other known serum cholesterol lowering agents.

The other hypolipidemic agent may be an ACAT inhibitor such as disclosed in 24 DRUGS OF THE FUTURE 9-15 (Avasimibe 1999), "The ACAT inhibitor, Cl-1011 is effective in the prevention and regression of aortic fatty streak area in hamsters", Nicolosi et al, Atherosclerosis (Shannon, Irel). (1998), 137 (1), 77-85; "The pharmacological profile of FCE 27677: a novel ACAT inhibitor with potent hypolipidemic activity mediated by selective suppression of the hepatic secretion of ApoB100-containing lipoprotein", Ghiselli, Giancarlo, Cardiovasc. Drug Rev. (1998), 16(1), 16-30; "RP 73163: a bioavailable alkylsulfinyl-diphenylimidazole ACAT inhibitor", Smith, C., et al, Bioorg. Med. Chem. Lett. (1996), 6(1), 47-50; "ACAT inhibitors: physiologic mechanisms for hypolipidemic and anti-atherosclerotic activities in experimental animals", Krause et al, Editor(s): Ruffolo, Robert R., Jr.; Hollinger, Mannfred A., Inflammation: Mediators Pathways (1995), 173-98, Publisher: CRC, Boca Raton, Fla.; "ACAT inhibitors: potential anti-atherosclerotic agents", Sliskovic et al, Curr. Med. Chem. (1994), 1(3), 204-25; "Inhibitors of acyl-CoA:cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl)methyl]ureas with enhanced hypocholesterolemic activity", Stout et al, Chemtracts: Org. Chem. (1995), 8(6), 359-62, or TS-962 (Taisho Pharmaceutical Co. Ltd).

The hypolipidemic agent may be an upregulator of LD2 receptor activity such as MD-700 (Taisho Pharmaceutical Co. Ltd) and LY295427 (Eli Lilly).

The hypolipidemic agent may be a cholesterol absorption inhibitor preferably Schering-Plough's SCH48461 as well as those disclosed in Atherosclerosis 115, 45-63 (1995) and J. Med. Chem. 41, 973 (1998).

The hypolipidemic agent may be an ileal $Na^+$/bile acid cotransporter inhibitor such as disclosed in Drugs of the Future, 24, 425-430 (1999).

The lipid-modulating agent may be a cholesteryl ester transfer protein (CETP) inhibitor such as Pfizer's CP 529,414 (WO/0038722 and EP 818448) and Pharmacia's SC-744 and SC-795.

The ATP citrate lyase inhibitor which may be employed in the combination of the invention may include, for example, those disclosed in U.S. Pat. No. 5,447,954.

Preferred hypolipidemic agents are pravastatin, lovastatin, simvastatin, atorvastatin, fluvastatin, cerivastatin, atavastatin and ZD-4522.

The above-mentioned U.S. patents are incorporated herein by reference. The amounts and dosages employed will be as indicated in the Physician's Desk Reference and/or in the patents set out above.

The compounds of the invention will be employed in a weight ratio to the hypolipidemic agent (where present), within the range from about 500:1 to about 1:500, preferably from about 100:1 to about 1:100.

The dose administered must be carefully adjusted according to age, weight and condition of the patient, as well as the route of administration, dosage form and regimen and the desired result.

The dosages and formulations for the hypolipidemic agent will be as disclosed in the various patents and applications discussed above.

The dosages and formulations for the other hypolipidemic agent to be employed, where applicable, will be as set out in the latest edition of the Physicians' Desk Reference.

For oral administration, a satisfactory result may be obtained employing the MTP inhibitor in an amount within the range of from about 0.01 mg/kg to about 500 mg and preferably from about 0.1 mg to about 100 mg, one to four times daily.

An oral dosage form, such as tablets or capsules, will contain the MTP inhibitor in an amount of from about 1 to about 500 mg, preferably from about 2 to about 400 mg, and more preferably from about 5 to about 250 mg, one to four times daily.

For oral administration, a satisfactory result may be obtained employing an HMG CoA reductase inhibitor, for example, pravastatin, lovastatin, simvastatin, atorvastatin, fluvastatin or cerivastatin in dosages employed as indicated in the PHYSICIAN'S DESK REFERENCE, such as in an amount within the range of from about 1 to 2000 mg, and preferably from about 4 to about 200 mg.

The squalene synthetase inhibitor may be employed in dosages in an amount within the range of from about 10 mg to about 2000 mg and preferably from about 25 mg to about 200 mg.

A preferred oral dosage form, such as tablets or capsules, will contain the HMG CoA reductase inhibitor in an amount from about 0.1 to about 100 mg, preferably from about 5 to about 80 mg, and more preferably from about 10 to about 40 mg.

A preferred oral dosage form, such as tablets or capsules will contain the squalene synthetase inhibitor in an amount of from about 10 to about 500 mg, preferably from about 25 to about 200 mg.

The other hypolipidemic agent may also be a lipoxygenase inhibitor including a 15-lipoxygenase (15-LO) inhibitor such as benzimidazole derivatives as disclosed in WO 97/12615, 15-LO inhibitors as disclosed in WO 97/12613, isothiazolones as disclosed in WO 96/38144, and 15-LO inhibitors as disclosed by Sendobry et al "Attenuation of diet-induced atherosclerosis in rabbits with a highly selective 15-lipoxygenase inhibitor lacking significant antioxidant properties", Brit. J. Pharmacology (1997) 120, 1199-1206, and Cornicelli et al, "15-Lipoxygenase and its Inhibition: A Novel Therapeutic Target for Vascular Disease", Current Pharmaceutical Design, 1999, 5, 11-20.

The compounds of the invention and the hypolipidemic agent may be employed together in the same oral dosage form or in separate oral dosage forms taken at the same time.

The compositions described above may be administered in the dosage forms as described above in single or divided doses of one to four times daily. It may be advisable to start a patient on a low dose combination and work up gradually to a high dose combination.

The preferred hypolipidemic agent is pravastatin, simvastatin, lovastatin, atorvastatin, fluvastatin or cerivastatin.

The other type of therapeutic agent which may be optionally employed with the DPP-IV inhibitors of the invention may be 1, 2, 3 or more of an anti-obesity agent including a beta 3 adrenergic agonist, a lipase inhibitor, a serotonin (and dopamine) reuptake inhibitor, a thyroid receptor beta drug, an anorectic agent and/or a fatty acid oxidation upregulator.

The beta 3 adrenergic agonist which may be optionally employed in combination with a compound of the invention may be AJ9677 (Takeda/Dainippon), L750355 (Merck), or CP331648 (Pfizer) or other known beta 3 agonists as disclosed in U.S. Pat. Nos. 5,541,204, 5,770,615, 5,491,134, 5,776,983 and 5,488,064, with AJ9677, L750,355 and CP331648 being preferred.

The lipase inhibitor which may be optionally employed in combination with a compound of the invention may be orlistat or ATL-962 (Alizyme), with orlistat being preferred.

The serotonin (and dopamine) reuptake inhibitor which may be optionally employed in combination with a compound of the invention may be sibutramine, topiramate (Johnson & Johnson) or axokine (Regeneron), with sibutramine and topiramate being preferred.

The thyroid receptor beta compound which may be optionally employed in combination with a compound of the invention may be a thyroid receptor ligand as disclosed in WO97/21993 (U. Cal SF), WO099/00353 (KaroBio) and GB98/284425 (KaroBio), with compounds of the KaroBio applications being preferred.

The anorectic agent which may be optionally employed in combination with a compound of the invention may be dexamphetamine, phentermine, phenylpropanolamine or mazindol, with dexamphetamine being preferred.

The fatty acid oxidation upregulator which may be optionally employed in combination with the compound of the invention can be famoxin (Genset).

The various anti-obesity agents described above may be employed in the same dosage form with the compound of the invention or in different dosage forms, in dosages and regimens as generally known in the art or in the PDR.

The infertility agent which may be optionally employed in combination with the DPP-IV inhibitor of the invention may be 1, 2, or more of clomiphene citrate (Clomid®, Aventis), bromocriptine mesylate (Parlodel®, Novartis), LHRH analogs, Lupron (TAP Pharm.), danazol, Danocrine (Sanofi), progestogens or glucocorticoids, which may be employed in amounts specified in the PDR.

The agent for polycystic ovary syndrome which may be optionally employed in combination with the DPP-IV inhibitor of the invention may be 1, 2, or more of gonadotropin releasing hormone (GnRH), leuprolide (Lupron®), Clomid®, Parlodel®, oral contraceptives or insulin sensitizers such as PPAR agonists, or other conventional agents for such use which may be employed in amounts specified in the PDR.

The agent for treating growth disorders and/or frailty which may be optionally employed in combination with the DPP-IV inhibitor of the invention may be 1, 2, or more of a growth hormone or growth hormone secretagogue such as MK-677 (Merck), CP-424,391 (Pfizer), and compounds disclosed in U.S. Ser. No. 09/506,749 filed Feb. 18, 2000, as well as selective androgen receptor modulators (SARMs), which is incorporated herein by reference, which may be employed in amounts specified in the PDR, where applicable.

The agent for treating arthritis which may be optionally employed in combination with the DPP-1V inhibitor of the invention may be 1, 2, or more of aspirin, indomethacin, ibuprofen, diclofenac sodium, naproxen, nabumetone (Relafen®, SmithKline Beecham), tolmetin sodium (Tolectin®, Ortho-McNeil), piroxicam (Feldene®, Pfizer), ketorolac tromethamine (Toradol®, Roche), celecoxib (Celebrex®, Searle), rofecoxib (Vioxx®, Merck) and the like, which may be employed in amounts specified in the PDR.

Conventional agents for preventing allograft rejection in transplantation such as cyclosporin, Sandimmune (Novartis), azathioprine, Immuran (Faro) or methotrexate may be optionally employed in combination with the DPP-IV inhibitor of the invention, which may be employed in amounts specified in the PDR.

Conventional agents for treating autoimmune diseases such as multiple sclerosis and immunomodulatory diseases such as lupus erythematosis, psoriasis, for example, azathioprine, Immuran, cyclophosphamide, NSAIDS such as ibuprofen, cox 2 inhibitors such as Vioxx and Celebrex, glucocorticoids and hydroxychloroquine, may be optionally employed in combination with the DPP-IV inhibitor of the invention, which may be employed in amounts specified in the PDR.

The AIDS agent which may be optionally employed in combination with the DPP-IV inhibitor of the invention may be a non-nucleoside reverse transcriptase inhibitor, a nucleoside reverse transcriptase inhibitor, a protease inhibitor and/or an AIDS adjunct anti-infective and may be 1, 2, or more of dronabinol (Marinol®, Roxane Labs), didanosine (Videx®, Bristol-Myers Squibb), megestrol acetate (Megace®, Bristol-Myers Squibb), stavudine (Zerit®, Bristol-Myers Squibb), delavirdine mesylate (Rescriptor®, Pharmacia), lamivudine/zidovudine (Combivir™, Glaxo), lamivudine (Epivir™, Glaxo), zalcitabine (Hivid®, Roche), zidovudine (Retrovir®, Glaxo), indinavir sulfate (Crixivan®, Merck), saquinavir (Fortovase™, Roche), saquinovir mesylate (Invirase®, Roche), ritonavir (Norvir®, Abbott), nelfinavir (Viracept®, Agouron).

The above anti-AIDS agents may be employed in amounts specified in the PDR.

The agent for treating inflammatory bowel disease or syndrome which may be optionally employed in combination with the DPP-IV inhibitor of the invention may be 1, 2, or more of sulfasalazine, salicylates, mesalamine (Asacol®, P&G) or Zelmac®, (Bristol-Myers Squibb), which may be employed in amounts specified in the PDR or otherwise known in the art.

The agent for treating osteoporosis which may be optionally employed in combination with the DPP-IV inhibitor of the invention may be 1, 2, or more of alendronate sodium (Fosamax®, Merck, tiludronate (Skelid®, Sanofi), etidronate disodium (Didronel®, P&G), raloxifene HCl (Evista®, Lilly), which may be employed in amounts specified in the PDR.

In carrying out the methods of the invention, a pharmaceutical composition may be employed containing the compounds of the invention, with or without another antidiabetic agent and/or other type therapeutic agent, in association with a pharmaceutical vehicle or diluent. The pharmaceutical composition can be formulated employing conventional solid or liquid vehicles or diluents and pharmaceutical additives of a type appropriate to the mode of desired administration. The compounds can be administered to mammalian species including humans, monkeys, dogs, etc. by an oral route, for example, in the form of tablets, capsules, granules or powders, or they can be administered by a parenteral route in the form of injectable preparations. The dose for adults is preferably between 10 and 1,000 mg per day, which can be administered in a single dose or in the form of individual doses from 1-4 times per day.

A typical capsule for oral administration contains compounds of the invention (250 mg), lactose (75 mg) and magnesium stearate (15 mg). The mixture is passed through a 60 mesh sieve and packed into a No. 1 gelatin capsule. A typical injectable preparation is produced by aseptically placing 250 mg of compounds of the invention into a vial, aseptically freeze-drying and sealing. For use, the contents of the vial are mixed with 2 mL of physiological saline, to produce an injectable preparation.

DPP-IV inhibitor activity of the compounds of the invention may be determined by use of an in vitro assay system which measures the potentiation of inhibition of DPP-IV. Inhibition constants (Ki values) for the DPP-IV inhibitors of the invention may be determined by the method described below.

Pharmaceutical Compositions

Pharmaceutical compositions containing a compound of the invention of the invention may be prepared by conventional techniques, e.g. as described in Remington: The Science and Practise of Pharmacy, 19th Ed., 1995. The compositions may appear in conventional forms, for example capsules, tablets, aerosols, solutions, suspensions or topical applications.

Typical compositions include a compound of the invention which inhibits the enzymatic activity of DPP-IV or a pharmaceutically acceptable basic addition salt or prodrug or hydrate thereof, associated with a pharmaceutically acceptable excipient which may be a carrier or a diluent or be diluted by a carrier, or enclosed within a carrier which can be in the form of a capsule, sachet, paper or other container. In making the compositions, conventional techniques for the preparation of pharmaceutical compositions may be used. For example, the active compound will usually be mixed with a carrier, or diluted by a carrier, or enclosed within a carrier which may be in the form of a ampoule, capsule, sachet, paper, or other container. When the carrier serves as a diluent, it may be solid, semi-solid, or liquid material that acts as a vehicle, excipient, or medium for the active compound. The active compound can be adsorbed on a granular solid container for example in a sachet. Some examples of suitable carriers are water, salt solutions, alcohols, polyethylene glycols, polyhydroxyethoxylated castor oil, peanut oil, olive oil, gelatin, lactose, terra alba, sucrose, dextrin, magnesium carbonate, sugar, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone. Similarly, the carrier or diluent may include any sustained release material known in the art, such as glyceryl monostearate or glyceryl distearate, alone or mixed with a wax. The formulations may also include wetting agents, emulsifying and suspending agents, preserving agents, sweetening agents or flavoring agents. The formulations of the invention may be formulated so as to provide quick, sustained, or delayed release of the active ingredient after administration to the patient by employing procedures well known in the art.

The pharmaceutical compositions can be sterilized and mixed, if desired, with auxiliary agents, emulsifiers, salt for influencing osmotic pressure, buffers and/or coloring substances and the like, which do not deleteriously react with the active compounds.

The route of administration may be any route, which effectively transports the active compound of the invention which inhibits the enzymatic activity of DPP-IV to the appropriate or desired site of action, such as oral, nasal, pulmonary, buccal, subdermal, intradermal, transdermal or parenteral, e.g., rectal, depot, subcutaneous, intravenous, intraurethral, intramuscular, intranasal, ophthalmic solution or an ointment, the oral route being preferred.

If a solid carrier is used for oral administration, the preparation may be tabletted, placed in a hard gelatin capsule in powder or pellet form or it can be in the form of a troche or lozenge. If a liquid carrier is used, the preparation may be in the form of a syrup, emulsion, soft gelatin capsule or sterile injectable liquid such as an aqueous or non-aqueous liquid suspension or solution.

For nasal administration, the preparation may contain a compound of the invention which inhibits the enzymatic activity of DPP-IV, dissolved or suspended in a liquid carrier, in particular an aqueous carrier, for aerosol application. The carrier may contain additives such as solubilizing agents, e.g., propylene glycol, surfactants, absorption enhancers such as lecithin (phosphatidylcholine) or cyclodextrin, or preservatives such as parabenes.

For parenteral application, particularly suitable are injectable solutions or suspensions, preferably aqueous solutions with the active compound dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

A typical tablet that may be prepared by conventional tabletting techniques may contain:

| Core: | Active compound (as free compound or salt thereof) | 250 mg |
|---|---|---|
| | Colloidal silicon dioxide (Aerosil) ® | 1.5 mg |
| | Cellulose, microcryst. (Avicel) ® | 70 mg |
| | Modified cellulose gum (Ac-Di-Sol) ® | 7.5 mg |
| | Magnesium stearate | Ad. |
| Coating: | HPMC approx. | 9 mg |
| | *Mywacett 9-40 T approx. | 0.9 mg |

*Acylated monoglyceride used as plasticizer for film coating.

The compounds of the invention may be administered to a mammal, especially a human in need of such treatment, prevention, elimination, alleviation or amelioration of the various diseases as mentioned above, e.g., type II diabetes, IGT, IFG, obesity, appetite regulation or as a blood glucose lowering agent, and especially type II diabetes. Such mammals include also animals, both domestic animals, e.g. household pets, and non-domestic animals such as wildlife.

The compounds of the invention are effective over a wide dosage range. For example, in the treatment of adult humans, dosages from about 0.05 to about 1000 mg, preferably from about 1 to about 500 mg, per day may be used. A typical dosage is about 10 mg to about 500 mg per day. In choosing a regimen for patients it may frequently be necessary to begin with a higher dosage and when the condition is under control to reduce the dosage. The exact dosage will depend upon the mode of administration, on the therapy desired, form in which administered, the subject to be treated and the body weight of the subject to be treated, and the preference and experience of the physician or veterinarian in charge.

Generally, the compounds of the invention are dispensed in unit dosage form comprising from about 0.05 to about 1000 mg of active ingredient together with a pharmaceutically acceptable carrier per unit dosage.

Usually, dosage forms suitable for oral, nasal, pulmonal or transdermal administration comprise from about 0.05 mg to about 1000 mg, preferably from about 0.5 mg to about 250 mg of the compounds admixed with a pharmaceutically acceptable carrier or diluent.

The invention also encompasses prodrugs of a compound of the invention which on administration undergo chemical conversion by metabolic processes before becoming active pharmacological substances. In general, such prodrugs will be functional derivatives of a compound of the invention which are readily convertible in vivo into a compound of the invention. Conventional procedures for the selection and preparation of suitable prodrug derivatives are described, for example, in "Design of Prodrugs", ed. H. Bundgaard, Elsevier, 1985.

The invention also encompasses active metabolites of a compound of the invention.

Thus, another aspect of the invention provides pharmaceutical compositions of the compounds of the invention, alone or in combination with another type antidiabetic agent and/or other type therapeutic agent.

In one example, the embodiments of the invention are represented by:

Pharmaceutical compositions comprising, as an active ingredient, at least one compound of the invention which inhibits the enzymatic activity of DPP-IV or a pharmaceutically acceptable salt or prodrug or hydrate thereof together with a pharmaceutically acceptable carrier or diluent;

Pharmaceutical compositions comprising a compound of the invention as described herein, in free form or in pharmaceutically acceptable acid addition salt form, together with at least one pharmaceutically acceptable carrier or diluent;

Pharmaceutical compositions comprising a compound of formula VA, VB, or a mixture thereof and a pharmaceutically acceptable carrier or diluent;

Pharmaceutical compositions comprising:
a. a substantially pure preparation of a compound of formula VB as described herein; and
b. a pharmaceutically acceptable carrier or diluent;

Methods of making a pharmaceutical composition comprising mixing a substantially pure preparation of a compound of formula VB with a pharmaceutically acceptable carrier or diluent;

Methods of making a pharmaceutical composition of a compound described herein wherein the pharmaceutically acceptable carrier or diluent is suitable for oral administration;

Methods of making a pharmaceutical composition of a compound described herein suitable for oral administration further comprising the step of formulating the composition into a tablet or capsule;

Methods of making a pharmaceutical composition of a compound described herein wherein the pharmaceutically acceptable carrier or diluent is suitable for parenteral administration;

Methods of making a pharmaceutical composition of a compound described herein suitable for parenteral administration further comprising the step of lyophilizing the composition to form a lyophilized preparation;

Pharmaceutical compositions for the treatment, prevention or control of atherosclerosis, comprising: (1) a compound of the invention, (2) an HMG-CoA reductase inhibitor, and (3) a pharmaceutically acceptable carrier;

Pharmaceutical compositions, comprising:
a) A compound of the invention;
b) One or more compounds selected from the group consisting of:
  i) Other dipeptidyl peptidase-IV inhibitors;
  ii) Insulin sensitizers selected from the group consisting of (i) PPAR agonists, (ii) biguanides, and (iii) protein phosphatase-1B inhibitors;
  iii) Insulin or insulin mimetics;
  iv) Sulfonylureas or other insulin secretagogues;
  v) α-glucosidase inhibitors;
  vi) glucagons receptor agonists;
  vii) GLP-1, GLP-1 mimetics, and GLP-1 receptor agonists;
  viii) GIP, GIP mimetics, and GIP receptor agonists;
  ix) PACAP, PACAP mimetics, and PACAP receptor 3 agonists;
  x) GLP-2, GLP-2 mimetics, and GLP-2 receptor agonists;
  xi) Cholesterol lowering agents selected from the group consisting of (i) HMG-CoA reductase inhibitors, (ii) sequestrants, (iii) nicotinyl alcohol, nicotinic acid or a salt thereof, (iv) PPARα agonists, (v) PPARα/γ dual agonists, (vi) inhibitors of cholesterol absorption, (vii) acyl CoA:cholesterol acyltransferase inhibitors, and (viii) anti-oxidants;
  xii) PPARδ agonists;
  xiii) Anti-obesity compounds;
  xiv) An ileal bile acid transporter inhibitor;
  xv) Anti-inflammatory agents;
  xvi) G-CSF, G-CSF mimetics, and G-CSF receptor agonists;
  xvii) EPO, EPO mimetics, and EPO receptor agonists; and
c) a pharmaceutically acceptable carrier.

Pharmaceutical combinations comprising a compound of the invention, an antidiabetic agent other than a DPP-IV inhibitor for treating diabetes and related diseases, and an anti-obesity agent or a lipid-modulating agent or both.

Pharmaceutical combinations comprising a compound of the invention and an antidiabetic agent;

Pharmaceutical combinations comprising a compound of the invention and an antidiabetic agent wherein the antidiabetic agent is 1, 2, 3 or more of a biguanide, a sulfonyl urea, a glucosidase inhibitor, a PPAR γ agonist, a PPAR α/γ dual agonist, an SGLT2 inhibitor, an aP2 inhibitor, a glycogen phosphorylase inhibitor, an AGE inhibitor, an insulin sensitizer, a glucagon-like peptide-1 (GLP-1) or mimetic thereof, insulin and/or a meglitinide;

Pharmaceutical combinations comprising a compound of the invention and an antidiabetic agent wherein the antidiabetic agent is 1, 2, 3 or more of metformin, glyburide, glimepiride, glipyride, glipizide, chlorpropamide, gliclazide, acarbose, miglitol, pioglitazone, troglitazone, rosiglitazone, insulin, G1-262570, isaglitazone, JTT-501, NN-2344, L895645, YM-440, R-119702, AJ9677, repaglinide, nateglinide, KAD1129, APR-HO39242, GW-409544, KRP297, AC2993, Exendin-4, LY307161, NN2211, and/or LY315902;

Pharmaceutical combinations comprising a compound of the invention and an antidiabetic agent wherein the compound is present in a weight ratio to the antidiabetic agent within the range from about 0.01 to about 100:1;

Pharmaceutical combinations comprising a compound of the invention and an antidiabetic agent wherein the anti-obesity agent is a beta 3 adrenergic agonist, a lipase inhibitor, a serotonin (and dopamine) reuptake inhibitor, a thyroid receptor beta compound, an anorectic agent, and/or a fatty acid oxidation upregulator;

Pharmaceutical combinations comprising a compound of the invention and an anti-obesity agent wherein the anti-obesity agent is orlistat, ATL-962, AJ9677, L750355, CP331648, sibutramine, topiramate, axokine, dexamphetamine, phentermine, phenylpropanolamine, famoxin, and/or mazindol;

Pharmaceutical combinations comprising a compound of the invention and a lipid-modulating agent wherein the lipid-modulating agent is an MTP inhibitor, an HMG CoA reductase inhibitor, a squalene synthetase inhibitor, a fibric acid derivative, an upregulator of LDL receptor activity, a lipoxygenase inhibitor, an ACAT inhibitor, a cholesteryl ester transfer protein inhibitor, or an ATP citrate lyase inhibitor;

Pharmaceutical combinations comprising a compound of the invention and a lipid-modulating agent wherein the lipid-modulating agent is pravastatin, lovastatin, simvastatin, atorvastatin, cerivastatin, fluvastatin, nisvastatin, visastatin, fenofibrate, gemfibrozil, clofibrate, implitapide, CP-529,414, avasimibe, TS-962, MD-700, and/or LY295427;

Pharmaceutical combinations comprising a compound of the invention and a lipid-modulating agent wherein the compound is present in a weight ratio to the lipid-modulating agent within the range from about 0.01 to about 100:1;

Pharmaceutical combinations comprising a compound of the invention and an agent for treating infertility, an agent for treating polycystic ovary syndrome, an agent for treating a growth disorder and/or frailty, an anti-arthritis agent, an agent for preventing inhibiting allograft rejection in transplantation, an agent for treating autoimmune disease, an anti-AIDS agent, an agent for treating inflammatory bowel disease/syndrome, an agent for treating anorexia nervosa, an anti-osteoporosis agent and/or an anti-obesity agent.

Methods For Measuring Activity

The following methods were used to measure the activities of the compounds of the invention which inhibit the enzymatic activity of DPP-IV. The compounds of the invention are tested for their ability to inhibit the enzyme activity of purified DPP-IV. Briefly, the activity of DPP-IV is measured in vitro by its ability to cleave the synthetic substrate Gly-Pro-p-nitroanilide (Gly-Pro-pNA). Cleavage of Gly-Pro-pNA by DPP-IV liberates the product p-nitroanilide (pNA), whose rate of appearance is directly proportional to the enzyme activity. Inhibition of the enzyme activity by specific enzyme inhibitors slows down the generation of pNA. Stronger interaction between an inhibitor and the enzyme results in a slower rate of generation of pNA. Thus, the degree of inhibition of the rate of accumulation of pNA is a direct measure of the strength of enzyme inhibition. The accumulation of pNA is measured spectrophotometrically. The inhibition constant, Ki, for each compound is determined by incubating fixed amounts of enzyme with several different concentrations of inhibitor and substrate.

Thus, DPP-IV enzyme activity was determined by a fluorometric assay with the substrate Gly-Pro-AMC which is cleaved by DPP-IV to release the fluorescent AMC leaving group. Free AMC (7-amino-4-methyl coumarin) was measured using an excitation wavelength of 380 nm and an emission wavelength of 460 nm with a Victor-II fluorescent reader. Stock solutions of DPP-IV (1 ng/μl, pH 8.0) and Gly-Pro-AMC substrate (400 μM) in 25 mM Tris buffer (pH 8.0) were prepared separately. Test compounds were dissolved in DMSO or in 50 mM glycine buffer (pH 3.0). The assay was performed by diluting the DPP-IV stock (10 μl) into 25 mM Tris buffer (77.5 μl) followed by addition of test compound (2.5 μl) at 26° C. After 10-minutes substrate was added (10 μl) and allowed to react for 20-minutes at 26° C. before free AMC was measured. $IC_{50}$ values were determined in triplicate, using a minimum of six different inhibitor concentrations. $IC_{50}$ values were calculated using Nonlinear Regression Analysis (GraphPad, Prism, San Diego, Calif.).

To determine the DPP-IV activity in the plasma of mice dosed with test compounds, plasma (10 μl) was diluted into 25 mM Tris buffer (80 μl, pH 8.0) followed by addition of Gly-Pro-AMC stock solution (10 μl) and the free AMC measured after 20-minutes at 26° C. Analysis was performed as described above.

The Zucker Diabetic Fatty (ZDF) rat model can be used to investigate the effects of the compounds of the invention on both the treatment and prevention of diabetes as rats of this sub-strain are initially pre-diabetic although they develop severe type 2 diabetes characterized by increased HbA1 c levels over a period of 6 weeks. The same strain can be used to predict the clinical efficacy of other anti-diabetic drug types. For example, the model predicts the potency and limited clinical efficacy of thiazolidinedione insulin sensitizer compounds.

The purification of porcine DPP-IV and the enzyme assay under steady state conditions are described in (1) Rahfeld, J. Schutkowski, M., Faust, J., Neubert., Barth, A., and Heins, J. (1991) Biol. Chem. Hoppe-Seyler, 372, 313-318; and (2) Nagatsu, T., Hino, M., Fuyamada, H., Hayakawa, T., Sakakibara, S., Nakagawa, Y., and Takemoto, T. (1976) Anal. Biochem., 74, 466-476, respectively.

Definitions

The term "DPP-IV" denotes dipeptidyl peptidase IV (EC 3.4.14.5; DPP-IV), also known as "CD-26." DPP-IV cleaves a dipeptide from the N terminus of a polypeptide chain containing a proline or alanine residue in the penultimate position.

The term "diabetes and related diseases" refers to Type II diabetes, Type I diabetes, impaired glucose tolerance, obesity, hyperglycemia, Syndrome X, dysmetabolic syndrome, diabetic complications, diabetic dyslipidemia, hyperinsulinemia, and the like.

The conditions, diseases and maladies collectively referred to as "diabetic complications" include retinopathy, neuropathy and nephropathy, and other known complications of diabetes.

The term "other type(s) of therapeutic agents" as employed herein refers to one or more antidiabetic agents (other than DPP-IV inhibitors of the invention), one or more anti-obesity agents, and/or one or more lipid-modulating agents (including anti-atherosclerosis agents), and/or one or more infertility agents, one or more agents for treating polycystic ovary syndrome, one or more agents for treating growth disorders, one or more agents for treating frailty, one or more agents for treating arthritis, one or more agents for preventing allograft rejection in transplantation, one or more agents for treating autoimmune diseases, one or more anti-AIDS agents, one or more anti-osteoporosis agents, one or more agents for treating immunomodulatory diseases, one or more agents for treating chronic inflammatory bowel disease or syndrome and/or one or more agents for treating anorexia nervosa.

The term "lipid-modulating" agent as employed herein refers to agents which lower LDL and/or raise HDL and/or lower triglycerides and/or lower total cholesterol and/or other known mechanisms for therapeutically treating lipid disorders.

The term "treatment" is defined as the management and care of a patient for the purpose of combating the disease, condition, or disorder and includes administering a compound of the present invention to prevent the onset of the symptoms or complications, or alleviating the symptoms or complications, or eliminating the disease, condition, or disorder.

The term "beta cell degeneration" is intended to mean loss of beta cell function, beta cell dysfunction, and death of beta cells, such as necrosis or apoptosis of beta cells.

By "substantially pure" in relation to compounds of the invention such as, but not limited to, those of formula VA and VB, it is meant that one isomer or the other, including all enantiomers, diastereoisomers, solvates, hydrates, and pharmaceutically acceptable salts thereof, represents at least 90% by weight of the composition. In some embodiments one isomer represents at least 98% by weight of the composition.

The term "boronic acid protecting group" as used herein refers to a moiety employed to block or protect the boronic acid functionality while reactions involving other functional sites of the compound are carried out. Typically, the boronic acid OH groups are protected as boronic acid esters derived from alchohols such as (+)-pinanediol; pinacol; 1,2-dicyclohexyl-ethanediol; 1,2-ethanediol; 2,2-diethanolamine; 1,3-propanediol; 2,3-butanediol, diisopropyl tartrate; 1,4-butanediol; diisopropylethanediol; (S,S,)-5,6-decanediol; 1,1,2-triphenyl-1,2-ethanediol; (2R,3R)-1,4-dimethyoxy-1,1,4,4-tetraphenyl-2,3-butanediol; methanol; ethanol; isopropanol; catechol; 1-butanol; and the like. As will be understood by those skilled in the art, alcohols having only a single hydroxy group, such as methanol, form diesters having the structure —B(OR)$_2$ in which R is the organic moiety from the alcohol (e.g., —B(OMe)$_2$). By comparison, diols such as pinacol form cyclic boronic diesters with —B(OH)$_2$ in which the organic moiety (e.g., —C(Me)$_2$-C(Me)$_2$-) is attached to both oxygens.

The term "N-protecting group" or "N-protected" as used herein refers to those groups intended to protect the N-terminus of an amino acid or peptide or to protect an amino group against undesirable reactions during synthetic procedures. Commonly used N-protecting groups are disclosed in T. W. Greene, P. G. Wuts, "Protective Groups In Organic Synthesis, 3$^{rd}$ Ed." (John Wiley & Sons, New York (1999)), which is hereby incorporated by reference. N-protecting groups comprise acyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-di methyl-3,5-dimethoxybenzyloxycarbonyl, benzhydryloxycarbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxycarbonyl, fluorenyl-9-methoxycarbonyl, cyclopentyloxycarbonyl, adamantyloxycarbonyl, cyclohexyloxycarbonyl, phenylthiocarbonyl and the like; alkyl groups such as benzyl, triphenylmethyl, benzyloxymethyl and the like; and silyl groups such as trimethylsilyl and the like. Preferred N-protecting groups are formyl, acetyl, benzoyl, pivaloyl, t-butyl acetyl, phenylsulfonyl, benzyl, 9-fluorenylmethyloxycarbonyl (Fmoc), t-butyloxycarbonyl (Boc) and benzyloxycarbonyl (Cbz).

The term "alkyl" or "$(C_{1-12})$alkyl", alone or in combination, refers to linear or branched chains and may include cyclic portions, having from 1-12 (the use of 1-12 herein implies each of 1, 2, 3, 4, 5, 6, 7, 8, 9, 10, 11 and 12) carbon atoms, such as but not limited to, e.g. methyl, ethyl, n-propyl, isopropyl, n-butyl, sec-butyl, isobutyl, tert-butyl, n-pentyl, 2-methylbutyl, 3-methylbutyl, n-hexyl, 4-methylpentyl, neopentyl, 2,2-dimethylpropyl, and the like.

The terms "$(C_{1-10})$alkyl", "$(C_{1-8})$alkyl" and "$(C_{1-6})$alkyl", alone or in combination, refers to linear or branched chains and may include cyclic portions, having from 1-10, 1-8, or 1-6 carbon atoms, respectively, such as but not limited to, e.g. methyl, ethyl, n-propyl, isopropyl, n-butyl, sec-butyl, isobutyl, tert-butyl, n-pentyl, 2-methylbutyl, 3-methylbutyl, n-hexyl, 4-methylpentyl, neopentyl, 2,2-dimethylpropyl, and the like.

The term "$(C_{1-4})$alkyl", alone or in combination, refers to linear or branched chains and may include cyclic portions, having from 1-4 carbon atoms, such as but not limited to, e.g. methyl, ethyl, n-propyl, isopropyl, n-butyl, sec-butyl, isobutyl, tert-butyl, and the like.

The terms "$(C_{2-12})$alkenyl" and "$(C_{2-10})$alkenyl", alone or in combination, refers to a straight or branched, unsaturated hydrocarbon chain having from 2-12 or 2-10 carbon atoms, respectively, and at least one double bond, such as, but not limited to, vinyl, 1-propenyl, allyl, isopropenyl, n-butenyl, n-pentenyl, n-hexenyl, and the like.

The terms "$(C_{2-12})$alkynyl" and "$(C_{2-10})$alkynyl", alone or in combination, refers to an unsaturated hydrocarbon chain having from 2-12 or 2-10 carbon atoms, respectively, and at least one triple bond, such as but not limited to —C≡CH, —C≡C—CH$_3$, —CH$_2$C≡CH, —CH$_2$—CH$_2$—C≡CH, —CH(CH$_3$)C≡CH, and the like.

The terms "$(C_{3-12})$cycloalkyl" and "$(C_{3-10})$cycloalkyl" refers to one or more saturated cyclic hydrocarbons having from 3-12 or 3-10 carbon atoms, respectively, such as, but not limited to, cyclopropyl, cyclobutyl, cyclopentyl, cyclohexyl, adamantyl, and the like.

The term "$(C_{5-10})$cycloalkenyl" refers to a radical of one or more cyclic hydrocarbon having at least one double bond having from 5-10 carbon atoms such as, but not limited to, cyclopentenyl, cyclohexenyl, and the like.

The term "cycloalkylene" refers to a "cycloalkyl" group which has single bonds for attachment at two different carbon atoms.

The terms "$(C_{1-6})$alkylaminocarbonyl" and "di-$(C_{1-6})$alkylaminocarbonyl" refer to straight or branched chain hydrocarbon groups having 1 to 6 carbon atoms connected to $NC(=O)$. Exemplary alkyl groups include but are not limited to methyl, ethyl, propyl, isopropyl, n-butyl, t-butyl, isobutyl, pentyl, hexyl, and the like.

The term "$(C_{1-6})$alkylcarbonyl" refers to linear or branched chain and cyclic hydrocarbon groups having 1 to 6 carbon atoms connected to $C(=O)$. Exemplary alkyl groups include but are not limited to methyl, ethyl, propyl, isopropyl, n-butyl, t-butyl, isobutyl, pentyl, hexyl, and the like.

The term $(C_{3-8})$cycloalkylcarbonyl refers to cyclic hydrocarbon groups having 3 to 8 carbon atoms connected to $C(=O)$. Exemplary cycloalkyl groups include but are not limited to cyclopropyl, cyclobutyl, cyclopentyl, cyclohexyl, and the like.

The terms "$(C_{1-10})$alkoxy", "$(C_{1-8})$alkoxy" and "$(C_{1-6})$alkoxy", alone or in combination, refers to "O" connected to alkyl, having linear or branched chains and may include cyclic portions, having from 1-10, 1-8 or 1-6 carbon atoms, respectively. Examples of linear alkoxy groups include but are not limited to methoxy, ethoxy, propoxy, butoxy, pentoxy, hexoxy, and the like. Examples of branched alkoxy include but are not limited to isoprpoxy, sec-butoxy, tert-butoxy, isopentoxy, isohexoxy, and the like. Examples of cyclic alkoxy include but are not limited to cyclopropyloxy, cyclobutyloxy, cyclopentyloxy, cyclohexyloxy, and the like.

The term "aryloxy" refers to an aryl group bonded to O.

The term "alkanoyl", alone or as part of another group, refers to alkyl linked to a carbonyl group.

The term "alkylene" refers to alkyl groups which have single bonds for attachment at two different carbon atoms.

The term "alkenylene" refers to alkenyl groups which have single bonds for attachement at two different carbon atoms.

The terms "alkynylene" refers to alkynyl groups which have single bonds for attachement at two different carbon atoms.

The term "aryl" refers to monocyclic, bicyclic, or tricyclic carbocyclic aromatic ring systems having 6 to 14 carbon atoms in the ring portion. Examples of aryl groups include but are not limited to phenyl, naphthyl, biphenyl, anthracenyl, azulenyl, and the like. Aryl is also intended to include the partially hydrogenated derivatives of the carbocyclic systems including 1,2,3,4-tetrahydro-naphthyl, indanyl and the like.

The term "heteroaryl" as used herein includes heterocyclic unsaturated ring systems containing one or more heteroatoms selected from nitrogen, oxygen and sulphur. Examples of heteroaryl groups include but are not limited to furyl, thienyl, pyrrolyl, and the like. Heteroaryl is also intended to include the partially hydrogenated derivatives of the heterocyclic systems enumerated below.

Examples of "aryl" and "heteroaryl" includes but are not limited to phenyl, biphenyl, indenyl, naphthyl (1-naphthyl, 2-naphthyl), N-hydroxytetrazolyl, N-hydroxytriazolyl, N-hydroxyimidazolyl, anthracenyl (1-anthracenyl, 2-anthracenyl, 3-anthracenyl), thiophenyl (2-thienyl, 3-thienyl), furyl (2-furyl, 3-furyl), indolyl, oxadiazolyl, isoxazolyl, quinazolinyl, fluorenyl, xanthenyl, isoindanyl, benzhydryl, acridinyl, thiazolyl, pyrrolyl (2-pyrrolyl), pyrazolyl (3-pyrazolyl), imidazolyl (1-imidazolyl, 2-imidazolyl, 4-imidazolyl, 5-imidazolyl), triazolyl (1,2,3-triazol-1-yl, 1,2,3-triazol-2-yl, 1,2,3-triazol-4-yl, 1,2,4-triazol-3-yl), oxazolyl (2-oxazolyl, 4-oxazolyl, 5-oxazolyl), thiazolyl (2-thiazolyl, 4-thiazolyl, 5-thiazolyl), pyridyl (2-pyridyl, 3-pyridyl, 4-pyridyl), pyrimidinyl (2-pyrimidinyl, 4-pyrimidinyl, 5-pyrimidinyl, 6-pyrimidinyl), pyrazinyl, pyridazinyl (3-pyridazinyl, 4-pyridazinyl, 5-pyridazinyl), quinolyl (2-quinolyl, 3-quinolyl, 4-quinolyl, 5-quinolyl, 6-quinolyl, 7-quinolyl, 8-quinolyl), isoquinolyl (1-isoquinolyl, 3-isoquinolyl, 4-isoquinolyl, 5-isoquinolyl, 6-isoquinolyl, 7-isoquinolyl, 8-isoquinolyl), benzo[b]furanyl (2-benzo[b]furanyl, 3-benzo[b]furanyl, 4-benzo[b]furanyl, 5-benzo[b]furanyl, 6-benzo[b]furanyl, 7-benzo[b]furanyl), 2,3-dihydro-benzo[b]furanyl (2-(2,3-dihydro-benzo[b]furanyl), 3-(2,3-dihydro-benzo[b]furanyl), 4-(2,3-dihydro-benzo[b]furanyl), 5-(2,3-dihydro-benzo[b]furanyl), 6-(2,3-dihydro-benzo[b]furanyl), 7-(2,3-dihydro-benzo[b]furanyl), benzo[b]thiophenyl (2-benzo[b]thiophenyl, 3-benzo[b]thiophenyl, 4-benzo[b]thiophenyl, 5-benzo[b]thiophenyl, 6-benzo[b]thiophenyl, 7-benzo[b]thiophenyl), 2,3-dihydro-benzo[b]thiophenyl, (2-(2,3-dihydro-benzo[b]thiophenyl), 3-(2,3-dihydro-benzo[b]thiophenyl), 4-(2,3-dihydro-benzo[b]thiophenyl), 5-(2,3-dihydro-benzo[b]thiophenyl), 6-(2,3-dihydro-benzo[b]thiophenyl), 7-(2,3-dihydro-benzo[b]thiophenyl), indolyl (1-indolyl, 2-indolyl, 3-indolyl, 4-indolyl, 5-indolyl, 6-indolyl, 7-indolyl), indazole (1-indazolyl, 3-indazolyl, 4-indazolyl, 5-indazolyl, 6-indazolyl, 7-indazolyl), benzimidazolyl (1-benzimidazolyl, 2-benzimidazolyl, 4-benzimidazolyl, 5-benzimidazolyl, 6-benzimidazolyl, 7-benzimidazolyl, 8-benzimidazolyl), benzoxazolyl (1-benzoxazolyl, 2-benzoxazolyl), benzothiazolyl (1-benzothiazolyl, 2-benzothiazolyl, 4-benzothiazolyl, 5-benzothiazolyl, 6-benzothiazolyl, 7-benzothiazolyl), carbazolyl (1-carbazolyl, 2-carbazolyl, 3-carbazolyl, 4-carbazolyl), 5H-dibenz[b,f]azepine (5H-dibenz[b,f]azepin-1-yl, 5H-dibenz[b,f]azepine-2-yl, 5H-dibenz[b,f]azepine-3-yl, 5H-dibenz[b,f]azepine-4-yl, 5H-dibenz[b,f]azepine-5-yl), 10,11-dihydro-5H-dibenz[b,f]azepine (10,11-dihydro-5H-dibenz[b,f]azepine-1-yl, 10,11-dihydro-5H-dibenz[b,f]azepine-2-yl, 10,11-dihydro-5H-dibenz[b,f]azepine-3-yl, 10,11-dihydro-5H-dibenz[b,f]azepine-4-yl, 10,11-dihydro-5H-dibenz[b,f]azepine-5-yl), and the like.

The terms "arylalkenyl" and "arylalkynyl" alone or as part of another group refer to alkenyl and alkynyl groups as described above having an aryl substituent.

The terms "halogen" and "halo" refers to chloro, fluoro, bromo or iodo.

The term "alkylamino", "arylamino", or "arylalkylamino" alone or as part of another group includes any of the above alkyl, aryl or arylalkyl groups linked to a nitrogen atom.

The term "substituted amino" as employed herein alone or as part of another group refers to amino substituted with one or two substituents, which may be the same or different, such as alkyl, aryl, arylalkyl, heteroaryl, heteroarylalkyl, cycloheteroalkyl, cycloheteroalkylalkyl, cycloalkyl, cycloalkylalkyl haloalkyl, hydroxyalkyl, alkoxyalkyl or thioalkyl. These substituents may be further substituted with any of the groups as set out above. In addition, the amino substituents may be taken together with the nitrogen atom to which they are attached to form 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl, 1-pyrrolidinyl, 1-piperidinyl, or 1-azepinyl, optionally substituted with alkyl, alkoxy, alkylthio, halo, trifluoromethyl or hydroxy.

The terms "alkylthio", "arylthio" or "aralkylthio" alone or as part of another group includes any of the above alkyl, aralkyl or aryl groups linked to a sulfur atom.

The term "acyl" by itself or part of another group refers to an organic radical linked to a carbonyl group; examples of acyl groups include any of the groups attached to a carbonyl, such as alkanoyl, alkenyl, aroyl, aralkanoyl, heteroaroyl, cycloalkanoyl, cycloheteroalkanoyl, and the like.

The term "cycloheteroalkyl" alone or as part of another group refers to a 3-, 4-, 5-, 6- or 7-membered saturated or partially unsaturated ring which includes 1 to 2 hetero atoms such as nitrogen, oxygen and/or sulfur, linked through a carbon atom or a heteroatom, where possible, optionally via the linker $(CH_2)_g$ (where g is 1, 2 or 3). The above groups may include 1 to 4 substituents such as alkyl, halo, oxo, and the like. In addition, any of the cycloheteroalkyl rings can be fused to a cycloalkyl, aryl, heteroaryl or cycloheteroalkyl ring.

The term "cycloheteroalkylalkyl" alone or as part of another group refers cycloheteroalkyl groups as defined above linked through a carbon atom or heteroatom to a $(CH_2)_r$ chain.

The term "heteroarylalkyl" or "heteroarylalkenyl" alone or as part of another group refers to a heteroaryl group as defined above linked through a C atom or heteroatom to a $(CH_2)_r$ chain, alkylene or alkenylene as defined above.

The phrase "naturally occurring α-amino acid sidechain" refers to the moieties (sidechains) attached to the α-amino carbon in the following naturally occurring α-amino acids: glycine, alanine, 2-aminobutyric acid, valine, leucine, isoleucine, tert-leucine, serine, threonine, cysteine, asparagine, aspartic acid, glutamine, glutamic acid, phenylalanine, histidine, tryptophan, tyrosine, phenylglycine, lysine, methionine, and arginine. The side chains of these amino acids are well known in the art. For example, the α-amino acid sidechain of alanine is methyl; the sidechain of phenylalanine is benzyl; and the sidechain of tert-leucine is tert-butyl.

The term "polyhaloalkyl" refers to an "alkyl" group as defined above which includes from 2 to 9, preferably from 2 to 5, halo substituents, such as F or Cl, preferably F, such as $CF_3CH_2$, $CF_3$ or $CF_3CF_2CH_2$.

The term "polyhaloalkoxy" refers to an "alkoxy" or "alkyloxy" group as defined above which includes from 2 to 9, preferably from 2 to 5, halo substituents, such as F or Cl, preferably F, such as $CF_3CH_2O$, $CF_3O$ or $CF_3CF_2CH_2O$.

The terms "polycyclic" and "polycycle" refer to two or more rings (e.g., cycloalkyls, cycloalkenyls, aryls, heteroaryls and/or cycloheteroalkyls) in which two or more carbons are common to two adjoining rings, e.g., the rings are "fused rings." Fused rings that are joined through nonadjacent atoms, are also known as "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, trifluoromethyl, cyano, or the like.

EXAMPLES

A further detailed description of the invention is given with reference to the following non-limiting examples.

Example 1

Synthesis of (2R)-boroPro-(1S,2S,3R,5S)-pinanediol ester, hydrochloride (2)

A flame dried round bottom flask equipped with a magnetic stir bar was charged with N-Boc-pyrrolidine (20 g, 117 mmol, 1 eq) and dry THF (60 mL) under a nitrogen atmosphere. The clear colorless solution was cooled to −78° C. and a solution of s-BuLi (100 mL of a 1.4 M solution in cyclohexane, 140 mmol) was added slowly over a 30 minute period. The light orange colored solution was stirred at −78° C. for 3 hours followed by treatment with $B(OMe)_3$ (39 mL, 350 mmol) after which the cooling bath was removed and the clear colorless solution slowly warmed to 0° C. Upon reaching 0° C., the reaction was quenched with a small amount of water (~2 mL), allowed to warm to room temp then extracted into 2 N NaOH (250 mL) and backwashed with additional EtOAc (150 mL). The aqueous phase was acidified to pH 3 by the addition of 2 N HCl and then extracted with EtOAc (3×120 mL). The organic extracts were combined and dried over $Na_2SO_4$ and concentrated to produce the free boronic acid (22.08 g, 103 mmol) as a sticky white solid in 88% yield. Without further purification the boronic acid was dissolved in tert-butyl methyl ether (150 mL) and with constant stirring (+)-pinanediol (17.5 g, 103 mmol) was added at room temperature. After 18 hr the ether was removed and the (+)-pinanediol boronic ester was purified by column chromatography (silica gel, 1:3 hexanes/EtOAc) to give a clear thick oil (26.84 g, 76.8 mmol, 76% yield, $R_f$=0.6 using a 2:1 hexane/ethyl acetate eluant, made visual via $I_2$ and/or PMA stain). Removal of the Boc protecting group was achieved by dissolving the oil in dry ether, cooling to 0° C. in an ice bath and with constant stirring dry HCl (g) was bubbled into the solution for 10 minutes. After 2 hours a white precipitate developed in the flask and the ether and excess HCl were removed in vacuo to afford the racemic HCl salt as a white solid. Crystallization and isolation of the desired isomer was performed by dissolving the HCl salt in a minimal amount of dichloromethane (250 mL) with gentle heating to facilitate a homogenous solution followed by continuous stirring for 8 hours to yield a fluffy white precipitate that was collected by vacuum filtration, dried and then dissolved in minimal 2-propanol (~200 mL) with gentle heating until homogenous. The alcoholic solution was stirred over night and the resulting white precipitate was collected by vacuum filtration affording isomerically pure 1 as a white solid. (7.0 g, 27 mmol, 23% yield). $^1H$ NMR (400 MHz, $D_2O$) δ 4.28 (d, J=8.0 Hz, 1H), 3.06 (m, 3H), 2.18 (m, 1H), 1.96 (m, 2H), 1.78 (m, 3 H), 1.62 (m, 2H), 1.21 (s, 3H), 1.05 (m, 5H), 0.84 (d, J=12 Hz, 2H), 0.71 (s, 2H), 0.62 (s, 3H).

Example 2

Synthesis Of Series A Compounds: (2R)-1-(2-Cyclopentylamino-acetyl)-boroPro-OH (4)

Step 1: (2R)-1-(2-Chloroacetyl)-boroPro-(1S,2S,3R, 5S)-pinanediol ester (3A)

To a solution of 2 (36.7 g, 129.3 mmol) dissolved in dry $CH_2Cl_2$ (200 mL) cooled to 0° C. was added chloroacetyl chloride (12.34 mL, 155.2 mmol) under a blanket of $N_2$. To this was slowly dripped 4-methylmorpholine (42.4 mL, 182 mmol) to give an almost clear light orange solution that was warmed to room temp. After 30 minutes the solution was cooled again to 0° C. and 200 mL of a 0.2 N solution of HCl was added and the organic layers separated, dried and concentrated to give a dark red oil that was a single spot by TLC (2:1 hex/EtOAc, $R_f$=0.22, made visual via $I_2$ and/or PMA stain) and was used in the next step without further purification. $^1$H NMR (400 MHz, CDCl$_3$) δ0.80 (s, 3 H), 1.25 (m, 1 H), 1.26 (s, 3 H), 1.42 (s, 3H), 1.75-1.96 (m, 4 H), 1.98-2.10 (m, 3 H), 2.12-2.20 (m, 1 H), 2.29-2.35 (m, 1 H), 3.12-3.16 (m, 1 H), 3.47-3.53 (m, 1 H), 3.58-3.63 (m, 1 H), 3.97-4.05 (q, 2 H), 4.30-4.32 (d, 1 H).

Step 2: (2R)-1-(2-Cyclopentylamino-acetyl)-boro-Pro-(1S,2S,3R,5S)-pinanediol ester (3B)

Compound 3A was dissolved in dry THF (~150 mL) followed by addition of K$_2$CO$_3$ (35 g) and cooled to 0° C. before addition of cyclopentylamine (21.93 g, 258 mmol). The reaction mixture was then allowed to warm to room temperature and stirred overnight. TLC indicated all starting material was consumed. The mixture was filtered through a celite and silica pad, washed with 5% MeOH in CH$_2$Cl$_2$ (200 mL) and concentrated to yield a sticky, light orange solid. The red sticky solid was dissolved in CH$_2$Cl$_2$ (150 mL) followed by addition of Et$_2$O (~200 mL) and the solution was stirred overnight. The resulting milky white solution was then filtered and the precipitate was washed with cold EtOAc (2×60 mL) and hexane (2×50 mL) and dried to give 3B (28.92 g, 120.5 mmol) as a fluffy white solid. The dark red mother liquor filtrate was concentrated and subjected to the previous recrystallization conditions to obtain a second crop of 3B (6.17 g, 25.7 mmol) for a combined overall yield of 3B (35.09 g, 93.8 mmol) of 73% yield. $R_f$=0.45 (10% MeOH in CH$_2$Cl$_2$). $^1$H NMR (400 MHz, CDCl$_3$) δ 4.18 (d, 1H), 3.95 (d, J=16 Hz, 1H), 3.6 (d, J=16 Hz, 1H), 3.46 (m, 3H), 2.74 (m, 1H), 2.36 (m, 1H), 2.16 (m, 2H), 2.04 (m, 4H), 1.90 (s, 1H), 1.74 (m, 6H), 1.61 (s, 1H), 1.46 (m, 2H), 1.34 (s, 3H), 1.30 (s, 3H), 0.88 (s, 3H).

Step 3: (2R)-1-(2-Cyclopentylamino-acetyl)-boro-Pro-OH (4)

To a solution of 3B (40.59 g, 108.5 mmol) in H$_2$O (200 mL, adjusted to pH 2 by addition of 2 N HCl) was added hexane (200 mL) and phenyl boronic acid (13.37 g, 109.5 mmol) and the bi-phasic mixture was stirred vigorously. The hexane layer was periodically removed and replaced with fresh hexane 6 times over a 24-hour period. The aqueous layer was separated and applied to a Dowex 50-X2-100 ion exchange column (H+ form) and eluted with water until the eluate was neutral. Elution with aqueous ammonium hydroxide (2 wt %) followed by lyophilization of the appropriate fractions yielded 4 (23.91 g, 99.6 mmol) as a white crystalline solid in a 92% yield. 4.TFA salt $^1$H NMR (400 MHz, D$_2$O) δ 3.88 (dd, J=8.0 Hz, 2H), 3.54 (m, 1H), 3.42 (m, 1H), 3.28 (m, 1H), 2.96 (m, 1H), 1.96 (m, 4H), 1.85 (m, 2H), 1.63 (m, 7H); MS (ESI) m/z 223 (M+H—H$_2$O)$^+$.

Example 3

Synthesis of 1-(2-Cyclopropylamino-acetyl)-pyrrolidine-(2R)-boronic acid. (A2)

The title compound was prepared according to the procedure of Example 2 using appropriate starting materials. $^1$H NMR (D$_2$O) δ 4.08 (dd, J=12 Hz, 2 H), 3.54 (m, 1H), 3.38 (m, 1H), 3.07 (m, 1H), 2.26 (m, 1H), 2.09 (m, 2H), 1.94 (m, 1H), 1.71 (m, 1H), 0.88 (s, 4H); MS (ESI) m/z 195.13 (MH$^+$—H$_2$O).

Example 4

Synthesis of 1-[2-(3-Hydroxy-adamantan-1-ylamino)-acetyl]-pyrrolidine-(2R)-boronic acid (A3)

The title compound was prepared according to the procedure of Example 2 using appropriate starting materials. $^1$H NMR (D$_2$O) δ 3.94 (d, J=8 Hz, 2H), 3.54 (m, 1H), 3.40 (m, 1H), 3.09 (m, 1H), 2.41 (s, 2H), 2.09 (m, 3H), 1.93 (m, 2H), 1.87 (m, 7H), 1.71 (m, 6H), 1.56 (m, 2 H); MS (ESI) m/z 305.21 (MH$^+$—H$_2$O).

Example 5

Synthesis of 1-(5R-Phenyl-pyrrolidine-2S-carbonyl)-pyrrolidine-(2R)-boronic acid (6)

Step 1: N-Boc-5-phenylPro-(2R)-boroPro-(1S,2S,3R,5S)-pinanediol ester (5)

To an ice-cooled (0° C.) solution of N-Boc-5-phenyl-Pro-OH (0.84 mmol) in dry CH$_2$Cl$_2$ was added EDAC (174 mg, 0.91 mmol) and HOBt (105 mg, 0.775 mmol). The reaction was stirred at 0° C. for 15-minutes and then 2 (200 mg, 0.7 mmol) and N-methyl morphiline (0.25 mL, 2.1 mmol) was added and the reaction was slowly warmed to room temperature and the reaction continued for 8 hours. The coupling reaction was then quenched with the addition of NaHCO$_3$ (10 mL), extracted into EtOAc (2×15 mL), washed with brine (15 mL), dried over Na$_2$SO$_4$, concentrated and further purified via column chromatography (silica gel, eluted with a gradient of EtOAc in hexanes, 30-50%) to afford 5 (320 mg, 0.62 mmol, 88%) as an off-white solid.

Step 2: 1-(5R-Phenyl-pyrrolidine-2S-carbonyl)-pyrrolidine-(2R)-boronic acid (6)

An ice-cooled solution of 5 (320 mg, 0.62 mmol) in dry ether was saturated with dry HCl (g) and allowed to stir for 1-hour. The solution was then concentrated under vacuum to afford a sticky white solid that was taken up in H$_2$O (10 mL, adjusted to pH 2 by addition of 2 N HCl) and hexane (10 mL) and phenyl boronic acid (74 mg, 0.62 mmol) and the bi-phasic mixture was stirred vigorously. The hexane layer was periodically removed and replaced with fresh hexane 6 times over a 24-hour period. The aqueous layer was separated and applied to a Dowex 50-X2-100 ion exchange column (H$^+$ form) and eluted with water until the eluate was neutral. Elution was continued with aqueous ammonium hydroxide (2 wt %) and the appropriate fractions were lyophilized to afford the free boronic acid B1 (76 mg, 0.26 mmol) as an amorphous white solid. $^1$H NMR (D$_2$O) δ 7.46 (m, 5H), 3.65 (m, 1H), 3.44 (m, 1H), 3.04 (m, 1H), 2.54 (m, 1H), 2.38 (m, 2H), 2.20 (m, 1H), 2.06 (m, 2H), 1.86 (m, 1H), 1.66 (m, 1H); MS (ESI) m/z 271 (MH$^+$—H$_2$O).

Example 6

Synthesis of 1-(Piperidine-2S-carbonyl)-pyrrolidin-(2R)-boronic acid (B2)

The title compound was prepared according to the procedure of Example 5 using appropriate starting materials. $^1$H NMR (D$_2$O) δ 4.07 (m, 1H), 3.61 (m, 1H), 3.34 (m, 2H), 2.94 (m, 2H), 2.16 (m, 1H), 2.03 (m, 2H), 1.87 (m, 3H), 1.56 (m, 4H); MS (ESI) m/z 209 (MH$^+$—H$_2$O).

Example 8

Synthesis of 1-(2,3-Dihydro-1H-indole-2S-carbonyl)-pyrrolidine-(2R)-boronic acid (B3)

The title compound was prepared according to the procedure of Example 5 using appropriate starting materials. $^1$H NMR (D$_2$O) δ 4.54 (m, 1H), 3.73 (m, 1H), 3.58 (m, 1H), 3.34 (m, 1H), 2.48 (m, 1H), 2.37 (m, 1H), 2.06 (m, 3H), 1.83 (m, 3H), 1.58 (m, 4H), 1.32 (m, 4H); MS (ESI) m/z 249 (MH$^+$—H$_2$O).

Example 9

Synthesis of 1-(4S-Phenyl-pyrrolidine-2S-carbonyl)-pyrrolidine-(2R)-boronic acid (B4)

The title compound was prepared according to the procedure of Example 5 using appropriate starting materials. $^1$H NMR (D$_2$O) δ 7.34 (d, J=13 Hz, 2H), 7.27 (m, 3H), 4.79 (m, 1H), 3.83 (m, 1H), 3.59 (m, 1H), 3.34 (m, 2H), 3.06 (m, 1H), 2.53 (m, 2H), 2.08 (m, 2H) 1.77 (m, 1H), 1.64 (m, 1H); MS (ESI) m/z 271 (MH$^+$—H$_2$O).

Example 10

Synthesis of (2R)-1-{2-[(3S)-Pyrrolidin-3-ylamino]-acetyl}-pyrrolidine-2-boronic acid (8)

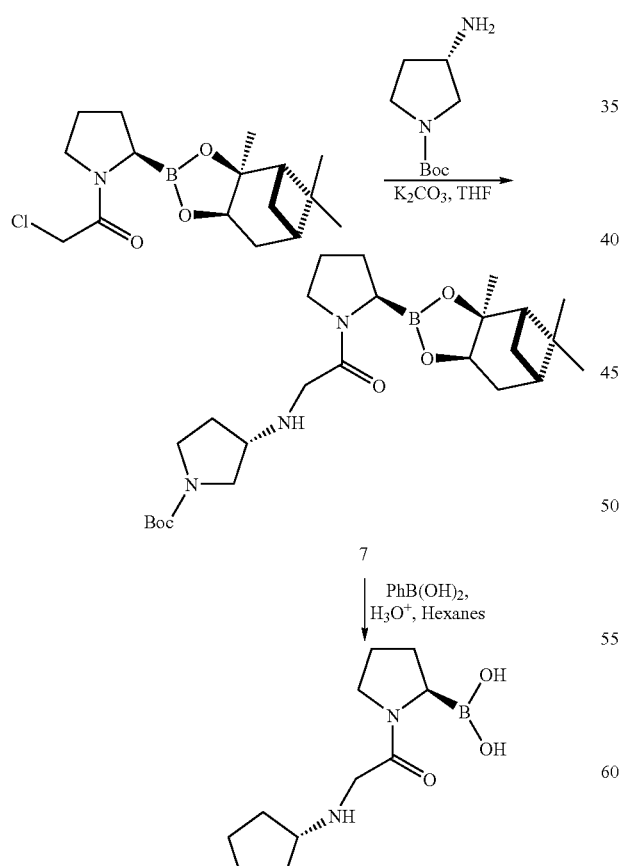

Step 1: (2R)-1-{2-[(3S)-1-tert-Butoxycarbonyl-pyrrolidin-3-ylamino]-acetyl}-pyrrolidine-2-boronic acid (1S,2S,3R,5S)-pinanediol ester (7)

The protocol described above for the synthesis of 3B was followed employing (3S)-3-amino-pyrrolidine-1-carboxylic acid tert-butyl ester in place of cyclopentylamine. Compound 7 was obtained as an oil.

(2R)-1-{2-[(3S)-Pyrrolidin-3-ylamino]-acetyl}-pyrrolidine-2-boronic acid (8)

The protocol described above for the deprotection of the pinanediol boronic ester 3B (Example 2, Step 3) was applied to 7. Compound 8 was obtained as a white solid. 8.TFA salt. $^1$H-NMR (500 MHz, CD$_3$OD) δ 4.12 (m, 3H), 3.76 (m, 1H), 3.54 (m, 3H), 3.41 (m, 2H), 3.26 (m, 1H), 2.55 (m, 1H), 2.28 (m, 1H), 2.05 (m, 3H), 1.74 (m, 1H). MS m/z (rel intensity) 241 (M) (27), 224 (100), 209 (73), 155 (47).

Example 11

Synthesis of (2R)-1-{2-[(3R)-Pyrrolidin-3-ylamino]-acetyl}-pyrrolidine-2-boronic acid (10)

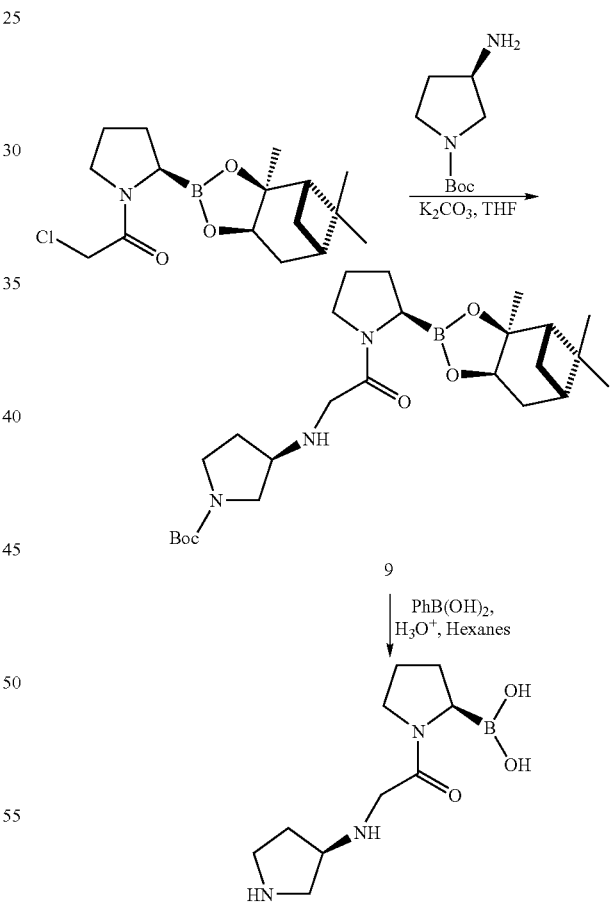

Step 1: (2R)-1-{2-[(3R)-1-tert-Butoxycarbonyl-pyrrolidin-3-ylamino]-acetyl}-pyrrolidine-2-boronic acid (1S,2S,3R,5S)-pinanediol ester (9)

The protocol described above for the synthesis of 3B was followed employing (3R)-3-amino-pyrrolidine-1-carboxylic acid tert-butyl ester in place of cyclopentylamine. Compound 9 was obtained as an oil. MS m/z (rel intensity) 476 (M+1)+ (100), 376 (74), 239 (38), 224 (67), 155 (55).

Step 2: (2R)-1-{2-[(3R)-Pyrrolidin-3-ylamino]-acetyl}-pyrrolidine-2-boronic acid (10)

The protocol described above for the deprotection of the pinanediol boronic ester 3B (Example 2, Step 3) was applied to 9. Compound 10 was obtained as a white solid. 10-TFA salt. $^1$H-NMR (500 MHz, CD$_3$OD) δ 4.13 (m, 1H), 4.08 (bs, 2H), 3.76 (dd, J=13.0, 8.0 Hz, 1H), 3.55 (m, 3H), 3.41 (m, 2H), 3.27 (m, 1H), 2.53 (m, 1H), 2.26 (m, 1H), 2.10 (m, 2H), 1.99 (m, 1H), 1.75 (m, 1H). MS m/z (rel intensity) 224 (M−17) (100), 206 (25), 180 (29), 155 (70).

Example 12

Synthesis of Series B Compounds: (2R)-1-[(2S)-Azetidine-2-carbonyl]-boroPro-OH (12)

Step 1: (2R)-1-[(2S)-1-tert-Butoxycarbonyl-azetidine-2-carbonyl]-boroPro-(1S,2S,3R,5S)-pinanediol ester (11)

To a solution of (2S)-azetidine-1,2-dicarboxylic acid 1-tert-butyl ester (169 mg, 0.8 mmol) in CH$_2$Cl$_2$ (5 mL) was added HOBt (105 mg, 0.8 mmol) and EDC (174 mg, 0.9 mmol). The reaction solution was then cooled to 0° C. in an ice bath for 10 min followed by sequential addition of 2 (200 mg, 0.7 mmol) and NMM (0.25 mL, 2.1 mmol). The reaction solution was allowed to warm up to room temperature and stirred overnight. The reaction mixture was diluted with additional CH$_2$Cl$_2$ (5 mL), washed with NaHCO$_3$ (2×10 mL), 0.1 M aqueous HCl (5 mL) and brine (10 mL). The organic layer was dried over Na$_2$SO$_4$ and evaporated under reduced pressure. The resulting oily residue was purified by column chromatography (silica gel, solvent eluent gradient from 1:4 EtOAc/hexane to 1:2 EtOAc/hexane) to afford 11 as a clear viscous oil.

Step 2: (2R)-1-[(2S)-Azetidine-2-carbonyl]-boroPro-OH (12)

A solution of compound 11 in 4N HCl in dioxane was stirred at room temperature for 4 h. The solvent was removed under vacuum and the resulting residue was submitted to the pinanediol ester deprotection protocol described above for the preparation of boronic acid 4. Compound 12 was obtained as a white solid. 12-TFA salt $^1$H-NMR (500 MHz, D$_2$O) δ 5.23 (m, 1H), 4.11 (m, 1H), 3.90 (m, 1H), 3.42 (m, 1H), 3.18 (m, 1H), 2.99 (m, 1H), 2.79 (m, 1H), 2.55 (m, 1H), 1.92 (m, 3H), 1.63 (m, 1H). MS m/z (rel intensity) 199 (M+1)+ (7), 181 (M−17) (100), 152 (53).

Example 13

Synthesis of Series C Compounds: (2R)-1-[(2S,4S)-4-Amino-pyrrolidine-2-carbonyl]-boroPro-OH (15)

Step 1: (2R)-1-[(2S,4S)-1-tert-Butoxycarbonyl-4-benzyloxycarbonylamino-pyrrolidine-2-carbonyl]-boroPro-(1S,2S,3R,5S)-pinanediol ester (13)

The protocol described for the synthesis of 11 was followed employing (2S,4S)-Fmoc-4-amino-1-boc-pyrrolidine-2-carboxylic acid (628 mg, 2.2 mmol) in place of azetidine-1,2-dicarboxylic acid 1-tert-butyl ester. Compound 13 was obtained as a clear colorless oil that was used in the next step without further purification.

Step 2: (2R)-1-[(2S,4S)-1-tert-Butoxycarbonyl-4-amino-pyrrolidine-2-carbonyl]-boroPro-(1S,2S,3R, 5S)-pinanediol ester (14)

To a solution of 13 dissolved in DCM (10 ml) was added diethyl amine (5 ml) at once and the resulting colorless solution was stirred overnight at room temperature. The reaction was evaporated to dryness and additional DCM was added followed by evaporation once again to dryness. The resulting oil was purified by column chromatography (silica gel, eluted with a gradient of 2.5 to 5% MeOH in DCM, made visible by I$_2$ and/or PMA) to give 14 as a clear colorless oil in a 48% yield over 2 steps.

Step 3: (2R)-1-[(2S,4S)-4-Amino-pyrrolidine-2-carbonyl]-boroPro-OH (15)

The protocol described above for the N-Boc deprotection and pinanediol ester hydrolysis in the synthesis of compound 12 was applied to 14. Compound 15 was obtained as a white solid. 15.TFA salt $^1$H-NMR (500 MHz, D$_2$O) δ 4.42 (dd, 1H), 3.87 (m, 1H), 3.5 (dd, 1H), 3.28 (m, 2H), 3.07 (m, 1H), 2.73 (m, 1H), 2.64 (m, 1H), 1.86 (m, 1H), 1.72 (br m, 2H), 1.55 (br m, 2H), 1.34 (m, 2H). MS m/z (rel intensity) 228 (M+1) (55), 210 (M+1−H$_2$O) (95).

Example 14

Synthesis of Series D Compounds: (2R)-1-[(2S)-4-Methanesulfonyl-piperazine-2-carbonyl]-boroPro-OH (19)

Step 1: (2R)-1-[(2S)-1-tert-Butoxycarbonyl-4-benzyloxycarbonyl-piperazine-2-carbonyl]-boroPro-(1S, 2S,3R,5S)-pinanediol ester (16)

The protocol described above for the synthesis of 11 was followed employing (2S)-N-1-Boc-N-4-Cbz-2-piperazine carboxylic acid (1 g, 2.6 mmol) in place of azetidine-1,2-dicarboxylic acid 1-tert-butyl ester. Compound 16 (690 mg, 1.5 mmol) was obtained in 57% yield as an oil after silica gel column chromatography. MS m/z (rel intensity) 618 (M+23)+ (17), 596 (M+1)+ (100), 496 (38).

Step 2: (2R)-1-[(2S)-1-tert-Butoxycarbonyl-piperazine-2-carbonyl]-boroPro-(1S,2S,3R,5S)-pinanediol ester (17)

To a solution of compound 16 (314 mg, 0.53 mmol) in MeOH (6 mL) was added Pd/C (40 mg). The mixture was stirred under a H$_2$ atmosphere for 2 h. Upon completion of the reaction, it was filtered through a plough of Celite. The solvents were removed under reduced pressure and the oily residue used in the next step without further purification. MS m/z (rel intensity) 462 (M+1)+ (100), 406 (12), 362 (11).

Step 3: (2R)-1-[(2S)-1-tert-Butoxycarbonyl-4-methanesulfonyl-piperazine-2-carbonyl]-boroPro-(1S,2S, 3R,5S)-pinanediol ester (18)

To a solution of compound 17 (214mg, 0.46 mmol) in CH$_2$Cl$_2$ (5 mL) cooled to 0° C. was sequentially added N-methylmorpholine (204 μL, 1.9 mmol) and methanesulfonyl chloride (72 μL, 0.93 mmol). The reaction mixture was allowed to warm up to room temperature and stir for 3 hours. The reaction was then diluted with $CH_2Cl_2$ (6 ml) and water (6 mL). The organic phase was isolated and dried over $MgSO_4$. After filtration, solvents were removed under reduced pressure. The oily residue was purified by column chromatography (silica gel) using a mixture of EtOAc/Hexanes as eluent. Compound 18 (112 mg, 0.21 mmol) was obtained in 45% yield. MS m/z (rel intensity) 562 $(M+23)^+$ (14), 540 (M+1) (100), 388 (75).

Step 4: (2R)-1-[(2S)-4-Methanesulfonyl-piperazine-2-carbonyl]-boroPro-OH (19)

The protocol described above for the N-Boc deprotection and pinanediol ester hydrolysis in the synthesis of compound 12 was applied to 18 (112 mg, 0.21 mg). Compound 19 (32 mg, 0.11 mmol) was obtained in 53% yield. 19.TFA salt $^1$H-NMR (500 MHz, $D_2O$) δ 4.32 (dd, J=11.0, 3.5 Hz, 1H), 4.05 (m, 1H), 3.93 (m, 1H), 3.77 (m, 1H), 3.60 (ddd, J=10.5, 8.0, 2.5 Hz, 1H), 3.47 (ddd, J=12.5, 3.0, 3.0, 1H), 3.35 (m, 2H), 3.16 (m, 2H), 3.02 (dd, J=13.8, 11.3 Hz, 1H), 2.93 (s, 3H), 1.96 (m, 2H), 1.81 (m, 1H), 1.72 (m, 1H), 1.56 (m, 1H). MS m/z (rel intensity) 575 (12), 328 $(M +23)^+$ (6), 288 (M−17) (100).

Example 15

Synthesis of Series F Compounds: (2R)-1-{2-[(3S)-Pyrrolidin-3-ylamino]-acetyl}-boroPro-OH (21)

Step 1: (2R)-1-{2-[(3S)-1-tert-Butoxycarbonyl-pyrrolidin-3-ylamino]-acetyl}-boroPro-(1S,2S,3R,5S)-pinanediol ester (20)

The protocol described above for the synthesis of 3B was followed employing (3S)-3-amino-pyrrolidine-1-carboxylic acid tert-butyl ester in place of cyclopentylamine. Compound 20 was obtained as an oil.

Step 2: (2R)-1-{2-[(3S)-Pyrrolidin-3-ylamino]-acetyl}-boroPro-OH (21)

The protocol described above for the N-Boc deprotection and pinanediol ester deprotection of compound 12 was applied to 20. Compound 21 was obtained as a white solid. 21-TFA salt $^1$H-NMR (500 MHz, $CD_3OD$) δ 4.12 (m, 3H), 3.76 (m, 1H), 3.54 (m, 3H), 3.41 (m, 2H), 3.26 (m, 1H), 2.55 (m, 1H), 2.28 (m, 1H), 2.05 (m, 3H), 1.74 (m, 1H). MS m/z (rel intensity) 241 (M) (27), 224 (100), 209 (73), 155 (47).

Example 16

Using the procedures illustrated above, the following compounds in the Table were prepared and characterized using liquid chromatography-mass spectroscopy (LC-MS).

TABLE

| Compound No. | Series | Structure | LC-MS |
|---|---|---|---|
| 22 | A | 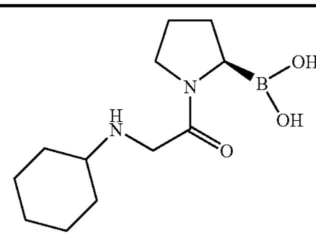 | 255 (M + 1) (13), 237 (100) |
| 23 | A | 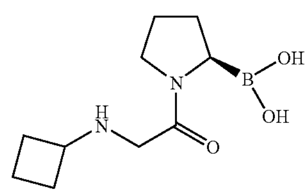 [SMILES: O=C(CNC1CCC1)N1CCC[C@H]1B(O)O] | 227 (M + 1) (10), 209 (100) |
| 24 | A | 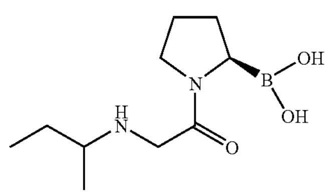 [SMILES: CCC(C)NCC(=O)N1CCC[C@H]1B(O)O] | 229 (M + 1) (18), 211 (100) |
| 25 | A | 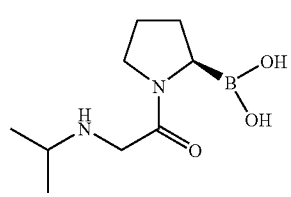 | 215 (M + 1) (12), 197 (100) |

TABLE-continued

| Compound No. | Series | Structure | LC-MS |
|---|---|---|---|
| 26 | A | 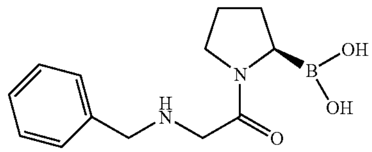 [SMILES: O=C(CNCc1ccccc1)N1CCC[C@H]1B(O)O] | 263 (M + 1) (5), 245 (100) |
| 27 | A | 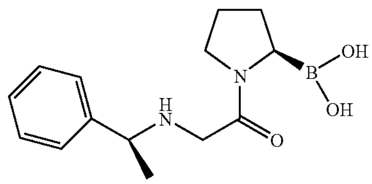 [SMILES: C[C@H](NCC(=O)N1CCC[C@H]1B(O)O)c1ccccc1] | 277 (M + 1) (4), 259 (100) |
| 28 | A | 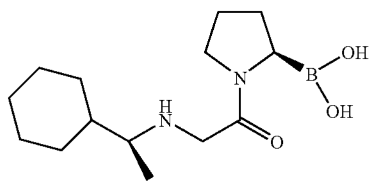 [SMILES: C[C@H](NCC(=O)N1CCC[C@H]1B(O)O)C1CCCCC1] | 283 (M + 1) (22), 265 (100) |
| 29 | A | 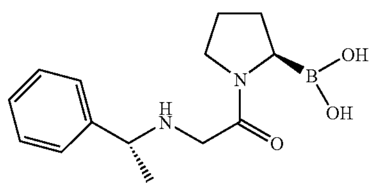 [SMILES: C[C@@H](NCC(=O)N1CCC[C@H]1B(O)O)c1ccccc1] | 277 (M + 1) (5), 259 (100) |
| 30 | A | 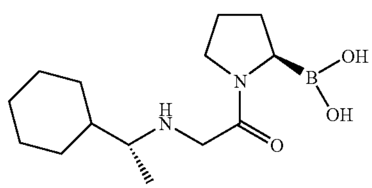 [SMILES: C[C@@H](NCC(=O)N1CCC[C@H]1B(O)O)C1CCCCC1] | 283 (M + 1) (21), 265 (100) |
| 31 | A | 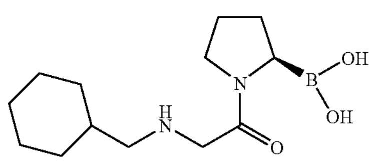 [SMILES: O=C(CNCC1CCCCC1)N1CCC[C@H]1B(O)O] | 269 (M + 1) (16), 251 (100) |
| 32 | A | 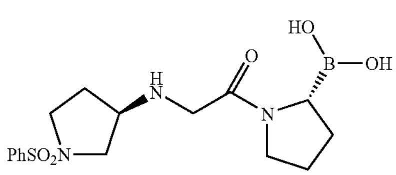 | 763 (6), 382 (M + 1) (100) |
| 33 | A | 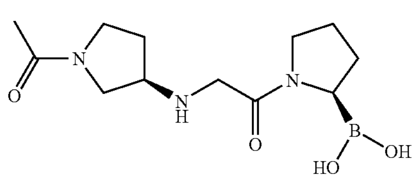 [SMILES: CC(=O)N1CC[C@@H](NCC(=O)N2CCC[C@H]2B(O)O)C1] | 284 (M + 1) (19), 266 (100) |

| Compound No. | Series | Structure | LC-MS |
|---|---|---|---|
| 34 | A | 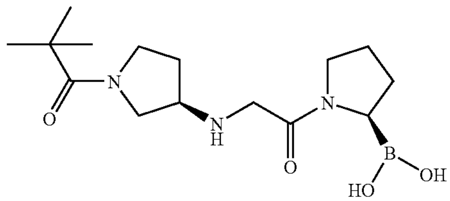 [SMILES: CC(C)(C)C(=O)N1CC[C@@H](NCC(=O)N2CCC[C@H]2B(O)O)C1] | 651 (28), 326 (M + 1) (57), 308 (100) |
| 35 | A | 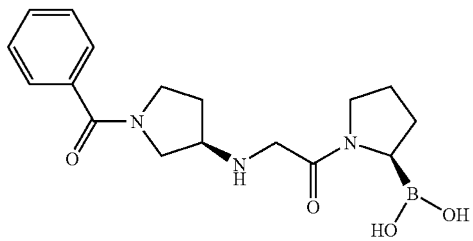 [SMILES: O=C(c1ccccc1)N1CC[C@@H](NCC(=O)N2CCC[C@H]2B(O)O)C1] | 691 (22), 346 (M + 1) (100), 328 (86) |
| 36 | A | 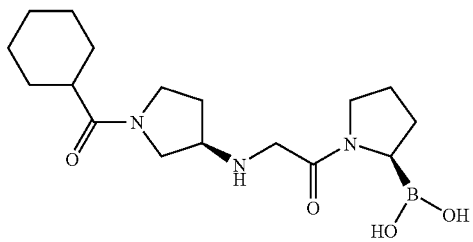 [SMILES: O=C(C1CCCCC1)N1CC[C@@H](NCC(=O)N2CCC[C@H]2B(O)O)C1] | 703 (28), 352 (M + 1) (18), 334 (100) |
| 37 | A | 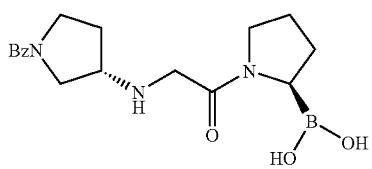 | 691 (49), 346 (M + 1) (14), 328 (100) |
| 38 | A | 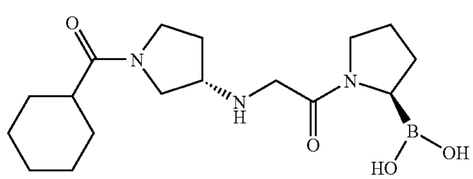 [SMILES: O=C(C1CCCCC1)N1CC[C@H](NCC(=O)N2CCC[C@H]2B(O)O)C1] | 703 (27), 352 (M+ 1) (3), 334 (100) |
| 39 | A | 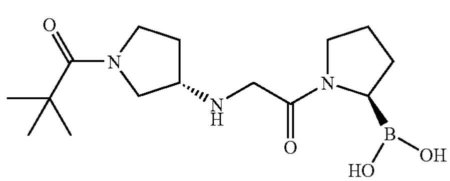 [SMILES: CC(C)(C)C(=O)N1CC[C@H](NCC(=O)N2CCC[C@H]2B(O)O)C1] | 651 (48), 326 (13), 308 (100) |
| 40 | A | 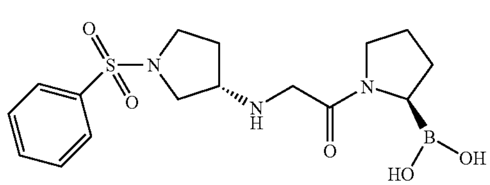 [SMILES: O=C(CN[C@H]1CCN(S(=O)(=O)c2ccccc2)C1)N1CCC[C@H]1B(O)O] | 382 (M+ 1) (100), 364 (7) |
| 41 | A | 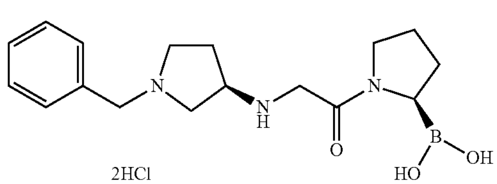 [SMILES: O=C(CN[C@@H]1CCN(Cc2ccccc2)C1)N1CCC[C@H]1B(O)O ; "2HCl"] | 332 (M+ 1) (100), 314 (10) |

TABLE-continued

| Compound No. | Series | Structure | LC-MS |
|---|---|---|---|
| 42 | A | 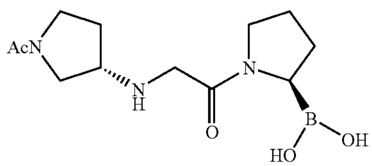 | 531 (15), 266 (M − 17) (100) |
| 43 | A | 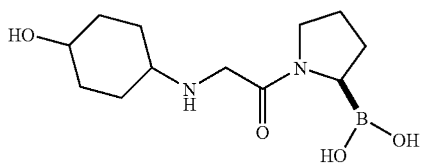 [SMILES: O=C(CNC1CCC(O)CC1)N1CCC[C@H]1B(O)O] | 271 (M + 1) (100), 253 (16) |
| 44 | A | 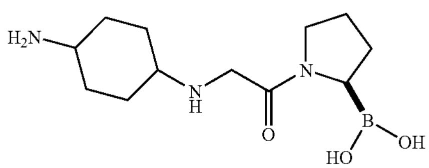 [SMILES: NC1CCC(NCC(=O)N2CCC[C@H]2B(O)O)CC1] | 270 (M + 1) (100), 252 (17) |
| 45 | A | 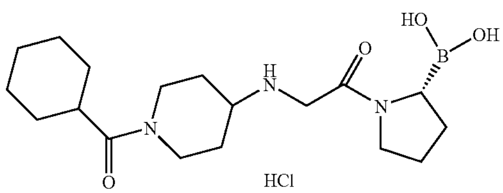 [SMILES: O=C(C1CCCCC1)N1CCC(NCC(=O)N2CCC[C@H]2B(O)O)CC1 ; Cl] | 731 (42), 366 (M + 1) (100), 348 (43) |
| 46 | A | 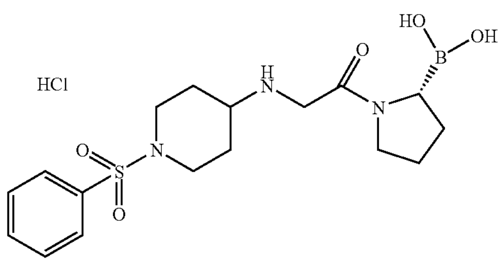 [SMILES: O=C(CNC1CCN(S(=O)(=O)c2ccccc2)CC1)N1CCC[C@H]1B(O)O ; Cl] | 791 (12), 396 (M + 1) |
| 47 | A | 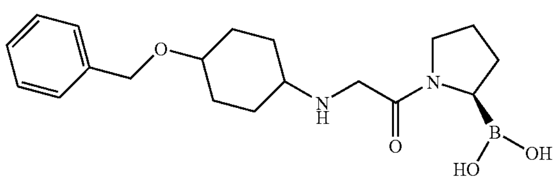 [SMILES: O=C(CNC1CCC(OCc2ccccc2)CC1)N1CCC[C@H]1B(O)O] | 721 (10), 361 (M + 1) (100) |
| 48 | A | 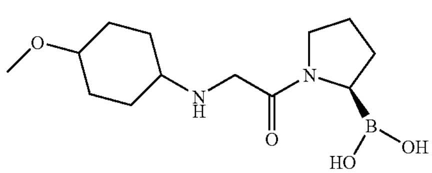 [SMILES: COC1CCC(NCC(=O)N2CCC[C@H]2B(O)O)CC1] | 285 (M + 1) (100), 267 (12) |
| 49 | A | 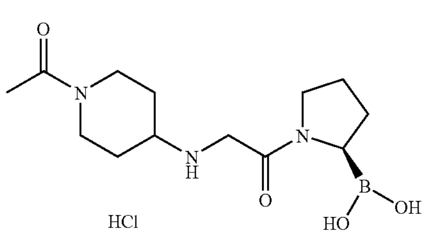 [SMILES: CC(=O)N1CCC(NCC(=O)N2CCC[C@H]2B(O)O)CC1 ; Cl] | 595 (48), 298 (M + 1) (100), 280 (80) |

| Compound No. | Series | Structure | LC-MS |
|---|---|---|---|
| 50 | A | 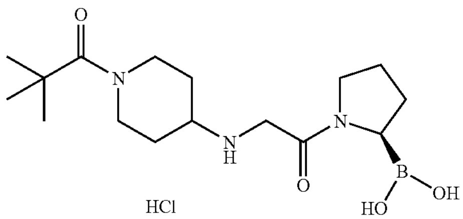 [SMILES: CC(C)(C)C(=O)N1CCC(NCC(=O)N2CCC[C@H]2B(O)O)CC1 ; Cl] | 679 (29),<br>340 (100) |
| 51 | A | 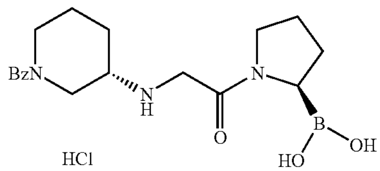 | 719 (92),<br>360 (M + 1) (65),<br>342 (100) |
| 52 | A | 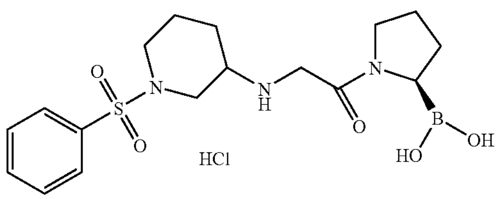 [SMILES: O=C(CNC1CCCN(S(=O)(=O)c2ccccc2)C1)N1CCC[C@H]1B(O)O ; Cl] | 791 (35),<br>396 (M + 1) (100),<br>378 (14) |
| 53 | A | 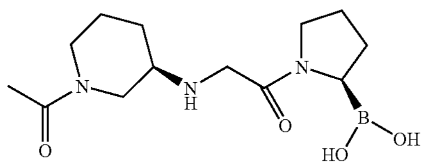 [SMILES: CC(=O)N1CCC[C@@H](NCC(=O)N2CCC[C@H]2B(O)O)C1] | 595 (89),<br>298 (M + 1) (44),<br>280 (100) |
| 54 | A | 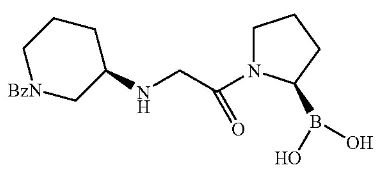 | 719 (72),<br>360 (M + 1) (40),<br>342 (100) |
| 55 | A | 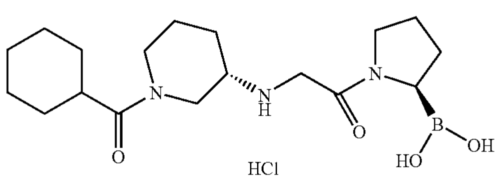 [SMILES: O=C(C1CCCCC1)N1CCC[C@H](NCC(=O)N2CCC[C@H]2B(O)O)C1 ; Cl] | 731 (100),<br>366 (M + 1) (34),<br>348 (86) |
| 56 | A | 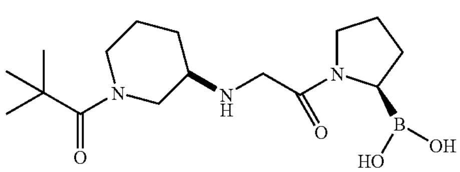 | 340 (M + 1) (5),<br>322 (100),<br>304 (18) |
| 57 | A | 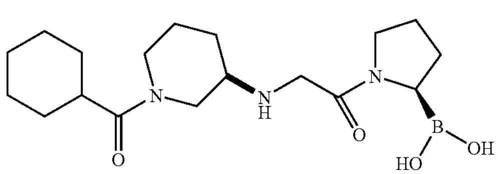 | 731 (100),<br>366 (M + 1) (52),<br>348 (94) |

TABLE-continued

| Compound No. | Series | Structure | LC-MS |
|---|---|---|---|
| 58 | A | 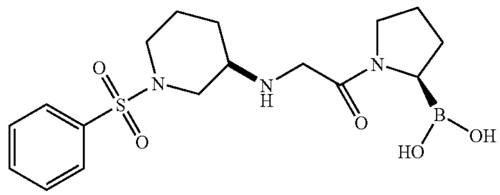 | 773 (33), 396 (M + 1) (100), 378 (16) |
| 59 | A | 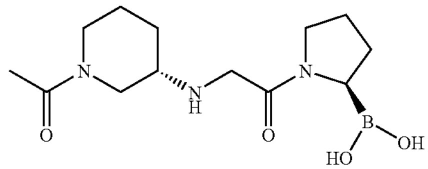 [SMILES: CC(=O)N1CCC[C@H](NCC(=O)N2CCC[C@H]2B(O)O)C1] | 595 (93), 298 (M + 1) (26), 280 (100) |
| 60 | A | 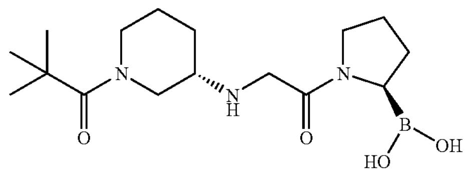 [SMILES: CC(C)(C)C(=O)N1CCC[C@H](NCC(=O)N2CCC[C@H]2B(O)O)C1] | 679 (100), 340 (98), 322 (70) |
| 61 | A | 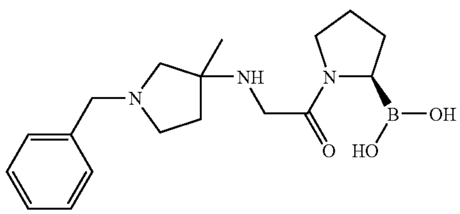 [SMILES: CC1(NCC(=O)N2CCC[C@H]2B(O)O)CCN(Cc2ccccc2)C1] | 346 (M + 1) (100), 328 (12) |
| 62 | B | 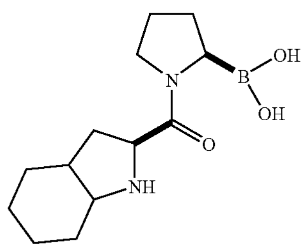 [SMILES: O=C([C@@H]1CC2CCCCC2N1)N1CCC[C@H]1B(O)O] | 249 (M − 17) major, 267 (M + 1) minor |
| 63 | B | 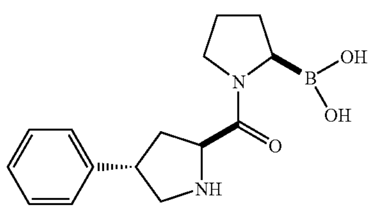 [SMILES: O=C([C@@H]1C[C@@H](c2ccccc2)CN1)N1CCC[C@H]1B(O)O] | 289 (M + 1) minor, 271 (M − 17) major |
| 64 | B | 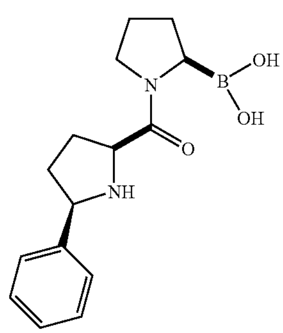 [SMILES: O=C([C@@H]1CC[C@H](c2ccccc2)N1)N1CCC[C@H]1B(O)O] | 289 (M + 1) minor, 271 (M − 17) major |

| Compound No. | Series | Structure | LC-MS |
|---|---|---|---|
| 65 | B | 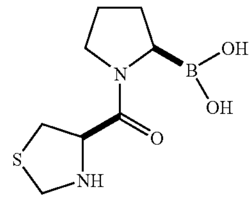 [SMILES: O=C([C@@H]1CSCN1)N1CCC[C@H]1B(O)O] | 213 (M − 17), 425 (2 M + 1) |
| 66 | B | 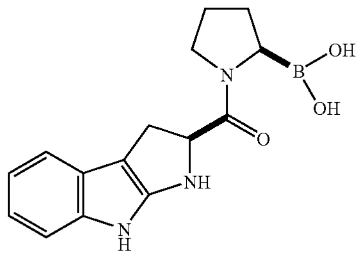 [SMILES: O=C([C@@H]1Cc2c([nH]c3ccccc23)N1)N1CCC[C@H]1B(O)O] | 282 (M − 17) major |
| 67 | | 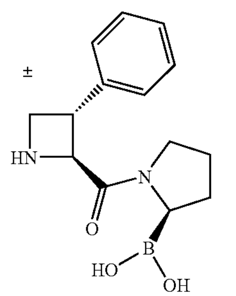 [SMILES: O=C([C@H]1NC[C@@H]1c1ccccc1)N1CCC[C@H]1B(O)O] | 257 (M − 17) major, 275 (M + 1) minor |
| 68 | B | 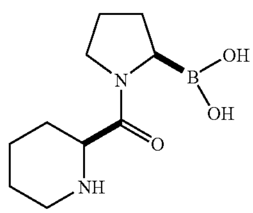 [SMILES: O=C([C@@H]1CCCCN1)N1CCC[C@H]1B(O)O] | 209 (M − 17) major, 227 (M + 1) minor |
| 69 | B | 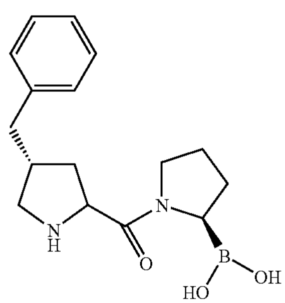 [SMILES: O=C(C1C[C@@H](Cc2ccccc2)CN1)N1CCC[C@H]1B(O)O] | 285 (M − 17) major, 303 (M + 1) minor |
| 70 | B | 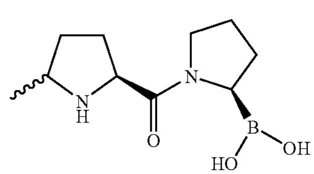 [SMILES: CC1CC[C@@H](C(=O)N2CCC[C@H]2B(O)O)N1] | 209 (M − 17) major, 227 (M + 1) minor |

TABLE-continued

| Compound No. | Series | Structure | LC-MS |
|---|---|---|---|
| 71 | B | (structure with 4-hydroxypyrrolidine-carbonyl-pyrrolidine boronic acid) | 211 (M − 17) major, 229 (M + 1) minor |
| 72 | B | (2-aminocyclopentyl carbonyl pyrrolidine boronic acid, cis) | 209 (M − 17) major, 227 (M + 1) minor |
| 73 | B | (2-aminocyclopentyl carbonyl pyrrolidine boronic acid, 1R,2R) | 209 (M − 17) major, 227 (M + 1) minor |
| 74 | B | HCl (aminoindane carbonyl pyrrolidine boronic acid) | 257 (M − 17) major, 275 (M + 1) minor |
| 75 | B | (2-aminocyclopentyl carbonyl pyrrolidine boronic acid, 1S,2S) | 209 (M − 17) major, 227 (M + 1) minor |
| 76 | B | (2-aminocyclohexyl carbonyl pyrrolidine boronic acid) | 223 (M − 17) major, 241 (M + 1) minor |
| 77 | B | (2-aminocyclohexyl carbonyl pyrrolidine boronic acid, ±) | 223 (M − 17) major, 241 (M + 1) minor |

| Compound No. | Series | Structure | LC-MS |
|---|---|---|---|
| 78 | B | 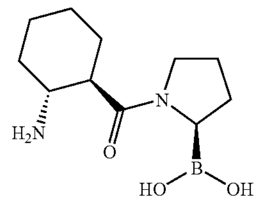 [SMILES: N[C@@H]1CCCC[C@H]1C(=O)N1CCC[C@H]1B(O)O] | 223 (M − 17) major, 241 (M + 1) minor |
| 79 | B | 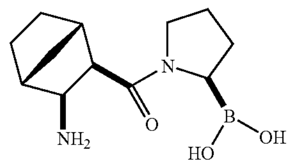 [SMILES: N[C@H]1[C@@H]2CC[C@@H](C2)[C@H]1C(=O)N1CCC[C@H]1B(O)O] | 235 (M − 17) major, 253 (M + 1) minor |
| 80 | B | 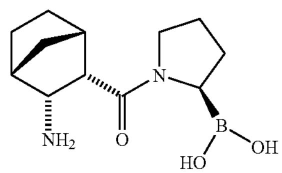 [SMILES: N[C@@H]1[C@@H]2CC[C@@H](C2)[C@@H]1C(=O)N1CCC[C@H]1B(O)O] | 235 (M − 17) major, 253 (M + 1) minor |
| 81 | B | (1R,2S) | 235 (M − 17) major, 253 (M + 1) minor |
| 82 | B | 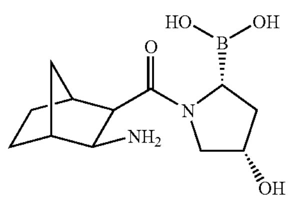 [SMILES: NC1C2CCC(C2)C1C(=O)N1C[C@@H](O)C[C@H]1B(O)O] | 251 (M − 17) major, 269 (M + 1) minor |
| 83 | B | 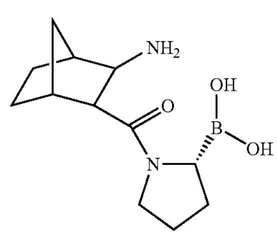 [SMILES: NC1C2CCC(C2)C1C(=O)N1CCC[C@H]1B(O)O] | 235 (M − 17) major, 253 (M + 1) minor |
| 84 | B | 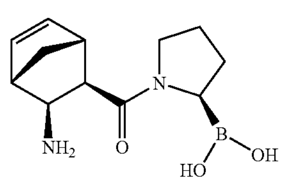 [SMILES: N[C@@H]1[C@H](C(=O)N2CCC[C@H]2B(O)O)[C@H]2C=C[C@@H]1C2] | 233 (M − 17) major, 251 (M + 1) minor |
| 85 | B | 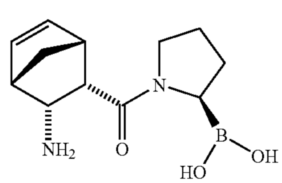 [SMILES: N[C@H]1[C@@H](C(=O)N2CCC[C@H]2B(O)O)[C@H]2C=C[C@@H]1C2] | 233 (M − 17) major, 251 (M + 1) minor |

TABLE-continued
| Compound No. | Series | Structure | LC-MS |
|---|---|---|---|
| 86 | B | 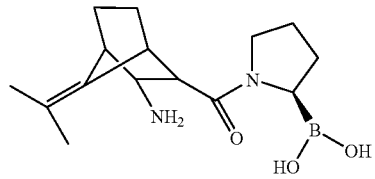 [SMILES: CC(C)=C1C2CCC1C(C(=O)N1CCC[C@H]1B(O)O)C2N] | 275 (M − 17) major, 293 (M + 1) minor |
| 87 | B | 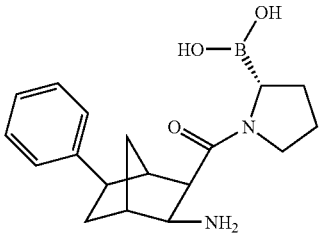 70% 6-Ph, 30% 5-Ph Predominate isomer drawn | 311 (M − 17) major, 329 (M + 1) minor |
| 88 | B | 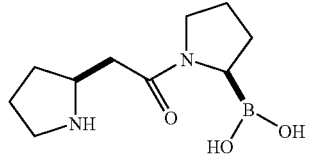 | 209 (M − 17) major, 227 (M + 1) minor |
| 89 | B | 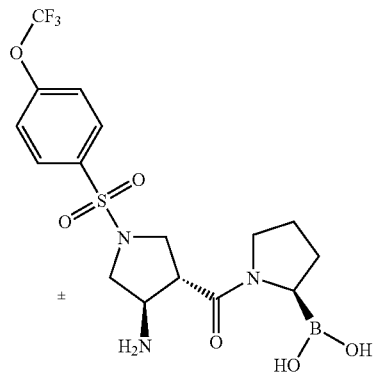 [SMILES: N[C@H]1CN(S(=O)(=O)c2ccc(OC(F)(F)F)cc2)C[C@@H]1C(=O)N1CCC[C@H]1B(O)O] | 434 (M − 17) major |
| 90 | B | 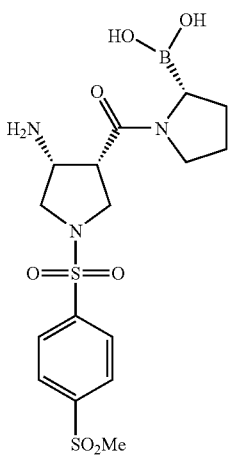 [SMILES: CS(=O)(=O)c1ccc(S(=O)(=O)N2C[C@H](N)[C@H](C(=O)N3CCC[C@H]3B(O)O)C2)cc1] | 446 (M + 1) (23), 428 (100) |

TABLE-continued
| Compound No. | Series | Structure | LC-MS |
|---|---|---|---|
| 91 | B | 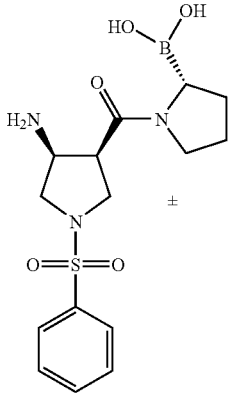 [SMILES: N[C@@H]1CN(S(=O)(=O)c2ccccc2)C[C@@H]1C(=O)N1CCC[C@H]1B(O)O] | 350 (M − 17) major, 368 (M + 1) minor |
| 92 | B | 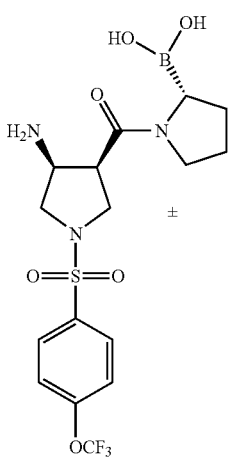 [SMILES: N[C@@H]1CN(S(=O)(=O)c2ccc(OC(F)(F)F)cc2)C[C@@H]1C(=O)N1CCC[C@H]1B(O)O] | 434 (M − 17) major |
| 93 | B | 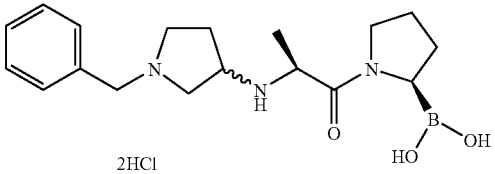 [SMILES: C[C@H](NC1CCN(Cc2ccccc2)C1)C(=O)N1CCC[C@H]1B(O)O ; "2HCl"] | 346 (M + 1) (100), 328 (14) |
| 94 | B | 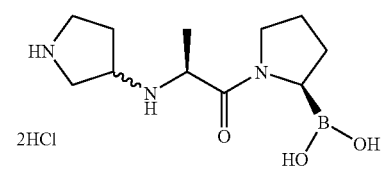 [SMILES: "2HCl" ; C[C@H](NC1CCNC1)C(=O)N1CCC[C@H]1B(O)O] | 511 (9), 256 (M + 1) (100), 238 (19) |
| 95 | B | 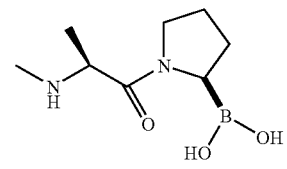 | 201 (M + 1) (100), 183 (22) |
| 96 | B | 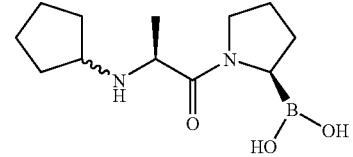 [SMILES: C[C@H](NC1CCCC1)C(=O)N1CCC[C@H]1B(O)O] | 255 (M + 1) (100), 237 (100) |

TABLE-continued

| Compound No. | Series | Structure | LC-MS |
|---|---|---|---|
| 97 | B | 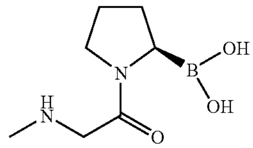 | 187 (M + 1) (5), 169 (100) |
| 98 | B | 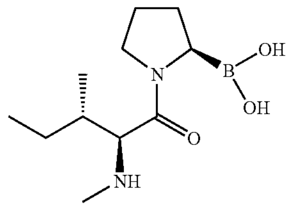 [SMILES: CC[C@H](C)[C@H](NC)C(=O)N1CCC[C@H]1B(O)O] | 243 (M + 1) (5), 225 (71) |
| 99 | B | 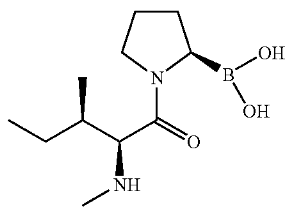 [SMILES: CC[C@@H](C)[C@H](NC)C(=O)N1CCC[C@H]1B(O)O] | 449 (5), 243 (M + 1) (7), 225 (100) |
| 100 | B | 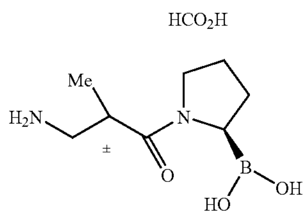 [SMILES: "HCO2H" ; CC(CN)C(=O)N1CCC[C@H]1B(O)O] | 223 (M + 23) (3), 183 (48) |
| 101 | B | 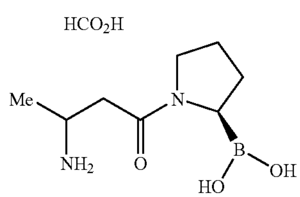 [SMILES: "HCO2H" ; CC(N)CC(=O)N1CCC[C@H]1B(O)O] | 223 (M + 23) (4), 183 (10) |
| 102 | C | 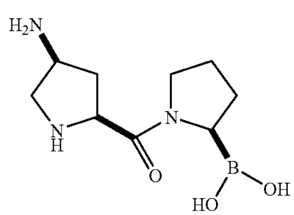 | 228 (M + 1) (55), 210 (M − 17) (95) |
| 103 | C | 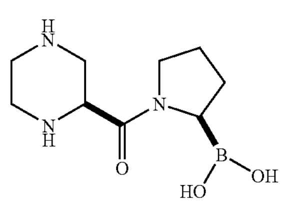 | 210 (M − 17) major, 228 (M + 1) minor |

TABLE-continued

| Compound No. | Series | Structure | LC-MS |
|---|---|---|---|
| 104 | C | 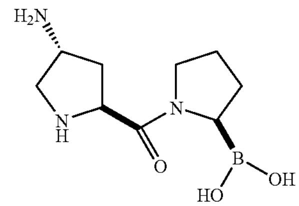 | 210 (M − 17) major, 228 (M + 1) minor |
| 105 | D | 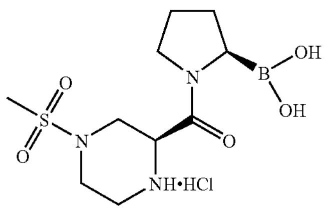 | 575 (12), 328 (M + 23) (6), 288 (100) |
| 106 | D | 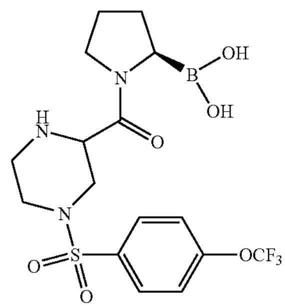 [SMILES: O=C(C1CN(S(=O)(=O)c2ccc(OC(F)(F)F)cc2)CCN1)N1CCC[C@H]1B(O)O] | 452 (M + 1) (3), 434 (100) |
| 107 | D | 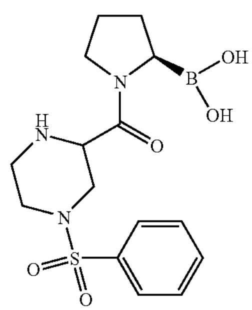 [SMILES: O=C(C1CN(S(=O)(=O)c2ccccc2)CCN1)N1CCC[C@H]1B(O)O] | 368 (M + 1) (2), 350 (100) |
| 108 | D | 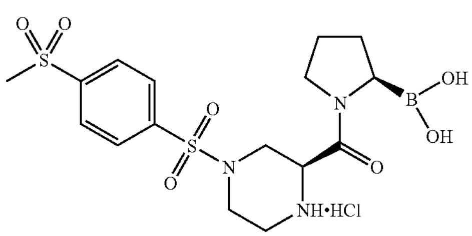 | 428 (M − 17) (100) |
| 109 | D | 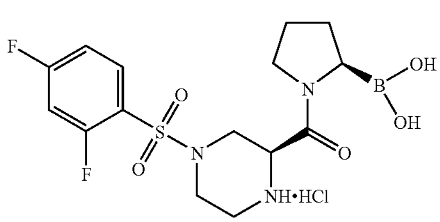 | 386 (M − 17) (100) |

| Compound No. | Series | Structure | LC-MS |
|---|---|---|---|
| 110 | D | 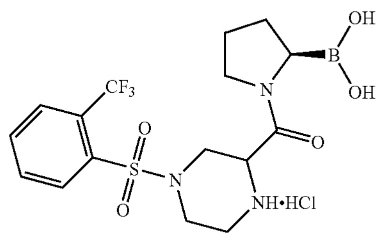 | 436 (M + 1) (10), 418 (100) |
| 111 | D | 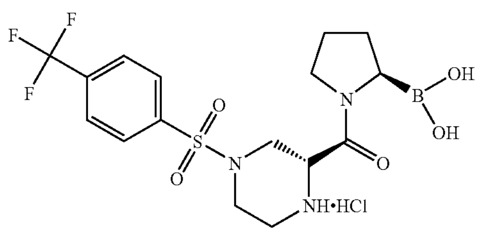 | 436 (M + 1) (4), 418 (100) |
| 112 | D | (formic acid salt) | 627 (25), 332 (M + 1) (10), 314 (100) |
| 113 | D | 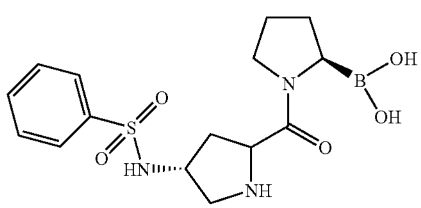 | 368 (M + 1) (38), 350 (100) |
| 114 | D | 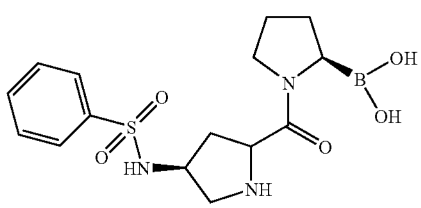 | 350 (M − 17) (100), 332 (22) |
| 115 | D | 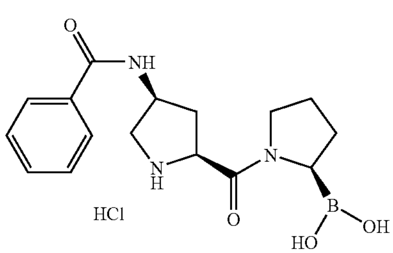 [SMILES: O=C(N[C@@H]1CN[C@H](C(=O)N2CCC[C@H]2B(O)O)C1)c1ccccc1 ; Cl] | 332 (M + 1) (4), 314 (93) |

TABLE-continued
| Compound No. | Series | Structure | LC-MS |
|---|---|---|---|
| 116 | D | 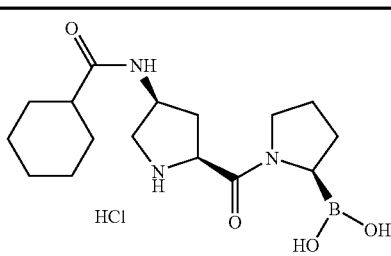 | 338 (M + 1) (3), 320 (98) |
| 117 | D | 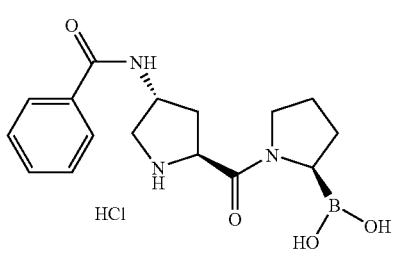 [SMILES: O=C(N[C@H]1CN[C@H](C(=O)N2CCC[C@H]2B(O)O)C1)c1ccccc1 ; Cl] | 332 (M + 1) (27), 314 (100) |
| 118 | D | 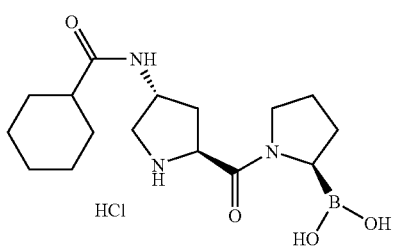 [SMILES: O=C(N[C@H]1CN[C@H](C(=O)N2CCC[C@H]2B(O)O)C1)C1CCCCC1 ; Cl] | 338 (M + 1) (21), 320 (100) |
| 119 | D | 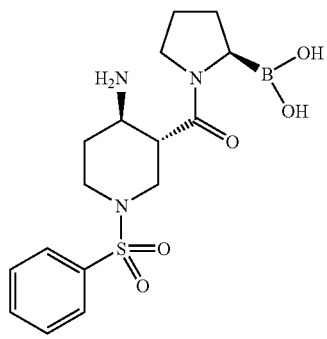 [SMILES: N[C@@H]1CCN(S(=O)(=O)c2ccccc2)C[C@H]1C(=O)N1CCC[C@H]1B(O)O] | 727 (8), 368 (M − 17) (56) |
| 120 | D | 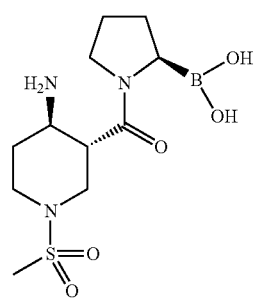 [SMILES: CS(=O)(=O)N1CC[C@@H](N)[C@H](C(=O)N2CCC[C@H]2B(O)O)C1] | 603 (24), 302 (M − 17) (73) |
| 121 | F | 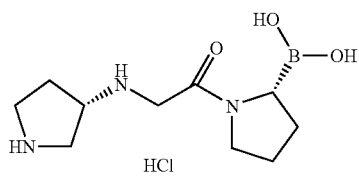 [SMILES: O=C(CN[C@H]1CCNC1)N1CCC[C@H]1B(O)O ; Cl] | 242 (M + 1) (100), 224 (19) |

TABLE-continued

| Compound No. | Series | Structure | LC-MS |
|---|---|---|---|
| 122 | F | 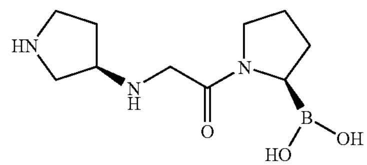 [SMILES: O=C(CN[C@@H]1CCNC1)N1CCC[C@H]1B(O)O] | 242 (M + 1) (100), 224 (9) |
| 123 | F | 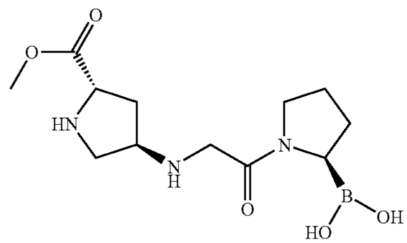 [SMILES: COC(=O)[C@@H]1C[C@@H](NCC(=O)N2CCC[C@H]2B(O)O)CN1] | 300 (M + 1) (11), 282 (100) |
| 124 | F | 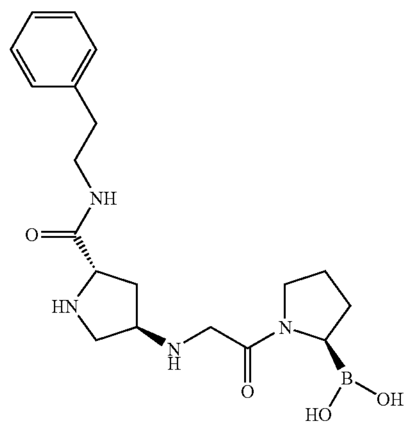 [SMILES: O=C(NCCc1ccccc1)[C@@H]1C[C@@H](NCC(=O)N2CCC[C@H]2B(O)O)CN1] | 371 (M − 17) major, 389 (M + 1) minor |
| 125 | F | 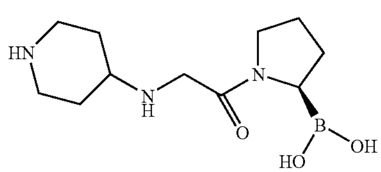 [SMILES: O=C(CNC1CCNCC1)N1CCC[C@H]1B(O)O] | 256 (M + 1) (100) |
| 126 | F | 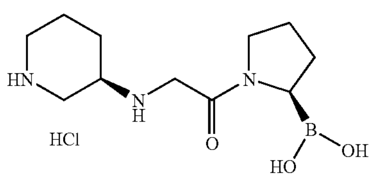 [SMILES: O=C(CN[C@@H]1CCCNC1)N1CCC[C@H]1B(O)O ; Cl] | 256 (M + 1) (100), 238 (8) |
| 127 | F | 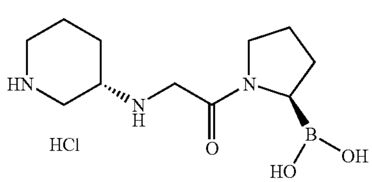 [SMILES: O=C(CN[C@H]1CCCNC1)N1CCC[C@H]1B(O)O ; Cl] | 256 (M + 1) (100), 238 (10) |
| 128 | F | 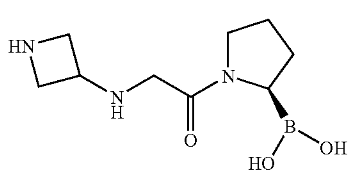 [SMILES: O=C(CNC1CNC1)N1CCC[C@H]1B(O)O] | 210 (M − 17) major, 228 (M + 1) minor |

TABLE-continued

| Compound No. | Series | Structure | LC-MS |
|---|---|---|---|
| 129 | F | 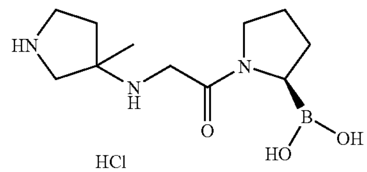 [SMILES: CC1(NCC(=O)N2CCC[C@H]2B(O)O)CCNC1 ; Cl] | 256 (M + 1) (100), 238 (10) |
| 130 | G | 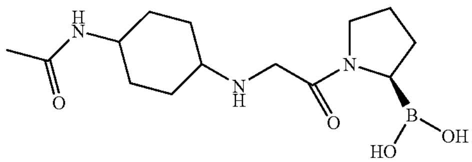 [SMILES: CC(=O)NC1CCC(NCC(=O)N2CCC[C@H]2B(O)O)CC1] | 623 (28), 312 (M + 1) (100), 294 (30) |
| 131 | G | 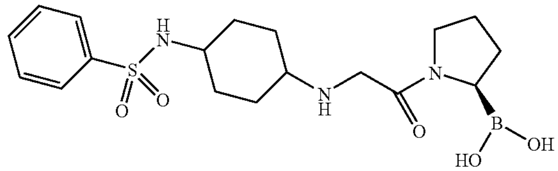 [SMILES: O=C(CNC1CCC(NS(=O)(=O)c2ccccc2)CC1)N1CCC[C@H]1B(O)O] | 819 (20), 410 (100) |
| 132 | G | 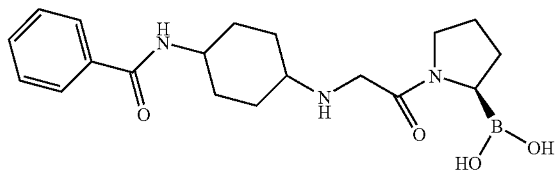 [SMILES: O=C(NC1CCC(NCC(=O)N2CCC[C@H]2B(O)O)CC1)c1ccccc1] | 374 (M + 1) (100), 356 (67) |
| 133 | G | 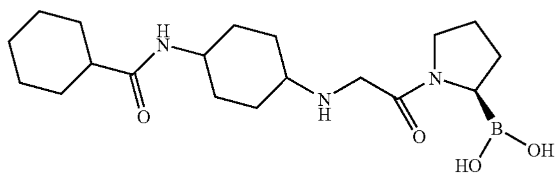 [SMILES: O=C(NC1CCC(NCC(=O)N2CCC[C@H]2B(O)O)CC1)C1CCCCC1] | 759 (57), 380 (M + 1) (100), 362 (64) |

Example 17

Dependence of Aminoboronate and Boronic Acid Forms of Inventive Compounds on pH

A 0.4 M stock solution of $Na_2HPO_4$ was prepared by dissolving 909 mg of salt in 16 mL of $D_2O$. pH was adjusted to the desired value by dropwise addition of either 20% DCl in $D_2O$ or 5% DCl in $D_2O$. The pH values were measured with a Fisher Scientific Accumet AB15 pH meter. Aliquots of the stock solution (4 mL) were prepared and 8 mg of compound 4 in the closed form (aminoboronate) were added to each one. The scintillation vials were capped, sealed with parafilm and allowed to stand in the dark for three days. After this time pH was measured again. The open/closed (i.e., linear/cyclic) ratio of compound 4 isomers at each pH was determined by recording the corresponding $^1$H-NMR spectra in a Varian AS 500 MHz instrument and measuring the ratio of the integrals of the peaks at 2.90-2.95 ppm and 2.40-2.50 ppm characteristic of the open and closed forms, respectively. FIG. 1 shows that the closed form predominates at higher pHs such as physiological pH, whereas the open form predominates at lower pHs.

Example 18

The final compounds of Examples 1-16 were tested in vitro as described herein and each displayed an $IC_{50}$ or $K_i$ of 10 μM or less.

While the invention has been described and exemplified in sufficient detail for those skilled in this art to make and use it, various alternatives, modifications, and improvements will be apparent to those skilled in the art without departing from the spirit and scope of the claims.

All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described.

Other embodiments are set forth within the following claims.

What is claimed is:

1. A method for inhibiting dipeptidyl peptidase-IV comprising contacting dipeptidyl peptidase-IV with an effective amount of a compound of formula (I):

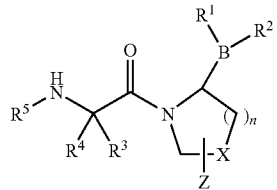

(I)

including all cyclic isomers thereof, stereoisomers thereof, solvates thereof, hydrates thereof and pharmaceutically acceptable salts thereof, wherein:
n is 1;
X is $CH_2$, $CF_2$ or $C(CH_3)_2$;
Z is H, halogen, hydroxyl, $(C_{1-6})$alkoxy, $(C_{1-12})$alkyl, $(C_{3-12})$cycloalkyl, phenyl, or heteroaryl; wherein the phenyl and heteroaryl groups are optionally mono- or independently plurisubstituted with $R^7$;
optionally, X together with an adjacent ring carbon and Z form a fused cyclopropyl;
optionally, one of the bonds in the ring containing X is a double bond;
$R^7$ is halogen, $(C_{1-10})$alkyl, $(C_{1-10})$alkoxy, $(C_{1-10})$alkylamino, $(C_{1-10})$dialkylamino, benzyl, benzyloxy, hydroxy$(C_{1-6})$alkyl, hydroxymethyl, nitro, trifluoromethyl, trifluoromethoxy, trifluoromethylthio, N-hydroxyamino, cyano, carboxy, acetamido, hydroxy, sulfamoyl, sulfonamido, or carbamoyl;
$R^1$ and $R^2$ are each independently —OH, a hydroxyl bearing a boronic acid protecting group, or a group capable of being hydrolyzed to a hydroxyl group in an aqueous solution at physiological pH or in biological fluids;
$R^3$, $R^4$ and $R^5$ are selected from the following Set I or Set II;
Set I: $R^3$ and $R^4$ independently are hydrogen, $C_1$ to $C_6$ alkyl or $C_3$ to $C_6$ cycloalkyl; and $R^5$ is heteroaryl; cycloheteroalkyl or cycloheteroalkylalkyl; all optionally mono- or independently plurisubstituted with halogen, alkyl, polyhaloalkyl, alkoxy, haloalkoxy, polyhaloalkoxy, alkoxycarbonyl, alkenyl, alkynyl, cycloalkyl, cycloalkylalkyl, polycycloalkyl, heteroarylamino, arylamino, cycloheteroalkyl, cycloheteroalkylalkyl, hydroxy, hydroxyalkyl, nitro, cyano, amino, substituted amino, alkylamino, dialkylamino, thiol, alkylthio, alkylcarbonyl, acyl, alkoxycarbonyl, aminocarbonyl, alkynylamino-carbonyl, alkylaminocarbonyl, alkenylaminocarbonyl, alkylcarbonyloxy, alkylcarbonylamino, arylcarbonylamino, alkylsulfonylamino, alkylaminocarbonyl-amino, alkoxycarbonylamino, alkylsulfonyl, aminosulfinyl, aminosulfonyl, alkylsulfinyl, or sulfonamido; or,
Set II: $R^3$ and $R^4$ are hydrogen and $R^5$ is:

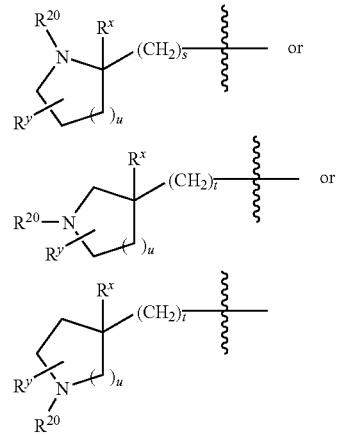

wherein
$R^{20}$ is hydrogen, $(C_{1-8})$alkyl, $(C_{1-6})$alkylcarbonyl, mono- or di-$(C_{1-6})$alkylaminocarbonyl, $(C_{3-8})$cycloalkylcarbonyl, benzyl, benzoyl, $(C_{1-6})$alkyloxycarbonyl, aralkyloxycarbonyl, pyridinyl, pyrimidinyl, phenyl, phenyl-substituted thiazolyl, phenylaminocarbonyl, alkylsulfonyl, or phenylsulfonyl; wherein the benzyl, benzoyl, pyridinyl, pyrimidinyl, phenyl, phenylaminocarbonyl, alkylsulfonyl, and phenylsulfonyl groups are optionally mono- or independently di-substituted with $R^{12}$;
$R^{12}$ is halogen, trifluoromethyl, cyano, nitro, $(C_{1-6})$alkyl, $(C_{1-6})$alkoxy, cycloalkyl, carboxy, acetamido, hydroxy, hydroxy$(C_{1-6})$alkyl, trifluoromethoxy, sulfamoyl, carbamoyl, sulfonamido, alkylsufonyl, phenylsulfonyl, aryl, or heteroaryl; wherein the aryl and heteroaryl groups are optionally mono- or independently plurisubstituted with $R^7$;
$R^x$ is hydrogen, $(C_{1-8})$alkyl, $(C_{3-12})$ cycloalkyl, benzyl, or phenyl; wherein the benzyl and phenyl groups are optionally mono- or independently di-substituted on the ring with $R^{12}$;
$R^y$ is absent or is halogen, $(C_{1-8})$alkyl, $(C_{1-8})$alkoxy, O-alkylcarboxylate, O-aralkylcarboxylate, N-alkylcarboxamido, N-aralkylcarboxamido, or phenyl;
s is 1 to 6; t is 0 to 6; and u is 0 to 3; and
wherein a bond bisected by a wavy line signifies a point of attachment.

2. A method according to claim 1, wherein the dipeptidyl peptidase-IV is within a mammal in need of treatment for a malcondition that can be regulated or normalized via inhibition of dipeptidyl peptidase-IV and the contacting step comprises administering to the mammal a therapeutically effective amount of the compound.

3. The method of claim 1 further comprising administering a therapeutically effective amount of a second medicament selected from the group consisting of a second medicament that increases insulin secretion, increases insulin sensitivity, reduces the uptake of sugar from the gastrointestinal tract, enhances the effect of endogenous peptides or proteins that affect glycemic control, or provides a replacement for endogenous peptides, proteins that affect glycemic control, or any combination thereof.

4. A method according to claim 3 wherein one or more second medicaments are administered and are selected from the group consisting of
  a) Other dipeptidyl peptidase-IV inhibitors;
  b) Insulin sensitizers selected from the group consisting of (i) PPAR agonists, (ii) biguanides, and (iii) protein phosphatase-1B inhibitors;
  c) Insulin or insulin mimetics;
  d) Sulfonylureas or other insulin secretagogues;
  e) α-glucosidase inhibitors;
  f) glucagons receptor agonists;
  g) GLP-1, GLP-1 mimetics, and GLP-1 receptor agonists;
  h) GLP-2, GLP-2 mimetics, and GLP-2 receptor agonists;
  i) GIP, GIP mimetics, and GIP receptor agonists;
  j) PACAP, PACAP mimetics, and PACAP receptor 3 agonists;
  k) Cholesterol lowering agents selected from the group consisting of (i) HMG-CoA reductase inhibitors, (ii) sequestrants, (iii) nicotinyl alcohol, nicotinic acid or a salt thereof, (iv) PPARα agonists, (v) PPARα/γ dual agonists, (vi) inhibitors of cholesterol absorption, (vii) acyl CoA:cholesterol acyltransferase inhibitors, and (viii) anti-oxidants;
  l) PPARδ agonists;
  m) Anti-obesity compounds;
  n) An ileal bile acid transporter inhibitor;
  o) Anti-inflammatory agents;
  p) G-CSF, G-CSF mimetics, and G-CSF receptor agonists; and
  q) EPO, EPO mimetics, and EPO receptor agonists.

5. The method of claim 1, wherein $R^1$ and $R^2$ are each hydroxyl.

6. The method of claim 1 wherein $R^1$ and $R^2$ are each hydroxyl that independently or together bear a boronic acid protecting group formed from (+)-pinanediol; pinacol; 1,2-dicyclohexyl-ethanediol; 1,2-ethanediol; 2,2-diethanolamine; 1,3-propanediol; 2,3-butanediol, diisopropyl tartrate; 1,4-butanediol; diisopropylethanediol; (S,S,)-5,6-decanediol; 1,1,2-triphenyl-1,2-ethanediol; (2R,3R)-1,4-dimethyoxy-1,1,4,4-tetraphenyl-2,3-butanediol; methanol; ethanol; isopropanol; catechol; or 1-butanol; or wherein $R^1$ and $R^2$ independently or together are a group capable of being hydrolyzed to form a boronic acid group —$B(OH)_2$ in an aqueous solution at physiological pH or in biological fluids.

7. The method of claim 1 wherein X is $CH_2$; the ring containing X is saturated; $R^1$ and $R^2$ are each hydroxyl, $R^3$ and $R^4$ are hydrogen; and $R^5$ is a group of Set I.

8. The method of claim 1 wherein X is $CH_2$; the ring containing X is saturated; $R^1$ and $R^2$ are each hydroxyl, $R^3$ and $R^4$ are hydrogen; and $R^5$ is a group of Set II.

9. The method of claim 1 wherein X is $CH_2$; the ring containing X is saturated; $R^1$ and $R^2$ are hydroxyl, $R^3$ and $R^4$ are hydrogen; and $R^5$ is a group of formula

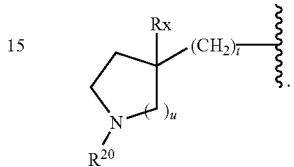

10. The method of of claim 8 wherein $R^x$ is hydrogen, $R^{20}$ is hydrogen, t is 0, and u is 1.

11. The method of 1 wherein the compound of formula (I) is

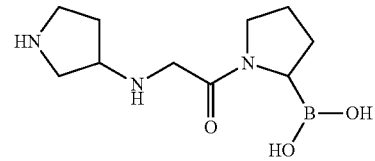 [SMILES: O=C(CNC1CCNC1)N1CCCC1B(O)O]

12. The method of 1 wherein the compound of formula (I) is

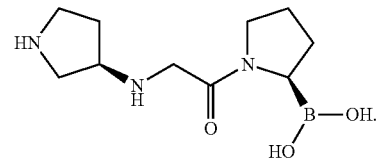 [SMILES: O=C(CN[C@@H]1CCNC1)N1CCC[C@H]1B(O)O]

* * * * *

UNITED STATES PATENT AND TRADEMARK OFFICE
CERTIFICATE OF CORRECTION

PATENT NO. : 8,415,295 B2  Page 1 of 13
APPLICATION NO. : 12/692276
DATED : April 9, 2013
INVENTOR(S) : Campbell et al.

It is certified that error appears in the above-identified patent and that said Letters Patent is hereby corrected as shown below:

On the Title page, in column 2, under Item (57) "Abstract", line 2, delete "$CH_2$," and insert --$CH_2$;--, therefor On the Title page, in column 2, under Item (57) "Abstract", line 6, delete "R7" and insert --$R^7$--, therefor On the Title page, in column 2, under Item (57) "Abstract", line 9, delete "$R^1$," and insert --$R^2$,--, therefor On Title page 2, in column 2, under Item (56) "Other Publications", line 10, delete "Filed" and insert --filed--, therefor On Title page 2, in column 2, under Item (56) "Other Publications", line 11, delete ""Chile" and insert --"Chilean--, therefor On Title page 2, in column 2, under Item (56) "Other Publications", line 15, delete "2006-539906 ," and insert --2006-539906,--, therefor On Title page 2, in column 2, under Item (56) "Other Publications", line 18, delete "Filed" and insert --filed--, therefor On Title page 2, in column 2, under Item (56) "Other Publications", line 21, delete "Mailed" and insert --mailed--, therefor On Title page 3, in column 1, under Item (56) "Other Publications", line 13, delete "11/381,090 ," and insert --11/381,090,--, therefor On Title page 3, in column 1, under Item (56) "Other Publications", line 15, delete "11/381,090" and insert --11/381,090,--, therefor Signed and Sealed this
Eighth Day of April, 2014

Michelle K. Lee
*Deputy Director of the United States Patent and Trademark Office*

CERTIFICATE OF CORRECTION (continued)
U.S. Pat. No. 8,415,295 B2

On Title page 3, in column 1, under Item (56) "Other Publications", line 17, delete "Mailed" and insert --mailed--, therefor On Title page 3, in column 1, under Item (56) "Other Publications", line 64, delete "Mailed" and insert --mailed--, therefor On Title page 3, in column 1, under Item (56) "Other Publications", line 71, delete "Mailed" and insert --mailed--, therefor On Title page 3, in column 2, under Item (56) "Other Publications", line 4, delete "Mailed" and insert --mailed--, therefor On Title page 3, in column 2, under Item (56) "Other Publications", line 5, delete "Mailed" and insert --mailed--, therefor On Title page 3, in column 2, under Item (56) "Other Publications", line 14, delete "pgs" and insert --pg--, therefor On Title page 3, in column 2, under Item (56) "Other Publications", line 27, delete "Mailed" and insert --mailed--, therefor On Title page 3, in column 2, under Item (56) "Other Publications", line 35, delete ""Israel" and insert --"Israeli--, therefor On Title page 3, in column 2, under Item (56) "Other Publications", line 37, delete "Mailed" and insert --mailed--, therefor On Title page 3, in column 2, under Item (56) "Other Publications", line 52, delete ""Taiwan" and insert --"Taiwanese--, therefor On Title page 3, in column 2, under Item (56) "Other Publications", line 54, delete "Mailed" and insert --mailed--, therefor On Title page 3, in column 2, under Item (56) "Other Publications", line 57, delete "CD 26)" and insert --CD26)--, therefor On Title page 3, in column 2, under Item (56) "Other Publications", line 57, delete "DPP IV" and insert --DPP-IV--, therefor On Title page 3, in column 2, under Item (56) "Other Publications", line 59, delete "Proteinases" and insert --Proteases--, therefor On Title page 3, in column 2, under Item (56) "Other Publications", line 60, delete "Hemophilus" and insert --Haemophilus--, therefor On Title page 4, in column 1, under Item (56) "Other Publications", line 3, delete "T," and insert --T.,-- therefor On Title page 4, in column 1, under Item (56) "Other Publications", line 3, delete "DPPIV" and insert --DPP-IV--, therefor On Title page 4, in column 1, under Item (56) "Other Publications", line 6, delete "L," and insert --L.,--, therefor On Title page 4, in column 1, under Item (56) "Other Publications", line 8, delete "U S A.," and insert --U S A,--, therefor On Title page 4, in column 1, under Item (56) "Other Publications", line 14, delete "J," and insert --J.,--, therefor On Title page 4, in column 1, under Item (56) "Other Publications", line 21, delete "H," and insert --H.,--, therefor On Title page 4, in column 1, under Item (56) "Other Publications", line 36, delete "Perspective"","  and insert --Perspective",--, therefor On Title page 4, in column 1, under Item (56) "Other Publications", line 40, delete "88.," and insert --88,--, therefor On Title page 4, in column 1, under Item (56) "Other Publications", line 55, delete "Denmark.," and insert --Denmark,--, therefor On Title page 4, in column 1, under Item (56) "Other Publications", line 57, delete "E," and insert --E.,--, therefor On Title page 4, in column 1, under Item (56) "Other Publications", line 65, delete "Discovery,Jul." and insert --Discovery, Jul.--, therefor On Title page 4, in column 1, under Item (56) "Other Publications", line 73, delete "Clin Exp" and insert --Clin. Exp.--, therefor On Title page 4, in column 2, under Item (56) "Other Publications", line 1, delete "A M," and insert --A. M.,--, therefor On Title page 4, in column 2, under Item (56) "Other Publications", line 3, delete "J Biol" and insert --J. Biol.--, therefor On Title page 4, in column 2, under Item (56) "Other Publications", line 5, delete "Lehninger,, A. .. L," and insert --Lehninger, A. L.,--, therefor On Title page 4, in column 2, under Item (56) "Other Publications", line 6, delete "A," and insert --A.,--, therefor On Title page 4, in column 2, under Item (56) "Other Publications", line 11, delete "R W," and insert --R. W.,--, therefor On Title page 4, in column 2, under Item (56) "Other Publications", line 16, delete "R," and insert --R.,--, therefor On Title page 4, in column 2, under Item (56) "Other Publications", line 23, delete "L," and insert --L.,--, therefor On Title page 4, in column 2, under Item (56) "Other Publications", line 24, delete "polymorphs,salts,co-crystals" and insert --polymorphs, salts, co-crystals--, therefor On Title page 4, in column 2, under Item (56) "Other Publications", line 25, delete "56.," and insert --56,--, therefor On Title page 4, in column 2, under Item (56) "Other Publications", line 40, delete "A," and insert --A.,--, therefor On Title page 4, in column 2, under Item (56) "Other Publications", line 43, delete "A," and insert --A.,--, therefor On Title page 5, in column 1, under Item (56) "Other Publications", line 6, delete "S," and insert --S.,--, therefor On Title page 5, in column 1, under Item (56) "Other Publications", line 24, delete "U.S." and insert --"U.S.--, therefor On Title page 5, in column 1, under Item (56) "Other Publications", line 25, delete "2010," and insert --2010",--, therefor On Title page 5, in column 1, under Item (56) "Other Publications", line 26, delete "U.S." and insert --"U.S.--, therefor On Title page 5, in column 1, under Item (56) "Other Publications", line 27, delete "2010," and insert --2010",--, therefor On Title page 5, in column 1, under Item (56) "Other Publications", line 28, delete "U.S." and insert --"U.S.--, therefor On Title page 5, in column 1, under Item (56) "Other Publications", line 29, delete "2010," and insert --2010",--, therefor

CERTIFICATE OF CORRECTION (continued)
U.S. Pat. No. 8,415,295 B2

On Title page 5, in column 1, under Item (56) "Other Publications", line 30, delete "Australian" and insert --"Australian--, therefor On Title page 5, in column 1, under Item (56) "Other Publications", line 31, delete "2010," and insert --2010",--, therefor On Title page 5, in column 1, under Item (56) "Other Publications", line 32, delete "Australian" and insert --"Australian--, therefor On Title page 5, in column 1, under Item (56) "Other Publications", line 33, delete "Filed" and insert --filed--, therefor On Title page 5, in column 1, under Item (56) "Other Publications", line 33, delete "2010," and insert --2010",--, therefor On Title page 5, in column 1, under Item (56) "Other Publications", line 34, delete "Japanese" and insert --"Japanese--, therefor On Title page 5, in column 1, under Item (56) "Other Publications", line 35, delete "2010," and insert --2010",--, therefor On Title page 5, in column 1, under Item (56) "Other Publications", line 36, delete "Japanese" and insert --"Japanese--, therefor On Title page 5, in column 1, under Item (56) "Other Publications", line 37, delete "2010," and insert --2010",--, therefor On Title page 5, in column 1, under Item (56) "Other Publications", line 38, delete "U.S." and insert --"U.S.--, therefor On Title page 5, in column 1, under Item (56) "Other Publications", line 38, delete "2010," and insert --2010",--, therefor On Title page 5, in column 1, under Item (56) "Other Publications", line 40, delete "U.S." and insert --"U.S.--, therefor On Title page 5, in column 1, under Item (56) "Other Publications", line 41, delete "2010," and insert --2010",--, therefor On Title page 5, in column 1, under Item (56) "Other Publications", line 42, delete "U.S." and insert --"U.S.--, therefor On Title page 5, in column 1, under Item (56) "Other Publications", line 43, delete "2010," and insert --2010",--, therefor On Title page 5, in column 1, under Item (56) "Other Publications", line 44, delete "Israeli" and insert --"Israeli--, therefor On Title page 5, in column 1, under Item (56) "Other Publications", line 44, delete "Filed" and insert --filed--, therefor On Title page 5, in column 1, under Item (56) "Other Publications", line 45, Delete "2010," and insert --2010",--, therefor On Title page 6, in column 2, under Item (56) "Other Publications", line 10, delete "2011to" and insert --2011 to--, therefor In the Specifications In column 1, line 33, after "aid", delete "to", therefor In column 4, line 19, after "hydroxy,", insert --($C_{1-8}$)alkyl--, therefor In column 4, line 48, after "are", delete "independently", therefor In column 5, line 35, delete "alkylsulfonyl," and insert --alkylsulfonyl;--, therefor In column 5, line 50, delete "Rx" and insert --$R^x$--, therefor In column 5, line 52, delete "Ry" and insert --$R^y$--, therefor In column 5, line 55, delete "Rx" and insert --$R^x$--, therefor In column 5, line 57, delete "Ry" and insert --$R^y$--, therefor In column 5, line 60, delete "Rx" and insert --$R^x$--, therefor In column 5, line 62, delete "Ry" and insert --$R^y$--, therefor In column 6, line 1, delete "$R^{29}$" and insert --$R^{20}$--, therefor In column 6, line 3, delete "arlkyloxycarbonyl," and insert --arlkyloxycarbonyl;--, therefor In column 6, line 9, delete "$R_x$" and insert --$R^x$--, therefor In column 6, line 9, delete "$R_y$" and insert --$R^y$--, therefor In column 6, line 37, delete "aryl," and insert --aryl;--, therefor In column 6, line 53, after "or", insert --$R^{ii}$-- therefor In column 6, line 65, delete "heteroaryl," and insert --heteroaryl;--, therefor In column 8, line 23, delete "mono-or" and insert --mono- or--, therefor In column 9, line 36, delete "Rx" and insert --$R^x$--, therefor In column 9, line 42, delete "Ry" and insert --$R^y$--, therefor In column 9, line 43, delete "Rx" and insert --$R^x$--, therefor In column 9, line 46, delete "Ry" and insert --$R^y$--, therefor In column 9, line 48, delete "Rx" and insert --$R^x$--, therefor In column 9, line 50, delete "Ry" and insert --$R^y$--, therefor In column 9, line 58, delete "arlkyloxycarbonyl," and insert --arlkyloxycarbonyl;--, therefor In column 9, line 64, delete "Rx" and insert --$R^x$--, therefor In column 9, line 67, delete "Ry" and insert --$R^y$--, therefor In column 10, line 3, delete "6;t" and insert --6; t--, therefor In column 10, line 24, delete "aryl," and insert --aryl;--, therefor In column 10, line 46, after "and", delete "¶", therefor In column 10, line 49, delete "heteroaryl," and insert --heteroaryl;--, therefor In column 11, line 30, delete "butanediol," and insert --butanediol;--, therefor In column 12, line 1, delete "$COR^S$;" and insert --$COR^8$;--, therefor In column 12, line 63, after "are", delete "independently", therefor In column 14, line 1, delete "Rx" and insert --$R^x$--, therefor In column 14, line 6, delete "Ry" and insert --$R^y$--, therefor In column 14, line 8, delete "Rx" and insert --$R^x$--, therefor In column 14, line 11, delete "Ry" and insert --$R^y$--, therefor

CERTIFICATE OF CORRECTION (continued)

U.S. Pat. No. 8,415,295 B2

In column 14, line 12, delete "Rx" and insert --$R^x$--, therefor

In column 14, line 28, delete "Rx" and insert --$R^x$--, therefor

In column 14, line 31, delete "Ry" and insert --$R^y$--, therefor

In column 14, line 35, delete "6;t" and insert --6; t--, therefor

In column 15, line 56, delete "aryl," and insert --aryl;--, therefor

In column 16, line 5, delete "$CR^iR^{ii}$is" and inset --$CR^iR^{ii}$ is--, therefor In column 16, line 7, delete "$(CH_2)$;" and insert --$(CH_2)_j$--, therefor In column 16, line 10, delete "$(CH_2)$" and insert --$(CH_2)_j$--, therefor In column 17, line 66, after "phenyl-$CH_2$—$C(CH_3)_2$—)", insert --,--, therefor In column 18, line 22, delete "aryl," and insert --aryl;--, therefor In column 18, line 38, delete "aryl," and insert --aryl;--, therefor In column 18, line 41, delete "(cc))" and insert --(ee))--, therefor In column 18, line 55, delete "Rx" and insert --$R^x$--, therefor In column 18, line 59, delete "Ry" and insert --$R^y$--, therefor In column 18, line 62, delete "Rx" and insert --$R^x$--, therefor In column 18, line 66, delete "Ry" and insert --$R^y$--, therefor In column 19, line 2, delete "Rx" and insert --$R^x$--, therefor In column 19, line 5, delete "Ry" and insert --$R^y$--, therefor In column 19, line 19, delete "Rx" and insert --$R^x$--, therefor In column 19, line 22, delete "Ry" and insert --$R^y$--, therefor In column 19, line 24, delete "aralkylcarboxamido;" and insert --aralkylcarboxamido,--, therefor In column 19, line 30, delete "Rx" and insert --$R^x$--, therefor In column 19, line 35, delete "Rx" and insert --$R^x$--, therefor In column 19, line 46, delete "Rx" and insert --$R^x$--, therefor In column 21, line 17, delete "aryl," and insert --aryl;--, therefor In column 21, line 37, delete "heteroaryl," and insert --heteroaryl;--, therefor In column 21, line 51, delete "$R^1$," and insert --$R^1$,--, therefor In column 23, line 16, delete "O" and insert --O,--, therefor In column 31, line 18, delete "CO2$R^8$," and insert --$CO_2R^8$,--, therefor In column 31, line 21, delete "($C_{1-10}$) dialkylamino;" and insert --($C_{1-10}$)dialkylamino;--, therefor In column 33, line 29, delete "arlkyloxycarbonyl," and insert --arlkyloxycarbonyl;--, therefor In column 35, line 24, delete "$R^2$;" and insert --$R^7$;--, therefor In column 35, line 59, delete "R26 $i_s$:" and insert --$R^{26}$ is:--, therefor In column 38, line 21, delete "R"" and insert --$R^{11}$--, therefor In column 38, line 22-23, delete "oxopyrro-lidinyl," and insert --oxopyrrolidinyl;--, therefor In column 38, line 23, delete "alkoxy," and insert --alkoxy;--, therefor In column 44, line 45, delete "Rx" and insert --$R^x$--, therefor In column 44, line 49, delete "Ry" and insert --$R^y$--, therefor In column 44, line 50, delete "Rx" and insert --$R^x$--, therefor In column 44, line 54, delete "Ry" and insert --$R^y$--, therefor In column 44, line 55, delete "Rx" and insert --$R^x$--, therefor In column 44, line 55, delete "Ry" and insert --$R^y$--, therefor In column 45, line 4, delete "$R_x$" and insert --$R^x$--, therefor In column 45, line 7, delete "$R_y$" and insert --$R^y$--, therefor In column 45, line 32, delete "aryl," and insert --aryl;--, therefor In column 45, line 59, delete "butanediol," and insert --butanediol;--, therefor In column 46, line 10, delete "aryl," and insert --aryl;--, therefor In column 46, line 31, delete "aryl," and insert --aryl;--, therefor In column 48, line 56, delete "Rx" and insert --$R^x$--, therefor In column 48, line 61, delete "Ry" and insert --$R^y$--, therefor In column 48, line 63, delete "Rx" and insert --$R^x$--, therefor In column 48, line 66, delete "Ry" and insert --$R^y$--, therefor In column 49, line 1, delete "Rx" and insert --$R^x$--, therefor In column 49, line 4, delete "Ry" and insert --$R^y$--, therefor In column 49, line 18, delete "$R_x$" and insert --$R^x$--, therefor In column 49, line 21, delete "$R_y$" and insert --$R^y$--, therefor In column 49, line 27, delete "Rx" and insert --$R^x$--, therefor In column 49, line 27, delete "Rx" and insert --$R^x$--, therefor In column 50, line 9, delete "aryl," and insert --aryl;--, therefor In column 50, line 26, delete "compoundshave" and insert --compounds have--, therefor In column 51, line 64, delete "as ," and insert --as,--, therefor In column 52, line 51, delete "$SOR^B$;" and insert --$SOR^8$;--, therefor In column 53, line 22, delete "$(CH2)_p$," and insert --$(CH_2)_p$--, therefor In column 53, line 32, delete "$(C_{1-4}$alkoxy," and insert --$(C_{1-4})$alkoxy,--, therefor In column 54, line 47, delete "Rx" and insert --$R^x$--, therefor In column 54, line 51, delete "Ry" and insert --$R^y$--, therefor In column 54, line 53, delete "Rx" and insert --$R^x$--, therefor In column 54, line 56, delete "Ry" and insert --$R^y$--, therefor In column 54, line 57, delete "Rx" and insert --$R^x$--, therefor In column 54, line 59, delete "Ry" and insert --$R^y$--, therefor In column 55, line 6, delete "$R_x$" and insert --$R^x$--, therefor In column 55, line 9, delete "$R_y$" and insert --$R^y$--, therefor In column 55, line 34, delete "aryl," and insert --aryl;--, therefor In column 55, line 63, delete "heteroaryl," and insert --heteroaryl;--, therefor In column 56, line 38, delete "$COR^S$;" and insert --$COR^8$;--, therefor In column 57, line 1, delete "ith" and insert --with--, therefor In column 58, line 42, delete "Rx" and insert --$R^x$--, therefor In column 58, line 45, delete "Ry" and insert --$R^y$--, therefor In column 58, line 46, delete "Rx" and insert --$R^x$--, therefor In column 58, line 50, delete "Ry" and insert --$R^y$--, therefor In column 58, line 51, delete "Rx" and insert --$R^x$--, therefor In column 58, line 51, delete "Rx" and insert --$R^x$--, therefor In column 58, line 52, delete "Ry" and insert --$R^y$--, therefor In column 58, line 67, delete "$R_x$" and insert --$R^x$--, therefor In column 59, line 3, delete "$R_y$" and insert --$R^y$--, therefor In column 59, line 33, delete "aryl," and insert --aryl;--, therefor In column 59, line 57, delete "aryl," and insert --aryl;--, therefor In column 66, line 21, delete "of" and insert --of:--, therefor In column 66, line 41, delete "PPAR" and insert --PPARδ--, therefor In column 69, line 16, delete "y" and insert --γ--, therefor In column 70, line 2, delete "H039242" and insert --HO39242--, therefor In column 70, line 38, delete "y" and insert --γ--, therefor In column 74, line 33, delete "DPP-1V" and insert --DPP-IV--, therefor In column 75, line 53, before "may", delete "of the invention", therefor In column 77, line 18, delete "include also" and insert --also include--, therefor In column 79, line 2, delete "both." and insert --both;--, therefor In column 81, line 50, delete "alchohols" and insert --alcohols--, therefor In column 81, line 62, delete "($Me_2$)-)is" and insert --($Me_2$)-) is--, therefor In column 83, line 34, delete "isoprpoxy," and insert --isopropoxy,--, therefor In column 83, line 44, delete "attachement" and insert --attachment--, therefor In column 83, line 46, delete "attachement" and insert --attachment--, therefor In column 85, line 10, delete "alkenyl," and insert --alkenoyl,--, therefor In column 90, line 6, delete "(35)" and insert --(3S)--, therefor In column 90, line 14, delete "8. TFA salt." and insert --8-TFA salt--, therefor In column 91, line 11, delete "salt." and insert --salt--, therefor In column 91, line 50, delete "12-TFA" and insert --12·TFA--, therefor In column 92, line 25, delete "15.TFA" and insert --15·TFA--, therefor In column 92, line 42, delete "(25)" and insert --(2S)--, therefor In column 92, line 46, delete "chormatography" and insert --chromatography--, therefor In column 93, line 3, after "reaction", insert --mixture--, therefor In column 93, line 21, delete "19.TFA" and insert --19·TFA--, therefor In column 94, line 19, delete "21-TFA" and insert --21·TFA--, therefor In column 121, Compound No. 119, delete "368" and insert --364--, therefor In column 125, Compound No. 129, delete "(10)" and insert --(28)--, therefor In the Claims In column 127, line 35, in Claim 1, before "including", insert --or of formula:

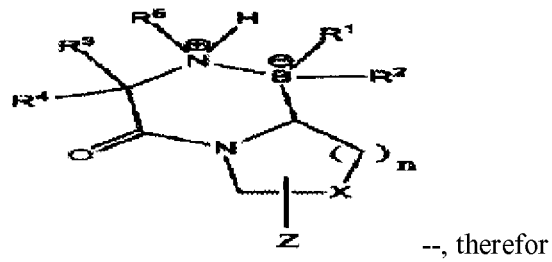

--, therefor

In column 127, line 35, in Claim 1, after "all", delete "cyclic isomers therefor,", therefor In column 128, line 59, in Claim 2, after "for", insert --the symptoms or complications of--, therefor In column 128, line 63, in Claim 2, delete "compound." and insert --compound, wherein the malcondition is impaired glycemic control or Type II diabetes.--, therefor In column 129, line 8, in Claim 4, delete "of" and insert --of:--, therefor In column 130, line 14, in Claim 9, delete "Rx" and insert --$R^x$--, therefor